(12) United States Patent
Abul-Husn et al.

(10) Patent No.: US 11,845,963 B2
(45) Date of Patent: Dec. 19, 2023

(54) HSD17B13 VARIANTS AND USES THEREOF

(71) Applicant: Regeneron Pharmaceuticals, Inc., Tarrytown, NY (US)

(72) Inventors: Noura S. Abul-Husn, Tarrytown, NY (US); Omri Gottesman, Tarrytown, NY (US); Alexander Li, Tarrytown, NY (US); Xiping Cheng, Tarrytown, NY (US); Yurong Xin, Tarrytown, NY (US); Jesper Gromada, Tarrytown, NY (US); Frederick E. Dewey, Tarrytown, NY (US); Aris Baras, Tarrytown, NY (US); Alan Shuldiner, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/875,192

(22) Filed: Jan. 19, 2018

(65) Prior Publication Data

US 2018/0216084 A1   Aug. 2, 2018

Related U.S. Application Data

(60) Provisional application No. 62/581,918, filed on Nov. 6, 2017, provisional application No. 62/472,972, filed (Continued)

(51) Int. Cl.

| | |
|---|---|
| C12Q 1/68 | (2018.01) |
| C12P 19/34 | (2006.01) |
| C12N 9/04 | (2006.01) |
| C12N 15/113 | (2010.01) |
| C12Q 1/6883 | (2018.01) |
| A61K 31/713 | (2006.01) |
| G01N 33/50 | (2006.01) |
| C12Q 1/32 | (2006.01) |
| C12Q 1/6827 | (2018.01) |
| C12Q 1/6876 | (2018.01) |
| A61K 47/61 | (2017.01) |
| A61P 1/16 | (2006.01) |
| A61K 38/44 | (2006.01) |
| A61K 38/46 | (2006.01) |

(Continued)

(52) U.S. Cl.
CPC .......... *C12N 9/0006* (2013.01); *A61K 31/713* (2013.01); *A61K 38/443* (2013.01); *A61K 38/465* (2013.01); *A61K 47/61* (2017.08); *A61P 1/16* (2018.01); *C12N 9/22* (2013.01); *C12N 9/96* (2013.01); *C12N 15/11* (2013.01); *C12N 15/113* (2013.01); *C12N 15/1137* (2013.01); *C12N 15/85* (2013.01); *C12N 15/907* (2013.01); *C12Q 1/32* (2013.01); *C12Q 1/6827* (2013.01); *C12Q 1/6876* (2013.01); *C12Q 1/6883* (2013.01); *C12Y 101/01051* (2013.01); *C12Y 101/01062* (2013.01); *G01N 33/5067* (2013.01); *A61K 48/00* (2013.01); *A61K 48/0066* (2013.01); *C12N 2310/14* (2013.01); *C12N 2310/20* (2017.05); *C12N 2310/531* (2013.01); *C12N 2320/30* (2013.01); *C12N 2320/34* (2013.01); *C12N 2800/24* (2013.01); *C12N 2800/80* (2013.01); *C12Q 2600/118* (2013.01); *C12Q 2600/156* (2013.01); *C12Q 2600/158* (2013.01); *G01N 2333/4704* (2013.01); *G01N 2800/085* (2013.01)

(58) Field of Classification Search
CPC .......... A61K 48/00; C12N 15/11; C12Q 1/32; C12Q 1/6883; C12Q 2600/118; C12Q 2600/156
See application file for complete search history.

(56) References Cited

U.S. PATENT DOCUMENTS

| | | | |
|---|---|---|---|
| 4,683,202 A | * | 7/1987 | Mullis ................... C12N 15/10 435/317.1 |
| 6,147,066 A | | 11/2000 | Petit et al. |

(Continued)

FOREIGN PATENT DOCUMENTS

| | | |
|---|---|---|
| CN | 104698108 | 6/2015 |
| CN | 103520724 B | 5/2016 |

(Continued)

OTHER PUBLICATIONS

RefSNP cluster report rs72613567 (printed Jun. 6, 2019 from ncbi.nlm.nih.gov).*

(Continued)

*Primary Examiner* — Stephen T Kapushoc
(74) *Attorney, Agent, or Firm* — Armstrong Teasdale LLP

(57) ABSTRACT

Provided are compositions related to HSD17B13 variants, including nucleic acid molecules and polypeptides related to variants of HSD17B13, and cells comprising those nucleic acid molecules and polypeptides. Also provided are methods related to HSD17B3 variants. Such methods include methods for detecting the presence of the HSD17B13 rs72613567 variant in a biological sample comprising genomic DNA, for detecting the presence or levels of any one of variant HSD17B13 Transcripts C, D, E, F, G, and H, and particularly D, in a biological sample comprising mRNA or cDNA, or for detecting the presence or levels of any one of variant HSD17B13 protein Isoforms C, D, E, F, G, or H, and particularly D, in a biological sample comprising protein. Also provided are methods for determining a subject's susceptibility to developing a liver disease or of diagnosing a subject with liver disease.

12 Claims, 23 Drawing Sheets
Specification includes a Sequence Listing.

Related U.S. Application Data on Mar. 17, 2017, provisional application No. 62/449,335, filed on Jan. 23, 2017.

(51) Int. Cl.

| | |
|---|---|
| *C12N 9/22* | (2006.01) |
| *C12N 9/96* | (2006.01) |
| *C12N 15/11* | (2006.01) |
| *C12N 15/85* | (2006.01) |
| *C12N 15/90* | (2006.01) |
| *A61K 48/00* | (2006.01) |

(56) References Cited

U.S. PATENT DOCUMENTS

| | | | |
|---|---|---|---|
| 7,820,380 | B2 | 10/2010 | Huang |
| 7,951,382 | B2 | 5/2011 | Gelber et al. |
| 7,951,776 | B2 | 5/2011 | Gelber |
| 8,071,302 | B2 | 12/2011 | Huang |
| 8,945,847 | B2 | 2/2015 | Benvenisty et al. |
| 9,051,567 | B2 | 6/2015 | Fitzgerald et al. |
| 9,072,743 | B2 | 7/2015 | Dilly et al. |
| 9,328,346 | B2 | 5/2016 | Lee et al. |
| 9,375,433 | B2 | 6/2016 | Dilly et al. |
| 9,526,720 | B2 | 12/2016 | Nagiec et al. |
| 9,574,241 | B2 | 2/2017 | Ferrando et al. |
| 9,585,887 | B2 | 3/2017 | Dilly et al. |
| 9,585,890 | B2 | 3/2017 | Dilly et al. |
| 9,617,514 | B2 | 4/2017 | Lunyak |
| 9,629,804 | B2 | 4/2017 | Heartlein et al. |
| 9,632,090 | B2 | 4/2017 | DePinho et al. |
| 9,677,138 | B2 | 6/2017 | Steiling et al. |
| 9,796,762 | B2 | 10/2017 | Kelly et al. |
| 9,808,462 | B2 | 11/2017 | Dilly et al. |
| 9,816,094 | B2 | 11/2017 | Lee et al. |
| 10,052,284 | B2 | 8/2018 | Heartlein et al. |
| 10,577,630 | B2 | 3/2020 | Zhang et al. |
| 10,767,175 | B2 | 9/2020 | Dellinger et al. |
| 10,787,647 | B2 | 9/2020 | Abul-Husn et al. |
| 10,961,583 | B1 | 3/2021 | Xin et al. |
| 2003/0004102 | A1* | 1/2003 | Ashkenazi ............ C07K 14/47 536/23.5 |
| 2005/0158376 | A1 | 7/2005 | Sardi et al. |
| 2007/0219169 | A1 | 9/2007 | Becourt et al. |
| 2008/0300170 | A1 | 12/2008 | Gelber et al. |
| 2009/0169585 | A1 | 7/2009 | Sardi |
| 2009/0203602 | A1 | 8/2009 | Gelber et al. |
| 2010/0028879 | A1 | 2/2010 | Labrie et al. |
| 2010/0056384 | A1 | 3/2010 | Hobbs et al. |
| 2010/0209427 | A1 | 8/2010 | Li et al. |
| 2010/0266618 | A1 | 10/2010 | Stojdl et al. |
| 2010/0267052 | A1 | 10/2010 | Gelber et al. |
| 2011/0130442 | A1 | 6/2011 | Kosaka et al. |
| 2011/0262462 | A1 | 10/2011 | Platt et al. |
| 2011/0129831 | A1 | 12/2011 | Cargill et al. |
| 2012/0015904 | A1 | 1/2012 | Sharp et al. |
| 2012/0028816 | A1 | 2/2012 | Warren et al. |
| 2012/0058088 | A1 | 3/2012 | Sardi |
| 2012/0276528 | A1 | 11/2012 | Cargill et al. |
| 2013/0005596 | A1 | 1/2013 | Gong et al. |
| 2013/0029873 | A1 | 1/2013 | de Perrot et al. |
| 2013/0079241 | A1 | 3/2013 | Luo et al. |
| 2013/0237454 | A1 | 9/2013 | Schutzer |
| 2013/0309769 | A1 | 11/2013 | Benvenisty et al. |
| 2014/0004153 | A1 | 1/2014 | Cowing et al. |
| 2014/0011889 | A1 | 1/2014 | Sardi |
| 2014/0045915 | A1 | 2/2014 | Skog et al. |
| 2014/0057800 | A1 | 2/2014 | Brattbakk et al. |
| 2014/0072957 | A1 | 3/2014 | Huang et al. |
| 2014/0088120 | A1 | 3/2014 | Dilly et al. |
| 2014/0163118 | A1 | 6/2014 | Giuliani et al. |
| 2014/0179536 | A1 | 6/2014 | Hobbs et al. |
| 2014/0295425 | A1 | 10/2014 | Nagy |
| 2014/0329704 | A1 | 11/2014 | Melton et al. |
| 2014/0363502 | A1 | 12/2014 | Sardi |
| 2014/0378425 | A1 | 12/2014 | Wilde et al. |
| 2015/0050728 | A1 | 2/2015 | Benvenisty et al. |
| 2015/0079061 | A1 | 3/2015 | Casey et al. |
| 2015/0079062 | A1 | 3/2015 | Casey et al. |
| 2015/0366997 | A1 | 12/2015 | Guild et al. |
| 2016/0024498 | A1 | 1/2016 | Fitzgerald et al. |
| 2016/0030585 | A1 | 2/2016 | Barnes et al. |
| 2016/0032388 | A1 | 2/2016 | Huang et al. |
| 2016/0032395 | A1 | 2/2016 | Davicioni et al. |
| 2016/0184458 | A1 | 6/2016 | Heartlein et al. |
| 2016/0237501 | A1 | 8/2016 | Sharp et al. |
| 2016/0320395 | A1 | 11/2016 | Ward et al. |
| 2016/0355806 | A1 | 12/2016 | Lee et al. |
| 2016/0355813 | A1 | 12/2016 | Lee et al. |
| 2016/0376598 | A1 | 12/2016 | Lee et al. |
| 2017/0022504 | A1 | 1/2017 | Lee et al. |
| 2017/0037396 | A1 | 2/2017 | Lee et al. |
| 2017/0044550 | A1 | 2/2017 | Lee et al. |
| 2017/0247758 | A1 | 8/2017 | Spiller et al. |
| 2017/0247759 | A1 | 8/2017 | Wilde et al. |
| 2017/0283770 | A1 | 10/2017 | Unyak |
| 2017/0335396 | A1 | 11/2017 | Kennedy et al. |
| 2017/0340661 | A1 | 11/2017 | Fitzgerald et al. |
| 2017/0349903 | A1 | 12/2017 | Liu et al. |
| 2017/0356002 | A1 | 12/2017 | Thompson et al. |
| 2018/0179553 | A1 | 6/2018 | Watson et al. |
| 2018/0179593 | A1 | 6/2018 | Melton et al. |
| 2018/0185516 | A1 | 7/2018 | Ansell et al. |
| 2018/0201936 | A1 | 7/2018 | Hinkle |
| 2018/0216084 | A1 | 8/2018 | Abul-Husn et al. |
| 2018/0216104 | A1 | 8/2018 | Abul-Husn et al. |
| 2018/0273955 | A1 | 9/2018 | Fitzgerald et al. |
| 2019/0002869 | A1 | 1/2019 | Yin et al. |
| 2019/0316121 | A1 | 10/2019 | Smith et al. |
| 2019/0365924 | A1 | 12/2019 | Conway et al. |
| 2019/0390195 | A1 | 12/2019 | Tondera et al. |
| 2020/0354693 | A1 | 11/2020 | Abul-Husn et al. |

FOREIGN PATENT DOCUMENTS

| | | |
|---|---|---|
| EP | 3011032 | 10/2019 |
| EP | 3620524 | 3/2020 |
| EP | 3011031 | 9/2020 |
| RU | 2545990 | 4/2015 |
| RU | 2562868 | 9/2015 |
| WO | 1995029255 | 11/1995 |
| WO | 9720942 | 6/1997 |
| WO | 1999046279 | 9/1999 |
| WO | 1999046281 | 9/1999 |
| WO | 2004110459 | 12/2004 |
| WO | 2005108415 | 11/2005 |
| WO | 2009039195 | 3/2009 |
| WO | 2010028110 | 3/2010 |
| WO | 2010040571 | 4/2010 |
| WO | 2010064702 | 6/2010 |
| WO | 2011006214 | 1/2011 |
| WO | 2011084747 | 7/2011 |
| WO | 2012052953 | 4/2012 |
| WO | 2012087983 | 6/2012 |
| WO | 2013126565 | 8/2013 |
| WO | 2013176772 | 11/2013 |
| WO | 2013177060 | 11/2013 |
| WO | 2013190075 | 12/2013 |
| WO | 2013166264 | 1/2014 |
| WO | 2014089313 | 6/2014 |
| WO | 2014196957 | 12/2014 |
| WO | 2015169971 | 11/2015 |
| WO | 2016004387 | 1/2016 |
| WO | 2016009246 | 1/2016 |
| WO | 2017048620 | 3/2017 |
| WO | 2017106210 | 6/2017 |
| WO | 2017106283 | 6/2017 |
| WO | 2017106292 | 6/2017 |
| WO | 2017106364 | 6/2017 |
| WO | 2017106370 | 6/2017 |
| WO | 2017106375 | 6/2017 |
| WO | 2017106382 | 6/2017 |
| WO | 2017156310 | 9/2017 |
| WO | 2017191274 | 11/2017 |

(56) References Cited

FOREIGN PATENT DOCUMENTS

| WO | 2017211947 | 12/2017 |
|---|---|---|
| WO | 2018107026 | 6/2018 |
| WO | 2018107028 | 6/2018 |
| WO | 2018136702 | 7/2018 |
| WO | 2018136758 | 7/2018 |
| WO | 2018220211 | 12/2018 |
| WO | 2019183164 | 9/2019 |
| WO | 2019183329 | 9/2019 |
| WO | 2019237069 | 12/2019 |
| WO | 2019246203 | 12/2019 |

OTHER PUBLICATIONS

GenBank accession DR004209 (submitted Jan. 2011, printed Jun. 10, 2019, from ncbi.nlm.nih.gov).*
New England Biolabs Catalog (1998/1999), pp. 121 and 284. (Year: 1998).*
Schiavinato, A. et al. The Journal of Biological Chemistry vol. 287, No. 14, pp. 11498-11515, Mar. 30, 2012.*
Submitted SNP(ss) Report in Submission Format for NCBI Assay Id (ss#): ss557289122. Nov. 22, 2012, 1 printed page from www.ncbi.nlm.nih.gov/ (Year: 2012).*
Kakuturu V. N. Rao, et al., "Genotyping single nucleotide polymorphisms directly from genomic DNA by invasive cleavage reaction on microspheres" Nucleic Acids Research, 2003, vol. 31, No. 11 (Year: 2003).*
Stevens, P.W. et al., "Analysis of single nucleotide polymorphisms with solid phase invasive cleavage reactions." Nucleic Acids Res 2001;29:77. (Year: 2001).*
Abul-Husn et al., "A Protein-Truncating HSD17B13 Variant and Protection from Chronic Liver Disease", N Engl J Med, 2018, 378, pp. 1096-1106.
Ford et al., "A New Assay for Picomole Levels of Androsterone and Testosterone Using Co-immobilized Luciferase, Oxidoreductase, and Steroid Dehydrogenase", Analytical Biochemistry, 1981, 110, pp. 43-48.
Krazeisen et al., "Phytoestrogens inhibit human 17β-hydroxysteroid dehydrogenase type 5", Molecular and Cellular Endocrinology, 2001, 171, pp. 151-162.
Promega "Technical Manual: NAD(P)H-Glo Detection System", 2017, TM398, pp. 1-15.
Adam, M., et al., "Hydroxysteroid (17b) dehydrogenase 13 deficiency triggers hepatic steatosis and inflammation in mice", The FASEB Journal, 2018, pp. 1-14.
Altschul, S. F., et al., "Basic Local Alignment Search Tool", J. Mol. Biol., 1990, pp. 403-410, 215.
Altschul, S. F., et al., "Gapped BLAST and PSI-BLAST: a new generation of protein database search programs", Nucleic Acids Research, 1997, pp. 3389-3402, 25 (17).
Brasaemle, D. L., et al., "Isolation of Lipid Droplets from Cells by Density Gradient Centrifugation", Current Protocols in Cell Biology, 2005, 3.15.1-3.15.12.
Browning, J. D., et al., "Prevalence of Hepatic Steatosis in an Urban Population in the United States: Impact of Ethnicity", Hepatology, 2004, pp. 1387-1395, 40(6).
Chambers, J. C., et al., "Genome-wide association study identifies loci influencing concentrations of liver enzymes in plasma" Nat Genet, 2011, pp. 1131-1138, 43(11).
Cohen, J. C., et al., "Human Fatty Liver Disease: Old Questions and New Insights", Science, 2011, pp. 1519-1523, 332.
Denny, J. C., et al., "PheWAS: demonstrating the feasibility of a phenome-wide scan to discover gene-disease associations", Bioinformatics, 2010, pp. 1205-1210, 26(9).
Denny, J. C., et al., "Systematic comparison of phenome-wide association study of electronic medical record data and genome-wide association study data", Nat Biotechnol, 2013, pp. 1102-1110, 31(12).
Dewey, F. E., et al., "Distribution and clinical impact of functional variants in 50,726 whole-exome sequences from the DiscovEHR Study", Science, 2016, pp. aaf6814, 354(6319).
Ding, Y., et al., "Isolating lipid droplets from multiple species", Nature Protocols, 2013, pp. 43-51, 8(1).
Kampf, C., et al., "The human liver-specific proteome defined by transcriptomics and antibody-based profiling", The FASEB Journal, 2014, pp. 2901-2914, 28(7).
Kleiner, D. E., et al., "Design and Validation of a Histological Scoring System for Nonalcoholic Fatty Liver Disease", Hepatology, 2005, pp. 1313-1321, 41(6).
Kochanek, K. D., et al., "Deaths: Final Data for 2014", National Viral Statistics Reports, 2016, pp. 1-122, 65(4).
Kozlitina, J., et al., "Exome-wide association study identifies a TM6SF2 variant that confers susceptibility to nonalcoholic fatty liver disease", Nat Genet, 2014, pp. 352-356, 46(4).
Lazo, M., et al., "Prevalence of Nonalcoholic Fatty Liver Disease in the United States: The Third National Health and Nutrition Examination Survey, 1988-1994", Am J Epidemiol, 2013, pp. 38-45, 178(1).
Li, H., et al., "Fast and accurate short read alignment with Burrows-Wheeler transform", Bioinformatics, 2009, pp. 1754-1760, 25(14).
Li, P., et al., "LTB4 causes macrophage-mediated inflammation and directly induces insulin resistance in obesity", Nat Med, 2015, pp. 239-247, 21(3).
Liu, S., et al., "Molecular cloning and expression analysis of a new gene for shortchain dehydrogenase/reductase 9", Acta Biochimica Polonica, 2007, pp. 213-218, 54(1).
Liu, Y.-L., et al., "TM6SF2 rs58542926 influences hepatic fibrosis progression in patients with non-alcoholic fatty liver disease", Nature Communications, 2014, pp. 1-6, 5(4309).
McKenna, A., et al., "The Genome Analysis Toolkit: A MapReduce framework for analyzing next-generation DNA sequencing data", Genome Research, 2010, pp. 1297-1303, 20.
Moeller, G., et al., "Integrated view on 17betahydroxysteroid dehydrogenases", Molecular and Cellular Endocrinology, 2009, pp. 7-19, 301.
Morgan, R. L., et al., "Eradication of Hepatitis C Virus Infection and the Development of Hepatocellular Carcinoma", Annals of Internal Medicine, 2013, pp. 329-337 and W-158-W-160, 158(5)(Part 1).
NCBI Reference Sequence: NM_178135, "*Homo spiens* hydroxysteroid 17-beta dehydrogenase 13 (HSD17B13), transcript variant A, mRNA" 2017, pp. 1-5.
NCBI Reference Sequence: NM_001136230, "*Homo sapiens* hydroxysteroid 17-beta dehydrogenase 13 (HSD17B13), transcript variant B, mRNA" 2017, pp. 1-5.
NCBI Reference Sequence: NP_835236, "17-beta-hydroxysteroid dehydrogenase 13 isoform A precursor [*Homo sapiens*]", 2017 pp. 1-4.
NCBI Reference Sequence: NP_001129702, "17-beta-hydroxysteroid dehydrogenase 13 isoform B [*Homo sapiens*]", 2017, pp. 1-4.
Pruim, R. J., et al., "LocusZoom: regional visualization of genome-wide association scan results", Bioinformatics, 2010, pp. 2336-2337, 26(18).
Reid, J. G., et al., "Launching genomics into the cloud: deployment of Mercury, a next generation sequence analysis pipeline", BMC Bioinformatics, 2014, pp. 1-11, 15(30).
Romeo, S., et al., "Genetic variation in PNPLA3 confers susceptibility to nonalcoholic fatty liver disease", Nat Genet, 2008, pp. 1461-1465, 40(12).
Rotman, Y., et al., "The Association of Genetic Variability in PNPLA3 with Histological Severity of Non-Alcoholic Fatty Liver Disease", Hepatology, 2010, pp. 894-903, 52(3).
Smith, T. F., et al., "Comparsion of Biosequences", Advances in Applied Mathematics, 1981, pp. 482-489, 2.
Sookoian, S., et al., "A nonsynonymous gene variant in the adiponutrin gene is associated with nonalcoholic fatty liver disease severity", Journal of Lipid Research, 2009, pp. 2111-2116, 50.
Sookoian, S., et al., "Genetic Variation in Transmembrane 6 Superfamily Member 2 and the Risk of Nonalcoholic Fatty Liver Disease and Histological Disease Severity", Hepatology, 2015, pp. 515-525, 61(2).

(56) References Cited

OTHER PUBLICATIONS

Speliotes, E. K., et al., "Genome-Wide Association Analysis Identifies Variants Associated with Nonalcoholic Fatty Liver Disease That Have Distinct Effects on Metabolic Traits", PLOS Genetics, 2011, e1001324, 7(3).
Su, W., et al., "Comparative proteomic study reveals 17!-HSD13 as a pathogenic protein in nonalcoholic fatty liver disease", PNAS, 2014, pp. 11437-11442, 111(31).
Trepo, E., et al., "PNPLA3 gene in liver diseases", Journal of Hepatology, 2016, pp. 399-412, 65.
UniProtKB-Q7Z5P4-1, "17-beta-hydroxysteroid dehydrogenase 13", 2003, pp. 6.
UniProtKB-Q7Z5P4-2, "17-beta-hydroxysteroid dehydrogenase 13", 2003, pp. 6-7.
Van Der Meer, A. J., et al., "Association Between Sustained Virological Response and All-Cause Mortality Among Patients With Chronic Hepatitis C and Advanced Hepatic Fibrosis", JAMA, 2012. pp. 2584-2593, 308(24).
Victor, R. G., et al., "The Dallas Heart Study: A Population-Based Probability Sample for the Multidisciplinary Study of Ethnic Differences in Cardiovascular Health", Am J Cardiol, 2004, pp. 1473-1480, 93.
Willer, C. J., et al., "METAL: fast and efficient meta-analysis of genomewide association scans", Bioinformatics, 2010, pp. 2190-2191, 26(17).
Williams, C. D., et al., "Clinical Advances in Liver, Pancreas, and Biliary Tract", Gastroenterology, 2011, pp. 124-131, 140.
Wong, R. J., et al., "Nonalcoholic Steatohepatitis Is the Second Leading Etiology of Liver Disease Among Adults Awaiting Liver Transplantation in the United States", Gastroenterology, 2015, pp. 547-555, 148.
Yang, J., et al., "GCTA: A Tool for Genome-wide Complex Trait Analysis", The American Journal of Human Genetics, 2011, pp. 76-82, 88.
Younossi, Z. M., et al., "Changes in the Prevalence of the Most Common Causes of Chronic Liver Diseases in the United States From 1988 to 2008", Clinical Gastroenterology and Hepatology, 2011, pp. 524-530, 9.
Yuan, X., et al., "Population-Based Genome-wide Association Studies Reveal Six Loci Influencing Plasma Levels of Liver Enzymes", The American Journal of Human Genetics, 2008, pp. 520-528, 83.
Zhang, J., et al., "PowerBLAST: A New Network BLAST Application for Interactive of Automated Sequence Analysis and Annotation", Genome Research, 1997, pp. 649-656, 7.
Edelman et al., "Genetic analysis of nonalcoholic fatty liver disease within a Caribbean-Hispanic population", Molecular Genetics & Genomic Medicine, 2015, 3(6), pp. 558-569.
Hotta et al., "R association of the rs738409 polymorphism in PNPLA3 with liver damage and the development of nonalcoholic fatty liver disease", BMC Medical Genetics, 2010, 11(172), pp. 1-10.
Kahali et al., "Insights from Genome-Wide Association Analyses of Nonalcoholic Fatty Liver Disease", Seminars in Liver Disease, 2015, 35(4), pp. 375-391.
Oniki et al., "Influence of the PNPLA3 rs738409 Polymorphism on Non-Alcoholic Fatty Liver Disease and Renal Function among Normal Weight Subjects", PLOS One, 2015, 10(7), pp. e0132640.
Shen et al., "The rs738409 (I148M) variant of the PNPLA3 gene and cirrhosis: a meta-analysis", Journal of Lipid Research, 2015, 56(1), pp. 167-175.
International Search Report and Written Opinion for PCT Application PCT/US2018/014637.
Brantly et al., "Crystal RG. Molecular basis of alpha-1-antitrypsin deficiency", Am J Med, 1988, pp. 13-31, 84.
Feitosa et al., "The ERLIN1-CHUK-CWF19L1 gene cluster influences liver fat deposition and hepatic inflammation in the NHLBI Family Heart Study", Atherosclerosis, 2013, pp. 175-180, 228.
Huang et al., "Expression and Characterization of a PNPLA3 Protein Isoform (I148M) Associated with Nonalcoholic Fatty Liver Disease", J Biol Chem, 2011, pp. 37085-37093, 286.

Kitamoto et al., "Genome-wide scan revealed that polymorphisms in the PNPLA3, SAMM50, and PARVB genes are associated with development and progression of nonalcoholic fatty liver disease in Japan", Hum Genet, 2013, pp. 783-792, 132.
Mahdessian et al., "TM6SF2 is a regulator of liver fat metabolism influencing triglyceride secretion and hepatic lipid droplet content", PNAS, 2014, pp. 8913-8918, 111.
Pirazzi et al., "Patatin-like phospholipase domain-containing 3 (PNPLA3) I148M (rs738409) affects hepatic VLDL secretion in humans and in vitro", J Hepatol, 2012, pp. 1276-1282, 57.
Shen et al., "The rs738409 (I148M) variant of the PNPLA3 gene and cirrhosis: a meta-analysis", J Lipid Res, 2015, pp. 167-175, 56.
Smagris et al., "Inactivation of Tm6sf2, a Gene Defective in Fatty Liver Disease, Impairs Lipidation but Not Secretion of Very Low Density Lipoproteins", J Biol Chem, 2016, pp. 10659-10676, 291.
Office Action dated Feb. 4, 2020 in related U.S. Appl. No. 15/913,366.
Leippe et al., "Bioluminescent Nicotinamide Adenine Dinucleotide Detection Assays Part 1: Technology and Features", 2014, hhttp://www.promega.com/resources/pubhub/bioluminescent-nicotinamide-adenine-dinucleotide-detection-assays/.
International Search Report/Written Opinion dated Jun. 26, 2019 received in application No. PCT/US19/23079.
G. Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBIO, 2015, 6(4):e01122-15.
S.Q. Tsai and K. Young, "Defining and improving the genome-wide specificities of CRISPR-Cas9 nucleases", Nature Reviews Genetics, 2016, 17:300-312.
Ghanbari, et al., "Genetic Variations in MicroRNA-Binding Sites Affect MicroRNA-Mediated Regulation of Several Genes Associated With Cardio-metabolic Phenotypes," Circ. Cardiovasc. Genet., 2015, 8(3), pp. 473-486.
Gieger, et al., "New gene functions in megakaryopoiesis and platelet formation," Nature, 2012, 480(7376), pp. 201-208 plus Supplementary Information.
Haapaniemi et al., "CRISPR-Cas9 genome editing induces a p53-mediated DNA damage response," Nat. Med. doi: 10.1038/s41591-018-0049-z, (Jun. 11, 2018, epub ahead of print).
Hry et al., "p53 inhibits CRISPR-Cas9 engineering in human pluripotent stem cells," Nat. Med. doi: 10.1038/s41591-018-0050-6 (Jun. 11, 2018, epub ahead of print).
Jiang et al., "Structural Biology. A Cas9-guide RNA complex preorganized for target DNA recognition," Science, 2015, 348(6242), pp. 1477-1481.
Jinek et al., "RNA-programmed genome editing in human cells," eLife, 2013, 2:e00471.
Komor et al., "CRISPR-Based Technologies for the Manipulation of Eukaryotic Genomes," Cell, 2017, 168(1-2), pp. 20-36.
Kosicki et al., "Repair of double-strand breaks induced by CRISPR-Cas9 leads to large deletions and complex rearrangements," Nat. Biotechnol., 2018, 36(8), pp. 765-771.
Nishimasu et al., "Crystal Structure of Cas9 in Complex with Guide RNA and Target DNA," Cell, 2014, 156(5), pp. 935-949.
PubMed NCBI Search Results for ((CRISPR[Title] OR Cas9[Title]) and ("Jan. 1, 2012"[PDate] : "Jan. 22, 2017")), https://www.ncbi.nlm.nih.gov/pubmed, retrieved on Sep. 22, 2019.
Quadri, et al., "Mutations in SLC30A10 Cause Parkinsonism and Dystonia with Hypermanganesemia, Polycthemia, and Chronic Liver Disease," The American Journal of Human Genetics, 2012, 90, pp. 467-477 plus Supplemental Material.
Ratziu, et al., "Current efforts and trends in the treatment of NASH," Journal of Hepatology, 2015, 62, pp S65-S75.
Santa Cruz Biotechnology, "17β-HSD13 Antibody (K-14): sc-161285" [Retrieved from the Internet Jun. 1, 2016: www.scbt.com/datasheet-161285-17betahsd13-k-14-antibody.html].
Santa Cruz Biotechnology, "17β-HSD13 siRNA (m), shRNA and Lentiviral Particle Gene Silencers" [Retrieved from the Internet Jun. 1, 2016: www.scbt.com/datasheet-108263-17beta-hsd13-sima-m.html].

(56) References Cited

OTHER PUBLICATIONS

Tang, et al., "A mouse knockout library for secreted and transmembrane proteins," Nature Biotechnology, 2010, 28 (7), pp. 749-755 plus Online Methods and Supplementary Information.
Non-Final Office Action dated Jul. 10, 2019 for U.S. Appl. No. 15/875,514.
Notice of Allowance dated Jan. 22, 2020 in U.S. Appl. No. 15/875,514.
International Search Report and Written Opinion of the International Searching Authority dated Jun. 6, 2018 for WIPO Application No. PCT/US2018/014454.
Business Wire, "Arrowhead Pharmaceuticals Initiates Phase 1/2 Study of ARO-HSD in Normal Healthy Volunteers and Patients with NASH of Suspected NASH", Mar. 3, 2020, pp. 1-2. businesswire. com/news/home/20200303005396/en/Arrowhead-Pharmaceuticals-Initiates-Phase-12-Study-ARO-HSD.
Zhang et al., "Omic studies reveal the pathogenic lipid droplet proteins in non-alcoholic fatty liver disease", Protein Cell, 2017, 8(1), pp. 4-13.
Non-Final Office Action dated Jun. 12, 2020 for U.S. Appl. No. 16/157,503.
Moeller et al., "Multifunctionality of human 17β-hydroxysteriod dehydrogenases", Molecular and Cellular Endocrinology, 2006, 248, pp. 47-55.
Final Office Action dated Sep. 22, 2020 for U.S. Appl. No. 15/913,366.
Notice of Allowance dated May 1, 2020 in U.S. Appl. No. 15/875,514.
Kitamoto et al., "Association of polymorphisms in GCKR and TRIB1 with nonalcoholic fatty liver disease and metabolic syndrome traits", Endocrine Journal, 2014, 61(7), pp. 683-689.
Notice of Allowance dated Nov. 19, 2020 for U.S. Appl. No. 16/157,503.
Brooks et al., "Basics of Enzymatic Assays for HTS", Assay Guidance Manual, 2012, pp. 1-12.
Doan et al., "Breast cancer prognosis predicted by nuclear receptor-coregulator networks", Molecular Oncology, 2014, 8, pp. 998-1013.
Ducharme et al., "Minireview: Lipid Droplets in Lipogenesis and Lipolysis", Endocrinology, 2008, 149(3), pp. 942-949.
Jequier et al., "Water as an essential nutrient: the physiological basis of hydration", European Journal of Clinical Nutrition, 2010, 64, pp. 115-123.
Karlson, "Introduction to Modern Biochemistry: Chapter V Enzymes and Biocatalysis", Fourth Edition, 1975, pp. 74-100.
Kuhl et al., "Pharmacology of estrogens and progestogens: influence of different routes of administration", Climacteric, 2005, 8, pp. 3-63.
Labrie, "Multiple intracrine hormonal targets in the prostate: opportunities and challenges", BJU Int, 2007, 100, pp. 48-51.
Mashek et al., "Hepatic Lipid Droplet Biology: Getting to the Root of Fatty Liver", Hepatology, 2015, 62, pp. 964-967.
Su et al., "Comparative proteomic study reveals 17beta-HSD13 as a pathogenic protein in nonalcoholic fatty liver disease", PNAS, 2014, 111(31), pp. 11437-11442.
Wolf et al., "To err is human: Patient misinterpretations of prescription drug label instructions", Patient Education and Counseling, 2007, 67, pp. 293-300.
Non-Final Office Action dated Sep. 8, 2021 in related U.S. Appl. No. 15/913,366.
Hassan et al., "Nonalcoholic fatty liver disease: A comprehensive review of a growing epidemic", World J Gastroenterology, 2014, 20(34), pp. 12082-12101.
Nemudryi et al., "TALEN and CRISPR/Cas Genome Editing Systems: Tools of Discovery", Acta Nature, 2014, 6 (No. 3 (22)), pp. 19-40.
Sun et al., "The CRSPR/Cas9 system for gene editing and its potential application in pain research", Transl Perioper Pain Med, 2016, 1(3), pp. 22-33.
Anstee et al., "Genetic Factors That Affect Risk of Alcoholic and Nonalcoholic Fatty Liver Disease", Gastroenterology, 2016, 150(8), pp. 1728-1744.
Final Office Action dated May 5, 2022 for U.S. Appl. No. 15/913,366.
Third Party Submission filed Feb. 25, 2022 in U.S. Appl. No. 16/978,947.
Elphick et al., "Conserved valproic-acid-induced lipid droplet formation in Dictyostelium and human hepatocytes identifies structurally active compounds", Disease Models & Mechanisms, 2012, pp. 231-240.
Del Ben et al., "Non-alcoholic fatty liver disease, metabolic syndrome and patatin-like phospholipase domain-containing protein3 gene variants", European Journal of Internal Medicine, 2014, 25, pp. 566-570.
Non-Final Office Action dated Sep. 26, 2022 in related U.S. Appl. No. 17/178,420.
Final Office Action dated Jan. 10, 2023 in related U.S. Appl. No. 17/178,420.

\* cited by examiner

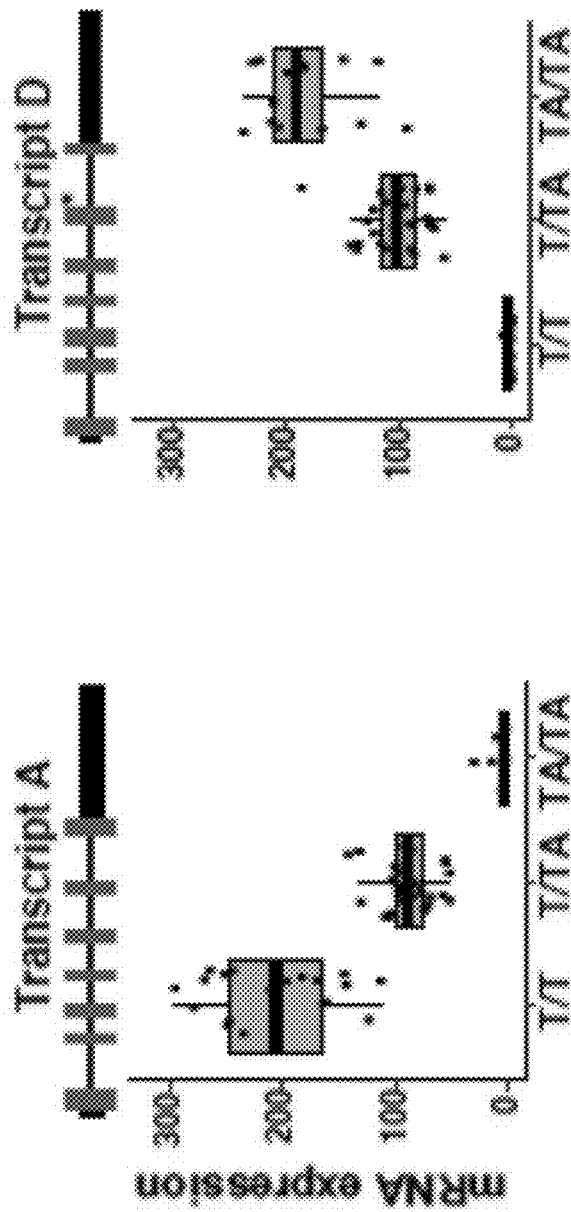
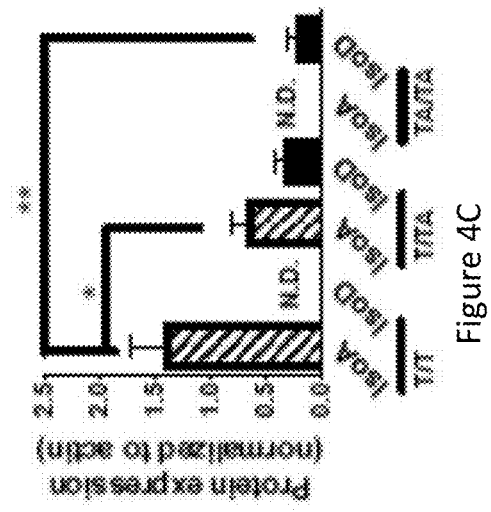
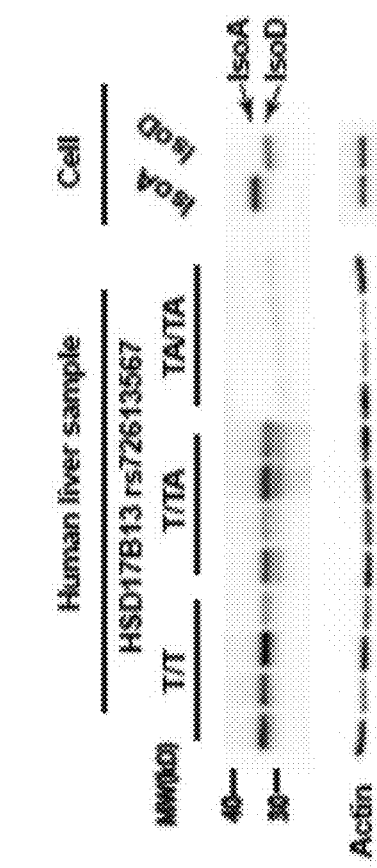
Figure 4A
Figure 4B
Figure 4C

HSD17B13 VARIANTS AND USES THEREOF

CROSS-REFERENCE TO RELATED APPLICATIONS

This application claims priority to U.S. Application No. 62/581,918, filed Nov. 6, 2017, to U.S. Application No. 62/472,972, filed Mar. 17, 2017, and to U.S. Application No. 62/449,335, filed Jan. 23, 2017, each of which is incorporated herein by reference in its entirety.

REFERENCE TO A SEQUENCE LISTING

This application includes a Sequence Listing submitted electronically as a text file named 18923800801SEQ, created on Jan. 19, 2018, with a size of 147 kilobytes. The Sequence Listing is incorporated herein by reference.

FIELD

The disclosure relates generally to the field of genetics. More particularly, the disclosure relates to gene alterations and polypeptide variants in hydroxysteroid 17-beta dehydrogenase 13 (HSD17B13) that associate with, for example, liver disease.

BACKGROUND

Various references, including patents, patent applications, accession numbers, technical articles, and scholarly articles are cited throughout the specification. Each reference is incorporated by reference herein, in its entirety and for all purposes.

Chronic liver disease and cirrhosis are leading causes of morbidity and mortality in the United States, accounting for 38,170 deaths (1.5% of total deaths) in 2014 (Kochanek et al., Natl. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530 e1; quiz e60, 2011), likely in conjunction with increased rates of obesity, its primary risk factor (Cohen et al., Science, 2011, 332, 1519-1523). While significant advances have been made in the treatment of hepatitis C (Morgan et al., Ann. Intern. Med., 2013, 158, 329-337; and van der Meer et al., J. Amer. Med. Assoc., 2012, 308, 2584-2593), there are currently no evidence-based treatments for alcoholic or nonalcoholic liver disease and cirrhosis.

Previous genome wide association studies (GWAS) have identified a limited number of genes and variants associated with chronic liver disease. The most robustly validated genetic association to date is to a common missense variant in the patatin-like phospholipase domain containing 3 gene (PNPLA3 p.Ile148Met, rs738409), initially found to be associated with increased risk of nonalcoholic fatty liver disease (NAFLD) (Romeo et al., Nat. Genet., 2008, 40, 1461-1465; and Speliotes et al., PLoS Genet., 2011, 7:e1001324), and subsequently found to be associated with disease severity (Rotman et al., Hepatology, 2010, 52, 894-903; and Sookoian et al., J. Lipid Res., 2009, 50, 2111-2116) and progression (Trepo et al., J. Hepatol., 2016, doi:10.1016/j.jhep.2016.03.011). Variation in the transmembrane 6 superfamily member 2 (TM6SF2) gene has also been shown to confer increased risk for NAFLD (Kozlitina et al., Nat. Genet., 2014, 46, 352-356; Liu et al., Nat. Commun., 2014, 5, 4309; and Sookoian et al., Hepatology, 2015, 61, 515-525). The normal functions of these two proteins are not well understood, though both have been proposed to be involved in hepatocyte lipid metabolism. How variants in PNPLA3 and TM6SF2 contribute to increased risk of liver disease has yet to be elucidated. GWAS have also identified several genetic factors to be associated with serum alanine aminotransferase (ALT) and aspartate aminotransferase (AST) (Chambers et al., Nat. Genet., 2011, 43, 1131-1138; and Yuan et al., Am. J. Hum. Genet., 2008, 83, 520-528), quantitative markers of hepatocyte injury and liver fat accumulation that are frequently measured clinically. To date, there are no described protective genetic variants for chronic liver disease. The discovery of protective genetic variants in other settings, such as loss-of-function variants in PCSK9 that reduce the risk of cardiovascular disease, has been the catalyst for development of new classes of therapeutics.

Knowledge of genetic factors underlying the development and progression of chronic liver disease could improve risk stratification and provide the foundation for novel therapeutic strategies. A better understanding of underlying genetic factors is needed to improve risk stratification and generate novel therapies for liver disease.

The present disclosure provides novel HSD17B13 variants that will aid in understanding the biology of HSD17B13, and will facilitate the diagnosis and treatment of subjects with liver disease.

SUMMARY

The present disclosure provides nucleic acid molecules, polypeptides, probes, primers, compositions, and methods related to the variant HSD17B13 rs72613567 gene, variant HSD17B13 transcripts, and variant HSD17B13 protein isoforms.

The present disclosure also provides nucleic acid molecules encoding variant HSD17B13 protein isoforms. In some embodiments, the nucleic acid molecule encodes the variant HSD17B13 protein Isoform C, Isoform D, Isoform F, Isoform G, or Isoform H. In some embodiments, the nucleic acid molecule encodes the variant HSD17B13 protein Isoform D.

The present disclosure also provides nucleic acid molecules comprising or consisting of at least 15 contiguous nucleotides of an HSD17B13 gene, wherein the contiguous nucleotides are at least about 90%, at least about 95%, at least about 96%, at least about 97%, at least about 98%, or at least about 99% identical to a corresponding sequence in SEQ ID NO:2, and having a thymine at a position corresponding to position 12666 of SEQ ID NO:2.

The present disclosure also provides nucleic acid molecules comprising or consisting of a nucleotide sequence that encodes a polypeptide having an amino acid sequence that is at least about 90%, at least about 95%, at least about 96%, at least about 97%, at least about 98%, at least about 99%, or 100% identical to the amino acid sequence of HSD17B13 Isoform D (SEQ ID NO:42). In some embodiments, the nucleic acid molecules comprise or consist of a nucleotide sequence that encodes a polypeptide comprising the amino acid sequence of HSD17B13 Isoform D (SEQ ID NO:42). In some embodiments, the nucleic acid molecules comprise or consist of a nucleotide sequence that is at least about 90%, at least about 95%, at least about 96%, at least about 97%, at least about 98%, at least about 99%, or 100% identical to a nucleotide sequence of a HSD17B13 Transcript D (SEQ ID NO:6, 15, 24, or 33). In some embodiments, the nucleic acid molecule is RNA and comprises or consists of SEQ ID NO:6, or a cDNA thereof comprising or consisting of SEQ ID NO:24, or wherein the nucleic acid molecule is mRNA and comprises or consists of SEQ ID NO:15, or a cDNA thereof comprising or consisting of SEQ ID NO:33.

The present disclosure also provides nucleic acid molecules, such as probes and primers, such as alteration-specific probes or alteration-specific primers, that hybridize to or near the alteration in the variant HSD17B13 rs72613567 gene or an HSD17B13 transcript.

The present disclosure also provides nucleic acid molecules comprising or consisting of from about 5 nucleotides up to about 50 nucleotides that specifically hybridize to a variant HSD17B13 gene at a region that includes a position corresponding to position 12666 in SEQ ID NO:2, or the complement thereof, and wherein the nucleic acid molecules specifically hybridize to a variant HSD17B13 gene having a thymine at a position corresponding to position 12666 of SEQ ID NO:2, or to the complement thereof.

The present disclosure also provides nucleic acid molecules comprising or consisting of from about 5 nucleotides up to about 50 nucleotides that specifically hybridize to variant HSD17B13 Transcript D, wherein the nucleic acid molecules specifically hybridize to: i) a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or ii) to the complement of the nucleotide sequence of i).

The present disclosure also provides nucleic acid molecules comprising or consisting of from about 5 nucleotides up to about 50 nucleotides comprising: i) a nucleic acid molecule which specifically hybridizes to a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or to the complement thereof; ii) a nucleic acid molecule which specifically hybridizes to exon 2 of Transcript D; and/or iii) a nucleic acid molecule which specifically hybridizes to the region which bridges exons 3 and 4 of Transcript D. In some embodiments, the nucleic acid molecule specifically hybridizes to an RNA molecule comprising or consisting of SEQ ID NO:6, or a cDNA thereof comprising or consisting of SEQ ID NO:24, or wherein the nucleic acid molecule specifically hybridizes to an mRNA comprising or consisting of SEQ ID NO:15, or a cDNA thereof comprising or consisting of SEQ ID NO:33, or the complement thereof. In some embodiments, the nucleic acid molecule is linked to a heterologous nucleic acid or comprises a heterologous label.

The present disclosure also provides vectors comprising any of these nucleic acid molecules.

The present disclosure also provides cells comprising any of these nucleic acid molecules.

The present disclosure also provides cells comprising any of these vectors.

The present disclosure also provides compositions comprising any of these nucleic acid molecules.

The present disclosure also provides compositions comprising any of these vectors.

The present disclosure also provides compositions comprising any of these cells.

The present disclosure also provides uses of any of these nucleic acid molecules for detecting a variant HSD17B13 gene or transcript, for determining a human subject's susceptibility or risk of developing a liver disease, or for determining a human subject's risk for progression to more clinically advanced stages of fatty liver disease.

The present disclosure also provides polypeptides corresponding with different variant HSD17B13 protein isoforms.

The present disclosure also provides polypeptides comprising or consisting of an amino acid sequence that is at least about 90%, at least about 95%, at least about 96%, at least about 97%, at least about 98%, at least about 99%, or 100% identical to the amino acid sequence of HSD17B13 Isoform D (SEQ ID NO:42). In some embodiments, the polypeptide comprises or consists of the amino acid sequence of SEQ ID NO:42. In some embodiments, the polypeptide is linked to a heterologous molecule.

The present disclosure also provides compositions comprising any of the polypeptides.

The present disclosure also provides methods of detecting a variant HSD17B13 rs72613567 gene, variant HSD17B13 transcripts (such as Transcript D), and variant HSD17B13 Isoforms (such as Isoform D).

The present disclosure also provides methods of detecting a variant HSD17B13 gene in a human subject, comprising performing an assay on a biological sample obtained from the human subject, wherein the assay determines whether a thymine is inserted between positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, wherein the presence of the thymine is indicative for a variant HSD17B13 gene. In some embodiments, the assay comprises sequencing a portion of the HSD17B13 gene including positions corresponding to positions 12665 and 12666 of SEQ ID NO:1, or including a position corresponding to position 12666 of SEQ ID NO:2. In some embodiments, the assay comprises or consists of: i) contacting the biological sample with a primer hybridizing to a region of the HSD17B13 gene that is within 50 nucleotides of a position corresponding to positions 12665 and 12666 of SEQ ID NO:1 of the wild type HSD17B13 gene, or within 50 nucleotides of a position corresponding to position 12666 of SEQ ID NO:2 of the variant HSD17B13 gene; ii) extending the primer at least through the position corresponding to positions 12665 and 12666 of SEQ ID NO:1 of the wild type HSD17B13 gene, or corresponding to position 12666 of SEQ ID NO:2 of the variant HSD17B13 gene; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the method further comprises determining whether the human subject is homozygous for the variant HSD17B13 gene.

The present disclosure also provides methods of detecting the presence of an HSD17B13 Transcript D in a human subject, comprising performing an assay on a biological sample obtained from the subject, wherein the assay determines the presence of an HSD17B13 Transcript D in the biological sample. In some embodiments, the assay comprises or consists of contacting the biological sample with one or more primers or probes that specifically hybridize to a nucleic acid sequence of HSD17B13 Transcript D, or to the complement thereof, and determining whether hybridization has occurred. In some embodiments, the method further comprises or consists of specifically detecting Transcript D by using a nucleic acid molecule comprising or consisting of from about 5 nucleotides up to about 50 nucleotides comprising or consisting of: i) a nucleic acid molecule which specifically hybridizes to a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or to the complement thereof; ii) a nucleic acid molecule which specifically hybridizes to exon 2 of Transcript D; and/or iii) a nucleic acid molecule which specifically hybridizes to the region which bridges exons 3 and 4 of Transcript D. In some embodiments, the HSD17B13 Transcript D comprises or consists of a nucleotide sequence that is at least about 90%, at least about 95%, at least about 96%, at least about 97%, at least about 98%, at least about 99%, or 100% identical to SEQ ID NO:6, 15, 24, or 33. In some embodiments, the one or more primers or probes specifically hybridize to SEQ ID NO:6. SEQ ID NO: 15, SEQ ID NO:24, and/or SEQ ID NO:33. In some embodiments, the assay further comprises using a primer or probe which specifically hybridizes to one or more of Transcripts A, B, C, E, F, F, G and/or H but not to Transcript D, and determining that hybridization has not occurred. In some embodiments, the assay comprises reverse transcription polymerase chain reaction (RT-PCR). In some embodiments, the assay comprises sequencing.

The present disclosure also provides methods of detecting the presence of HSD17B13 Isoform D in a human subject, comprising performing an assay on a biological sample obtained from the human subject, wherein the assay determines the presence of HSD17B13 Isoform D in the biological sample. In some embodiments, the HSD17B13 Isoform D comprises or consists of an amino acid sequence that is at least about 90%, at least about 95%, at least about 96%, at least about 97%, at least about 98%, at least about 99%, or 100% identical to SEQ ID NO:42. In some embodiments, the assay comprises sequencing.

The present disclosure also provides methods of determining a subject's susceptibility to developing a liver disease and/or methods of diagnosing a subject with a liver disease by determining whether the variant HSD17B13 rs72613567 gene, variant HSD17B13 transcripts (such as Transcript D), and variant HSD17B13 Isoforms (such as Isoform D) is present in a biological sample from the subject.

The present disclosure also provides methods of determining a human subject's susceptibility or risk of developing a liver disease, comprising or consisting of: a) performing an assay on a biological sample obtained from the human subject, wherein the assay determines whether a thymine is inserted between positions of the HSD17B13 gene corresponding to positions 12665 and 12666 of SEQ ID NO: 1, or whether a thymine is present at a position of the variant HSD17B13 gene corresponding to position 12666 of SEQ ID NO:2; and b) classifying the human subject as being at decreased risk for developing the liver disease if a thymine is inserted between the positions corresponding to positions 12665 and 12666 of SEQ ID NO:1 of the wild type HSD17B13 gene or if a thymine is present at a position corresponding to position 12666 of SEQ ID NO:2 of the variant HSD17B13 gene, or classifying the human subject as being at increased risk for developing the liver disease if a thymine is not inserted between the positions of the HSD17B13 gene corresponding to positions 12665 and 12666 of SEQ ID NO:1 or if a thymine is not present at a position of the variant HSD17B13 gene corresponding to position 12666 of SEQ ID NO:2. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the assay comprises or consists of: i) contacting the biological sample with a primer hybridizing to a region of the HSD17B13 gene that is within 50 nucleotides of positions of the HSD17B13 gene corresponding to positions 12665 and 12666 of SEQ ID NO:1, or corresponding to position 12666 of SEQ ID NO:2; ii) extending the primer at least through the positions of the HSD17B13 gene corresponding to positions 12665 and 12666 of SEQ ID NO:1, or corresponding to position 12666 of SEQ ID NO:2; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the assay comprises or consists of contacting the biological sample with a primer or probe that specifically hybridizes to the variant HSD17B13 gene having a thymine at a position corresponding to position 12666 of SEQ ID NO:2, and does not hybridize to the corresponding wild type HSD17B13 gene under stringent conditions, and determining whether hybridization has occurred. In some embodiments, the variant HSD17B13 gene is detected by sequencing. In some embodiments, the method further comprises determining whether the human subject is homozygous for the variant HSD17B13 gene.

The present disclosure also provides methods of determining a human subject's susceptibility or risk for developing a liver disease, comprising or consisting of: a) performing an assay on a biological sample obtained from the human subject, wherein the assay determines the presence of an HSD17B13 Transcript D in the biological sample, and b) classifying the human subject as being at decreased risk for developing the liver disease if an HSD17B13 Transcript D is present in the biological sample, or classifying the human subject as being at increased risk for developing the liver disease if an HSD17B13 Transcript D is not present in the biological sample. In some embodiments, the HSD17B13 Transcript D comprises or consists of a nucleotide sequence that is at least about 90%, at least about 95%, at least about 96%, at least about 97%, at least about 98%, at least about 99%, or 100% identical to SEQ ID NO:6, 15, 24, or 33. In some embodiments, the HSD17B13 Transcript D is RNA and comprises or consists of SEQ ID NO:6, or a cDNA thereof comprising or consisting of SEQ ID NO:24, or wherein the HSD17B13 Transcript D is mRNA and comprises or consists of SEQ ID NO:15, or a cDNA thereof comprising or consisting of SEQ ID NO:33. In some embodiments, the assay determines the expression level of HSD17B13 Transcript D in the biological sample, wherein an increased expression level of HSD17B13 Transcript D compared to a control sample from a control human subject homozygous for a wild type HSD17B13 allele indicates a decreased risk for developing the liver disease, and wherein the same or a decreased expression level of HSD17B13 Transcript D compared to the control sample indicates an increased risk for developing the liver disease. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the assay comprises or consists of contacting the biological sample with one or more primers or probes that specifically hybridize to a nucleic acid sequence of an HSD17B13 Transcript D, or to the complement thereof, and determining whether hybridization has occurred. In some embodiments, the method further comprises specifically detecting Transcript D by using a nucleic acid molecule comprising from about 5 nucleotides up to about 50 nucleotides comprising: i) a nucleic acid molecule which specifically hybridizes to a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or to the complement thereof; ii) a nucleic acid molecule which specifically hybridizes to exon 2 of Transcript D; and/or iii) a nucleic acid molecule which specifically hybridizes to the region which bridges exons 3 and 4 of Transcript D. In some embodiments, the HSD17B13 Transcript D comprises or consists of a nucleotide sequence that is at least about 90%, at least about 95%, at least about 96%, at least about 97%, at least about 98%, at least about 99%, or 100% identical to SEQ ID NO:6, 15, 24, or 33. In some embodiments, the one or more primers or probes specifically hybridize to SEQ ID NO:6, SEQ ID NO:15, SEQ ID NO:24, and/or SEQ ID NO:33. In some embodiments, the assay further comprises using a primer or probe which specifically hybridizes to one or more of Transcripts A, B, C, E, F, F, G and/or H but not to Transcript D, and determining that hybridization has not occurred. In some embodiments, the assay comprises reverse transcription polymerase chain reaction (RT-PCR) or quantitative RT-PCR (qRT-PCR). In some embodiments, the assay comprises sequencing.

The present disclosure also provides methods of determining a human subject's susceptibility or risk for developing a liver disease, comprising or consisting of: a) detecting whether HSD17B13 Isoform D is present in a biological sample obtained from the human subject; and b) classifying the human subject as being at decreased risk for developing the liver disease if HSD17B13 Isoform D is detected in the biological sample, or classifying the human subject as being at decreased risk for developing the liver disease if HSD17B13 Isoform D is not detected in the biological sample. In some embodiments, the HSD17B13 Isoform D comprises or consists of an amino acid sequence that is at least about 90%, at least about 95%, at least about 96%, at least about 97%, at least about 98%, at least about 99%, or 100% identical to SEQ ID NO:42. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the detecting comprises sequencing.

The present disclosure also provides methods of determining a human subject's risk for progression to more clinically advanced stages of fatty liver disease, comprising or consisting of: a) performing an assay on a biological sample obtained from the human subject, wherein the assay determines whether a thymine is inserted between positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene; and b) classifying the human subject as being at decreased risk for progression to more clinically advanced stages of fatty liver disease if a thymine is inserted between the positions corresponding to positions 12665 and 12666 of SEQ ID NO:1 of the wild type HSD17B13 gene or if a thymine is present at a position corresponding to position 12666 of SEQ ID NO:2 of the variant HSD17B13 gene, or classifying the human subject as being at increased risk for progression to more clinically advanced stages of fatty liver disease if a thymine is not inserted between the positions of the HSD17B13 gene corresponding to positions 12665 and 12666 of SEQ ID NO:1, or if a thymine is not present at a position of the variant HSD17B13 gene corresponding to position 12666 of SEQ ID NO:2. In some embodiments, the assay comprises or consists of: i) contacting the biological sample with a primer hybridizing to a region of the HSD17B13 gene that is within 50 nucleotides of positions of the HSD17B13 gene corresponding to positions 12665 and 12666 of SEQ ID NO:1, or corresponding to position 12666 of SEQ ID NO:2; ii) extending the primer at least through the positions of the HSD17B13 gene corresponding to positions 12665 and 12666 of SEQ ID NO:1, or corresponding to position 12666 of SEQ ID NO:2; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the assay comprises or consists of contacting the biological sample with a primer or probe that specifically hybridizes to the variant HSD17B13 gene having a thymine at a position corresponding to position 12666 of SEQ ID NO:2, and not to the corresponding wild type HSD17B13 gene under stringent conditions, and determining whether hybridization has occurred. In some embodiments, the variant HSD17B13 gene is detected by sequencing. In some embodiments, the method further comprises determining whether the human subject is homozygous for the variant HSD17B13 gene.

The present disclosure also provides methods of determining a human subject's risk for progression to more clinically advanced stages of fatty liver disease, comprising or consisting of: a) performing an assay on a biological sample obtained from the human subject, wherein the assay determines the presence of an HSD17B13 Transcript D in the biological sample; and b) classifying the human subject as being at decreased risk for progression to more clinically advanced stages of fatty liver disease if an HSD17B13 Transcript D is present in the biological sample, or classifying the human subject as being at increased risk for progression to more clinically advanced stages of fatty liver disease if an HSD17B3 Transcript D is not present in the biological sample. In some embodiments, the HSD17B13 Transcript D comprises or consists of a nucleotide sequence that is at least about 90%, at least about 95%, at least about 96%, at least about 97%, at least about 98%, at least about 99%, or 100% identical to SEQ ID NO:6, 15, 24, or 33. In some embodiments, the HSD17B13 Transcript D is RNA and comprises or consists of SEQ ID NO:6, or a cDNA thereof comprising or consisting of SEQ ID NO:24, or wherein the HSD17B13 Transcript D is mRNA and comprises or consists of SEQ ID NO:15, or a cDNA thereof comprising or consisting of SEQ ID NO:33. In some embodiments, the assay determines the expression level of HSD17B13 Transcript D in the biological sample, wherein an increased expression level of HSD17B13 Transcript D compared to a control sample from a control human subject homozygous for a wild type HSD17B13 allele indicates a decreased risk for progression to more clinically advanced stages of fatty liver disease, and wherein the same or a decreased expression level of HSD17B13 Transcript D compared to the control sample indicates an increased risk for progression to more clinically advanced stages of fatty liver disease. In some embodiments, the assay comprises or consists of contacting the biological sample with one or more primers or probes that specifically hybridize to a nucleic acid sequence of HSD17B13 Transcript D, or to the complement thereof, and determining whether hybridization has occurred. In some embodiments, the method further comprises specifically detecting Transcript D by using a nucleic acid molecule comprising from about 5 nucleotides up to about 50 nucleotides comprising: i) a nucleic acid molecule which specifically hybridizes to a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or to the complement thereof; ii) a nucleic acid molecule which specifically hybridizes to exon 2 of Transcript D; and/or iii) a nucleic acid molecule which specifically hybridizes to the region which bridges exons 3 and 4 of Transcript D. In some embodiments, the one or more primers or probes specifically hybridize to SEQ ID NO:6, SEQ ID NO:15, SEQ ID NO:24, and/or SEQ ID NO:33. In some embodiments, the assay further comprises using a primer or probe which specifically hybridizes to one or more of Transcripts A, B, C, E, F, F', G and/or H but not to Transcript D, and determining that hybridization has not occurred. In some embodiments, the assay comprises reverse transcription polymerase chain reaction (RT-PCR) or quantitative RT-PCR (qRT-PCR). In some embodiments, the assay comprises sequencing.

The present disclosure also provides methods of determining a human subject's risk for progression to more clinically advanced stages of fatty liver disease, comprising: a) detecting whether HSD17B13 Isoform D is present in a biological sample obtained from the human subject; and b) classifying the human subject as being at decreased risk for progression to more clinically advanced stages of liver disease if HSD17B13 Isoform D is detected in the biological sample. In some embodiments, the HSD17B13 Isoform D comprises an amino acid sequence that is at least about 90%, at least about 95%, at least about 96%, at least about 97%, at least about 98%, at least about 99%, or 100% identical to SEQ ID NO:42. In some embodiments, the detecting comprises sequencing.

BRIEF DESCRIPTION OF THE DRAWINGS

The accompanying figures, which are incorporated in and constitute a part of this specification, illustrate several aspects and together with the description serve to explain the principles of the present disclosure.

FIGS. 4A, 4B, 4C, 4D, 4E, and 4F show expression, subcellular localization, and enzymatic activity of a novel HSD17B13 transcript; 4A: expression of HSD17B13 transcripts A and D in homozygous reference (T/T), heterozygous (T/TA), and homozygous alternate (TA/TA) carriers of the HSD17B13 rs72613567 splice variant; coding regions in HSD17B13 gene are indicated in vertical rectangles, untranslated regions as thick lines, and introns as thin lines; the asterisk in transcript D indicates the A insertion from rs72613567; mRNA expression is displayed in FPKM units (Fragments Per Kilobase of transcript per Million mapped reads); 4B: HSD17B13 Western blot from fresh frozen human liver and HEK293 cell samples; human liver samples are from homozygous reference (T/T), heterozygous (T/TA), and homozygous alternate (TA/TA) carriers of the HSD17B13 rs72613567 splice variant; cell samples are from HEK293 cells overexpressing non-tagged HSD17B13 transcripts A and D; HSD17B13 transcript D was translated to a truncated protein IsoD with lower molecular weight than HSD17B13 IsoA; 4C: HSD17B13 IsoD protein levels were lower than IsoA protein levels from both human liver (left) and cell (right) samples; protein level normalized to Actin was shown in the bar columns; ** $P<0.001$, *$P<0.05$; 4D: both HSD17B13 isoforms A and D are localized on lipid droplet membrane; HepG2 stably overexpressing HSD17B13 transcripts A or D were labelled with BODIPY to show lipid droplets and anti-Myc to show HSD17B13 localization; all figures are magnified to the same extent; scale bar indicates 10 µm; insets represent 4× amplification of the original images; 4E: enzymatic activity of HSD17B13 isoforms A and D to 17-beta estradiol (estradiol), leukotriene B4 (LTB4), and 13-Hydroxyoctadecadienoic acid (13(S)-HODE; HSD17B13 isoform D show <10% enzymatic activity of the corresponding values for isoform A; 4F: HSD17B13 isoform D when overexpressed in HEK293 cells did not show much conversion of estradiol (substrate) to estrone (product) when measured in the culture media, while overexpressed HSD17B13 isoform A showed robust conversion.

FIGS. 7A and 7B show a protein sequence alignment of all identified HSD17B13 isoforms (A-H), isoform A (SEQ ID NO:39), isoform B (SEQ ID NO:40), isoform C (SEQ ID NO:41), isoform D (SEQ ID NO:42), isoform E (SEQ ID NO:43), isoform F (SEQ ID NO:44), isoform G (SEQ ID NO:46), and isoform H (SEQ ID NO:47).

Figure 1A:
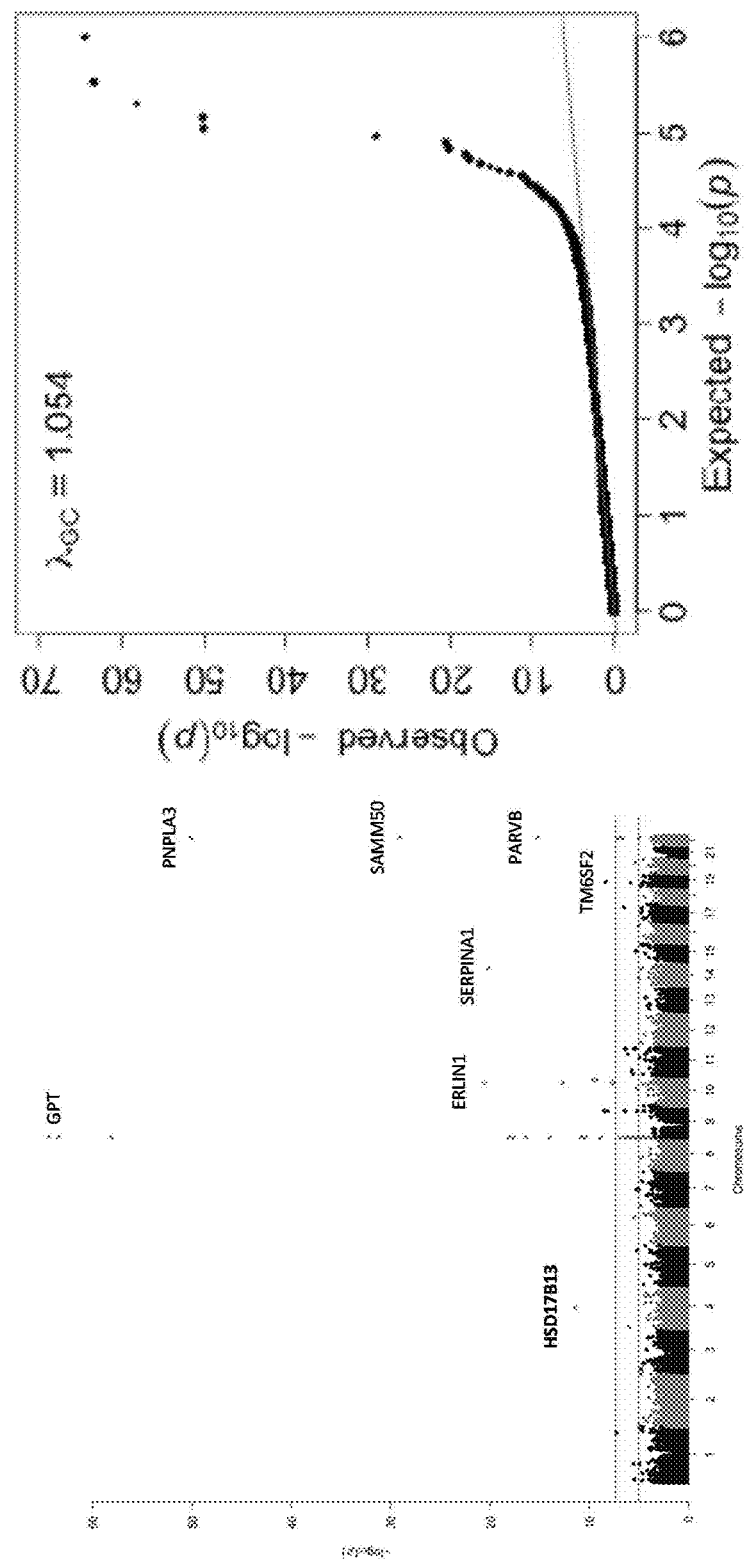
FIGS. 1A and 1B show Manhattan plots (left) and quantile-quantile plots (right) of single nucleotide variant associations with serum transaminase levels in the GHS discovery cohort; 1A: variants in genes significantly associated with alanine aminotransferase (ALT) levels at $P<1.0\times10^{-7}$: 1B: variants in genes significantly associated with aspartate aminotransferase (AST) levels at $P<1.0\times10^{-7}$: the association tests were well calibrated, as shown by exome-wide quantile-quantile plots and genomic control lambda values.

Additional advantages of the present disclosure will be set forth in part in the description which follows, and in part will be apparent from the description, or can be learned by practice of the embodiments disclosed herein. Advantages of the present disclosure will be realized and attained by means of the elements and combinations particularly pointed out in the appended claims. It is to be understood that both the foregoing general description and the following detailed description are exemplary and explanatory only and are not restrictive of the embodiments, as claimed.

DESCRIPTION

Various terms relating to aspects of disclosure are used throughout the specification and claims. Such terms are to be given their ordinary meaning in the art, unless otherwise indicated. Other specifically defined terms are to be construed in a manner consistent with the definition provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the terms "subject" and "patient" are used interchangeably. A subject may include any animal, including mammals. Mammals include, without limitation, farm animals (e.g., horse, cow, pig, sheep, etc.), companion animals (e.g., dog, cat, etc.), laboratory animals (e.g., mouse, rat, rabbits, etc.), and non-human primates (e.g., monkeys, apes, etc.). In some embodiments, the subject is a human.

As used herein, a "nucleic acid," a "nucleic acid molecule," a "nucleotide sequence," "polynucleotide," or "oligonucleotide" can comprise a polymeric form of nucleotides of any length, may comprise DNA and/or RNA, and can be single-stranded, double-stranded, or multiple stranded. One strand of a nucleic acid also refers to its complement.

The term "comprising" throughout the present disclosure may be replaced with "consisting" or "consisting essentially of" in particular embodiments as desired.

As used herein, the phrase "corresponding to" or grammatical variations thereof when used in the context of the numbering of a particular amino acid or nucleotide sequence or position refers to the numbering of a specified reference sequence when the particular amino acid or nucleotide sequence is compared to the reference sequence (e.g., with the reference sequence herein being the nucleic acid molecule or polypeptide of (wild type or full length) HSD17B13). In other words, the residue (e.g., amino acid or nucleotide) number or residue (e.g., amino acid or nucleotide) position of a particular polymer is designated with respect to the reference sequence rather than by the actual numerical position of the residue within the particular amino acid or nucleotide sequence. For example, a particular amino acid sequence can be aligned to a reference sequence by introducing gaps to optimize residue matches between the two sequences. In these cases, although the gaps are present, the numbering of the residue in the particular amino acid or nucleotide sequence is made with respect to the reference sequence to which it has been aligned.

For example, a nucleic acid molecule having a thymine inserted between positions of the HSD17B13 gene corresponding to positions 12665 and 12666 of SEQ ID NO:1 (or position 12666 of SEQ ID NO:2) can be identified by performing a sequence alignment between the particular HSD17B13 nucleic acid of interest and the nucleotide sequence of SEQ ID NO:1 and/or SEQ ID NO:2. A variety of computational algorithms exist that can be used for performing sequence alignments. For example, by using the NCBI BLAST algorithm (Altschul et al., 1997, Nucleic acid molecules Res., 25, 3389-3402) or CLUSTALW software (Sievers et al., 2014. Methods Mol. Biol., 1079, 105-116) sequence alignments may be performed. However, sequences can also be aligned manually.

It has been observed in accordance with the present disclosure that certain variations in HSD17B13 associate with a decreased risk of developing a liver disease. A variant in the HSD17B13 gene segregating with the phenotype of a decreased risk of developing a liver disease in affected family members has been identified in accordance with the present disclosure. For example, a genetic alteration that results in a thymine inserted between positions of the HSD17B13 gene corresponding to positions 12665 and 12666 of SEQ ID NO:1 (or position 12666 of SEQ ID NO:2) has been observed to indicate that the human having such an alteration may have a decreased risk of developing a liver disease. Therefore, human subjects that do not possess this thymine insertion and, therefore may have an increased risk of developing a liver disease, or have a liver disease, may be treated such that liver disease is inhibited, the symptoms thereof are reduced, and/or development of symptoms is repressed. Accordingly, the present disclosure provides recombinant variant HSD17B13 nucleic acid molecules, including RNA, or cDNA derived therefrom, or mRNA, or cDNA derived therefrom, as well as recombinant variant HSD17B13 polypeptides. Additionally, the disclosure provides methods for leveraging the identification of such variants in subjects to identify or stratify risk in such subjects of developing liver disease, or to diagnose subjects as having liver disease, such that subjects at risk or subjects with active disease may be treated.

Provided herein is an HSD17B13 variant discovered to be associated with reduced alanine and aspartate transaminase levels; a reduced risk of chronic liver diseases including nonalcoholic and alcoholic liver fatty liver disease, cirrhosis, and hepatocellular carcinoma; and reduced progression from simple steatosis to more clinically advanced stages of chronic liver disease. Also provided herein are previously unidentified transcripts of the HSD17B13 gene associated with the variant.

Nucleic acid molecules and polypeptides related to variants of HSD17B13, and cells comprising those nucleic acid molecules and polypeptides are provided herein. Also provided are methods for detecting the presence of the HSD17B13 rs72613567 variant gene in a biological sample comprising genomic DNA, for detecting the presence or levels of any one of HSD17B13 transcripts C, D, E, F, F', G, and H (RNA or cDNA derived therefrom, and/or mRNA or cDNA derived therefrom), and particularly Transcript D (RNA or cDNA derived therefrom, and/or mRNA or cDNA derived therefrom), in a biological sample comprising RNA or cDNA derived therefrom, mRNA or cDNA derived therefrom, and for detecting the presence or levels of any one of HSD17B13 protein isoforms C, D, E, F, F, G, or H, and particularly D, in a biological sample comprising protein. Also provided are methods for determining a subject's susceptibility to or risk of developing a liver disease. Also provided are methods for diagnosing a subject with liver disease or at risk for developing a liver disease. Also provided are methods for determining a subject's risk for progression to more clinically advanced stages of fatty liver disease. Also provided are methods for modifying a cell through use of expression vectors for expressing a recombinant HSD17B13 gene or a nucleic acid encoding an HSD17B13 protein.

The present disclosure provides nucleic acid molecules and polypeptides related to variants of HSD17B13 (also known as hydroxysteroid 17-beta dehydrogenase 13, 17-beta-hydroxysteroid dehydrogenase 13, 17β-hydroxysteroid dehydrogenase-13, 17β-HSD13, short-chain dehydrogenase/reductase 9, SCDR9, HMFN0376, NIL497, and SDR16C3). The human HSD17B13 gene is approximately 19 kb in length and includes seven exons and six introns located at 4q22.1 in the genome. Exemplary human HSD17B13 protein sequences are assigned UniProt Accession No. Q7Z5P4 (Q7Z5P4-1 and Q7Z5P4-2, respectively) and NCBI Reference Sequence Nos. NP_835236 and NP_001129702. Exemplary human HSD17B13 nucleic acid molecules are assigned NCBI Reference Sequence Nos. NM_178135 and NM_001136230.

In particular, provided herein is a splice variant of HSD17B13 (rs72613567) having an insertion of an adenine adjacent to the donor splice site in intron 6. The adenine is an insertion on the forward (plus) strand of the chromosome, which corresponds to an inserted thymine on the reverse (minus) strand of the chromosome. Because the human HSD17B13 gene is transcribed in the reverse direction, this nucleotide insertion is reflected as an inserted thymine in the exemplary variant HSD17B13 rs72613567 sequence provided in SEQ ID NO:2 relative to the exemplary wild type HSD17B13 gene sequence provided in SEQ ID NO:1. The insertion will therefore be referred to herein as a thymine inserted between positions 12665 and 12666 in SEQ ID NO:1 or at position 12666 in SEQ ID NO:2.

Two transcripts (A and B; SEQ ID NOs:21 and 22, respectively) were previously identified to be expressed in subjects with the wild type HSD17B13 gene. Transcript A includes all seven exons of the HSD17B13 gene, whereas exon 2 is skipped in Transcript B. Transcript A is the dominant transcript in wild type subjects. Provided herein, however, are six additional, previously unidentified, HSD17B3 transcripts that are expressed (C, D, E, F, G, and H, SEQ ID NOs: 23, 24, 25, 26, 28, and 29, respectively). In Transcript C, exon 6 is skipped compared to Transcript A. In Transcript D, there is an insertion of a guanine 3' of exon 6, resulting in a frameshift in and premature truncation of exon 7 compared to Transcript A. In Transcript E, there is an additional exon between exons 3 and 4 compared to Transcript A. In Transcript F, which is expressed only in HSD17B13 rs72613567 variant carriers, there is read-through from exon 6 into intron 6 compared to Transcript A. In Transcript G, exon 2 is skipped, and there is an insertion of a guanine 3' of exon 6, resulting in a frameshift in and premature truncation of exon 7 compared to Transcript A. In Transcript H, there is an additional exon between exons 3 and 4, and there is an insertion of a guanine 3' of exon 6, resulting in a frameshift in and premature truncation of exon 7 compared to Transcript A. Transcripts C, D, F, G, and H are dominant in HSD17B13 rs72613567 variant carriers, with Transcript D being the most abundant transcript in carriers of the HSD17B13 rs72613567 variant. Also provided herein is one additional, previously unidentified, HSD17B13 transcript that is expressed at low levels (F', SEQ ID NO:27). Like Transcript F, Transcript F' also includes a read-through from exon 6 into intron 6 compared to Transcript A, but, in contrast to Transcript F, the read-through does not include the inserted thymine present in the HSD17B13 rs72613567 variant gene.

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO:1 is the wild type HSD17B13 genomic sequence (Human Genome Assembly GRCh38). Transcripts more prevalent in subjects with wild type HSD17B13 gene include Transcript A, Transcript B, Transcript E, and Transcript F'.

SEQ ID NO:2 is an HSD17B13 genomic sequence variant (Human Genome Assembly GRCh38; rs72613567; insertion of T at chr4: 87310241-87310240; insertion of T at position 12666). Transcripts more prevalent in subjects with the variant rs72613567 HSD17B13 gene include Transcript C, Transcript D, Transcript F, Transcript G, and Transcript H.

SEQ ID NO:53 is an endogenous HSD17B13 Promoter (−499 to 100 relative to transcription start site (TSS)).

As used herein, the term "transcript" means any one or more of the RNA or mRNA molecule, or the corresponding cDNA molecule derived therefrom, disclosed in the table below, unless otherwise indicated by the context of its use.

The sequence identifier nomenclature for the various transcripts is listed in the table below. The RNA transcript is shown along with its cDNA counterpart, and the mRNA transcript is shown along with its cDNA counterpart.

| Transcript | RNA | cDNA (RNA) | mRNA | cDNA (mRNA) | Protein |
|---|---|---|---|---|---|
| A | SEQ ID NO: 3 | SEQ ID NO: 21 | SEQ ID NO: 12 | SEQ ID NO: 30 | SEQ ID NO: 39 |
| B | SEQ ID NO: 4 | SEQ ID NO: 22 | SEQ ID NO: 13 | SEQ ID NO: 31 | SEQ ID NO: 40 |
| C | SEQ ID NO: 5 | SEQ ID NO: 23 | SEQ ID NO: 14 | SEQ ID NO: 32 | SEQ ID NO: 41 |
| D | SEQ ID NO: 6 | SEQ ID NO: 24 | SEQ ID NO: 15 | SEQ ID NO: 33 | SEQ ID NO: 42 |
| E | SEQ ID NO: 7 | SEQ ID NO: 25 | SEQ ID NO: 16 | SEQ ID NO: 34 | SEQ ID NO: 43 |
| F | SEQ ID NO: 8 | SEQ ID NO: 26 | SEQ ID NO: 17 | SEQ ID NO: 35 | SEQ ID NO: 44 |
| F' | SEQ ID NO: 9 | SEQ ID NO: 27 | SEQ ID NO: 18 | SEQ ID NO: 36 | SEQ ID NO: 45 |
| G | SEQ ID NO: 10 | SEQ ID NO: 28 | SEQ ID NO: 19 | SEQ ID NO: 37 | SEQ ID NO: 46 |
| H | SEQ ID NO: 11 | SEQ ID NO: 29 | SEQ ID NO: 20 | SEQ ID NO: 38 | SEQ ID NO: 47 |

Accordingly, as used herein, the term "Transcript A" means any one or more of SEQ ID NO:3, SEQ ID NO:12, SEQ ID NO:21, and/or SEQ ID NO:30; "Transcript B" means any one or more of SEQ ID NO:4. SEQ ID NO: 13, SEQ ID NO:22, and/or SEQ ID NO:31; "Transcript C" means any one or more of SEQ ID NO:5, SEQ ID NO:14, SEQ ID NO:23, and/or SEQ ID NO:32; "Transcript D" means any one or more of ii) SEQ ID NO:6, SEQ ID NO:15, SEQ ID NO:24, and/or SEQ ID NO:33; "Transcript E" means any one or more of SEQ ID NO:7, SEQ ID NO:16, SEQ ID NO:25, and/or SEQ ID NO:34; "Transcript F" means any one or more of SEQ ID NO:8, SEQ ID NO:17, SEQ ID NO:26, and/or SEQ ID NO:35; "Transcript F'" means any one or more of SEQ ID NO:9, SEQ ID NO:18, SEQ ID NO:27, and/or SEQ ID NO:36; "Transcript G" means any one or more of SEQ ID NO: 10. SEQ ID NO:19, SEQ ID NO:28, and/or SEQ ID NO:37; and "Transcript H" means any one or more of SEQ ID NO:11, SEQ ID NO:20, SEQ ID NO:29, and/or SEQ ID NO:38, unless otherwise indicated b the context.

The nucleotide positions of the exons within the HSD17B13 genes for each Transcript are provided below.

| Nucleotide Positions in SEQ ID NO: 1 for Exons of HSD17B13 Transcripts More Prevalent in Subjects Homozygous for Wild Type HSD17B13 Gene. | | | | |
|---|---|---|---|---|
| | Transcript A | Transcript B | Transcript E | Transcript F' |
| Exon 1 | 1-275 | 1-275 | 1-275 | 1-275 |
| Exon 2 | 4471-4578 | skipped | 4471-4578 | 4471-4578 |
| Exon 3 | 5684-5835 | 5684-5815 | 5684-5815 | 5684-5815 |
| Exon 3' | not present | not present | 6210-6281 | not present |
| Exon 4 | 7308-7414 | 7308-7414 | 7308-7414 | 7308-7414 |
| Exon 5 | 8947-9084 | 8947-9084 | 8947-9084 | 8947-9084 |
| Exon 6 | 12548-12664 | 12548-12664 | 12548-12664 | 12548-13501* |
| Exon 7 | 17599-19118 | 17599-19118 | 17599-19118 | skipped |

*Includes read-through from exon 6 into intron 6; read-through = positions 12665-13501

Nucleotide Positions in SEQ ID NO: 2 for Exons of HSD17B13 Transcripts More Prevalent in Subjects Homozygous for rs72613567 HSD17B13 Variant Gene (Insertion of T at Position 12666).

|  | Transcript C | Transcript D | Transcript F | Transcript G | Transcript H |
|---|---|---|---|---|---|
| Exon 1 | 1-275 | 1-275 | 1-275 | 1-275 | 1-275 |
| Exon 2 | 4471-4578 | 4471-4578 | 4471-4578 | skipped | 4471-4578 |
| Exon 3 | 5684-5815 | 5684-5815 | 5684-5815 | 5684-5815 | 5684-5815 |
| Exon 3' | not present | not present | not present | not present | 6210-6281 |
| Exon 4 | 7308-7414 | 7308-7414 | 7308-7414 | 7308-7414 | 7308-7414 |
| Exon 5 | 8947-9084 | 8947-9084 | 8947-9084 | 8947-9084 | 8947-9084 |
| Exon 6 | Skipped | 12548-12665^ | 12548-13502* | 12548-12665^ | 12548-12665^ |
| Exon 7 | 17600-19119 | 17600-19119 | skipped | 17600-19119 | 17600-19119 |

^Includes additional residue 12665 at 3' end compared to Transcript A
*Includes read-through from exon 6 into intron 6; read-through = positions 12665-13502.

The corresponding HSD17B13 isoform proteins include: i) Isoform A (SEQ ID NO:39; region encoded by Exon 1=1-70, region encoded by Exon 2=71-106, region encoded by Exon 3=107-150, region encoded by Exon 4=151-185, region encoded by Exon 5=186-232, region encoded by Exon 6v1=233-271, and region encoded by Exon 7=272-300); ii) Protein Isoform B (SEQ ID NO:40; region encoded by Exon 1=1-70, Exon 2=skipped, region encoded by Exon 3=71-114, region encoded by Exon 4=115-149, region encoded by Exon 5=150-196, region encoded by Exon 6v1=197-235, and region encoded by Exon 7=236-264); iii) Protein Isoform C (SEQ ID NO:41; region encoded by Exon 1=1-70, region encoded by Exon 2=71-106, region encoded by Exon 3=107-150, region encoded by Exon 4=151-185, region encoded by Exon 5=186-232, Exon 6=skipped, and region encoded by Exon 7=233-261); iv) Protein Isoform D (SEQ ID NO:42; region encoded by Exon 1=1-70, region encoded by Exon 2=71-106, region encoded by Exon 3=107-150, region encoded by Exon 4=151-185, region encoded by Exon 5=186-232, region encoded by Exon 6v2=233-271, and region encoded by Exon 7=272-274); v) Protein Isoform E (SEQ ID NO:43; region encoded by Exon 1=1-70, region encoded by Exon 2=71-106, region encoded by Exon 3=107-150, region encoded by Exon 3'=151-174, region encoded by Exon 4=175-209, region encoded by Exon 5=210-256, region encoded by Exon 6v1=257-295, and region encoded by Exon 7=296-324); vi) Protein Isoform F (SEQ ID NO:44; region encoded by Exon 1=1-70, region encoded by Exon 2=71-106, region encoded by Exon 3=107-150, region encoded by Exon 4=151-185, region encoded by Exon 5=186-232, region encoded by Exon 6v3=233-284, and region encoded by read-through into Intron 6=272-284); vii) Protein Isoform F' (SEQ ID NO:45; region encoded by Exon 1=1-70, region encoded by Exon 2=71-106, region encoded by Exon 3=107-150, region encoded by Exon 4=151-185, region encoded by Exon 5=186-232, and region encoded by Exon 6v4=233-271); viii) Protein Isoform G (SEQ ID NO:46; region encoded by Exon 1=1-70, Exon 2=skipped, region encoded by Exon 3=71-114, region encoded by Exon 4=115-149, region encoded by Exon 5=150-196, region encoded by Exon 6v2=197-235, and region encoded by Exon 7=236-238); and ix) Protein Isoform H (SEQ ID NO:47; region encoded by Exon 1=1-70, region encoded by Exon 2=71-106, region encoded by Exon 3=107-150, region encoded by Exon 3'=151-174, region encoded by Exon 4=175-209, region encoded by Exon 5=210-256, region encoded by Exon 6v2=257-295, and region encoded by Exon 7=296-298).

As explained in more detail elsewhere herein, the variant HSD17B13 rs72613567 is associated with reduced alanine and aspartate transaminase levels and a reduced risk of chronic liver diseases including nonalcoholic and alcoholic liver fatty liver disease, cirrhosis, and hepatocellular carcinoma. The variant HSD17B13 rs72613567 is also associated with reduced progression from simple steatosis to more clinically advanced stages of chronic liver disease.

Disclosed herein are variant HSD17B13 nucleic acid molecules, including a variant HSD17B13 gene and variant HSD17B13 transcripts. Also disclosed are nucleic acid molecules that hybridize under stringent or moderate conditions with any of the nucleic acid molecules disclosed herein. Such nucleic acid molecules can be useful, for example, to express HSD17B13 variant proteins or as primers, probes, antisense RNAs, shRNAs, and siRNAs, each of which is described in more detail elsewhere herein. In any of the embodiments described herein, the nucleic acid molecules and/or polypeptides can be isolated nucleic acid molecules or isolated polypeptides.

The present disclosure provides nucleic acid molecules comprising or consisting of at least 15 contiguous nucleotides of an HSD17B13 gene, wherein the contiguous nucleotides are at least about 90%, at least about 95%, at least about 96%, at least about 97%, at least about 98%, or at least about 99% identical to a corresponding sequence in SEQ ID NO:2, and having a thymine at a position corresponding to position 12666 of SEQ ID NO:2. In some embodiments, the nucleic acid molecules comprise or consist of at least 15 contiguous nucleotides of an HSD17B13 gene, wherein the contiguous nucleotides are at least about 90% identical to a corresponding sequence in SEQ ID NO:2, and having a thymine at a position corresponding to position 12666 of SEQ ID NO:2.

The present disclosure provides nucleic acid molecules comprising or consisting of a nucleotide sequence that encodes a polypeptide having an amino acid sequence that is at least about 90%, at least about 95%, at least about 96%, at least about 97%, at least about 98%, at least about 99%, or 100% identical to the amino acid sequence of HSD17B13 Isoform D (SEQ ID NO:42). In some embodiments, the nucleic acid molecules comprise or consist of a nucleotide sequence that encodes a polypeptide having an amino acid sequence that is at least about 90% identical to the amino acid sequence of HSD17B13 Isoform D (SEQ ID NO:42). In some embodiments, the nucleic acid molecule comprises or consists of a nucleotide sequence that encodes a polypeptide having the amino acid sequence of HSD17B13 Isoform D (SEQ ID NO:42). In some embodiments, these nucleic acid molecules encode a polypeptide having 274 amino acids. In some embodiments, these nucleic acid molecules encode a polypeptide having a C-terminal Val-Ser-Ser. In some embodiments, these nucleic acid molecules encode a polypeptide associated with a decreased risk of developing any of the liver diseases described herein or decreased risk of progression to more clinically advanced stages of fatty liver disease.

The present disclosure provides nucleic acid molecules comprising at least 15 contiguous nucleotides of an HSD17B3 gene and having a thymine at a position corresponding to position 12666 (or thymines at positions corresponding to positions 12666 and 12667) of the HSD17B13 rs72613567 variant gene (SEQ ID NO:2). That is, disclosed herein are nucleic acid molecules comprising at least 15 contiguous nucleotides of an HSD17B13 gene and having a thymine inserted between nucleotides corresponding to positions 12665 and 12666 of the wild type HSD17B13 gene (SEQ ID NO:1). Such nucleic acid molecules can be useful, for example, to express HSD17B13 variant transcripts and isoform proteins.

The HSD17B13 gene can be an HSD17B13 gene from any organism. For example, the HSD17B13 gene can be a human HSD17B13 gene or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible. As one example, the at least 15 contiguous nucleotides can be at least about 90%, at least about 95%, at least about 96%, at least about 97%, at least about 98%, or at least about 99% identical to a corresponding sequence in the HSD17B13 rs72613567 variant (SEQ ID NO:2) including position 12666 or positions 12666 and 12667 of SEQ ID NO:2. In some embodiments, the at least 15 contiguous nucleotides can be at least about 90% identical to a corresponding sequence in the HSD17B13 rs72613567 variant (SEQ ID NO:2) including position 12666 or positions 12666 and 12667 of SEQ ID NO:2. In some embodiments, the nucleic acid molecule comprises at least 15 contiguous nucleotides of SEQ ID NO:2 including position 12666 or positions 12666 and 12667 of SEQ ID NO:2. In some embodiments, the at least 15 contiguous nucleotides can be at least about 90%, at least about 95%, at least about 96%, at least about 97%, at least about 98%, or at least about 99% identical to a corresponding sequence in the wild type HSD17B13 gene (SEQ ID NO:1) including positions 12665 and 12666 of SEQ ID NO:1, wherein a thymine is present between the positions corresponding to positions 12665 and 12666 of SEQ ID NO:1. In some embodiments, the at least 15 contiguous nucleotides can be at least about 90% identical to a corresponding sequence in the wild type HSD17B13 gene (SEQ ID NO:1) including positions 12665 and 12666 of SEQ ID NO: 1, wherein a thymine is present between the positions corresponding to positions 12665 and 12666 of SEQ ID NO:1. In some embodiments, the nucleic acid molecule comprises at least 15 contiguous nucleotides of SEQ ID NO:1 including positions 12665 and 12666 of SEQ ID NO: 1, wherein a thymine is present between the positions corresponding to positions 12665 and 12666 of SEQ ID NO:1.

In some cases, the isolated nucleic acid molecule can comprise an HSD17B13 minigene in which one or more nonessential segments of the gene have been deleted with respect to a corresponding wild type HSD17B13 gene. As one example, the deleted segments comprise one or more intronic sequences. In some embodiments, the HSD17B13 minigenes can comprise, for example, exons corresponding to exons 1-7 from HSD17B13 Transcript D and an intron corresponding to intron 6 in SEQ ID NO:2. In some embodiments, an HSD17B13 minigene may comprise exons 1-7 and intron 6 from SEQ ID NO:2. Minigenes are described in more detail elsewhere herein.

The present disclosure provides nucleic acid molecules corresponding to all or part of an RNA transcript, such as Transcript A, Transcript B, Transcript C, Transcript D, Transcript E, Transcript F, Transcript F', Transcript G, and Transcript H, or a corresponding cDNA thereof, or an mRNA transcript, such as Transcript A, Transcript B, Transcript C, Transcript D, Transcript E, Transcript F, Transcript F', Transcript G, and Transcript H, or a corresponding cDNA thereof.

The present disclosure provides nucleic acid molecules corresponding to all or part of an RNA transcript, such as Transcript C, Transcript D, Transcript E, Transcript F, Transcript F', Transcript G, and Transcript H, or a corresponding cDNA thereof, or an mRNA transcript, such as Transcript C, Transcript D, Transcript E, Transcript F, Transcript F', Transcript G, and Transcript H, or a corresponding cDNA thereof.

The present disclosure provides nucleic acid molecules corresponding to all or part of an RNA transcript, such as Transcript C, Transcript D, Transcript F, Transcript G, and Transcript H, or a corresponding cDNA thereof, or an mRNA transcript, such as Transcript C, Transcript D, Transcript F, Transcript G, and Transcript H, or a corresponding cDNA thereof.

The present disclosure provides nucleic acid molecules corresponding to all or part of RNA Transcript D, or a corresponding cDNA, or an mRNA Transcript D, or a corresponding cDNA.

Such isolated nucleic acid molecules can be useful, for example, to express HSD17B13 variant transcripts and proteins.

In some embodiments, the nucleic acid molecule comprises or consists of a nucleotide sequence that is at least about 90%, at least about 95%, at least about 96%, at least about 97%, at least about 98%, at least about 99%, or 100% identical to a nucleotide sequence of an HSD17B13 Transcript D (SEQ ID NO:6, 15, 24, or 33). In some embodiments, the nucleic acid molecule is RNA and comprises or consists of SEQ ID NO:6, or a cDNA thereof comprising or consisting of SEQ ID NO:24, or wherein the nucleic acid molecule is mRNA and comprises or consists of SEQ ID NO: 15, or a cDNA thereof comprising or consisting of SEQ ID NO:33.

HSD17B13 Transcript D, Transcript G, and Transcript H include an insertion of a guanine at the 3' end of exon 6, resulting in a frameshift in exon 7 and premature truncation of the region of the HSD17B13 protein encoded by exon 7 compared to Transcript A. Accordingly, provided herein are nucleic acid molecules comprising a segment (e.g., at least 15 contiguous nucleotides) present in Transcripts D, G, and H (or fragments or homologs thereof) that is not present in Transcript A (or a fragment or homolog thereof). Also provided herein are nucleic acid molecules comprising a segment (e.g., at least 15 contiguous nucleotides) present in Transcripts D (or fragments or homologs thereof) that is not present in Transcript A (or a fragment or homolog thereof). Such regions can be readily identified by comparing the sequences of the Transcripts. For example, provided herein are nucleic acid molecules comprising or consisting of at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region spanning the exon 6-exon 7 boundary in Transcript D, Transcript G, or Transcript H, and the segment includes a guanine at a residue corresponding to residue 878 at the 3' end of exon 6 in Transcript D (i.e., an insertion of a guanine at the 3' end of exon 6 relative to Transcript A in addition to the guanine at the start of exon 7), a residue corresponding to residue 770 at the 3' end of exon 6 in Transcript G (i.e., an insertion of a guanine at the 3' end of exon 6 relative to Transcript B in addition to the guanine at the start of exon 7), or a residue corresponding to residue 950 at the 3' end of exon 6 in Transcript H (i.e., an insertion of a guanine at the 3' end of exon 6 relative to Transcript E in addition to the guanine at the start of exon 7). It is understood that such a nucleic acid would include a sufficient number of nucleotides in each of exons 6 and 7 to distinguish the inserted guanine from other features in the HSD17B13 Transcripts (e.g., from the guanine at the start of exon 7, from the read-through into intron 6 in Transcript F, or from the deleted exon 6 in Transcript C).

As one example, the nucleic acid molecule can comprise or consist of at least 15 contiguous nucleotides (e.g., at least 20 contiguous nucleotides or at least 30 contiguous nucleotides) of Transcript D spanning the exon 6-exon 7 boundary, optionally comprising exons 6 and 7 of Transcript D, and optionally comprising the entire sequence of Transcript D.

In some embodiments, the nucleic acid molecule further comprises a segment present in Transcript D (or a fragment or homolog thereof) that is not present in Transcript G (or a fragment or homolog thereof), and the nucleic acid molecule further comprises a segment present in Transcript D (or a fragment or homolog thereof) that is not present in Transcript H (or a fragment or homolog thereof). Such regions can be readily identified by comparing the sequences of the Transcripts. For example, such nucleic acid molecules can comprise or consist of a segment of the contiguous nucleotides (e.g., at least 5 contiguous nucleotides, at least 10 contiguous nucleotides or at least 15 contiguous nucleotides) that is at least about 90%, at least about 95%, at least about 96%, at least about 97%, at least about 98%, or at least about 99% identical to a region spanning the boundary of exons 3 and 4 of Transcript D to distinguish from Transcript H. Likewise, such nucleic acid molecules can comprise or consist of a segment of the contiguous nucleotides (e.g., at least 5 contiguous nucleotides, at least 10 contiguous nucleotides or at least 15 contiguous nucleotides) that is at least about 90%, at least about 95%, at least about 96%, at least about 97%, at least about 98%, or at least about 99% identical to a region within exon 2 of Transcript D, a region spanning the exon 1-exon 2 boundary of Transcript D, or a region spanning the exon 2-exon 3 boundary of Transcript D to distinguish from Transcript G. In some embodiments, the nucleic acid molecules can comprise or consist of a sequence at least about 90%, at least about 95%, at least about 96%, at least about 97%, at least about 98%, or at least about 99% identical to the sequence set forth in Transcript D and encodes an HSD17B13 isoform protein comprising the sequence set forth in Isoform D. Like Transcript D, Transcript H includes an insertion of a guanine 3' of exon 6 compared to Transcript A. Transcript H further includes an additional exon (exon 3') between exons 3 and 4 compared to Transcript A and Transcript D. Accordingly, provided herein are nucleic acid molecules as described above comprising a segment present in Transcripts D, G, and H (or fragments or homologs thereof) that is not present in Transcript A (or a fragment or homolog thereof) but further comprising a segment (e.g., at least 15 contiguous nucleotides) of Transcript H (or a fragment or homolog thereof) that is not present in Transcript D (or a fragment or homolog thereof). Such regions can be readily identified by comparing the sequences of the Transcripts. For example, provided herein are nucleic acid molecules as described for Transcript D, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region within exon 3' of Transcript H, a region spanning the exon 3-exon 3' boundary of Transcript H, or a region spanning the exon 3'-exon 4 boundary of Transcript H. It is understood that such nucleic acid molecules would include a sufficient number of nucleotides in each of exons 3 and 3' or each of exons 3' and 4 to distinguish from other features in the HSD17B13 transcripts (e.g., from the boundary of exons 3 and 4). For example, the region of exon 3' can comprise the entire exon 3'. Optionally, the nucleic acid molecules can comprise or consist of a sequence at least about 90%, at least about 95%, at least about 96%, at least about 97%, at least about 98%, or at least about 99% identical to the sequence set forth in Transcript H and encodes an HSD17B13 protein comprising Isoform H.

As one example, the nucleic acid molecules can comprise or consist of at least 15 contiguous nucleotides (e.g., at least 20 contiguous nucleotides or at least 30 contiguous nucleotides) of Transcript H including a region within exon 3', a region spanning the exon 3-exon 3' boundary, or a region spanning the exon 3'-exon 4 boundary, optionally comprising the entire exon 3' of Transcript H, and optionally comprising the entire sequence of Transcript H.

Like Transcript D, Transcript G includes an insertion of a guanine 3' of exon 6 compared to Transcript A. In addition, however, Transcript G is missing exon 2 compared to Transcript A and Transcript D (i.e., Transcript G includes an exon 1-exon 3 boundary not present in Transcripts A and D). Accordingly, provided herein are nucleic acid molecules as described above comprising or consisting of a segment present in Transcripts D, G, and H (or fragments or homologs thereof) that is not present in Transcript A (or a fragment or homolog thereof) but further comprising a segment (e.g., at least 15 contiguous nucleotides) from Transcript G (or a fragment or homolog thereof) that is not present in Transcript D (or a fragment or homolog thereof). Such regions can be readily identified by comparing the sequences of the Transcripts. For example, provided herein are nucleic acid molecules as described for Transcript D, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region spanning the exon 1-exon 3 boundary in Transcript G. It is understood that such nucleic acid molecules would include a sufficient number of nucleotides in each of exons 1 and 3 to distinguish from other features in the HSD17B13 Transcripts (e.g., the boundary of exons 1 and 2 or the boundary of exons 2 and 3). For example, the region can comprise the entirety of exons 1 and 3 in Transcript G. Optionally, the nucleic acid molecules comprise or consist of a sequence at least about 90%, at least about 95%, at least about 96%, at least about 97%, at least about 98%, or at least about 99% identical to the sequence set forth in Transcript G and encodes an HSD17B13 protein comprising the sequence set forth in Isoform G.

As one example, the nucleic acid molecules can comprise or consist of at least 15 contiguous nucleotides (e.g., at least 20 contiguous nucleotides or at least 30 contiguous nucleotides) of Transcript G including a region spanning the exon 1-exon 3 boundary, optionally comprising the exons 1 and 3 of Transcript G, and optionally comprising the entire sequence of Transcript G.

Also provided herein are nucleic acid molecules comprising or consisting of a segment (e.g., at least 15 contiguous nucleotides) present in Transcript E (or a fragment or homolog thereof) that is not present in Transcript A (or a fragment or homolog thereof). Such regions can be readily identified by comparing the sequences of the Transcripts. Transcript E includes an additional exon between exons 3 and 4 compared to Transcript A. Accordingly, provided herein are nucleic acid molecules comprising or consisting of at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region within exon 3' of Transcript E, a region spanning the exon 3-exon 3' boundary of Transcript E, or a region spanning the exon 3'-exon 4 boundary of Transcript E. It is understood that such nucleic acid molecules would include a sufficient number of nucleotides in each of exons 3 and 3' or each of exons 3' and 4 to distinguish from other features in the HSD17B13 transcripts (e.g., from the boundary of exons 3 and 4). For example, the region of exon 3' can comprise the entire exon 3'. Optionally, the nucleic acid molecules further comprise a segment (e.g., at least 15 contiguous nucleotides) from Transcript E (or a fragment or homolog thereof) that is not present in Transcript H (or a fragment or homolog thereof). Such regions can be readily identified by comparing the sequences of the Transcripts. For example, provided herein are nucleic acid molecules as described above, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region spanning the exon 6-exon 7 boundary in Transcript E. It is understood that such nucleic acid molecules would include a sufficient number of nucleotides in each of exons 6 and 7 to distinguish from other features in the HSD17B13 Transcripts (particularly the additional guanine at the 3' end of exon 6 in Transcript H)). For example, the region can comprise the entirety of exons 6 and 7 in Transcript E. Optionally, the isolated nucleic acid comprises or consist of a sequence at least about 90%, at least about 95%, at least about 96%, at least about 97%, at least about 98%, or at least about 99% identical to the sequence set forth in Transcript E and encodes an HSD17B13 protein comprising the sequence set forth in Isoform E.

As one example, the nucleic acid molecules can comprise or consist of at least 15 contiguous nucleotides (e.g., at least 20 contiguous nucleotides or at least 30 contiguous nucleotides) of Transcript E including a region within exon 3', a region spanning the exon 3-exon 3' boundary, or a region spanning the exon 3'-exon 4 boundary, optionally comprising the entire exon 3' of Transcript E, and optionally comprising the entire sequence of Transcript E.

Also provided herein are nucleic acid molecules comprising or consisting of a segment (e.g., at least 15 contiguous nucleotides) present in Transcript F (or a fragment or homolog thereof) that is not present in Transcript A (or a fragment or homolog thereof). Such regions can be readily identified by comparing the sequences of the Transcripts. Transcript F includes a read-through from exon 6 into intron 6 compared to Transcript A, and the read-through includes the inserted thymine present in the HSD17B3 rs72613567 variant gene. Accordingly, provided herein are nucleic acid molecules comprising or consisting of at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region within the read-through into intron 6 in Transcript F or a region spanning the boundary between the read-through into intron 6 and the rest of exon 6 in Transcript F. It is understood that such nucleic acid molecules would include a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F (i.e., the inserted thymine) that is not present in Transcript F'. Transcript F' also includes a read-through from exon 6 into intron 6 compared to Transcript A, but the read-through does not include the inserted thymine present in the HSD17B13 rs72613567 variant gene. For example, the region can be the entire read-through into intron 6 in Transcript F. Optionally, the isolated nucleic acid molecules comprise or consist of a sequence at least about 90%, at least about 95%, at least about 96%, at least about 97%, at least about 98%, or at least about 99% identical to the sequence set forth in Transcript F and encodes an HSD17B13 protein comprising the sequence set forth in Protein Isoform F.

As one example, the nucleic acid molecules can comprise or consist of at least 15 contiguous nucleotides (e.g., at least 20 contiguous nucleotides or at least 30 contiguous nucleotides) of Transcript F including a region within the read-through into intron 6 or a region spanning the boundary between the read-through into intron 6 and the rest of exon 6, optionally comprising the entire read-through into intron 6, and optionally comprising the entire sequence of Transcript F.

Also provided herein are nucleic acid molecules comprising or consisting of a segment (e.g., at least 15 contiguous nucleotides) present in Transcript F' (or a fragment or homolog thereof) that is not present in Transcript A (or a fragment or homolog thereof). Such regions can be readily identified by comparing the sequences of the Transcripts. Transcript F' includes a read-through from exon 6 into intron 6 compared to Transcript A, and the read-through does not include the inserted thymine present in the HSD17B13 rs72613567 variant gene. Accordingly, provided herein are nucleic acid molecules comprising or consisting of at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region within the read-through into intron 6 in Transcript F' or a region spanning the boundary between the read-through into intron 6 and the rest of exon 6 in Transcript F'. It is understood that such nucleic acid molecules would include a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F' that is not present in Transcript F. The read-through in Transcript F includes the inserted thymine present in the HSD17B13 rs72613567 variant gene, whereas the read-through in Transcript F' does not. For example, the region can be the entire read-through into intron 6 in Transcript F'. Optionally, the isolated nucleic acid molecules comprise or consist of a sequence at least about 90%, at least about 95%, at least about 96%, at least about 97%, at least about 98%, or at least about 99% identical to the sequence set forth in Transcript F' and encodes an HSD17B13 protein comprising, consisting essentially of, or consisting of the sequence set forth in Isoform F'.

As one example, the nucleic acid molecules can comprise or consist of at least 15 contiguous nucleotides (e.g., at least 20 contiguous nucleotides or at least 30 contiguous nucleotides) of Transcript F' including a region within the read-through into intron 6 or a region spanning the boundary between the read-through into intron 6 and the rest of exon 6, optionally comprising the entire read-through into intron 6, and optionally comprising the entire sequence of Transcript F'.

Also provided herein are nucleic acid molecules comprising or consisting of a segment (e.g., at least 15 contiguous nucleotides) present in Transcript C (or a fragment or homolog thereof) that is not present in Transcript A (or a fragment or homolog thereof). Such regions can be readily identified by comparing the sequences of the Transcripts. Transcript C is missing exon 6 compared to Transcript A (i.e., Transcript C includes an exon 5-exon 7 boundary not present in Transcript A). Accordingly, provided herein are nucleic acid molecules comprising or consisting of at least 15 contiguous nucleotides (e.g., at least 20 contiguous nucleotides or at least 30 contiguous nucleotides) encoding all or part of an HSD17B13 protein, wherein a segment of the contiguous nucleotides (e.g., at least 5 contiguous nucleotides, at least 10 contiguous nucleotides or at least 15 contiguous nucleotides) is at least about 90%, at least about 95%, at least about 96%, at least about 97%, at least about 98%, or at least about 99% identical to a region spanning the exon 5-exon 7 boundary in Transcript C. It is understood that such nucleic acid molecules would include a sufficient number of nucleotides in each of exons 5 and 7 to distinguish from other features in the HSD17B13 Transcripts (e.g., from boundary of exons 5 and 6 or of exons 6 and 7 in other HSD17B13 Transcripts). For example, the region can comprise the entirety of exons 5 and 7 in Transcript C. Optionally, the nucleic acid molecules comprise or consist of a sequence at least about 90%, at least about 95%, at least about 96%, at least about 97%, at least about 98%, or at least about 99% identical to the sequence set forth in Transcript C and encodes an HSD17B13 protein comprising the sequence set forth in Isoform C.

As one example, the nucleic acid molecules can comprise or consist of at least 15 contiguous nucleotides (e.g., at least 20 contiguous nucleotides or at least 30 contiguous nucleotides) of Transcript C including a region spanning the exon 5-exon 7 boundary, optionally comprising the entirety of exons 5 and 7 in Transcript C, and optionally comprising the entire sequence of Transcript C.

In some embodiments, the nucleic acid molecule comprises less nucleotides than the entire HSD17B3 transcript sequence. In some embodiments, the nucleic acid molecules comprise or consist of at least about 5, at least about 8, at least about 10, at least about 12, at least about 15, at least about 20, at least about 25, at least about 30, at least about 35, at least about 40, at least about 45, at least about 50, at least about 60, at least about 70, at least about 80, at least about 90, at least about 100, at least about 200, at least about 300, at least about 400, at least about 500, or at least about 600 contiguous nucleotides of a particular transcript. In some embodiments, the nucleic acid molecules comprise or consist of at least about 200 to at least about 500 contiguous nucleotides of a particular transcript. In this regard, the longer nucleic acid molecules are preferred over the shorter ones. In some embodiments, the nucleic acid molecules comprise or consist of at least about 50, at least about 60, at least about 70, at least about 80, at least about 90, at least about 100, at least about 200, at least about 300, at least about 400, or at least about 500 contiguous nucleotides of a particular transcript. In this regard, the longer nucleic acid molecules are preferred over the shorter ones.

In some embodiments, the nucleic acid molecules can be useful, for example, as primers, and probes.

The present disclosure provides nucleic acid molecules comprising or consisting of from about 5 nucleotides up to about 50 nucleotides that specifically hybridizes to an HSD17B13 gene at a region that includes a position corresponding to position 12666 in SEQ ID NO:2, or the complement thereof, and wherein the nucleic acid molecule specifically hybridizes to an HSD17B13 gene having a thymine at a position corresponding to position 12666 of SEQ ID NO:2, or to the complement thereof.

The present disclosure provides nucleic acid molecules comprising or consisting of from about 5 nucleotides up to about 50 nucleotides that specifically hybridizes to variant HSD17B13 Transcript D, wherein the nucleic acid molecule specifically hybridizes to: i) a nucleotide sequence that is at least about 90%, at least about 95%, at least about 96%, at least about 97%, at least about 98%, at least about 99%, or 100% identical to a nucleotide sequence of a SEQ ID NO:6, 15, 24, or 33, or ii) to the complement of the nucleotide sequence of i). In some embodiments, the nucleic acid molecules comprise or consist of from about 5 nucleotides up to about 50 nucleotides that specifically hybridizes to variant HSD17B13 Transcript D, wherein the nucleic acid molecule specifically hybridizes to: i) a nucleotide sequence that is at least about 90% identical to a nucleotide sequence of a SEQ ID NO:6, 15, 24, or 33, or ii) to the complement of the nucleotide sequence of i).

The present disclosure provides nucleic acid molecules comprising or consisting of from about 5 nucleotides up to about 50 nucleotides comprising or consisting of: i) a nucleotide sequence that is at least about 90%, at least about 95%, at least about 96%, at least about 97%, at least about 98%, at least about 99%, or 100% identical (or at least about 90% identical) to a nucleotide sequence of a SEQ ID NO:6, 15, 24, or 33, or to the complement thereof; ii) a nucleic acid molecule which specifically hybridizes to exon 2 of Transcript D (RNA or cDNA derived therefrom, and/or mRNA or cDNA derived therefrom; preferably RNA or cDNA derived therefrom); and/or iii) a nucleic acid molecule which specifically hybridizes to the region which bridges exons 3 and 4 of Transcript D (RNA or cDNA derived therefrom, and/or mRNA or cDNA derived therefrom; preferably RNA or cDNA derived therefrom). In some embodiments, the nucleic acid molecule specifically hybridizes to an RNA molecule comprising or consisting of SEQ ID NO:6, or a cDNA thereof comprising or consisting of SEQ ID NO:24, or wherein the nucleic acid molecule specifically hybridizes to an mRNA comprising or consisting of SEQ ID NO: 15, or a cDNA thereof comprising or consisting of SEQ ID NO:33, or the complement thereof. In some embodiments, the nucleic acid molecule is linked to a heterologous nucleic acid or comprises a heterologous label.

In some embodiments, such nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 11000, or at least about 11500. In some embodiments, the nucleic acid molecule comprises or consists of at least 15 nucleotides. In some embodiments, the nucleic acid molecule comprises or consists of at least 15 nucleotides to at least about 35 nucleotides. In some embodiments, such nucleic acid molecules hybridize to variant HSD17B3 genomic DNA, variant HSD17B13 minigenes, variant HSD17B3 RNA (or cDNA derived therefrom), or variant HSD17B13 mRNA (or cDNA derived therefrom) under stringent conditions. Such nucleic acid molecules may be used, for example, as probes, as primers, or as alteration-specific probes or primers as described or exemplified herein.

Also disclosed herein are nucleic acid molecules comprising or consisting of at least 15 contiguous nucleotides that hybridize to an HSD17B13 gene (e.g., an HSD17B13 minigene) at a segment that includes or is within 1000, 500, 400, 300, 200, 100, 50, 45, 40, 35, 30, 25, 20, 15, 10, or 5 nucleotides of a position corresponding to position 12666 or positions 12666 and 12667 of the HSD17B13 rs72613567 variant (SEQ ID NO:2). Such nucleic acid molecules can be useful, for example, as primers or probes.

In some embodiments, the at least 15 contiguous nucleotides can hybridize to a segment of the HSD17B13 gene or HSD17B13 minigene that is at least about 90%, at least about 95%, at least about 96%, at least about 97%, at least about 98%, or at least about 99% (or at least about 90% identical) identical to a corresponding sequence in the HSD17B13 rs72613567 variant (SEQ ID NO:2), and having a thymine at a position corresponding to position 12666 of SEQ ID NO:2. In some embodiments, the nucleic acid molecule can hybridize to at least 15 contiguous nucleotides of SEQ ID NO:2. In some embodiments, the nucleic acid molecule hybridizes to a segment including position 12666 or positions 12666 and 12667 in SEQ ID NO:2 or a position corresponding to position 12666 or positions 12666 and 12667 in SEQ ID NO:2.

In some embodiments, the segment to which the nucleic acid molecules can hybridize can comprise, for example, at least 20, 25, 30, 35, 40, 45, 50, 55, 60, 65, 70, 75, 80, 75, 90, 95, 100, 200, 300, 400, 500, 600, 700, 800, 900, 1000, or 2000 contiguous nucleotides of nucleic acid molecule encoding a variant HSD17B13 protein isoform. In some embodiments, the segment to which the nucleic acid molecules can hybridize can be, for example, up to 20, 25, 30, 35, 40, 45, 50, 55, 60, 65, 70, 75, 80, 75, 90, 95, 100, 200, 300, 400, 500, 600, 700, 800, 900, or 1000 contiguous nucleotides of a nucleic acid encoding a variant HSD17B13 protein isoform. In some embodiments, the nucleic acid molecules can comprise, for example, at least 1000, 2000, 3000, 4000, 5000, 6000, 7000, 8000, 9000, 10000, 11000, 12000, 13000, 14000, 15000, 16000, 17000, 18000, or 19000 contiguous nucleotides of a variant HSD17B13 gene. In some embodiments, the segment to which the nucleic acid molecules can hybridize can be, for example, up to 20, 25, 30, 35, 40, 45, 50, 55, 60, 65, 70, 75, 80, 75, 90, 95, 100, 200, 300, 400, 500, 600, 700, 800, 900, or 1000 contiguous nucleotides of a variant HSD17B13 gene. In some embodiments, the segment can be about 15 to 100 nucleotides in length, or about 15 to 35 nucleotides in length.

Also provided are nucleic acid molecules hybridizing to segments of an RNA transcript, such as Transcript A, Transcript B, Transcript C, Transcript D, Transcript E, Transcript F, Transcript F', Transcript G, and Transcript H, or a corresponding cDNA thereof, or an mRNA transcript, such as Transcript A, Transcript B, Transcript C, Transcript D, Transcript E, Transcript F, Transcript F', Transcript G, and Transcript H, or a corresponding cDNA thereof.

Also provided are nucleic acid molecules hybridizing to segments of an RNA transcript, such as Transcript C, Transcript D, Transcript E, Transcript F, Transcript F', Transcript G, and Transcript H. or a corresponding cDNA thereof, or an mRNA transcript, such as Transcript C, Transcript D, Transcript E, Transcript F, Transcript F', Transcript G, and Transcript H, or a corresponding cDNA thereof.

Also provided are nucleic acid molecules hybridizing to segments of an RNA transcript, such as Transcript C, Transcript D, Transcript F, Transcript G, and Transcript H, or a corresponding cDNA thereof, or an mRNA transcript, such as Transcript C, Transcript D, Transcript F, Transcript G, and Transcript H, or a corresponding cDNA thereof.

Also provided are nucleic acid molecules hybridizing to segments of RNA Transcript D. or a corresponding cDNA, or an mRNA Transcript D, or a corresponding cDNA.

Provided herein are nucleic acid molecules comprising or consisting of a region (e.g., at least 15 contiguous nucleotides) that hybridizes to a segment present in Transcripts D, G, and H (RNA or cDNA derived therefrom, and/or mRNA or cDNA derived therefrom; preferably RNA or cDNA derived therefrom), or fragments or homologs thereof, that is not present in Transcript A (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. For example, provided herein are nucleic acid molecules that hybridize to at least 15 contiguous nucleotides of a nucleic acid encoding an HSD17B13 protein, wherein contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region spanning the exon 6-exon 7 boundary in Transcript D (RNA or cDNA derived therefrom, and/or mRNA or cDNA derived therefrom; preferably RNA or cDNA derived therefrom), and the segment includes a guanine at a residue corresponding to residue 878 at the 3' end of exon 6 in Transcript D (RNA or cDNA derived therefrom, and/or mRNA or cDNA derived therefrom; preferably RNA or cDNA derived therefrom) (i.e., an insertion of a guanine at the 3' end of exon 6 relative to Transcript A in addition to the guanine at the start of exon 7). Alternatively, provided herein are nucleic acid molecules that hybridize to at least 15 contiguous nucleotides of a segment of a nucleic acid encoding an HSD17B13 protein, wherein the contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region spanning the exon 6-exon 7 boundary in Transcript G, and the segment includes a guanine at a residue corresponding to residue 770 at the 3' end of exon 6 in Transcript G (RNA or cDNA derived therefrom, and/or mRNA or cDNA derived therefrom; preferably RNA or cDNA derived therefrom) (i.e., an insertion of a guanine at the 3' end of exon 6 relative to Transcript B in addition to the guanine at the start of exon 7). Alternatively, provided herein are nucleic acid molecules that hybridize to at least 15 contiguous nucleotides of a nucleic acid encoding an HSD17B13 protein, wherein the contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region spanning the exon 6-exon 7 boundary in Transcript H (RNA or cDNA derived therefrom, and/or mRNA or cDNA derived therefrom; preferably RNA or cDNA derived therefrom), and the segment includes a guanine at a residue corresponding to residue 950 at the 3' end of exon 6 in Transcript H (i.e., an insertion of a guanine at the 3' end of exon 6 relative to Transcript E in addition to the guanine at the start of exon 7). It is understood that such nucleic acid molecules would be designed to hybridize to a sufficient number of nucleotides in each of exons 6 and 7 to distinguish the inserted guanine from other features in the HSD17B13 Transcripts (e.g., from the read-through into intron 6 in Transcript F or from the deleted exon 6 in Transcript C).

As one example, the segment can comprise or consist of a region of Transcript D (RNA or cDNA derived therefrom, and/or mRNA or cDNA derived therefrom; preferably RNA or cDNA derived therefrom) spanning the exon 6-exon 7 boundary (i.e., including the guanine at residue 878 of Transcript D). As another example, the segment can comprise or consist of a region of Transcript G (RNA or cDNA derived therefrom, and/or mRNA or cDNA derived therefrom; preferably RNA or cDNA derived therefrom) spanning the exon 6-exon 7 boundary (i.e., including the guanine at residue 770 of Transcript G). As another example, the segment can comprise or consist of a region of Transcript H (RNA or cDNA derived therefrom, and/or mRNA or cDNA derived therefrom; preferably RNA or cDNA derived therefrom) spanning the exon 6-exon 7 boundary (i.e., including the guanine at residue 950 of Transcript H).

In some embodiments, the nucleic acid molecules further comprise or consist of a region (e.g., 15 contiguous nucleotides) that hybridizes to a segment present in Transcript D (RNA or cDNA derived therefrom, and/or mRNA or cDNA derived therefrom; preferably RNA or cDNA derived therefrom), or a fragment or homolog thereof, that is not present in Transcript G (RNA or cDNA derived therefrom, and/or mRNA or cDNA derived therefrom; preferably RNA or cDNA derived therefrom), or a fragment or homolog thereof, and the nucleic acid molecules further comprise or consist of a region that hybridizes to a segment present in Transcript D (RNA or cDNA derived therefrom, and/or mRNA or cDNA derived therefrom; preferably RNA or cDNA derived therefrom), or a fragment or homolog thereof, that is not present in Transcript H (RNA or cDNA derived therefrom, and/or mRNA or cDNA derived therefrom; preferably RNA or cDNA derived therefrom), or a fragment or homolog thereof. Such segments can be readily identified by comparing the sequences of the Transcripts. For example, the segment (e.g., at least 5 contiguous nucleotides, at least 10 contiguous nucleotides or at least 15 contiguous nucleotides) present in Transcript D (RNA or cDNA derived therefrom, and/or mRNA or cDNA derived therefrom, preferably RNA or cDNA derived therefrom), or a fragment or homolog thereof, that is not present in Transcript H (RNA or cDNA derived therefrom, and/or mRNA or cDNA derived therefrom; preferably RNA or cDNA derived therefrom), or a fragment or homolog thereof, can be at least about 90%, at least about 95%, at least about 96%, at least about 97%, at least about 98%, or at least about 99% identical (or at least about 90% identical) to a region spanning the boundary of exons 3 and 4 of Transcript D (RNA or cDNA derived therefrom, and/or mRNA or cDNA derived therefrom; preferably RNA or cDNA derived therefrom) to distinguish from Transcript H. Likewise, the segment (e.g., at least 5 contiguous nucleotides, at least 10 contiguous nucleotides or at least 15 contiguous nucleotides) present in Transcript D (RNA or cDNA derived therefrom, and/or mRNA or cDNA derived therefrom; preferably RNA or cDNA derived therefrom), or a fragment or homolog thereof, that is not present in Transcript G (RNA or cDNA derived therefrom, and/or mRNA or cDNA derived therefrom; preferably RNA or cDNA derived therefrom), or a fragment or homolog thereof, can be at least about 90%, at least about 95%, at least about 96%, at least about 97%, at least about 98%, or at least about 99% identical (or at least about 90% identical) to a region within exon 2 of Transcript D (RNA or cDNA derived therefrom, and/or mRNA or cDNA derived therefrom; preferably RNA or cDNA derived therefrom), a region spanning the exon 1-exon 2 boundary of Transcript D (RNA or cDNA derived therefrom, and/or mRNA or cDNA derived therefrom; preferably RNA or cDNA derived therefrom), or a region spanning the exon 2-exon 3 boundary of Transcript D (RNA or cDNA derived therefrom, and/or mRNA or cDNA derived therefrom; preferably RNA or cDNA derived therefrom) to distinguish from Transcript G.

Provided herein are nucleic acid molecules as described above comprising or consisting of a region that hybridizes to a segment present in Transcripts D, G, and H (RNA or cDNA derived therefrom, and/or mRNA or cDNA derived therefrom, preferably RNA or cDNA derived therefrom), or fragments or homologs thereof, that is not present in Transcript A (RNA or cDNA derived therefrom, and/or mRNA or cDNA derived therefrom; preferably RNA or cDNA derived therefrom), or a fragment or homolog thereof, but further comprising a region (e.g., at least 15 contiguous nucleotides) that hybridizes to a segment that is present in Transcript H (RNA or cDNA derived therefrom, and/or mRNA or cDNA derived therefrom; preferably RNA or cDNA derived therefrom), or a fragment or homolog thereof, but not in Transcript D (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. For example, the segment can be at least about 90%, at least about 95%, at least about 96%, at least about 97%, at least about 98%, at least about 99%, or 100% identical (or at least about 90% identical) to a region (e.g., at least 5 contiguous nucleotides, at least 10 contiguous nucleotides or at least 15 contiguous nucleotides) within exon 3' of Transcript H (RNA or cDNA derived therefrom, and/or mRNA or cDNA derived therefrom; preferably RNA or cDNA derived therefrom), a region spanning the exon 3-exon 3' boundary of Transcript H (RNA or cDNA derived therefrom, and/or mRNA or cDNA derived therefrom; preferably RNA or cDNA derived therefrom), or a region spanning the exon 3'-exon 4 boundary of Transcript H (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in each of exons 3 and 3' or each of exons 3' and 4 to distinguish from other features in the HSD17B13 transcripts (e.g., from the boundary of exons 3 and 4). As one example, the segment can comprise or consist of a region of Transcript H (RNA or cDNA derived therefrom, and/or mRNA or cDNA derived therefrom; preferably RNA or cDNA derived therefrom) within exon 3', spanning the exon 3-exon 3' boundary, or spanning the exon 3'-exon 4 boundary.

Provided herein are nucleic acid molecules as described above comprising or consisting of a region that hybridizes to a segment present in Transcripts D, G, and H (RNA or cDNA derived therefrom, and/or mRNA or cDNA derived therefrom; preferably RNA or cDNA derived therefrom), or fragments or homologs thereof, that is not present in Transcript A (RNA or cDNA derived therefrom, and/or mRNA or cDNA derived therefrom; preferably RNA or cDNA derived therefrom), or a fragment or homolog thereof, but further comprising a region (e.g., at least 15 contiguous nucleotides) that hybridizes to a segment present in Transcript G (RNA or cDNA derived therefrom, and/or mRNA or cDNA derived therefrom; preferably RNA or cDNA derived therefrom), or a fragment or homolog thereof, but not in Transcript D (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. For example, the segment can be at least about 90%, at least about 95%, at least about 96%, at least about 97%, at least about 98%, at least about 99%, or 100% identical (or at least about 90% identical) to a region (e.g., at least 5 contiguous nucleotides, at least 10 contiguous nucleotides or at least 15 contiguous nucleotides) spanning the exon 1-exon 3 boundary in Transcript G (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in each of exons 1 and 3 to distinguish from other features in the HSD17B13 Transcripts (e.g., the boundary of exons 1 and 2 or the boundary of exons 2 and 3). As one example, the segment can comprise or consist of a region of Transcript G (RNA or cDNA derived therefrom, and/or mRNA or cDNA derived therefrom; preferably RNA or cDNA derived therefrom) spanning the exon 1-exon 3 boundary.

Also provided are nucleic acid molecules comprising or consisting of a region (e.g., at least 15 contiguous nucleotides) that hybridizes to a segment of a nucleic acid encoding an HSD17B13 protein that is present in Transcript E (RNA or cDNA derived therefrom, and/or mRNA or cDNA derived therefrom; preferably RNA or cDNA derived therefrom), or a fragment or homolog thereof, but not in Transcript A (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. Transcript E includes an additional exon between exons 3 and 4 compared to Transcript A. Accordingly, provided herein are nucleic acid molecules that hybridize to at least 15 contiguous nucleotides of a nucleic acid encoding an HSD17B13 protein, wherein the contiguous nucleotides comprise or consist of a segment that is at least about 90%, at least about 95%, at least about 96%, at least about 97%, at least about 98%, at least about 99%, or 100% identical (or at least about 90% identical) to a region (e.g., at least 5 contiguous nucleotides, at least 10 contiguous nucleotides or at least 15 contiguous nucleotides) within exon 3' of Transcript E (RNA or cDNA derived therefrom, and/or mRNA or cDNA derived therefrom; preferably RNA or cDNA derived therefrom), a region spanning the exon 3-exon 3' boundary of Transcript E (RNA or cDNA derived therefrom, and/or mRNA or cDNA derived therefrom; preferably RNA or cDNA derived therefrom), or a region spanning the exon 3'-exon 4 boundary of Transcript E (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in each of exons 3 and 3' or each of exons 3' and 4 to distinguish from other features in the HSD17B13 transcripts (e.g., from the boundary of exons 3 and 4). As one example, the segment can comprise or consist of a region of Transcript E (RNA or cDNA derived therefrom, and/or mRNA or cDNA derived therefrom; preferably RNA or cDNA derived therefrom) within exon 3', spanning the exon 3-exon 3' boundary of Transcript E (RNA or cDNA derived therefrom, and/or mRNA or cDNA derived therefrom; preferably RNA or cDNA derived therefrom), or spanning the exon 3'-exon 4 boundary (RNA or cDNA derived therefrom, and/or mRNA or cDNA derived therefrom; preferably RNA or cDNA derived therefrom).

In some embodiments, the nucleic acid molecules further comprise or consist of a region (e.g., 15 contiguous nucleotides) that hybridizes to a segment present in Transcript E (RNA or cDNA derived therefrom, and/or mRNA or cDNA derived therefrom; preferably RNA or cDNA derived therefrom), or a fragment or homolog thereof, that is not present in Transcript H (RNA or cDNA derived therefrom, and/or mRNA or cDNA derived therefrom; preferably RNA or cDNA derived therefrom), or a fragment or homolog thereof. Such segments can be readily identified by comparing the sequences of the Transcripts. For example, the segment (e.g., at least 5 contiguous nucleotides, at least 10 contiguous nucleotides or at least 15 contiguous nucleotides) present in Transcript E (RNA or cDNA derived therefrom, and/or mRNA or cDNA derived therefrom; preferably RNA or cDNA derived therefrom), or a fragment or homolog thereof, that is not present in Transcript H (RNA or cDNA derived therefrom, and/or mRNA or cDNA derived therefrom; preferably RNA or cDNA derived therefrom), or a fragment or homolog thereof, can be at least about 90%, at least about 95%, at least about 96%, at least about 97%, at least about 98%, or at least about 99% identical (or at least about 90% identical) to a region spanning the boundary of exons 6 and 7 of Transcript E (RNA or cDNA derived therefrom, and/or mRNA or cDNA derived therefrom; preferably RNA or cDNA derived therefrom) to distinguish from Transcript G. It is understood that such nucleic acid molecules would be designed to hybridize to a sufficient number of nucleotides in each of exons 6 and 7 to distinguish from other features in the HSD17B13 Transcripts (particularly the additional guanine at the 3' end of exon 6 in Transcript H).

Also provided are nucleic acid molecules comprising or consisting of a region (e.g., at least 15 contiguous nucleotides) that hybridizes to a segment of a nucleic acid encoding an HSD17B13 protein that is present in Transcript F (RNA or cDNA derived therefrom, and/or mRNA or cDNA derived therefrom; preferably RNA or cDNA derived therefrom), or a fragment or homolog thereof, but not in Transcript A (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. Transcript F includes a read-through from exon 6 to intron 6 compared to Transcript A. Accordingly, provided herein are nucleic acid molecules that hybridize to at least 15 contiguous nucleotides of a nucleic acid encoding an HSD17B13 protein, wherein the contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region within the read-through into intron 6 in Transcript F (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise or consist of a sequence present in Transcript F (RNA or cDNA derived therefrom, and/or mRNA or cDNA derived therefrom; preferably RNA or cDNA derived therefrom) (i.e., the inserted thymine) that is not present in Transcript F' (RNA or cDNA derived therefrom, and/or mRNA or cDNA derived therefrom; preferably RNA or cDNA derived therefrom). Transcript F' also includes a read-through from exon 6 into intron 6 compared to Transcript A, but the read-through does not include the inserted thymine present in the HSD17B13 rs72613567 variant gene. As one example, the segment can comprise or consist of a region of Transcript F (RNA or cDNA derived therefrom, and/or mRNA or cDNA derived therefrom; preferably RNA or cDNA derived therefrom) within the read-through into intron 6 or spanning the boundary between the read-through into intron 6 and the rest of exon 6.

Also provided are nucleic acid molecules comprising or consisting of a region (e.g., at least 15 contiguous nucleotides) that hybridizes to a segment of a nucleic acid encoding an HSD17B13 protein that is present in Transcript F' (RNA or cDNA derived therefrom, and/or mRNA or cDNA derived therefrom; preferably RNA or cDNA derived therefrom), or a fragment or homolog thereof, but not in Transcript A (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. Transcript F' includes a read-through from exon 6 to intron 6 compared to Transcript A. Accordingly, provided herein are nucleic acid molecules that hybridize to at least 15 contiguous nucleotides of a nucleic acid encoding an HSD17B13 protein, wherein the contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region within the read-through into intron 6 in Transcript F' (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F' (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise or consist of a sequence present in Transcript F' (RNA or cDNA derived therefrom, and/or mRNA or cDNA derived therefrom; preferably RNA or cDNA derived therefrom) that is not present in Transcript F (RNA or cDNA derived therefrom, and/or mRNA or cDNA derived therefrom; preferably RNA or cDNA derived therefrom). The read-through in Transcript F includes the inserted thymine present in the HSD17B13 rs72613567 variant gene, whereas the read-through in Transcript F' does not. As one example, the segment can comprise or consist of a region of Transcript F' (RNA or cDNA derived therefrom, and/or mRNA or cDNA derived therefrom; preferably RNA or cDNA derived therefrom) within the read-through into intron 6 or spanning the boundary between the read-through into intron 6 and the rest of exon 6.

Also provided are nucleic acid molecules comprising or consisting of a region (e.g., at least 15 contiguous nucleotides) that hybridizes to a segment of a nucleic acid encoding an HSD17B13 protein that is present in Transcript C (RNA or cDNA derived therefrom, and/or mRNA or cDNA derived therefrom; preferably RNA or cDNA derived therefrom), or a fragment or homolog thereof, but not in Transcript A (RNA or cDNA derived therefrom, and/or mRNA or cDNA derived therefrom; preferably RNA or cDNA derived therefrom), or a fragment or homolog thereof. Such regions can be readily identified by comparing the sequences of the Transcripts. Transcript C is missing exon 6 compared to Transcript A (i.e., Transcript C includes an exon 5-exon 7 boundary not present in Transcript A). Accordingly, provided herein are nucleic acid molecules that hybridize to at least 15 contiguous nucleotides of a nucleic acid encoding an HSD17B13 protein, wherein the contiguous nucleotides comprise or consist of a segment (e.g., at least 5 contiguous nucleotides, at least 10 contiguous nucleotides or at least 15 contiguous nucleotides) that is at least about 90%, at least about 95%, at least about 96%, at least about 97%, at least about 98%, at least about 99%, or 100% identical (or at least about 90% identical) to a region spanning the exon 5-exon 7 boundary in Transcript C (RNA or cDNA derived therefrom, and/or mRNA or cDNA derived therefrom; preferably RNA or cDNA derived therefrom). It is understood that such nucleic acid molecules would be designed to hybridize to a sufficient number of nucleotides in exons 5 and 7 to distinguish from other features in the HSD17B13 Transcripts (e.g., from boundary of exons 5 and 6 or of exons 6 and 7 in other HSD17B13 Transcripts). As one example, the segment can comprise or consist of a region from Transcript C (RNA or cDNA derived therefrom, and/or mRNA or cDNA derived therefrom; preferably RNA or cDNA derived therefrom) spanning the exon 5-exon 7 boundary.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern.

Solid-state substrates for use in solid supports can include any solid material to which molecules can be coupled. This includes materials such as acrylamide, agarose, cellulose, nitrocellulose, glass, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A form for a solid-state substrate is a microtiter dish, such as a standard 96-well type. In some embodiments, a multiwell glass slide can be employed that normally contain one array per well. In some embodiments, the support is a microarray.

The nucleic acid molecules disclosed herein can comprise RNA. DNA, or both RNA and DNA. The nucleic acid molecules can also be linked or fused to a heterologous nucleotide sequence, such as in a vector, or a heterologous label. For example, the nucleic acid molecules disclosed herein can be in a vector or exogenous donor sequence comprising the nucleic acid molecule and a heterologous nucleotide sequence. The nucleic acid molecules can also be linked or fused to a heterologous label, such as a fluorescent label. Other examples of labels are disclosed elsewhere herein.

The label can be directly detectable (e.g., fluorophore) or indirectly detectable (e.g., hapten, enzyme, or fluorophore quencher). Such labels can be detectable by spectroscopic, photochemical, biochemical, immunochemical, or chemical means. Such labels include, for example, radiolabels that can be measured with radiation-counting devices; pigments, dyes or other chromogens that can be visually observed or measured with a spectrophotometer; spin labels that can be measured with a spin label analyzer, and fluorescent labels (e.g., fluorophores), where the output signal is generated by the excitation of a suitable molecular adduct and that can be visualized by excitation with light that is absorbed by the dye or can be measured with standard fluorometers or imaging systems. The label can also be, for example, a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term "label" can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish pernnxidate (HRP) to bind to the tag, and then use a calorimetric substrate (e.g., tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels are known and include, for example, particles, fluorophores, haptens, enzymes and their calorimetric, fluo genic and chemiluminescent substrates and other labels.

The nucleic acid molecules can be modified nucleic acid molecules and comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain nucleotide analogs such as, for example, 5-substituted pyrimidines, 6-azapyrimidines, and N-2, N-6 and O-6 substituted purines including, but not limited to, 2-aminopropyladenine, 5-propynyluracil, 5-propynylcytosine, and 5-methylcytosine can increase the stability of duplex formation. Often, base modifications can be combined with, for example, a sugar modification, such as 2'-O-methoxyethyl, to achieve unique properties such as increased duplex stability.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $-O[(CH_2)_nO]_mCH_3$, $-O(CH_2)_nOCH_3$, $-O(CH_2)_nNH_2$, $-O(CH_2)_nCH_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include, but are not limited to, C$_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included.

Nucleotide substitutes also include nucleotides or nucleotide analogs that have had the phosphate moiety or sugar moieties replaced. In some embodiments, nucleotide substitutes may not contain a standard phosphorus atom. Substitutes for the phosphate can be, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and CH$_2$ component parts.

It is also understood in a nucleotide substitute that both the sugar and the phosphate moieties of the nucleotide can be replaced by, for example, an amide type linkage (aminoethylglycine) (PNA).

It is also possible to link other types of molecules (conjugates) to nucleotides or nucleotide analogs to enhance, for example, cellular uptake. Conjugates can be chemically linked to the nucleotide or nucleotide analogs. Such conjugates include, for example, lipid moieties such as a cholesterol moiety, cholic acid, a thioether such as hexyl-S-tritylthiol, a thiocholesterol, an aliphatic chain such as dodecandiol or undecyl residues, a phospholipid such as di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety, or an octadecylamine or hexylamino-carbonyl-oxycholesterol moiety.

Also disclosed herein are polypeptides encoded by the nucleic acid molecules disclosed herein and compositions comprising a nucleic acid or polypeptide disclosed herein and a carrier increasing the stability of the isolated nucleic acid or protein (e.g., prolonging the period under given conditions of storage (e.g., −, 20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Also provided herein are functional polynucleotides that can interact with the disclosed nucleic acid molecules. Functional polynucleotides are nucleic acid molecules that have a specific function, such as binding a target molecule or catalyzing a specific reaction. Examples of functional polynucleotides include, but are not limited to, antisense molecules, aptamers, ribozymes, triplex forming molecules, and external guide sequences. The functional polynucleotides can act as effectors, inhibitors, modulators, and stimulators of a specific activity possessed by a target molecule, or the functional polynucleotides can possess a de novo activity independent of any other molecules.

Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant (k$_d$) less than or equal to about $10^{-6}$, less than or equal to about $10^{-8}$, less than or equal to about $10^{-10}$, or less than or equal to about $10^{-12}$. Examples of antisense molecules include, but are not limited to, antisense RNAs, small interfering RNAs (siRNAs), and short hairpin RNAs (shRNAs).

In some embodiments, any of the nucleic acid molecules, genomic DNA molecules, minigenes, RNA molecules, mRNA molecules, or cDNA molecules disclosed herein can be purified, e.g., are at least about 90% pure. In some embodiments, any of the nucleic acid molecules disclosed herein can be purified, e.g., are at least about 95% pure. In some embodiments, any of the nucleic acid molecules disclosed herein can be purified, e.g., are at least about 99% pure. Purification is according to the hands of a human, with human-made purification techniques.

The present disclosure also provides vectors comprising any one or more of the nucleic acid molecules disclosed herein. In some embodiments, the vectors comprise any one or more of the nucleic acid molecules disclosed herein and a heterologous nucleic acid. The vectors can be viral or nonviral vectors capable of transporting a nucleic acid molecule. In some embodiments, the vector is a plasmid or cosmid. In some embodiments, the vector is a viral vector, wherein additional DNA segments can be ligated into the viral genome. In some embodiments, the vector can autonomously replicate in a host cell into which it is introduced. In some embodiments, the vector can be integrated into the genome of a host cell upon introduction into the host cell and thereby are replicated along with the host genome. Moreover, particular vectors can direct the expression of genes to which they are operatively linked. Such vectors are referred to herein as "recombinant expression vectors" or "expression vectors." Such vectors can also be targeting vectors.

In some embodiments, the proteins encoded by the various genetic variants disclosed herein are expressed by inserting nucleic acid molecules encoding the disclosed genetic variants into expression vectors, such that the genes are operatively linked to expression control sequences, such as transcriptional and translational control sequences. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art. In some embodiments, nucleic acid molecules comprising the disclosed genetic variants can be ligated into a vector such that transcriptional and translational control sequences within the vector serve their intended function of regulating the transcription and translation of the genetic variant.

In addition to a nucleotide sequence comprising the disclosed genetic variants, the recombinant expression vectors can carry regulatory sequences that control the expression of the genetic variant in a host cell such as, for example, promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. Methods of expressing polypeptides in bacterial cells or fungal cells (e.g., yeast cells) are also well known.

A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter).

In addition to a nucleotide sequence comprising the disclosed genetic variants and regulatory sequences, the recombinant expression vectors can carry additional sequences, such as sequences that regulate replication of the vector in host cells and selectable marker genes. Exemplary selectable marker genes include, but are not limited to, the dihydrofolate reductase (DHFR) gene (for use in dhfr-host cells with methotrexate selection/amplification), the neo gene (for G418 selection), and the glutamate synthetase (GS) gene.

The present disclosure also provides cells (e.g., recombinant host cells) comprising any one or more of the nucleic acid molecules, including vectors comprising the nucleic acid molecules, and/or any one or more of the polypeptides disclosed herein. The cells can be in vitro, ex vivo, or in vivo. Nucleic acid molecules can be linked to a promoter and other regulatory sequences so they are expressed to produce an encoded protein. Cell lines of such cells are further provided.

In some embodiments, the cell is a totipotent cell or a pluripotent cell (e.g., an embryonic stem (ES) cell such as a rodent ES cell, a mouse ES cell, or a rat ES cell). Pluripotent and/or totipotent cells can be, for example, ES cells or ES-like cells, such as an induced pluripotent stem (iPS) cells. In accordance with the present disclosure, the embryonic stem cells may be non-human embryonic stem cells. In some embodiments, the cell is a primary somatic cell, or a cell that is not a primary somatic cell. Such cells can be isolated by conventional techniques and include, for example, somatic cells, hematopoietic cells, endothelial cells, epithelial cells, fibroblasts, mesenchymal cells, keratinocytes, melanocytes, monocytes, mononuclear cells, adipocytes, preadipocytes, neurons, glial cells, hepatocytes, skeletal myoblasts, and smooth muscle cells. For example, primary cells can be derived from connective tissues, muscle tissues, nervous system tissues, or epithelial tissues.

In some embodiments, the cells may normally not proliferate indefinitely but, due to mutation or alteration, have evaded normal cellular senescence and instead can keep undergoing division. Such mutations or alterations can occur naturally or be intentionally induced. Examples of immortalized cells include, but are not limited to, Chinese hamster ovary (CHO) cells, human embryonic kidney cells (e.g., HEK 293 cells), and mouse embryonic fibroblast cells (e.g., 3T3 cells). In some embodiments, the cell is a differentiated cell, such as a liver cell (e.g., a human liver cell).

The cell can be from any source. For example, the cell can be a eukaryotic cell, an animal cell, a plant cell, or a fungal (e.g., yeast) cell. Such cells can be fish cells or bird cells, or such cells can be mammalian cells, such as human cells, non-human mammalian cells, rodent cells, mouse cells or rat cells. Mammals include, but are not limited to, humans, non-human primates, monkeys, apes, cats dogs, horses, bulls, deer, bison, sheep, rodents (e.g., mice, rats, hamsters, guinea pigs), livestock (e.g., bovine species such as cows, steer, etc.; ovine species such as sheep, goats, etc.; and porcine species such as pigs and boars). Birds include, but are not limited to, chickens, turkeys, ostrich, geese, ducks, etc. Domesticated animals and agricultural animals are also included. The term "non-human animal" excludes humans. In some embodiments, the cell is a human cell.

The present disclosure provides use of any of the nucleic acid molecules described herein as probes or primers for detecting a variant HSD17B13 gene or variant HSD17B13 transcript, for determining a human subject's susceptibility or risk of developing a liver disease, or for determining a human subject's risk for progression to more clinically advanced stages of fatty liver disease.

The present disclosure provides HSD17B13 isoform polypeptides and fragments thereof, and particularly HSD17B13 isoform polypeptides and fragments thereof produced by the HSD17B13 rs72613567 variant.

The present disclosure provides polypeptides comprising or consisting of an amino acid sequence that is at least about 90%, at least about 95%, at least about 96%, at least about 97%, at least about 98%, at least about 99%, or 100% identical to the amino acid sequence of HSD17B13 Isoform D (SEQ ID NO:42). In some embodiments, the polypeptides comprise or consist of an amino acid sequence that is at least about 90% identical to the amino acid sequence of HSD17B13 Isoform D (SEQ ID NO:42). In some embodiments, the polypeptide comprises or consists of the amino acid sequence of SEQ ID NO:42. In some embodiments, these polypeptides have 274 amino acids. In some embodiments, these polypeptides have a C-terminal Val-Ser-Ser. In some embodiments, these polypeptides are associated with a decreased risk of developing any of the liver diseases described herein or decreased risk of progression to more clinically advanced stages of fatty liver disease.

In some embodiments, the polypeptides comprise or consist of an amino acid sequence at least about 90%, at least about 95%, at least about 96%, at least about 97%, at least about 98%, at least about 99%, or 100% identical (or at least about 90%) to Isoform A, Isoform B, Isoform C, Isoform D, Isoform E, Isoform F, Isoform F', Isoform G, or Isoform H. In some embodiments, the HSD17B13 protein is Isoform A, Isoform B, Isoform C, Isoform D, Isoform E, Isoform F, Isoform F', Isoform G, or Isoform H.

In some embodiments, the polypeptides comprise or consist of an amino acid sequence at least about 90%, at least about 95%, at least about 96%, at least about 97%, at least about 98%, at least about 99%, or 100% identical (or at least about 90%) to Isoform C, Isoform D, Isoform E, Isoform F, Isoform F', Isoform G, or Isoform H. In some embodiments, the polypeptide is Isoform C, Isoform D, Isoform E, Isoform F, Isoform F', Isoform G, or Isoform H.

In some embodiments, the polypeptides comprise or consist of an amino acid sequence at least about 90%, at least about 95%, at least about 96%, at least about 97%, at least about 98%, at least about 99%, or 100% identical (or at least about 90%) to Isoform C, Isoform D, Isoform F, Isoform G, or Isoform H. In some embodiments, the polypeptide is Isoform C, Isoform D, Isoform F, Isoform G, or Isoform H.

In some embodiments, the polypeptides comprise or consist of an amino acid sequence at least about 90%, at least about 95%, at least about 96%, at least about 97%, at least about 98%, at least about 99%, or 100% identical to Isoform D. In some embodiments, the polypeptides comprise or consist of an amino acid sequence at least about 90% identical to Isoform D. In some embodiments, the polypeptide is Isoform D.

In some embodiments, the polypeptides comprise or consist of, for example, at least 5, 6, 8, 10, 12, 14, 15, 16, 18, 20, 22, 24, 25, 30, 35, 40, 45, 50, 60, 70, 80, 90, 100, 150, 200, 250, or 300 contiguous amino acids of: i) HSD17B13 Isoform A, B, C, D, E, F, F', G, or H or a fragment thereof; ii) HSD17B13 Isoform C, D, E, F, F', G, or H or a fragment thereof; iii) HSD17B13 Isoform C, D, F, G, or H or a fragment thereof; or iv) HSD17B13 Isoform D or a fragment thereof. It is understood that gene sequences within a population and proteins encoded by such genes can vary due to polymorphisms such as single-nucleotide polymorphisms. The sequences provided herein for each HSD17B13 isoform are only exemplary sequences. Other sequences are also possible.

As one example, the polypeptides can comprise or consist of a segment (e.g., at least 8 contiguous amino acids) that is at least about 90%, at least about 95%, at least about 96%, at least about 97%, at least about 98%, at least about 99%, or 100% identical (or at least about 90%) to a segment including at least a portion of the region encoded by exon 7 in Isoform D, Isoform G, or Isoform H, (or fragments or homologs thereof) that is not present in Isoform A (or a fragment or homolog thereof). Such regions can be readily identified by comparing the sequences of the Isoforms. The region encoded by exon 7 in Isoforms D, G, and H is frameshifted and truncated compared to the region encoded by exon 7 in Isoform A.

Such polypeptides can further comprise or consist of a segment present in Isoform D (or a fragment or homolog thereof) that is not present in Isoform G (or a fragment or homolog thereof), and can further comprise a segment present in Isoform D (or a fragment or homolog thereof) that is not present in Isoform H (or a fragment or homolog thereof). Such regions can be readily identified by comparing the sequences of the Isoforms. For example, such polypeptides can comprise or consist of a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least about 90%, at least about 95%, at least about 96%, at least about 97%, at least about 98%, or at least about 99% identical (or at least about 90%) to a segment spanning the boundary of the regions encoded by exons 3 and 4 of Isoform D to distinguish from Isoform H. Likewise, such polypeptides can comprise or consist of a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least about 90%, at least about 95%, at least about 96%, at least about 97%, at least about 98%, or at least about 99% identical (or at least about 90%) to a segment within the region encoded by exon 2 in Isoform D, a segment spanning the boundary of the regions encoded by exons 1 and 2 in Isoform D, or a segment spanning the boundary of the regions encoded by exons 2 and 3 in Isoform D to distinguish from Isoform G.

Like Isoform D, the region encoded by exon 7 in Isoform H is frameshifted and truncated compared to Isoform A. In addition, however, Isoform H includes a region encoded by an additional exon (exon 3') between exons 3 and 4 compared to Isoforms A and D. Accordingly, such polypeptides can be as described above comprising or consisting of a segment that is present in Isoforms D, G, and H (or fragments or homologs thereof) that is not present in Isoform A (or a fragment or homolog thereof) but further comprising a segment (e.g., at least 8 contiguous amino acids) from Isoform H (or a fragment or homolog thereof) that is not present in Isoform D (or a fragment or homolog thereof). Such regions can be readily identified by comparing the sequences of the Isoforms. For example, such polypeptides can further comprise or consist of a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least about 90%, at least about 95%, at least about 96%, at least about 97%, at least about 98%, at least about 99%, or 100% identical (or at least about 90%) to a segment including at least a portion of the region encoded by exon 3' in Isoform H.

Like Isoform D, the region encoded by exon 7 in Isoform G is frameshifted and truncated compared to Isoform A. In addition, however, Isoform G is missing the region encoded by exon 2 compared to Isoforms A and D and thus includes an exon 1-exon 3 boundary not present in Isoforms A and D. Accordingly, such polypeptides can be as described above comprising or consisting of a segment that is present in Isoforms D, G, and H (or fragments or homologs thereof) that is not present in Isoform A (or a fragment or homolog thereof) but further comprising a segment (e.g., at least 8 contiguous amino acids) from Isoform G (or a fragment or homolog thereof) that is not present in Isoform D (or a fragment or homolog thereof). Such regions can be readily identified by comparing the sequences of the Isoforms. For example, such polypeptides can further comprise or consist of a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least about 90%, at least about 95%, at least about 96%, at least about 97%, at least about 98%, at least about 99%, or 100% identical (or at least about 90%) to a segment spanning the boundary of the regions encoded by exons 1 and 3 in Isoform G.

Also provided herein are polypeptides comprising or consisting of a segment (e.g., at least 8 contiguous amino acids) that is present in Isoform E (or a fragment or homolog thereof) that is not present in Isoform A (or a fragment or homolog thereof). Isoform E includes a region encoded by an additional exon (exon 3') between exons 3 and 4 that is not present in Isoform A. Such regions can be readily identified by comparing the sequences of the Isoforms. Accordingly, the polypeptides can comprise or consist of at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 isoform protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least about 90%, at least about 95%, at least about 96%, at least about 97%, at least about 98%, at least about 99%, or 100% identical (or at least about 90%) to a segment including at least a portion of the region encoded by exon 3' in Isoform E or Isoform H. Optionally, such polypeptides can further comprise or consist of a segment (e.g., at least 8 contiguous amino acids) from Isoform E (or a fragment or homolog thereof) that is not present in Isoform H (or a fragment or homolog thereof). Such regions can be readily identified by comparing the sequences of the Isoforms. For example, such polypeptides can further comprise or consist of a segment of the contiguous amino acids (e.g., at least 3 contiguous amino acids, at least 5 contiguous amino acids, at least 8 contiguous amino acids, at least 10 contiguous amino acids, or at least 15 contiguous amino acids) that is at least about 90%, at least about 95%, at least about 96%, at least about 97%, at least about 98%, at least about 99%, or 100% identical (or at least about 90%) a segment spanning the boundary of the regions encoded by exons 6 and 7 in Isoform E.

Also provided herein are polypeptides comprising or consisting of a segment (e.g., at least 8 contiguous amino acids) present in Isoform F (or a fragment or homolog thereof) that is not present in Isoform A (or a fragment or homolog thereof). Isoform F includes a region encoded by read-through from exon 6 into intron 6 that is not present in Isoform A. Such regions can be readily identified by comparing the sequences of the Isoforms. Accordingly, the polypeptides can comprise or consist of at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 isoform protein (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least about 90%, at least about 95%, at least about 96%, at least about 97%, at least about 98%, at least about 99%, or 100% identical (or at least about 90%) to a segment including at least a portion of the region encoded by the read-through into intron 6 in Isoform F.

Also provided herein are polypeptides comprising or consisting of a segment (e.g., at least 8 contiguous amino acids) present in Isoform C (or a fragment or homolog thereof) that is not present in Isoform A (or a fragment or homolog thereof). Isoform C is missing the region encoded by exon 6 compared to Isoform A and includes an exon 5-exon 7 boundary not present in Isoform A. Such regions can be readily identified by comparing the sequences of the Isoforms. Accordingly, the polypeptides can comprise at least 5, 6, 8, 10, 12, 14, 15, 16, 18, 20, 22, 24, 25, 30, 35, 40, 45, 50, 60, 70, 80, 90, 100, 150, or 200 contiguous amino acids of an HSD17B13 protein isoform (e.g., at least 8 contiguous amino acids, at least 10 contiguous amino acids, or at least 15 contiguous amino acids of an HSD17B13 protein), wherein a segment of the contiguous amino acids (e.g., at least 3 contiguous amino acids, at least 5 contiguous amino acids, at least 8 contiguous amino acids, at least 10 contiguous amino acids, or at least 15 contiguous amino acids) is at least about 90%, at least about 95%, at least about 96%, at least about 97%, at least about 98%, at least about 99%, or 100% identical (or at least about 90%) to a segment spanning the boundary of the regions encoded by exons 5 and 7 in Isoform C.

Any of the isolated polypeptides disclosed herein can be linked to a heterologous molecule or heterologous label. Examples of such heterologous molecules or labels are disclosed elsewhere herein. For example, the heterologous molecule can be an immunoglobulin Fc domain, a peptide tag as disclosed elsewhere herein, poly(ethylene glycol), polysialic acid, or glycolic acid.

The present disclosure also provides methods of producing any of the polypeptides or fragments thereof disclosed herein. For example, polypeptides or fragments thereof can be produced from host cells comprising nucleic acid molecules (e.g., recombinant expression vectors) encoding such polypeptides or fragments thereof. Such methods can comprise culturing a host cell comprising a nucleic acid molecule (e.g., recombinant expression vector) encoding a polypeptide or fragment thereof under conditions sufficient to produce the polypeptide or fragment thereof, thereby producing the polypeptide or fragment thereof. The nucleic acid can be operably linked to a promoter active in the host cell, and the culturing can be carried out under conditions whereby the nucleic acid is expressed. Such methods can further comprise recovering the expressed polypeptide or fragment thereof. The recovering can further comprise purifying the polypeptide or fragment thereof.

Examples of suitable systems for protein expression include host cells such as, for example: bacterial cell expression systems (e.g., *Escherichia coli, Lactococcus lactis*), yeast cell expression systems (e.g., *Saccharomyces cerevisiae, Pichia pastoris*), insect cell expression systems (e.g., baculovirus-mediated protein expression), and mammalian cell expression systems.

In some embodiments, the nucleic acid molecules encode a tag in frame with the polypeptide or fragment thereof to facilitate protein purification. Examples of tags are disclosed elsewhere herein. Such tags can, for example, bind to a partner ligand (e.g., immobilized on a resin) such that the tagged protein can be isolated from all other proteins (e.g., host cell proteins).

Other methods can also be used to produce polypeptides or fragments thereof. For example, two or more peptides or polypeptides can be linked together by protein chemistry techniques. For example, peptides or polypeptides can be chemically synthesized using either Fmoc (9-fluorenylmethyloxycarbonyl) or Boc (tert-butyloxycarbonoyl) chemistry. Alternately, the peptide or polypeptide can be independently synthesized in vivo as described herein. Once isolated, these independent peptides or polypeptides may be linked to form a peptide or fragment thereof via similar peptide condensation reactions.

In some embodiments, the polypeptides can possess post-expression modifications such as, for example, glycosylations, acetylations, and phosphorylations, as well as other modifications known in the art, both naturally occurring and non-naturally occurring. A polypeptide may be an entire protein, or a subsequence thereof.

The present disclosure also provides methods of producing any of the polypeptides disclosed herein, comprising culturing a host cell comprising a recombinant expression vectors comprising nucleic acid molecules comprising a polynucleotide capable of encoding one or more of the polypeptides disclosed herein, or its complement, thereby producing the polypeptide.

The polypeptides disclosed herein can comprise an amino acid sequence of a naturally occurring HSD17B13 isoform protein, or can comprise a non-naturally occurring sequence. In one example, the non-naturally occurring sequence can differ from the non-naturally occurring sequence due to conservative amino acid substitutions. For example, the sequence can be identical with the exception of conservative amino acid substitutions.

Any of the polypeptides disclosed herein can further have one or more substitutions (such as conservative amino acid substitutions), insertions, or deletions. Insertions include, for example, amino or carboxyl terminal fusions as well as intrasequence insertions of single or multiple amino acid residues. Techniques for making substitutions at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e. a deletion of 2 residues or insertion of 2 residues. Substitutions, deletions, insertions or any combination thereof may be combined to arrive at a final construct. In some embodiments, the mutations do not place the sequence out of reading frame and do not create complementary regions that could produce secondary mRNA structure.

In some embodiments, the polypeptides disclosed herein are linked or fused to heterologous polypeptides or heterologous molecules or labels, numerous examples of which are disclosed elsewhere herein. For example, the proteins can be fused to a heterologous polypeptide providing increased or decreased stability. The fused domain or heterologous polypeptide can be located at the N-terminus, the C-terminus, or internally within the polypeptide. A fusion partner may, for example, assist in providing T helper epitopes (an immunological fusion partner), or may assist in expressing the polypeptide (an expression enhancer) at higher yields than the native recombinant polypeptide. Certain fusion partners are both immunological and expression enhancing fusion partners. Other fusion partners may be selected to increase the solubility of the polypeptide or to facilitate targeting the polypeptide to desired intracellular compartments. Some fusion partners include affinity tags, which facilitate purification of the polypeptide.

In some embodiments, a fusion protein is directly fused to the heterologous molecule or is linked to the heterologous molecule via a linker, such as a peptide linker. For example, peptide linker sequences may contain Gly, Asn and Ser residues. Other near neutral amino acids, such as Thr and Ala may also be used in the linker sequence. A linker sequence may generally be, for example, from 1 to about 50 amino acids in length. Linker sequences are generally not required when the first and second polypeptides have non-essential N-terminal amino acid regions that can be used to separate the functional domains and prevent steric interference.

In some embodiments, the polypeptides are operably linked to a cell-penetrating domain. For example, the cell-penetrating domain can be derived from the HIV-1 TAT protein, the TLM cell-penetrating motif from human hepatitis B virus. MPG, Pep-1, VP22, a cell-penetrating peptide from Herpes simplex virus, or a polyarginine peptide sequence. The cell-penetrating domain can be located at the N-terminus, the C-terminus, or anywhere within the protein.

In some embodiments, the polypeptides are operably linked to a heterologous polypeptide for ease of tracking or purification, such as a fluorescent protein, a purification tag, or an epitope tag. Examples of fluorescent proteins include, but are not limited to, green fluorescent proteins (e.g., GFP, GFP-2, tagGFP, turboGFP, eGFP, Emerald, Azami Green. Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include, but are not limited to, glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, SI, T7, V5, VSV-G, histidine (His), biotin carboxyl carrier protein (BCCP), and calmodulin. In some embodiments, the heterologous molecule is an immunoglobulin Fc domain, a peptide tag, a transduction domain, poly(ethylene glycol), polysialic acid, or glycolic acid.

In some embodiments, isolated polypeptides comprise non-natural or modified amino acids or peptide analogs. For example, there are numerous D-amino acids or amino acids which have a different functional substituent than the naturally occurring amino acids. The opposite stereo isomers of naturally occurring peptides are disclosed, as well as the stereo isomers of peptide analogs.

In some embodiments, the isolated polypeptides are peptide mimetics, which can be produced to resemble peptides, but which are not connected via a natural peptide linkage. For example, linkages for amino acids or amino acid analogs include, but are not limited to, —CH$_2$NH—, —CH$_2$S—, —CH$_2$—, —CH=CH— (cis and trans), —COCH$_2$—, —CH(OH)CH$_2$—, and —CHH$_2$SO—. Peptide analogs can have more than one atom between the bond atoms, such as b-alanine, gaminobutyric acid, and the like.

In some embodiments, the polypeptides comprise D-amino acids, which can be used to generate more stable peptides because D amino acids are not recognized by peptidases. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together.

The present disclosure also provides nucleic acid molecules encoding any of the polypeptides disclosed herein. This includes all degenerate sequences related to a specific polypeptide sequence (all nucleic acid molecules having a sequence that encodes one particular polypeptide sequence as well as all nucleic acids, including degenerate nucleic acids, encoding the disclosed variants and derivatives of the protein sequences). Thus, while each particular nucleotide sequence may not be written out herein, each and every sequence is in fact disclosed and described herein through the disclosed polypeptide sequences.

Percent identity (or percent complementarity) between particular stretches of nucleotide sequences within nucleic acid molecules or amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package. Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

The present disclosure also provides compositions comprising any one or more of the nucleic acid molecules and/or any one or more of the polypeptides disclosed herein and a carrier and/or excipient. In some embodiments, the carrier increases the stability of the nucleic acid molecule and/or polypeptide (e.g., prolonging the period under given conditions of storage (e.g., −20° C., 4° C., or ambient temperature) for which degradation products remain below a threshold, such as below 0.5% by weight of the starting nucleic acid or protein; or increasing the stability in vivo). Examples of carriers include, but are not limited to, poly(lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

The nucleic acid molecules and polypeptides disclosed herein can be introduced into a cell by any means. Non-limiting transfection methods include chemical-based transfection methods using liposomes, nanoparticles, calcium, dendrimers, and cationic polymers such as DEAE-dextran or polyethylenimine. Viral methods can also be used for transfection by, for example, adenovirus, adeno-associated virus, lentivirus, retrovirus, by transfection, by lipid-mediated transfection, or by nucleofection. In some embodiments, nucleofection is performed using the LONZA® NUCLEOFECTOR™ system. Introduction of nucleic acid molecules or proteins into a cell can also be accomplished by micro-injection. Non-chemical methods include electroporation, sono-poration, optical transfection, particle-based transfection including use of a gene gun, or magnet-assisted transfection, intracytoplasmic injection. Introduction of nucleic acid molecules and proteins into cells can also be accomplished by hydrodynamic delivery (HDD). In some embodiments, a nucleic acid or protein can be introduced into a cell in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule.

The introduction of nucleic acid molecules or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

The present disclosure provides methods for detecting the presence of the variant HSD17B13 rs72613567 gene in a biological sample comprising genomic DNA, for detecting the presence or levels of any one of or a combination of HSD17B13 Transcripts C, D, E, F, F', G, and H, and particularly D, in a biological sample comprising RNA, or cDNA derived therefrom, or comprising mRNA, or cDNA derived therefrom, or for detecting the presence or levels of any one of or a combination of HSD17B13 protein Isoforms C, D, E, F, F', G, or H, and particularly D, in a biological sample comprising protein. It is understood that gene sequences within a population and RNAs. mRNAs, and proteins encoded by such genes can vary due to polymorphisms such as single-nucleotide polymorphisms. The sequences provided herein for the HSD17B13 gene and for each HSD17B13 Transcript and HSD17B13 Isoform are only exemplary sequences for the HSD17B13 gene and for each HSD17B13 Transcript (RNA, mRNA, and cDNA derived therefrom) and HSD17B13 isoform. Other sequences for the HSD17B13 gene and for each HSD17B13 Transcript and HSD17B13 Isoform are also possible.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample.

A biological sample can be processed differently depending on the assay being employed. For example, when detecting the HSD17B13 rs72613567 variant nucleic acid molecule, preliminary processing designed to isolate or enrich the sample for the genomic DNA can be employed. A variety of known techniques may be used for this purpose. When detecting the level of HSD17B13 Transcript C, D, E, F, G, or H mRNA, different techniques can be used to enrich the biological sample with mRNA. Various methods to detect the presence or level of a particular HSD17B13 rs72613567 variant nucleic acid molecule can be used.

The present disclosure provides methods for detecting a variant HSD17B13 rs72613567 gene in a cell or in a subject such as a human subject.

The present disclosure provides methods of detecting a variant HSD17B13 gene in a human subject, comprising or consisting of performing an assay on a biological sample obtained from the human subject, wherein the assay determines whether a thymine is inserted between positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, wherein the presence of said thymine is indicative for a variant HSD17B13 gene. In some embodiments, the assay comprises or consists of sequencing a portion of the HSD17B13 gene including positions corresponding to positions 12665 and 12666 of SEQ ID NO:1, or including a position corresponding to position 12666 of SEQ ID NO:2. In some embodiments, the assay comprises or consists of: i) contacting the biological sample with a primer hybridizing to a region of the HSD17B13 gene that is within 50 nucleotides of a position of the HSD17B13 gene corresponding to positions 12665 and 12666 of SEQ ID NO: 1, or within 50 nucleotides of a position of the HSD17B13 gene corresponding to position 12666 of SEQ ID NO:2; ii) extending the primer at least through the position of the HSD17B13 gene corresponding to positions 12665 and 12666 of SEQ ID NO:1, or corresponding to position 12666 of SEQ ID NO:2; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the method further comprises determining whether the human subject is homozygous for the variant HSD17B13 gene.

In some embodiments, the methods comprise or consist of, for example, obtaining a biological sample from the subject comprising an HSD17B13 gene, and performing an assay on the biological sample that determines that a position corresponding to position 12666 of SEQ ID NO:2 of the variant HSD17B13 gene is occupied by a thymine or that a thymine is inserted between positions corresponding to positions 12665 and 12666 of SEQ ID NO:1 of the wild type HSD17B13 gene. It is understood that determining that a position of the HSD17B13 gene corresponding to position 12666 of SEQ ID NO:2 is occupied by a thymine means that the identity of a sufficient number of nucleotides is determined in the positions flanking the positions corresponding to positions 12665 and 12666 of SEQ ID NO:1 that it can be determined that a thymine is inserted between the positions corresponding to positions 12665 and 12666 of SEQ ID NO:1. Such assays can comprise, for example determining the identity of positions corresponding to position 12666 of SEQ ID NO:2 of the variant HSD17B13 gene (or positions 12665 and 12666 of SEQ ID NO:1 of the wild type HSD17B13 gene) and one or more surrounding positions (e.g., at least 1, 2, 3, 4, 5, 6, 7, 8, 9, or 10 positions flanking one side or each side of position 12666 of SEQ ID NO:2 of the variant HSD17B13 gene or positions 12665 and 12666 of SEQ ID NO:1 of the wild type HSD17B13 gene).

The assay in such a method can comprise, for example, sequencing a portion of the HSD17B13 gene including a position corresponding to position 12666 or positions 12666 and 12667 of SEQ ID NO:2. Likewise, the assay can comprise sequencing a portion of the HSD17B13 gene including positions corresponding to positions 12665 and 12666 of SEQ ID NO:1. As an example, this method can comprise: i) contacting the biological sample with a primer, such as an alteration-specific primer, hybridizing to a segment of the HSD17B13 gene that is proximate to a position of the HSD17B13 gene corresponding to position 12666 or positions 12666 and 12667 of SEQ ID NO:2; ii) extending the primer at least through the position of the HSD17B13 gene corresponding to position 12666 or positions 12666 and 12667 of SEQ ID NO:2; and iii) determining the identity of the position of the HSD17B13 gene corresponding to position 12666 or positions 12666 and 12667 of SEQ ID NO:2 in an extension product of the primer. As another example, this method can comprise: i) contacting the biological sample with a primer, such as an alteration-specific primer, hybridizing to a segment of the HSD17B13 gene that is proximate to positions of the HSD17B13 gene corresponding 12665 and 12666 of SEQ ID NO: 1 ii) extending the primer at least through the positions of the HSD17B13 gene corresponding to 12665 and 12666 of SEQ ID NO:2; and iii) determining the whether a thymine is present between the positions of the HSD17B13 gene corresponding to positions 12665 and 12666 of SEQ ID NO:1 in an extension product of the primer. In some embodiments, the alteration-specific probe or alteration-specific primer comprises or consists of a nucleotide sequence which is complementary to and/or hybridizes, or specifically hybridizes, to a particular HSD17B13 gene or transcript, such as Transcript D, but which does not hybridize, or specifically hybridize, to a wild type HSD17B13 gene (SEQ ID NO: 1). As used herein. "proximate" means within about 50, within about 45, within about 40, within about 35, within about 30, within about 25, within about 20, within about 15, within about 10, or within about 5, nucleotides of the particular stated position.

Alternatively, the assay in such a method can comprise contacting the biological sample with a primer or probe that specifically hybridizes to the HSD17B13 rs72613567 variant and not the corresponding wild type HSD17B13 sequence (e.g., under stringent conditions), and determining whether hybridization has occurred.

The present disclosure provides methods of detecting the presence of an HSD17B13 Transcript in a human subject.

The present disclosure provides methods of detecting the presence of an HSD17B13 Transcript D (RNA or cDNA derived therefrom, and/or mRNA or cDNA derived therefrom; preferably RNA or cDNA derived therefrom) in a human subject, comprising or consisting of performing an assay on a biological sample obtained from the subject, wherein the assay determines the presence of an HSD17B13 Transcript D in the biological sample. In some embodiments, the assay comprises or consists of contacting the biological sample with one or more primers or probes that specifically hybridize to a nucleic acid sequence of an HSD17B13 Transcript D (RNA or cDNA derived therefrom, and/or mRNA or cDNA derived therefrom; preferably RNA or cDNA derived therefrom), or to the complement thereof, and determining whether hybridization has occurred. In some embodiments, the method further comprises specifically detecting Transcript D (RNA or cDNA derived therefrom, and/or mRNA or cDNA derived therefrom; preferably RNA or cDNA derived therefrom) by using a nucleic acid molecule comprising or consisting of from about 5 nucleotides up to about 50 nucleotides comprising or consisting of: i) a nucleotide sequence that is at least about 90%, at least about 95%, at least about 96%, at least about 97%, at least about 98%, at least about 99%, or 100% identical (or at least about 90%) to a nucleotide sequence of a SEQ ID NO:6, 15, 24, or 33, or to the complement thereof; ii) a nucleic acid molecule which specifically hybridizes to exon 2 of Transcript D (RNA or cDNA derived therefrom, and/or mRNA or cDNA derived therefrom; preferably RNA or cDNA derived therefrom); and/or iii) a nucleic acid molecule which specifically hybridizes to the region which bridges exons 3 and 4 of Transcript D (RNA or cDNA derived therefrom, and/or mRNA or cDNA derived therefrom; preferably RNA or cDNA derived therefrom). In some embodiments, the HSD17B13 Transcript D comprises or consists of a nucleotide sequence that is at least about 90%, at least about 95%, at least about 96%, at least about 97%, at least about 98%, at least about 99%, or 100% identical (or at least about 90%) to SEQ ID NO:6, 15, 24, or 33. In some embodiments, the one or more primers or probes specifically hybridize to SEQ ID NO:6, SEQ ID NO:15, SEQ ID NO:24, and/or SEQ ID NO:33. In some embodiments, the assay comprises reverse transcription polymerase chain reaction (RT-PCR). In some embodiments, the assay comprises sequencing.

The present disclosure provides methods for detecting the presence of one or a combination of HSD17B13 Transcripts C, D, E, F, F', G, or H (RNA or cDNA derived therefrom, and/or mRNA or cDNA derived therefrom; preferably RNA or cDNA derived therefrom) in a cell or in a subject such as a human subject. Such methods can comprise or consist of, for example, obtaining a biological sample from the subject comprising RNA, or cDNA derived therefrom, or comprising mRNA, or cDNA derived therefrom, and performing an assay on the sample that determines the presence of Transcript C, D, E, F, F', G, or H (RNA or cDNA derived therefrom, and/or mRNA or cDNA derived therefrom; preferably RNA or cDNA derived therefrom) in the subject. For example, such an assay can detect a region or combination of regions that is present in (e.g., is unique to) one or more of Transcripts C, D, E, F, F', G, or H (RNA or cDNA derived therefrom, and/or mRNA or cDNA derived therefrom; preferably RNA or cDNA derived therefrom) that is not present in Transcripts A and B (RNA or cDNA derived therefrom, and/or mRNA or cDNA derived therefrom; preferably RNA or cDNA derived therefrom). Such a region may be unique to a particular Transcript (e.g., unique to Transcript C (RNA or cDNA derived therefrom, and/or mRNA or cDNA derived therefrom; preferably RNA or cDNA derived therefrom)) or unique to a combination of Transcripts (e.g., unique to Transcripts D, G, and H (RNA or cDNA derived therefrom, and/or mRNA or cDNA derived therefrom; preferably RNA or cDNA derived therefrom)). Such regions can be readily identified by comparing the sequences of Transcripts A-H and are described in further detail elsewhere herein.

As one example, the assay can comprise RNA sequencing (RNA-Seq). As another example, the assay can comprise or consist of contacting the biological sample with one or more primers or probes that specifically hybridize to one or more sequences, the combination of which is unique to one or a combination of Transcripts C, D, E, F, F', G, or H (RNA or cDNA derived therefrom, and/or mRNA or cDNA derived therefrom; preferably RNA or cDNA derived therefrom) among HSD17B13 Transcripts A, B, C, D, E, F, F', G, and H (i.e., that is not present in Transcripts A and B (RNA or cDNA derived therefrom, and/or mRNA or cDNA derived therefrom; preferably RNA or cDNA derived therefrom)), and determining whether hybridization has occurred. Optionally, the assay can comprise reverse transcription polymerase chain reaction (RT-PCR). Such assays can be specific for a particular HSD17B13 Transcript or for a particular combination of HSD17B13 Transcripts. For example, Transcripts D, G, and H each include an additional guanine inserted at the 3' end of exon 6 compared to Transcripts A, B, and E (Transcript C does not include exon 6), and Transcripts D, G, and H each include exon 7, whereas Transcript F reads through from exon 6 to intron 6. Thus, a primer or probe hybridizing to the region spanning the boundary of exon 6 and exon 7 in Transcript D (RNA or cDNA derived therefrom, and/or mRNA or cDNA derived therefrom; preferably RNA or cDNA derived therefrom) can specifically detect the combination of Transcripts D, G, and H (RNA or cDNA derived therefrom, and/or mRNA or cDNA derived therefrom; preferably RNA or cDNA derived therefrom). It is understood that such a primer or probe would be designed to hybridize to a sufficient number of nucleotides in each of exons 6 and 7 to distinguish the inserted guanine from other features in the HSD17B13 Transcripts (e.g., from the read-through into intron 6 in Transcript F (RNA or cDNA derived therefrom, and/or mRNA or cDNA derived therefrom; preferably RNA or cDNA derived therefrom) or from the deleted exon 6 in Transcript C (RNA or cDNA derived therefrom, and/or mRNA or cDNA derived therefrom; preferably RNA or cDNA derived therefrom)). Likewise, Transcripts E and H each include exon 3' compared to all of the other transcripts. Thus, a primer or probe specifically hybridizing to a region within exon 3' or its boundary with exon 3 or exon 4 can specifically detect the combination of Transcripts E and H (RNA or cDNA derived therefrom, and/or mRNA or cDNA derived therefrom; preferably RNA or cDNA derived therefrom). It is understood that such a primer or probe would be designed to hybridize to a sufficient number of nucleotides in each of exons 3 and 3' or each of exons 3' and 4 to distinguish from other features in the HSD17B13 transcripts (e.g., from the boundary of exons 3 and 4). Likewise, Transcripts B and G are each missing exon 2. Thus, a primer or probe specifically hybridizing to a region spanning the boundary of exons 1 and 3 can specifically detect the combination of Transcripts B and G (RNA or cDNA derived therefrom, and/or mRNA or cDNA derived therefrom; preferably RNA or cDNA derived therefrom). It is understood that a primer or probe would be designed to hybridize to a sufficient number of nucleotides in each of exons 1 and 3 to distinguish from other features in the HSD17B13 Transcripts (e.g., the boundary of exons 1 and 2 or the boundary of exons 2 and 3).

In one specific example, the one or more primers or probes specifically hybridize to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H (RNA or cDNA derived therefrom, and/or mRNA or cDNA derived therefrom; preferably RNA or cDNA derived therefrom) (i.e., including the additional guanine at the 3' end of exon 6 that is not present in exon 6 in other HSD17B13 Transcripts). Optionally, the one or more primers or probes further specifically hybridize to a region within exon 3' of Transcript H (RNA or cDNA derived therefrom, and/or mRNA or cDNA derived therefrom; preferably RNA or cDNA derived therefrom), a region spanning the exon 3-exon 3' boundary of Transcript H (RNA or cDNA derived therefrom, and/or mRNA or cDNA derived therefrom; preferably RNA or cDNA derived therefrom), or a region spanning the exon 3'-exon 4 boundary of Transcript H (RNA or cDNA derived therefrom, and/or mRNA or cDNA derived therefrom; preferably RNA or cDNA derived therefrom) or further specifically hybridize to a region spanning the exon 1-exon 3 boundary in Transcript G (RNA or cDNA derived therefrom, and/or mRNA or cDNA derived therefrom; preferably RNA or cDNA derived therefrom). Optionally, the one or more primers or probes further specifically hybridize to a region within exon 1 of any of Transcripts A-H (RNA or cDNA derived therefrom, and/or mRNA or cDNA derived therefrom; preferably RNA or cDNA derived therefrom) (common to Transcripts A-H). For example, a primer specifically hybridizing to a region within exon 1 of any of Transcripts A-H (RNA or cDNA derived therefrom, and/or mRNA or cDNA derived therefrom; preferably RNA or cDNA derived therefrom) and a primer specifically hybridizing to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H (RNA or cDNA derived therefrom, and/or mRNA or cDNA derived therefrom; preferably RNA or cDNA derived therefrom) can be used to amplify the intervening sequence and distinguish between Transcripts D, G, and H based on the size of the amplified product, as Transcript G is missing exon 2 compared to Transcript D, and Transcript H includes an additional exon between exons 3 and 4 compared to Transcript D.

In another specific example, the one or more primers or probes specifically hybridize to a region within exon 3' of Transcript E (RNA or cDNA derived therefrom, and/or mRNA or cDNA derived therefrom; preferably RNA or cDNA derived therefrom) or Transcript H (RNA or cDNA derived therefrom, and/or mRNA or cDNA derived therefrom; preferably RNA or cDNA derived therefrom), a region spanning the exon 3-exon 3' boundary of Transcript E (RNA or cDNA derived therefrom, and/or mRNA or cDNA derived therefrom; preferably RNA or cDNA derived therefrom) or Transcript H (RNA or cDNA derived therefrom, and/or mRNA or cDNA derived therefrom; preferably RNA or cDNA derived therefrom), or a region spanning the exon 3'-exon 4 boundary of Transcript E (RNA or cDNA derived therefrom, and/or mRNA or cDNA derived therefrom; preferably RNA or cDNA derived therefrom) or Transcript H (RNA or cDNA derived therefrom and/or mRNA or cDNA derived therefrom; preferably RNA or cDNA derived therefrom). Optionally, the one or more primers or probes can further specifically hybridize to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H(RNA or cDNA derived therefrom, and/or mRNA or cDNA derived therefrom; preferably RNA or cDNA derived therefrom). Alternatively, the one or more primers or probes can further specifically hybridize to a region spanning the boundary of exons 6 and 7 in Transcript E (RNA or cDNA derived therefrom, and/or mRNA or cDNA derived therefrom; preferably RNA or cDNA derived therefrom). For example, a primer specifically hybridizing to a region within exon 3' of Transcript E (RNA or cDNA derived therefrom, and/or mRNA or cDNA derived therefrom; preferably RNA or cDNA derived therefrom) or Transcript H (RNA or cDNA derived therefrom, and/or mRNA or cDNA derived therefrom; preferably RNA or cDNA derived therefrom), a region spanning the exon 3-exon 3' boundary of Transcript E (RNA or cDNA derived therefrom, and/or mRNA or cDNA derived therefrom; preferably RNA or cDNA derived therefrom) or Transcript H (RNA or cDNA derived therefrom, and/or mRNA or cDNA derived therefrom; preferably RNA or cDNA derived therefrom), or a region spanning the exon 3'-exon 4 boundary of Transcript E (RNA or cDNA derived therefrom, and/or mRNA or cDNA derived therefrom; preferably RNA or cDNA derived therefrom) or Transcript H (RNA or cDNA derived therefrom, and/or mRNA or cDNA derived therefrom; preferably RNA or cDNA derived therefrom) and a primer specifically hybridizing to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H (RNA or cDNA derived therefrom, and/or mRNA or cDNA derived therefrom; preferably RNA or cDNA derived therefrom) can be used to amplify the intervening sequence and distinguish between Transcripts E and H, because only Transcript H and not Transcript E includes the additional guanine at the 3' end of exon 6.

In another specific example, the one or more primers or probes specifically hybridize to a region within the read-through into intron 6 in Transcript F (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F (RNA or cDNA derived therefrom, and/or mRNA or cDNA derived therefrom; preferably RNA or cDNA derived therefrom). It is understood that such a primer or probe would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F (RNA or cDNA derived therefrom, and/or mRNA or cDNA derived therefrom; preferably RNA or cDNA derived therefrom) (i.e., the inserted thymine) that is not present in Transcript F' (RNA or cDNA derived therefrom, and/or mRNA or cDNA derived therefrom; preferably RNA or cDNA derived therefrom). Transcript F' also includes a read-through from exon 6 into intron 6 compared to Transcript A, but the read-through does not include the inserted thymine present in the HSD17B13 rs72613567 variant gene.

In another specific example, the one or more primers or probes specifically hybridize to a region within the read-through into intron 6 in Transcript F' (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F' (RNA or cDNA derived therefrom, and/or mRNA or cDNA derived therefrom; preferably RNA or cDNA derived therefrom). It is understood that such a primer or probe would be designed to hybridize to a sufficient number of nucleotides in the read-through to distinguish the read-through from other features in the HSD17B13 Transcripts (e.g., from boundary of exons 6 and 7 in other HSD17B13 Transcripts). Optionally, the contiguous nucleotides comprise a sequence present in Transcript F' (RNA or cDNA derived therefrom, and/or mRNA or cDNA derived therefrom; preferably RNA or cDNA derived therefrom) that is not present in Transcript F (RNA or cDNA derived therefrom, and/or mRNA or cDNA derived therefrom; preferably RNA or cDNA derived therefrom). The read-through in Transcript F includes the inserted thymine present in the HSD17B13 rs72613567 variant gene, whereas the read-through in Transcript F' does not.

In yet another specific example, the one or more primers or probes specifically hybridize to a region spanning the exon 5-exon 7 boundary in Transcript C (RNA or cDNA derived therefrom, and/or mRNA or cDNA derived therefrom; preferably RNA or cDNA derived therefrom). It is understood that such a primer or probe would be designed to hybridize to a sufficient number of nucleotides in exons 5 and 7 to distinguish from other features in the HSD17B13 Transcripts (e.g., from boundary of exons 5 and 6 or of exons 6 and 7 in other HSD17B13 Transcripts).

Certain methods utilize probes and primers (described in more detail elsewhere herein) of sufficient nucleotide length to bind to the target DNA sequence and specifically detect and/or identify a polynucleotide comprising the HSD17B13 rs72613567 variant or specific HSD17B13 RNA or mRNA transcripts, or cDNA derived therefrom. The hybridization conditions or reaction conditions can be determined by the operator to achieve this result. This length may be any length that is sufficient to be useful in a detection method of choice. Such probes and primers can hybridize specifically to a target sequence under high stringency hybridization conditions. Probes and primers may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, about 85%, about 90%, about 91%, about 92%, about 93%, about 94%, about 95%, about 96%, about 97%, about 98%, about 99%, or 100% sequence identity or complementarity to the target polynucleotide. In some embodiments, the probes and primers can share about 90%, about 91%, about 92%, about 93%, about 94%, about 95%, about 96%, about 97%, about 98%, about 99%, or 100% sequence identity or complementarity to the target polynucleotide. In some embodiments, the probes and primers can share about 95%, about 96%, about 97%, about 98%, about 99%, or 100% sequence identity or complementarity to the target polynucleotide.

Specific primers can be used to amplify the HSD17B13 rs72613567 variant gene and/or specific HSD17B13 RNA or mRNA transcripts to produce an amplicon that can be used as a "specific probe" or can itself be detected for identifying the HSD17B13 rs72613567 variant gene or for determining the level of specific HSD17B13 RNA or mRNA transcripts in a biological sample. The HSD17B13 variant gene can be used to denote a genomic nucleic acid sequence including a position corresponding to residue 12666 in SEQ ID NO:2 (insertion of a thymine relative to the wild type genomic locus set forth in SEQ ID NO:1 (i.e., inserted between positions 12665 and 12666 in SEQ ID NO:1)). When the probe is hybridized with the polynucleotides of a biological sample under conditions that allow for the binding of the probe to the sample, this binding can be detected and thus allow for an indication of the presence of the HSD17B13 rs72613567 variant gene or the presence or the level of specific HSD17B13 RNA or mRNA transcripts in the biological sample. Such identification of a bound probe has been described. The specific probe may comprise a sequence of at least about 80%, from about 80% to about 85%, from about 85% to about 90%, from about 90% to about 95%, and from about 95% to about 100% identical (from about 90% to about 95% or from about 95% to about 100% identical) (or complementary) to a specific region of the HSD17B13 gene, an HSD17B13 RNA or mRNA transcript, or an HSD17B13 cDNA derived therefrom.

To determine whether a nucleic acid molecule within a biological sample comprises the inserted thymine at residue 12666 in the HSD17B3 rs72613567 variant gene (e.g., SEQ ID NO:2) (i.e., an inserted thymine between residues 12665 and 12666 in the wild type HSD17B13 locus (SEQ ID NO:1)), the biological sample may be subjected to a polynucleotide amplification method using a primer pair that includes a first primer derived from the 5' flanking sequence adjacent to the inserted thymine and a second primer derived from the 3' flanking sequence adjacent to the inserted thymine to produce an amplicon that is diagnostic for the presence of the inserted thymine at residue 12666 in the HSD17B13 rs72613567 variant gene (SEQ ID NO:2) (i.e., an inserted thymine between residues 12665 and 12666 in the wild type HSD17B13 gene (SEQ ID NO:1)). In some cases, the amplicon may range in length from the combined length of the primer pairs plus one nucleotide base pair to any length of amplicon producible by a DNA amplification protocol. This distance can range from one nucleotide base pair up to the limits of the amplification reaction, or about twenty thousand nucleotide base pairs. Optionally, the primer pair flanks a region including the inserted thymine and at least 1, 2, 3, 4, 5, 6, 7, 8, 9, 10, or more nucleotides on each side of the thymine.

PCR primer pairs can be derived from a known sequence, for example, by using computer programs intended for that purpose such as the PCR primer analysis tool in Vector NTI version 10 (Informax Inc., Bethesda Md.); PrimerSelect (DNASTAR Inc., Madison, Wis.), and Primer3 (Version 0.4.0.COPYRGT., 1991, Whitehead Institute for Biomedical Research, Cambridge, Mass.). Additionally, the sequence can be visually scanned and primers manually identified using known guidelines.

As outlined in further detail below, any conventional nucleic acid hybridization or amplification or sequencing method can be used to specifically detect the presence of the HSD17B13 rs72613567 variant locus and/or the level of specific HSD17B13 RNA or mRNA transcripts. By "specifically detect" is intended that the polynucleotide can be used either as a primer to amplify a region of the HSD17B13 polynucleotide or the polynucleotide can be used as a probe that hybridizes under stringent conditions to a polynucleotide comprising the HSD17B13 rs72613567 variant gene or a polynucleotide comprising a specific HSD17B13 transcript, particularly Transcript C, D, E, F, G, or H (RNA or cDNA derived therefrom, and/or mRNA or cDNA derived therefrom, preferably RNA or cDNA derived therefrom).

A variety of techniques are available in the art including, for example, nucleic acid sequencing, nucleic acid hybridization, and nucleic acid amplification. Illustrative examples of nucleic acid sequencing techniques include, but are not limited to, chain terminator (Sanger) sequencing and dye terminator sequencing.

Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid may be amplified prior to or simultaneous with detection. Illustrative examples of nucleic acid amplification techniques include, but are not limited to, polymerase chain reaction (PCR), ligase chain reaction (LCR), strand displacement amplification (SDA), and nucleotide sequence based amplification (NASBA). Other methods include, but are not limited to, ligase chain reaction, strand displacement amplification, and thermophilic SDA (tSDA).

Any method can be used for detecting either the non-amplified or amplified polynucleotides including, for example. Hybridization Protection Assay (HPA), quantitative evaluation of the amplification process in real-time, and determining the quantity of target sequence initially present in a sample, but which is not based on a real-time amplification.

Also provided are methods for identifying nucleic acid molecules which do not necessarily require sequence amplification and are based on, for example, the known methods of Southern (DNA:DNA) blot hybridizations, in situ hybridization (ISH), and fluorescence in situ hybridization (FISH) of chromosomal material. Southern blotting can be used to detect specific nucleotide sequences. In such methods, nucleic acid that is extracted from a sample is fragmented, electrophoretically separated on a matrix gel, and transferred to a membrane filter.

Examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology. Conventional assays for screening for targeted modifications, such as long-range PCR, Southern blotting, or Sanger sequencing, can also be used. Next generation sequencing (NGS) can also be used for screening. Next-generation sequencing can also be referred to as "NGS" or "massively parallel sequencing" or "high throughput sequencing."

In hybridization techniques, stringent conditions can be employed such that a probe or primer will specifically hybridize to its target. In some embodiments, a polynucleotide primer or probe under stringent conditions will hybridize to its target sequence (e.g., the variant HSD17B13 gene, variant HSD17B13 RNA or cDNA corresponding thereto, or variant HSD17B13 mRNA or cDNA corresponding thereto) to a detectably greater degree than to other sequences (e.g., the corresponding wild type HSD17B13 gene, wild type HSD17B13 RNA or cDNA corresponding thereto, or wild type HSD17B13 mRNA or cDNA corresponding thereto), such as, at least 2-fold, at least 3-fold, at least 4-fold, or more over background, including over 10-fold over background. In some embodiments, a polynucleotide primer or probe under stringent conditions will hybridize to its target sequence to a detectably greater degree than to other sequences by at least 2-fold. In some embodiments, a polynucleotide primer or probe under stringent conditions will hybridize to its target sequence to a detectably greater degree than to other sequences by at least 3-fold. In some embodiments, a polynucleotide primer or probe under stringent conditions will hybridize to its target sequence to a detectably greater degree than to other sequences by at least 4-fold. In some embodiments, a polynucleotide primer or probe under stringent conditions will hybridize to its target sequence to a detectably greater degree than to other sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for longer probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in IX to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure provides methods of detecting the presence of HSD17B13 Isoform D in a human subject, comprising or consisting of performing an assay on a biological sample obtained from the human subject, wherein the assay determines the presence of HSD17B13 Isoform D in the biological sample. In some embodiments, the HSD17B13 Isoform D comprises or consists of an amino acid sequence that is at least about 90%, at least about 95%, at least about 96%, at least about 97%, at least about 98%, at least about 99%, or 100% identical to SEQ ID NO:42. In some embodiments, the assay comprises sequencing.

The present disclosure provides methods for detecting the presence or quantifying the levels of variant HSD17B13 polypeptide in a biological sample, including, for example, protein sequencing and immunoassays. In some embodiments, the method of detecting the presence of variant HSD17B13 polypeptide in a human subject comprises performing an assay on a biological sample from the human subject that detects the presence of the variant HSD17B13 polypeptide in the biological sample.

Illustrative non-limiting examples of protein sequencing techniques include, but are not limited to, mass spectrometry and Edman degradation. Illustrative examples of immunoassays include, but are not limited to, immunoprecipitation, Western blot, immunohistochemistry, ELISA, immunocytochemistry, flow cytometry, and immuno-PCR. Polyclonal or monoclonal antibodies detectably labeled using various known techniques (e.g., calorimetric, fluorescent, chemiluminescent, or radioactive) are suitable for use in the immunoassays. Regarding immunoassays, the variant HSD17B13 isoforms have different sizes as compared to the HSD17B13 isoforms which correspond to the wild type condition and, therefore, run at a different molecular weights on a protein gel. Thus, by using the same antibody, the HSD17B13 HSD17B13 isoforms which correspond to the wild type condition can be distinguished from the variant HSD17B13 isoforms in, for example, a Western Blot assay.

In some embodiments, the HSD17B13 isoform detected is not displaced from the cell membrane. In some embodiments, the HSD17B13 isoform is a membrane-bound protein. Such association may aid in the processing of particular biological samples (i.e., obtaining membrane preparation samples).

The present disclosure also provides kits for making the compositions and utilizing the methods described herein. The kits described herein can comprise an assay or assays for detecting one or more genetic variants in a sample of a subject.

In some embodiments, the kits for human identification of HSD17B13 variants utilize the compositions and methods described above. In some embodiments, a basic kit can comprise a container having at least one pair of oligonucleotide primers or probes, such as alteration-specific probes or alteration-specific primers, for hybridization to any of the nucleic acid molecules disclosed herein. A kit can also optionally comprise instructions for use. A kit can also comprise other optional kit components, such as, for example, one or more of an allelic ladder directed to each of the loci amplified, a sufficient quantity of enzyme for amplification, amplification buffer to facilitate the amplification, divalent cation solution to facilitate enzyme activity, dNTPs for strand extension during amplification, loading solution for preparation of the amplified material for electrophoresis, genomic DNA as a template control, a size marker to insure that materials migrate as anticipated in the separation medium, and a protocol and manual to educate the user and limit error in use.

In some embodiments, any of the kits disclosed herein may further comprise any one or more of: a nucleotide ladder, protocol, an enzyme (such as an enzyme used for amplification, such as polymerase chain reaction (PCR)), dNTPs, a buffer, a salt or salts, and a control nucleic acid sample. In some embodiments, any of the kits disclosed herein may further comprise any one or more of: a detectable label, products and reagents required to carry out an annealing reaction, and instructions. In some embodiments, a kit can comprise one or more of the primers or probes disclosed herein. For example, a kit can comprise one or more probes that hybridize to one or more of the disclosed genetic variants. In some embodiments, a kit can comprise one of the disclosed cells or cell lines. A kit can further comprise media for cell culture.

The present disclosure provides methods for determining a subject's susceptibility or risk of developing a liver disease (e.g., a chronic liver disease) or of diagnosing a subject with liver disease (e.g., a fatty liver disease, NAFLD, or simple steatosis) or at risk of developing liver disease. The subject can be any organism, including, for example, a human, a non-human mammal, a rodent, a mouse, or a rat Such methods can comprise or consist of, for example, detecting the presence of the HSD17B13 rs72613567 variant gene in a biological sample comprising genomic DNA, detecting the presence or levels of any one of HSD17B3 Transcripts C, D, F, G, and H (RNA or cDNA derived therefrom, and/or mRNA or cDNA derived therefrom; preferably RNA or cDNA derived therefrom), and particularly D (RNA or cDNA derived therefrom, and/or mRNA or cDNA derived therefrom, preferably RNA or cDNA derived therefrom), in a biological sample comprising RNA, or cDNA derived therefrom, or comprising mRNA, or cDNA derived therefrom, or detecting the presence or levels of any one of HSD17B13 Isoforms C, D, F, G, or H, and particularly D, in a biological sample comprising protein. It is understood that gene sequences within a population and RNAs, mRNAs, and proteins encoded by such genes can vary due to polymorphisms such as single-nucleotide polymorphisms. The sequences provided herein for the HSD17B3 gene and for each HSD17B13 Transcript and HSD17B13 Isoform are only exemplary sequences for the HSD17B13 gene and for each HSD17B13 Transcript and HSD17B13 isoform. Other sequences for the HSD17B13 gene and for each HSD17B13 Transcript and HSD17B13 Isoform are also possible.

In any of the methods or uses described herein, the liver disease can be a chronic liver disease, fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, or non-alcoholic steatohepatitis (NASH). In some embodiments, the liver disease is fatty liver disease, NAFLD, or simple steatosis. In some embodiments, the liver disease is a chronic liver disease. In some embodiments, the liver disease is fatty liver disease. In some embodiments, the liver disease is NAFLD. In some embodiments, the liver disease is alcoholic liver fatty liver disease. In some embodiments, the liver disease is fibrosis. In some embodiments, the liver disease is cirrhosis. In some embodiments, the liver disease is viral hepatitis. In some embodiments, the liver disease is NASH. In some embodiments, the liver disease is hepatocellular carcinoma. In some embodiments, the liver disease is simple steatosis. In some embodiments, the liver disease is steatohepatitis. In some embodiments, the liver disease is fibrosis, NASH, or cirrhosis.

Liver diseases, such as chronic liver diseases, include diseases of the liver which last over a period of six months and can include, for example, diseases of the liver involving progressive destruction and regeneration of the liver parenchyma that can lead to fibrosis and cirrhosis. Liver pathologies encompassed by chronic liver diseases can include, for example, inflammation (e.g., chronic hepatitis), liver cirrhosis, and hepatocellular carcinoma. Types of chronic liver disease are disclosed elsewhere herein and include, for example, fatty liver disease, viral hepatitis, nonalcoholic fatty liver disease, alcoholic fatty liver disease, cirrhosis, and hepatocellular carcinoma. Symptoms and signs of chronic liver diseases are known and can include, for example, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice). Testing for chronic liver diseases can involve blood tests, imaging of the liver, and biopsy of the liver. An individual is at increased risk of a chronic liver disease if the subject has at least one known risk-factor (e.g., genetic factor such as a disease-causing mutation) placing individuals with that risk factor at a statistically significant greater risk of developing the disease than individuals without the risk factor. Risk factors for chronic liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

The present disclosure provides methods of determining a human subject's susceptibility or risk of developing a liver disease, comprising or consisting of: a) performing an assay on a biological sample obtained from the human subject, wherein the assay determines whether a thymine is inserted between positions corresponding to positions 12665 and 12666 of SEQ ID NO:1 of the wild type HSD17B13 gene, or whether a thymine is present at a position corresponding to position 12666 of SEQ ID NO:2 of the variant HSD17B3 gene; and b) classifying the human subject as being at decreased risk for developing the liver disease if a thymine is inserted between the positions corresponding to positions 12665 and 12666 of SEQ ID NO:1 of the wild type HSD17B13 gene or if a thymine is present at a position corresponding to position 12666 of SEQ ID NO:2 of the variant HSD17B13 gene, or classifying the human subject as being at increased risk for developing the liver disease if a thymine is not inserted between the positions of the HSD17B13 gene corresponding to positions 12665 and 12666 of SEQ ID NO:1 or if a thymine is not present at a position of the HSD17B13 gene corresponding to position 12666 of SEQ ID NO:2. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the assay comprises or consists of: i) contacting the biological sample with a primer hybridizing to a region of the HSD17B13 gene that is within 50 nucleotides of positions of the HSD17B13 gene corresponding to positions 12665 and 12666 of SEQ ID NO:1, or corresponding to position 12666 of SEQ ID NO:2; ii) extending the primer at least through the positions of the HSD17B13 gene corresponding to positions 12665 and 12666 of SEQ ID NO:1, or corresponding to position 12666 of SEQ ID NO:2; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the assay comprises or consists of contacting the biological sample with a primer or probe that specifically hybridizes to the variant HSD17B13 gene having a thymine at a position corresponding to position 12666 of SEQ ID NO:2, and does not hybridize to the corresponding wild type HSD17B13 gene under stringent conditions, and determining whether hybridization has occurred. In some embodiments, the variant HSD17B13 gene is detected by sequencing. In some embodiments, the method further comprises determining whether the human subject is homozygous for the variant HSD17B13 gene.

In some embodiments, the methods comprise or consist of detecting the presence of the HSD17B13 rs72613567 variant gene in a biological sample comprising genomic DNA. Such methods can comprise or consist of: a) performing an assay on a biological sample comprising an HSD17B13 gene obtained from the subject, wherein the assay determines the identity of the nucleotide occupying a position of the HSD17B13 gene corresponding to position 12666 or positions 12666 and 12667 of SEQ ID NO:2; and b) classifying the subject as being at decreased risk for developing the liver disease if the position corresponding to position 12666 of SEQ ID NO:2 is occupied by a thymine or positions 12666 and 12667 of SEQ ID NO:2 are occupied by thymines. Alternatively, the subject can be classified as being at increased risk for developing the liver disease if the position is not occupied by a thymine. Likewise, such methods can comprise performing an assay on the biological sample that determines the identity of the nucleotides occupying positions of the HSD17B13 gene corresponding to positions 12665 and 12666 of SEQ ID NO: 1. The subject can be classified as being at decreased risk for developing the liver disease if a thymine is inserted between the positions corresponding to positions 12665 and 12666 of SEQ ID NO:1 of the wild type HSD17B13 gene. Alternatively, the subject can be classified as being at increased risk for developing the chronic liver disease if there is no thymine inserted between the positions corresponding to positions 12665 and 12666 of SEQ ID NO:1 of the wild type HSD17B13 gene.

Any assay for determining the identity of the nucleotide occupying a position of the HSD17B13 gene corresponding to position 12666 or positions 12666 and 12667 of SEQ ID NO:2 (or corresponding to positions 12665 and 12666 of SEQ ID NO:1) can be used. As one example, the assay can comprise or consist of sequencing a portion of the HSD17B13 gene including a position corresponding to position 12666 or positions 12666 and 12667 of SEQ ID NO:2. Sequencing can comprise or consist of: i) contacting the biological sample with a primer hybridizing to a segment of the HSD17B13 gene that is proximate to a position of the HSD17B13 gene corresponding to position 12666 or positions 12666 and 12667 of SEQ ID NO:2; ii) extending the primer at least through the position of the HSD17B13 gene corresponding to position 12666 or positions 12666 and 12667 of SEQ ID NO:2; and iii) determining the identity of the position of the HSD17B13 gene corresponding to position 12666 or positions 12666 and 12667 of SEQ ID NO:2 in an extension product of the primer. As used herein, "proximate" means within about 50, within about 45, within about 40, within about 35, within about 30, within about 25, within about 20, within about 15, within about 10, or within about 5, nucleotides of the particular stated position.

As another example, the assay can comprise or consist of contacting the biological sample with a primer or probe, such as an alteration-specific primer or an alteration-specific probe, that specifically hybridizes to the variant HSD17B13 rs72613567 gene and not the corresponding wild type HSD17B13 gene under stringent conditions, and determining whether hybridization has occurred.

The present disclosure provides methods of determining a human subject's susceptibility or risk for developing a liver disease, comprising or consisting of: a) performing an assay on a biological sample obtained from the human subject, wherein the assay determines the presence of an HSD17B13 Transcript D (RNA or cDNA derived therefrom, and/or mRNA or cDNA derived therefrom; preferably RNA or cDNA derived therefrom) in the biological sample; and b) classifying the human subject as being at decreased risk for developing the liver disease if an HSD17B13 Transcript D is present in the biological sample, or classifying the human subject as being at increased risk for developing the liver disease if an HSD17B13 Transcript D is not present in the biological sample. In some embodiments, the HSD17B13 Transcript D comprises or consists of a nucleotide sequence that is at least about 90%, at least about 95%, at least about 96%, at least about 97%, at least about 98%, at least about 99%, or 100% identical (at least about 90% identical) to SEQ ID NO:6, 15, 24, or 33. In some embodiments, the HSD17B13 Transcript D is RNA and comprises or consists of SEQ ID NO:6, or a cDNA thereof comprising or consisting of SEQ ID NO:24, or wherein the HSD17B13 Transcript D is mRNA and comprises or consists of SEQ ID NO: 15, or a cDNA thereof comprising or consisting of SEQ ID NO:33. In some embodiments, the assay determines the expression level of HSD17B13 Transcript D (RNA or cDNA derived therefrom, and/or mRNA or cDNA derived therefrom; preferably RNA or cDNA derived therefrom) in the biological sample, wherein an increased expression level of HSD17B13 Transcript D compared to a control sample from a control human subject homozygous for a wild type HSD17B13 allele indicates a decreased risk for developing the liver disease, and wherein the same or a decreased expression level of HSD17B13 Transcript D compared to the control sample indicates an increased risk for developing the liver disease. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the assay comprises or consists of contacting the biological sample with one or more primers or probes that specifically hybridize to a nucleic acid sequence of HSD17B13 Transcript D (RNA or cDNA derived therefrom, and/or mRNA or cDNA derived therefrom; preferably RNA or cDNA derived therefrom), or to the complement thereof, and determining whether hybridization has occurred. In some embodiments, the method further comprises specifically detecting Transcript D (RNA or cDNA derived therefrom, and/or mRNA or cDNA derived therefrom; preferably RNA or cDNA derived therefrom) by using a nucleic acid molecule comprising or consisting of from about 5 nucleotides up to about 50 nucleotides comprising or consisting of: i) a nucleotide sequence that is at least about 90%, at least about 95%, at least about 96%, at least about 97%, at least about 98%, at least about 99%, or 100% identical (or at least about 90% identical) to a nucleotide sequence of a SEQ ID NO:6, 15, 24, or 33, or to the complement thereof; ii) a nucleic acid molecule which specifically hybridizes to exon 2 of Transcript D (RNA or cDNA derived therefrom, and/or mRNA or cDNA derived therefrom; preferably RNA or cDNA derived therefrom); and/or iii) a nucleic acid molecule which specifically hybridizes to the region which bridges exons 3 and 4 of Transcript D (RNA or cDNA derived therefrom, and/or mRNA or cDNA derived therefrom; preferably RNA or cDNA derived therefrom). In some embodiments, the HSD17B13 Transcript D comprises or consists of a nucleotide sequence that is at least about 90%, at least about 95%, at least about 96%, at least about 97%, at least about 98%, at least about 99%, or 100% identical (or at least about 90% identical) to SEQ ID NO:6, 15, 24, or 33. In some embodiments, the one or more primers or probes specifically hybridize to SEQ ID NO:6, SEQ ID NO: 15, SEQ ID NO:24, and/or SEQ ID NO:33. In some embodiments, the assay comprises reverse transcription polymerase chain reaction (RT-PCR) or quantitative RT-PCR (qRT-PCR). In some embodiments, the assay comprises sequencing.

In some embodiments, the methods comprise or consist of: a) performing an assay on a biological sample comprising RNA, or cDNA derived therefrom, or comprising mRNA, or cDNA derived therefrom, obtained from the subject, wherein the assay determines the presence of Transcript C, D, F, G, or H (RNA or cDNA derived therefrom, and/or mRNA or cDNA derived therefrom; preferably RNA or cDNA derived therefrom) in the biological sample; and b) classifying the subject as being at decreased risk for developing the liver disease if Transcript C, D, F, G, or H is present in the biological sample. Such an assay can, for example, detect a region or combination of regions that is present in (e.g., is unique to) one or more of Transcripts C, D, F, G, and H (RNA or cDNA derived therefrom, and/or mRNA or cDNA derived therefrom; preferably RNA or cDNA derived therefrom) that is not present in Transcripts A and B (RNA or cDNA derived therefrom, and/or mRNA or cDNA derived therefrom; preferably RNA or cDNA derived therefrom) or that is not present in Transcripts A, B, and E (RNA or cDNA derived therefrom, and/or mRNA or cDNA derived therefrom; preferably RNA or cDNA derived therefrom) or that is not present in Transcripts A, B, E, and F' (RNA or cDNA derived therefrom, and/or mRNA or cDNA derived therefrom; preferably RNA or cDNA derived therefrom). Such regions can be readily identified by comparing the sequences of Transcripts A-H and are described in more detail elsewhere herein. Alternatively, the subject can be classified as being at increased risk for developing the liver disease if Transcript C, D, F, G, or H is not present in the biological sample. In a specific example, the assay can determine the expression level of Transcript C, D, F, G, or H (RNA or cDNA derived therefrom, and/or mRNA or cDNA derived therefrom; preferably RNA or cDNA derived therefrom), and particularly Transcript D (RNA or cDNA derived therefrom, and/or mRNA or cDNA derived therefrom; preferably RNA or cDNA derived therefrom), in the biological sample, wherein an increased expression level of Transcript C, D, F, G, or H, and particularly Transcript D, in the biological sample compared to a control sample from a control subject homozygous for a wild type HSD17B13 allele indicates a decreased risk for developing the liver disease. Alternatively, a decreased expression level or no change in expression level of Transcript C, D, F, G, or H, and particularly Transcript D, in the biological sample compared to a control sample from a control subject homozygous for a wild type HSD17B13 allele indicates an increased risk for developing the liver disease. In another specific example, the assay can comprise determining the expression level of Transcript C, D, F, G, or H (RNA or cDNA derived therefrom, and/or mRNA or cDNA derived therefrom; preferably RNA or cDNA derived therefrom), and particularly Transcript D (RNA or cDNA derived therefrom, and/or mRNA or cDNA derived therefrom; preferably RNA or cDNA derived therefrom), relative to Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom), and particularly Transcript A (RNA or cDNA derived therefrom, and/or mRNA or cDNA derived therefrom; preferably RNA or cDNA derived therefrom), in the biological sample, wherein an increased ratio of Transcript C, D, F, G, or H, and particularly Transcript D, expression relative to Transcript A, B, or E or Transcript A, B, E, or F', and particularly Transcript A, expression compared to the ratio in a control sample from a control subject homozygous for a wild type HSD17B13 allele indicates a decreased risk for developing the liver disease. Alternatively, a decreased ratio or no change in the ratio of Transcript C, D, F, G, or H, and particularly Transcript D, expression relative to Transcript A, B, or E or Transcript A, B, E, and F', and particularly Transcript A, expression compared to the ratio in a control sample from a control subject homozygous for a wild type HSD17B13 allele indicates an increased risk for developing the liver disease.

In some methods for detecting the presence or levels of any one of Transcripts C, D, F, G, or H (RNA or cDNA derived therefrom, and/or mRNA or cDNA derived therefrom; preferably RNA or cDNA derived therefrom), and particularly D (RNA or cDNA derived therefrom, and/or mRNA or cDNA derived therefrom; preferably RNA or cDNA derived therefrom), the assay can comprise or consist of contacting the biological sample with one or more primers or probes (e.g., alteration-specific primers or alteration-specific probes) that specifically hybridize to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H (RNA or cDNA derived therefrom, and/or mRNA or cDNA derived therefrom; preferably RNA or cDNA derived therefrom) (i.e., including the additional guanine at the 3' end of exon 6 that is not present in exon 6 in other HSD17B13 Transcripts), and determining whether hybridization has occurred. In addition or alternatively, the assay can comprise contacting the biological sample with one or more primers or probes that specifically hybridize to a region within the read-through into intron 6 in Transcript F (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F (RNA or cDNA derived therefrom, and/or mRNA or cDNA derived therefrom; preferably RNA or cDNA derived therefrom), and determining whether hybridization has occurred. In addition or alternatively, the assay can comprise contacting the biological sample with one or more primers or probes that specifically hybridize to a region spanning the exon 5-exon 7 boundary in Transcript C (RNA or cDNA derived therefrom, and/or mRNA or cDNA derived therefrom; preferably RNA or cDNA derived therefrom), and determining whether hybridization has occurred.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of Transcript C, D, F, G, or H, and particularly Transcript D, in the biological sample.

Other methods can comprise detecting the presence or levels of any one of HSD17B13 Transcripts A, B, and E (RNA or cDNA derived therefrom, and/or mRNA or cDNA derived therefrom; preferably RNA or cDNA derived therefrom) or Transcripts A, B, E, and F' (RNA or cDNA derived therefrom, and/or mRNA or cDNA derived therefrom; preferably RNA or cDNA derived therefrom) in a biological sample. Such methods can comprise or consist of: a) performing an assay on a biological sample obtained from the subject, wherein the assay determines the presence of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) in the biological sample; and b) classifying the subject as being at increased risk for developing the liver disease if Transcript A, B, or E or Transcript A, B, E, or F' is present in the biological sample. Such an assay can, for example, detect a region or combination of regions that is present in (e.g., is unique to) one or more of Transcripts A, B, or E (RNA or cDNA derived therefrom, and/or mRNA or cDNA derived therefrom; preferably RNA or cDNA derived therefrom) or Transcripts A, B, E, or F (RNA or cDNA derived therefrom, and/or mRNA or cDNA derived therefrom; preferably RNA or cDNA derived therefrom) that is not present in Transcripts C, D, F, G, and H (RNA or cDNA derived therefrom, and/or mRNA or cDNA derived therefrom; preferably RNA or cDNA derived therefrom). Such regions can be readily identified by comparing the sequences of Transcripts A-H and are described in more detail elsewhere herein. Alternatively, the subject can be classified as being at decreased risk for developing the liver disease if Transcript A, B, or E or Transcript A, B, E, or F' is not present in the biological sample. In a specific example, the assay can determine the expression level of Transcript A, B, or E (RNA or cDNA derived therefrom, and/or mRNA or cDNA derived therefrom; preferably RNA or cDNA derived therefrom) or Transcript A, B, E, or F (RNA or cDNA derived therefrom, and/or mRNA or cDNA derived therefrom; preferably RNA or cDNA derived therefrom) in the biological sample, wherein an increased expression level of Transcript A, B, or E or Transcript A, B, E, or F' in the biological sample compared to a control sample from a control subject homozygous for the HSD17B13 rs72613567 variant allele indicates an increased risk for developing the liver disease. Alternatively, a decreased expression level or no change in expression level of Transcript A, B, or E or Transcript A, B, E, or F' in the biological sample compared to a control sample from a control subject homozygous for the HSD17B13 rs72613567 variant allele indicates a decreased risk for developing the liver disease. In another specific example, the assay can comprise determining the expression level of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) relative to Transcript C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), in the biological sample, wherein an increased ratio of Transcript A, B, or E or Transcript A, B, E, or F expression relative to Transcript C, D, F, G, or H, particularly Transcript D, expression compared to the ratio in a control sample from a control subject homozygous for the HSD17B13 rs72613567 variant allele indicates an increased risk for developing the liver disease. Alternatively, a decreased ratio or no change in the ratio of Transcript A, B, or E or Transcript A, B, E, or F expression relative to Transcript C, D, F, G, or H, particularly Transcript D, expression compared to the ratio in a control sample from a control subject homozygous for the HSD17B13 rs72613567 variant allele indicates a decreased risk for developing the liver disease.

In some methods for detecting the presence or levels of any one of Transcripts A, B, or E (RNA or cDNA derived therefrom, and/or mRNA or cDNA derived therefrom; preferably RNA or cDNA derived therefrom) or Transcripts A, B, E, or F' (RNA or cDNA derived therefrom, and/or mRNA or cDNA derived therefrom; preferably RNA or cDNA derived therefrom), the assay can comprise or consist of contacting the biological sample with one or more primers or probes, such as alteration-specific primers or alteration-specific probes, that specifically hybridize to a region within exon 3', spanning the boundary of exons 3 and 3', or spanning the boundary of exons 3' and 4 in Transcript E (RNA or cDNA derived therefrom, and/or mRNA or cDNA derived therefrom; preferably RNA or cDNA derived therefrom) to distinguish Transcript E from Transcripts A, B, C, D, F, and G, and further contacting the biological sample with one or more primers and probes, such as alteration-specific primers or alteration-specific probes, that specifically hybridize to a region spanning the boundary of exons 6 and 7 in Transcript E (RNA or cDNA derived therefrom, and/or mRNA or cDNA derived therefrom; preferably RNA or cDNA derived therefrom) to distinguish Transcript E from Transcript H, and determining whether hybridization has occurred. In addition or alternatively, the assay can comprise or consist of contacting the biological sample with one or more primers or probes, such as alteration-specific primers or alteration-specific probes, that specifically hybridize to a region spanning the boundaries of exon 1 and 3 in Transcript B (RNA or cDNA derived therefrom, and/or mRNA or cDNA derived therefrom; preferably RNA or cDNA derived therefrom) to distinguish transcript B from Transcripts A, C, D, E, F, and H, and further contacting the biological sample with one or more primers or probes, that specifically hybridize to a region spanning the boundary of exons 6 and 7 in Transcript B (RNA or cDNA derived therefrom, and/or mRNA or cDNA derived therefrom; preferably RNA or cDNA derived therefrom) to distinguish Transcript B from Transcript G, and determining whether hybridization has occurred. In addition or alternatively, the assay can comprise or consist of contacting the biological sample with one or more primers or probes, such as alteration-specific primers or alteration-specific probes, that specifically hybridize to a region spanning the exon 6-exon 7 boundary in Transcript A (RNA or cDNA derived therefrom, and/or mRNA or cDNA derived therefrom; preferably RNA or cDNA derived therefrom) to distinguish Transcript A from Transcripts D, F, G, and H, and further contacting the biological sample with one or more primers or probes, such as alteration-specific primers or alteration-specific probes, that specifically hybridize to a region within exon 6, spanning the exon 5-exon 6 boundary, or spanning the exon 6-exon 7 boundary in Transcript A (RNA or cDNA derived therefrom, and/or mRNA or cDNA derived therefrom; preferably RNA or cDNA derived therefrom) to distinguish Transcript A from Transcript C, and determining whether hybridization has occurred. Optionally, the assay can further comprise contacting the biological sample with one or more primers or probes, such as alteration-specific primers or alteration-specific probes, that specifically hybridize to a region within exon 2, spanning exon 1-exon 2 boundary, or spanning the exon 2-exon 3 boundary in Transcript A (RNA or cDNA derived therefrom, and/or mRNA or cDNA derived therefrom; preferably RNA or cDNA derived therefrom) to distinguish Transcript A from Transcripts B and H, and further contacting the biological sample with one or more primers or probes, such as alteration-specific primers or alteration-specific probes, that specifically hybridize to a region spanning the exon 3-exon 4 boundary in Transcript A (RNA or cDNA derived therefrom, and/or mRNA or cDNA derived therefrom; preferably RNA or cDNA derived therefrom) to distinguish Transcript A from Transcripts E and H, and determining whether hybridization has occurred.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of Transcript A, B, or E or Transcript A, B, E, or F' in the biological sample.

The present disclosure provides methods of determining a human subject's susceptibility or risk for developing a liver disease, comprising or consisting of: a) detecting whether HSD17B13 Isoform D is present in a biological sample obtained from the human subject; and b) classifying the human subject as being at decreased risk for developing the liver disease if HSD17B13 Isoform D is detected in the biological sample, or classifying the human subject as being at decreased risk for developing the liver disease if HSD17B13 Isoform D is not detected in the biological sample. In some embodiments, the HSD17B13 Isoform D comprises or consists of an amino acid sequence that is at least about 90%, at least about 95%, at least about 96%, at least about 97%, at least about 98%, at least about 99%, or 100% identical (or at least about 90% identical) to SEQ ID NO:42. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the detecting comprises sequencing.

In some embodiments, the methods comprise or consist of detecting the presence or levels of any one of HSD17B13 Isoforms C, D, F, G, or H, and particularly D, in a biological sample comprising protein. Such epitopes can be readily identified by comparing the sequences of Isoforms A-H and are described in more detail elsewhere herein. Alternatively, the subject can be classified as being at increased risk for developing the liver disease if Isoform C, D, F, G, or H is not present in the biological sample.

In some embodiments, the detecting determines the expression level of Isoform C, D, F, G, or H in the biological sample, wherein an increased expression level of Isoform C, D, F, G, or H compared to a control sample from a control subject homozygous for a wild type HSD17B13 allele indicates a decreased risk for developing the liver disease. Alternatively, a decreased expression level or no change in expression level of Isoform C, D, F, G, or H compared to a control sample from a control subject homozygous for a wild type HSD17B13 allele indicates an increased risk for developing the liver disease.

In some embodiments, the detecting determines the expression level of Isoform A, B, or E or Isoform A, B, E, or F' in the biological sample, wherein an increased expression level of Isoform A, B, or E or Isoform A, B, E, or F' compared to a control sample from a control subject homozygous for the HSD17B13 rs72613567 variant allele indicates an increased risk for developing the liver disease. Alternatively, a decreased expression level or no change in expression level of Isoform A, B, or E or Isoform A, B, E, or F' compared to a control sample from a control subject homozygous for the HSD17B13 rs72613567 variant allele indicates a decreased risk for developing the liver disease.

The present disclosure provides methods of determining a human subject's risk for progression to more clinically advanced stages of fatty liver disease.

The present disclosure provides methods of determining a human subject's risk for progression to more clinically advanced stages of fatty liver disease, comprising or consisting of: a) performing an assay on a biological sample obtained from the human subject, wherein the assay determines whether a thymine is inserted between positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene; and b) classifying the human subject as being at decreased risk for progression to more clinically advanced stages of fatty liver disease if a thymine is inserted between the positions corresponding to positions 12665 and 12666 of SEQ ID NO:1 of the wild type HSD17B13 gene or if a thymine is present at a position corresponding to position 12666 of SEQ ID NO:2 of the variant HSD17B13 gene, or classifying the human subject as being at increased risk for progression to more clinically advanced stages of fatty liver disease if a thymine is not inserted between the positions of the HSD17B13 gene corresponding to positions 12665 and 12666 of SEQ ID NO: 1, or if a thymine is not present at a position of the HSD17B13 gene corresponding to position 12666 of SEQ ID NO:2. In some embodiments, the assay comprises or consists of: i) contacting the biological sample with a primer hybridizing to a region of the HSD17B13 gene that is within 50 nucleotides of positions of the HSD17B13 gene corresponding to positions 12665 and 12666 of SEQ ID NO:1, or corresponding to position 12666 of SEQ ID NO:2; ii) extending the primer at least through the positions of the HSD17B13 gene corresponding to positions 12665 and 12666 of SEQ ID NO:1, or corresponding to position 12666 of SEQ ID NO:2; and iii) determining whether a thymine is inserted between the positions corresponding to positions 12665 and 12666 of SEQ ID NO:1 of the wild type HSD17B13 gene, or whether a thymine is present at a position corresponding to position 12666 of SEQ ID NO:2 of the variant HSD17B13 gene, in an extension product of the primer. In some embodiments, the assay comprises or consists of contacting the biological sample with a primer or probe that specifically hybridizes to the variant HSD17B13 gene having a thymine at a position corresponding to position 12666 of SEQ ID NO:2, and not to the corresponding wild type HSD17B13 gene under stringent conditions, and determining whether hybridization has occurred. In some embodiments, the variant HSD17B13 gene is detected by sequencing. In some embodiments, the method further comprises determining whether the human subject is homozygous for the variant HSD17B13 gene.

In some embodiments, the methods comprise or consist of a) performing an assay on a biological sample comprising an HSD17B13 gene obtained from the subject, wherein the assay determines the identity of the nucleotide occupying a position of the HSD17B13 gene corresponding to position 12666 or positions 12666 and 12667 of SEQ ID NO:2; and b) classifying the subject as being at decreased risk for progression to more clinically advanced stages of the liver disease (e.g., for progression from simple steatosis to one or more of steatohepatitis, fibrosis, cirrhosis, and hepatocellular carcinoma) if the position corresponding to position 12666 of SEQ ID NO:2 is occupied by a thymine or positions 12666 and 12667 of SEQ ID NO:2 are occupied by thymines. Alternatively, the subject can be classified as being at increased risk for progression to more clinically advanced stages of liver disease (e.g., for histopathological progression from simple steatosis to one or more of steatohepatitis, fibrosis, cirrhosis, and hepatocellular carcinoma) if the position is not occupied by a thymine. Likewise, such methods can comprise or consist of performing an assay on the biological sample that determines the identity of the nucleotides occupying positions of the HSD17B13 gene corresponding to positions 12665 and 12666 of SEQ ID NO:1. The subject can be classified as being at decreased risk for progression to more clinically advanced stages of liver disease (e.g., for histopathological progression from simple steatosis to one or more of steatohepatitis, fibrosis, cirrhosis, and hepatocellular carcinoma) if the thymine is inserted between the positions corresponding to positions 12665 and 12666 of SEQ ID NO:1 of the wild type HSD17B13 gene. Alternatively, the subject can be classified as being at increased risk for progression to more clinically advanced stages of liver disease (e.g., for histopathological progression from simple steatosis to one or more of steatohepatitis, fibrosis, cirrhosis, and hepatocellular carcinoma) if there is no thymine inserted between the positions corresponding to positions 12665 and 12666 of SEQ ID NO:1 of the wild type HSD17B13 gene.

In some embodiments, if a subject is determined to have HSD17B13 protein isoforms or transcripts for A, B, E, or F', then the subject is at an increased risk for developing fibrosis, which may manifest as late-stage NASH. In contrast, if a subject is determined to have HSD17B13 protein isoforms or transcripts for C, D, F, G, or H, then the subject is at a decreased risk for developing fibrosis. In some embodiments, the histopathologic features of NASH including, for example, lobular inflammation and hepatocyte ballooning, can also be examined in subjects having or suspected of having an increased risk for developing fibrosis. Subjects having HSD17B13 protein isoforms or transcripts for C, D, F, G, or H, are at a decreased risk for developing lobular inflammation and hepatocyte ballooning.

Any assay, such as the assays described herein, for determining the identity of the nucleotide occupying a position of the HSD17B13 gene corresponding to position 12666 or positions 12666 and 12667 of SEQ ID NO:2 (or corresponding to positions 12665 and 12666 of SEQ ID NO:1) can be used. In addition, any assay, such as the assays described herein, comprising or consisting of contacting the biological sample with a primer or probe, such as an alteration-specific primer or an alteration-specific probe, that specifically hybridizes to the HSD17B13 rs72613567 variant and not the corresponding wild type HSD17B13 sequence under stringent conditions, and determining whether hybridization has occurred.

The present disclosure provides methods of determining a human subject's risk for progression to more clinically advanced stages of fatty liver disease, comprising or consisting of: a) performing an assay on a biological sample obtained from the human subject, wherein the assay determines the presence of an HSD17B13 Transcript D (RNA or cDNA derived therefrom, and/or mRNA or cDNA derived therefrom; preferably RNA or cDNA derived therefrom) in the biological sample; and b) classifying the human subject as being at decreased risk for progression to more clinically advanced stages of fatty liver disease if an HSD17B13 Transcript D is present in the biological sample, or classifying the human subject as being at increased risk for progression to more clinically advanced stages of fatty liver disease if an HSD17B13 Transcript D is not present in the biological sample. In some embodiments, the HSD17B13 Transcript D comprises or consists of a nucleotide sequence that is at least about 90%, at least about 95%, at least about 96%, at least about 97%, at least about 98%, at least about 99%, or 100% identical (or at least about 90% identical) to SEQ ID NO:6, 15, 24, or 33. In some embodiments, the HSD17B13 Transcript D is RNA and comprises or consists of SEQ ID NO:6, or a cDNA thereof comprising or consisting of SEQ ID NO:24, or wherein the HSD17B13 Transcript D is mRNA and comprises or consists of SEQ ID NO:15, or a cDNA thereof comprising or consisting of SEQ ID NO:33. In some embodiments, the assay determines the expression level of HSD17B13 Transcript D (RNA or cDNA derived therefrom, and/or mRNA or cDNA derived therefrom; preferably RNA or cDNA derived therefrom) in the biological sample, wherein an increased expression level of HSD17B13 Transcript D compared to a control sample from a control human subject homozygous for a wild type HSD17B13 allele indicates a decreased risk for progression to more clinically advanced stages of fatty liver disease, and wherein the same or a decreased expression level of HSD17B13 Transcript D compared to the control sample indicates an increased risk for progression to more clinically advanced stages of fatty liver disease. In some embodiments, the assay comprises or consists of contacting the biological sample with one or more primers or probes that specifically hybridize to a nucleic acid sequence of HSD17B13 Transcript D (RNA or cDNA derived therefrom, and/or mRNA or cDNA derived therefrom; preferably RNA or cDNA derived therefrom), or to the complement thereof, and determining whether hybridization has occurred. In some embodiments, the method further comprises specifically detecting Transcript D (RNA or cDNA derived therefrom, and/or mRNA or cDNA derived therefrom; preferably RNA or cDNA derived therefrom) by using a nucleic acid molecule comprising from about 5 nucleotides up to about 50 nucleotides comprising or consisting of: i) a nucleotide sequence that is at least about 90%, at least about 95%, at least about 96%, at least about 97%, at least about 98%, at least about 99%, or 100% identical (or at least about 90% identical) to a nucleotide sequence of a SEQ ID NO:6, 15, 24, or 33, or to the complement thereof; ii) a nucleic acid molecule which specifically hybridizes to exon 2 of Transcript D (RNA or cDNA derived therefrom, and/or mRNA or cDNA derived therefrom; preferably RNA or cDNA derived therefrom); and/or iii) a nucleic acid molecule which specifically hybridizes to the region which bridges exons 3 and 4 of Transcript D (RNA or cDNA derived therefrom, and/or mRNA or cDNA derived therefrom; preferably RNA or cDNA derived therefrom). In some embodiments, the one or more primers or probes specifically hybridize to SEQ ID NO:6. SEQ ID NO:15, SEQ ID NO:24, and/or SEQ ID NO:33. In some embodiments, the assay comprises reverse transcription polymerase chain reaction (RT-PCR) or quantitative RT-PCR (qRT-PCR). In some embodiments, the assay comprises sequencing.

In some embodiments, the methods comprise or consist of: performing an assay on a biological sample obtained from the subject, wherein the assay determines the presence of Transcript C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), in the biological sample; and b) classifying the subject as being at decreased risk for progression to more clinically advanced stages of liver disease (e.g., for histopathological progression from simple steatosis to one or more of steatohepatitis, fibrosis, cirrhosis, and hepatocellular carcinoma) if Transcript C, D, F, G, or H, and particularly Transcript D, is present in the biological sample. Alternatively, the subject can be classified as being at increased risk for progression to more clinically advanced stages of liver disease (e.g., for histopathological progression from simple steatosis to one or more of steatohepatitis, fibrosis, cirrhosis, and hepatocellular carcinoma) if Transcript C, D, F, G, or H, particularly Transcript D, is not present in the biological sample. In a specific example, the assay can determine the expression level of Transcript C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), in the biological sample, wherein an increased expression level of Transcript C, D, F, G, or H, particularly Transcript D, in the biological sample compared to a control sample from a control subject homozygous for a wild type HSD17B13 allele indicates a decreased risk for progression to more clinically advanced stages of liver disease (e.g., for histopathological progression from simple steatosis to one or more of steatohepatitis, fibrosis, cirrhosis, and hepatocellular carcinoma). Alternatively, a decreased expression level or no change in expression level of Transcript C, D, F, G, or H, particularly Transcript D, in the biological sample compared to a control sample from a control subject homozygous for a wild type HSD17B13 allele indicates an increased risk for progression to more clinically advanced stages of liver disease (e.g., for histopathological progression from simple steatosis to one or more of steatohepatitis, fibrosis, cirrhosis, and hepatocellular carcinoma). In another specific example, the assay can comprise or consist of determining the expression level of Transcript C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), relative to Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom), particularly Transcript A (RNA or cDNA derived therefrom, and/or mRNA or cDNA derived therefrom; preferably RNA or cDNA derived therefrom), in the biological sample, wherein an increased ratio of Transcript C, D, F, G, or H, particularly Transcript D, expression relative to Transcript A, B, or E or Transcript A, B, E, or F', particularly Transcript A, expression compared to the ratio in a control sample from a control subject homozygous for a wild type HSD17B13 allele indicates a decreased risk for progression to more clinically advanced stages of liver disease (e.g., for histopathological progression from simple steatosis to one or more of steatohepatitis, fibrosis, cirrhosis, and hepatocellular carcinoma). Alternatively, a decreased ratio or no change in the ratio of Transcript C, D, F, G, or H, particularly Transcript D, expression relative to Transcript A, B, or E or Transcript A, B, E, or F', particularly Transcript A, expression compared to the ratio in a control sample from a control subject homozygous for a wild type HSD17B13 allele indicates an increased risk for progression to more clinically advanced stages of liver disease (e.g., for histopathological progression from simple steatosis to one or more of steatohepatitis, fibrosis, cirrhosis, and hepatocellular carcinoma).

In some embodiments, for detecting the presence or levels of any one of Transcripts C, D, F, G, or H (RNA or cDNA derived therefrom, and/or mRNA or cDNA derived therefrom; preferably RNA or cDNA derived therefrom), and particularly D (RNA or cDNA derived therefrom, and/or mRNA or cDNA derived therefrom; preferably RNA or cDNA derived therefrom), the assay can comprise or consist of contacting the biological sample with one or more primers or probes (e.g., alteration-specific primers or alteration-specific probes) that specifically hybridize to a region spanning the boundary of exons 6 and 7 in Transcript D (RNA or cDNA derived therefrom, and/or mRNA or cDNA derived therefrom; preferably RNA or cDNA derived therefrom), Transcript G (RNA or cDNA derived therefrom, and/or mRNA or cDNA derived therefrom; preferably RNA or cDNA derived therefrom), or Transcript H (RNA or cDNA derived therefrom, and/or mRNA or cDNA derived therefrom; preferably RNA or cDNA derived therefrom) (i.e., including the additional guanine at the 3' end of exon 6 that is not present in exon 6 in other HSD17B13 Transcripts), and determining whether hybridization has occurred. In addition or alternatively, the assay can comprise or consist of contacting the biological sample with one or more primers or probes that specifically hybridize to a region within the read-through into intron 6 in Transcript F (RNA or cDNA derived therefrom, and/or mRNA or cDNA derived therefrom; preferably RNA or cDNA derived therefrom) or a region spanning the boundary between the read-through into intron 6 and the rest of exon 6 in Transcript F (RNA or cDNA derived therefrom, and/or mRNA or cDNA derived therefrom; preferably RNA or cDNA derived therefrom), and determining whether hybridization has occurred. In addition or alternatively, the assay can comprise or consist of contacting the biological sample with one or more primers or probes that specifically hybridize to a region spanning the exon 5-exon 7 boundary in Transcript C (RNA or cDNA derived therefrom, and/or mRNA or cDNA derived therefrom; preferably RNA or cDNA derived therefrom), and determining whether hybridization has occurred.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of Transcript C, D, F, G, or H, and particularly Transcript D, in the biological sample.

In some embodiments, the methods comprise or consist of: a) performing an assay on a biological sample obtained from the subject, wherein the assay determines the presence of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) in the biological sample; and b) classifying the subject as being at increased risk for progression to more clinically advanced stages of liver disease (e.g., for histopathological progression from simple steatosis to one or more of steatohepatitis, fibrosis, cirrhosis, and hepatocellular carcinoma) if Transcript A, B, or E or Transcript A, B, E, or F' is present in the biological sample. Alternatively, the subject can be classified as being at decreased risk for progression to more clinically advanced stages of liver disease (e.g., for histopathological progression from simple steatosis to one or more of steatohepatitis, fibrosis, cirrhosis, and hepatocellular carcinoma) if Transcript A, B, or E or Transcript A, B, E, or F' is not present in the biological sample. In a specific example, the assay can determine the expression level of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) in the biological sample, wherein an increased expression level of Transcript A, B, or E or Transcript A, B, E, or F' in the biological sample compared to a control sample from a control subject homozygous for the HSD17B13 rs72613567 variant allele indicates an increased risk for progression to more clinically advanced stages of liver disease (e.g., for histopathological progression from simple steatosis to one or more of steatohepatitis, fibrosis, cirrhosis, and hepatocellular carcinoma). Alternatively, a decreased expression level or no change in expression level of Transcript A, B, or E or Transcript A, B, E, or F' in the biological sample compared to a control sample from a control subject homozygous for the HSD17B13 rs72613567 variant allele indicates a decreased risk for progression to more clinically advanced stages of liver disease (e.g., for histopathological progression from simple steatosis to one or more of steatohepatitis, fibrosis, cirrhosis, and hepatocellular carcinoma). In another specific example, the assay can comprise determining the expression level of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) relative to Transcript C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), in the biological sample, wherein an increased ratio of Transcript A, B, or E or Transcript A, B, E, or F expression relative to Transcript C, D, F, G, or H, particularly Transcript D, expression compared to the ratio in a control sample from a control subject homozygous for the HSD17B13 rs72613567 variant allele indicates an increased risk for progression to more clinically advanced stages of liver disease (e.g., for histopathological progression from simple steatosis to one or more of steatohepatitis, fibrosis, cirrhosis, and hepatocellular carcinoma). Alternatively, a decreased ratio or no change in the ratio of Transcript A, B, or E (RNA or cDNA derived therefrom, and/or mRNA or cDNA derived therefrom; preferably RNA or cDNA derived therefrom) or Transcript A, B, E, or F' (RNA or cDNA derived therefrom, and/or mRNA or cDNA derived therefrom; preferably RNA or cDNA derived therefrom) expression relative to C, D, F, G, or H (RNA or cDNA derived therefrom, and/or mRNA or cDNA derived therefrom; preferably RNA or cDNA derived therefrom), particularly Transcript D (RNA or cDNA derived therefrom, and/or mRNA or cDNA derived therefrom; preferably RNA or cDNA derived therefrom), expression compared to the ratio in a control sample from a control subject homozygous for the HSD17B13 rs72613567 variant allele indicates a decreased risk for progression to more clinically advanced stages of liver disease (e.g., for histopathological progression from simple steatosis to one or more of steatohepatitis, fibrosis, cirrhosis, and hepatocellular carcinoma).

In some embodiments, for detecting the presence or levels of any one of Transcripts A, B, or E (RNA or cDNA derived therefrom, and/or mRNA or cDNA derived therefrom; preferably RNA or cDNA derived therefrom) or Transcripts A, B, E, or F' (RNA or cDNA derived therefrom, and/or mRNA or cDNA derived therefrom; preferably RNA or cDNA derived therefrom), the assay can comprise or consist of contacting the biological sample with one or more primers or probes, such as alteration-specific primers or alteration-specific probes, that specifically hybridize to a region within exon 3', spanning the boundary of exons 3 and 3', or spanning the boundary of exons 3' and 4 in Transcript E (RNA or cDNA derived therefrom, and/or mRNA or cDNA derived therefrom; preferably RNA or cDNA derived therefrom) to distinguish Transcript E from Transcripts A, B, C, D, F, and G, and further contacting the biological sample with one or more primers and probes, such as alteration-specific primers or alteration-specific probes, that specifically hybridize to a region spanning the boundary of exons 6 and 7 in Transcript E (RNA or cDNA derived therefrom, and/or mRNA or cDNA derived therefrom; preferably RNA or cDNA derived therefrom) to distinguish Transcript E from Transcript H, and determining whether hybridization has occurred. In addition or alternatively, the assay can comprise or consist of contacting the biological sample with one or more primers or probes, such as alteration-specific primers or alteration-specific probes, that specifically hybridize to a region spanning the boundaries of exon 1 and 3 in Transcript B (RNA or cDNA derived therefrom, and/or mRNA or cDNA derived therefrom; preferably RNA or cDNA derived therefrom) to distinguish transcript B from Transcripts A, C, D, E, F, and H, and further contacting the biological sample with one or more primers or probes, that specifically hybridize to a region spanning the boundary of exons 6 and 7 in Transcript B (RNA or cDNA derived therefrom, and/or mRNA or cDNA derived therefrom; preferably RNA or cDNA derived therefrom) to distinguish Transcript B from Transcript G, and determining whether hybridization has occurred. In addition or alternatively, the assay can comprise or consist of contacting the biological sample with one or more primers or probes, such as alteration-specific primers or alteration-specific probes, that specifically hybridize to a region spanning the exon 6-exon 7 boundary in Transcript A (RNA or cDNA derived therefrom, and/or mRNA or cDNA derived therefrom; preferably RNA or cDNA derived therefrom) to distinguish Transcript A from Transcripts D, F, G, and H, and further contacting the biological sample with one or more primers or probes, such as alteration-specific primers or alteration-specific probes, that specifically hybridize to a region within exon 6, spanning the exon 5-exon 6 boundary, or spanning the exon 6-exon 7 boundary in Transcript A (RNA or cDNA derived therefrom, and/or mRNA or cDNA derived therefrom; preferably RNA or cDNA derived therefrom) to distinguish Transcript A from Transcript C, and determining whether hybridization has occurred. Optionally, the assay can further comprise or consist of contacting the biological sample with one or more primers or probes, such as alteration-specific primers or alteration-specific probes, that specifically hybridize to a region within exon 2, spanning exon 1-exon 2 boundary, or spanning the exon 2-exon 3 boundary in Transcript A (RNA or cDNA derived therefrom, and/or mRNA or cDNA derived therefrom; preferably RNA or cDNA derived therefrom) to distinguish Transcript A from Transcripts B and H, and further contacting the biological sample with one or more primers or probes, such as alteration-specific primers or alteration-specific probes, that specifically hybridize to a region spanning the exon 3-exon 4 boundary in Transcript A (RNA or cDNA derived therefrom, and/or mRNA or cDNA derived therefrom; preferably RNA or cDNA derived therefrom) to distinguish Transcript A from Transcripts E and H, and determining whether hybridization has occurred.

Other assays that can be used in the methods disclosed herein include, for example, reverse transcription polymerase chain reaction (RT-PCR) or quantitative RT-PCR (qRT-PCR). Yet other assays that can be used in the methods disclosed herein include, for example, RNA sequencing (RNA-Seq) followed by determination of the presence and quantity of Transcript A, B, or E or Transcript A, B, E, or F' in the biological sample.

The present disclosure provides methods of determining a human subject's risk for progression to more clinically advanced stages of fatty liver disease, comprising or consisting of: a) detecting whether HSD17B13 Isoform D is present in a biological sample obtained from the human subject; and b) classifying the human subject as being at decreased risk for progression to more clinically advanced stages of liver disease if HSD17B13 Isoform D is detected in the biological sample. In some embodiments, the HSD17B13 Isoform D comprises or consists of an amino acid sequence that is at least about 90%, at least about 95%, at least about 96%, at least about 97%, at least about 98%, at least about 99%, or 100% identical (or at least about 90% identical) to SEQ ID NO:42. In some embodiments, the detecting comprises sequencing.

In some embodiments, the detecting determines the expression level of Isoform C, D, F, G, or H in the biological sample, wherein an increased expression level of Isoform C, D, F, G, or H compared to a control sample from a control human subject homozygous for a wild type HSD17B13 allele indicates a decreased risk for progression to more clinically advanced stages of liver disease (e.g., for histopathological progression from simple steatosis to one or more of steatohepatitis, fibrosis, cirrhosis, and hepatocellular carcinoma). Alternatively, a decreased expression level or no change in expression level of Isoform C, D, F, G, or H compared to a control sample from a control subject homozygous for a wild type HSD17B13 allele indicates an increased risk for progression to more clinically advanced stages of liver disease (e.g., for histopathological progression from simple steatosis to one or more of steatohepatitis, fibrosis, cirrhosis, and hepatocellular carcinoma).

In some embodiments, the detecting determines the expression level of Isoform A, B, or E or Isoform A, B, E, or F' in the biological sample, wherein an increased expression level of Isoform A, B, or E or Isoform A, B, E, or F' compared to a control sample from a control human subject homozygous for the HSD17B13 rs72613567 variant allele indicates an increased risk for progression to more clinically advanced stages of liver disease (e.g., for histopathological progression from simple steatosis to one or more of steatohepatitis, fibrosis, cirrhosis, and hepatocellular carcinoma). Alternatively, a decreased expression level or no change in expression level of Isoform A, B, or E or Isoform A, B, E, or F compared to a control sample from a control subject homozygous for the HSD17B13 rs72613567 variant allele indicates a decreased risk for progression to more clinically advanced stages of liver disease (e.g., for histopathological progression from simple steatosis to one or more of steatohepatitis, fibrosis, cirrhosis, and hepatocellular carcinoma).

Any one or more of the methods described herein can be carried out in vitro.

In any of the methods disclosed herein, a primer or probe may either hybridize to its intended target nucleic acid molecule or specifically hybridize to its intended target nucleic acid molecule. In some embodiments, a primer or probe that specifically hybridizes to a particular target does not hybridize to a wild type nucleic acid molecule (such as, for example, SEQ ID NO:1, or a Transcript that has functional activity associated with wild type HSD17B13).

In any of the methods disclosed herein in which a subject is classified as being at increased risk for progression to more clinically advanced stages of liver disease (e.g., for histopathological progression from simple steatosis to one or more of steatohepatitis, fibrosis, cirrhosis, and hepatocellular carcinoma) or as being at increased risk for developing liver disease (e.g., chronic liver disease), the method can further comprise a therapeutic or prophylactic method. Alternatively, the method can further comprise administering a therapeutic agent to prevent or alleviate one or more symptoms associated with progression to more clinically advanced stages of liver disease (e.g., progression from simple steatosis to more clinically advanced stages of liver disease, or progression from simple steatosis to one or more of steatohepatitis, fibrosis, cirrhosis, and hepatocellular carcinoma). For example, such treatments could be focused on preventing or reducing inflammation or preventing or reducing fibrosis. Examples of such therapeutics in development include, but are not limited to obeticholic acid, GS-9674, Simtuzumab, GS-4997, NDI-010976, GFT505/Elafibranor, Aramchol, Cenicriviroc, GR-MD-02, TD139, SHP626, PXS4728A, and RP103—Cysteamine bitartrate. The present disclosure provides a therapeutic agent selected from the group consisting of the therapeutic agents disclosed above for use in the treatment, prevention or alleviation of a liver disease in a human subject which does not carry an HSD17B13 variant gene. In one aspect, the human subject has been tested negative for a variant HSD17B13 gene. In one aspect, the treatment comprises the step of determining whether or not the human subject carries a variant HSD17B13 gene. In one aspect, the human patient has been determined as having a variant HSD17B13 gene in accordance with any of the methods described herein. The present disclosure also provides a therapeutic agent selected from the group consisting of the therapeutic agents disclosed above for use in the treatment, prevention or alleviation of a fatty liver disease in a human subject which has been determined as having a risk for progression to more clinically advances stages of fatty liver disease in accordance with any of the methods of the present disclosure.

Various methods are provided for modifying a cell through use of any combination of antisense molecules such as antisense RNA, siRNA, and shRNA, HSD17B13 proteins or fragments thereof, and expression vectors for expressing a recombinant HSD17B13 gene or a nucleic acid encoding an HSD17B13 protein. The methods can occur in vitro, ex vivo, or in vivo. The antisense molecules such as antisense RNA, siRNA, and shRNA, HSD17B13 proteins or fragments thereof, and expression vectors can be introduced into the cell in any form and by any means as described elsewhere herein, and all or some can be introduced simultaneously or sequentially in any combination.

Antisense molecules can be used to alter expression of an HSD17B13 gene or a nucleic acid encoding an HSD17B13 isoform protein. Examples of antisense molecules include antisense RNAs, small interfering RNAs (siRNAs), and short hairpin RNAs (shRNAs). Such antisense RNAs, siRNAs, or shRNAs can be designed to target any region of an mRNA. For example, the antisense RNAs, siRNAs, or shRNAs can be designed to target a region unique to one or more of the HSD17B13 transcripts disclosed herein, or a region common to one or more of the HSD17B13 transcripts disclosed herein.

Subjects can be, for example, a subject (e.g., a human) who is not a carrier of the HSD17B13 rs72613567 variant (or is only a heterozygous carrier of the HSD17B13 rs72613567 variant) and has or is susceptible to developing a liver disease.

The following representative embodiments are presented:

Embodiment 1

A nucleic acid molecule comprising or consisting of at least 15 contiguous nucleotides of an HSD17B13 gene, and having a thymine inserted between nucleotides at positions corresponding to positions 12665 and 12666 of SEQ ID NO:1.

Embodiment 2

The nucleic acid molecule of embodiment 1, wherein the contiguous nucleotides are at least about 90%, at least about 95%, at least about 96%, at least about 97%, at least about 98%, or at least about 99% identical to a corresponding sequence in SEQ ID NO:2, including the position corresponding to position 12666 of SEQ ID NO:2.

Embodiment 3

The nucleic acid molecule of embodiment 1 or 2, wherein the HSD17B13 gene is a human HSD17B13 gene.

Embodiment 4

The nucleic acid molecule of any one of embodiments 1 to 3, wherein the isolated nucleic acid molecule comprises or consists of at least 15, at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, or at least 19000 nucleotides corresponding to contiguous nucleotides of SEQ ID NO:2.

Embodiment 5

The nucleic acid molecule of any one of embodiments 1 to 4, wherein the isolated nucleic acid molecule comprises or consists of an HSD17B13 minigene in which one or more nonessential segments of the gene have been deleted with respect to a corresponding wild type HSD17B13 gene.

Embodiment 6

The nucleic acid molecule of embodiment 5, wherein the deleted segments comprise one or more intronic sequences.

Embodiment 7

The nucleic acid molecule of embodiment 5 or 6, wherein the isolated nucleic acid molecule further comprises an intron corresponding to intron 6 of SEQ ID NO:2.

Embodiment 8

The nucleic acid molecule of embodiment 7, wherein the intron is intron 6 of SEQ ID NO:2.

Embodiment 9

A nucleic acid molecule comprising or consisting of at least 15 contiguous nucleotides encoding all or part of an HSD17B13 protein, wherein the contiguous nucleic acid molecules comprise a segment that is at least about 90%, at least about 95%, at least about 96%, at least about 97%, at least about 98%, at least about 99%, or 100% identical to a corresponding segment present in: i) SEQ ID NO:6, SEQ ID NO: 15, SEQ ID NO:24, or SEQ ID NO:33 (Transcript D); ii) SEQ ID NO:10, SEQ ID NO:19, SEQ ID NO:28, or SEQ ID NO:37 (Transcript G); or iii) SEQ ID NO:11, SEQ ID NO:20. SEQ ID NO:29, or SEQ ID NO:38 (Transcript H), that is not present in SEQ ID NO:3, SEQ ID NO:12, SEQ ID NO:21, or SEQ ID NO:30 (Transcript A).

Embodiment 10

The nucleic acid molecule of embodiment 9, wherein the contiguous nucleotides further comprise or consists of a segment that is at least about 90%, at least about 95%, at least about 96%, at least about 97%, at least about 98%, at least about 99%, or 100% identical to a corresponding segment present in SEQ ID NO:6, SEQ ID NO:15, SEQ ID NO:24, or SEQ ID NO:33 (Transcript D) that is not present in SEQ ID NO: 11, SEQ ID NO:20, SEQ ID NO:29, or SEQ ID NO:38 (Transcript H), and wherein the contiguous nucleotides further comprise or consists of a segment that is at least about 90%, at least about 95%, at least about 96%, at least about 97%, at least about 98%, at least about 99%, or 100% identical to a corresponding segment present in SEQ ID NO:6, SEQ ID NO:15, SEQ ID NO:24, or SEQ ID NO:33 (Transcript D) that is not present in SEQ ID NO:10, SEQ ID NO:19, SEQ ID NO:28, or SEQ ID NO:37 (Transcript G).

Embodiment 11

The nucleic acid molecule of embodiment 9, wherein the contiguous nucleotides further comprise or consists of a segment that is at least about 90%, at least about 95%, at least about 96%, at least about 97%, at least about 98%, at least about 99%, or 100% identical to a corresponding segment present in SEQ ID NO:11, SEQ ID NO:20. SEQ ID NO:29, or SEQ ID NO:38 (Transcript H) that is not present in SEQ ID NO:6. SEQ ID NO:15, SEQ ID NO:24, or SEQ ID NO:33 (Transcript D).

Embodiment 12

The nucleic acid molecule of embodiment 9, wherein the contiguous nucleotides further comprise or consists of a segment that is at least about 90%, at least about 95%, at least about 96%, at least about 97%, at least about 98%, at least about 99%, or 100% identical to a corresponding segment present in SEQ ID NO: 10, SEQ ID NO:19, SEQ ID NO:28, or SEQ ID NO:37 (Transcript G) that is not present in SEQ ID NO:6, SEQ ID NO:15, SEQ ID NO:24, or SEQ ID NO:33 (Transcript D).

Embodiment 13

An nucleic acid molecule comprising at least 15 contiguous nucleotides encoding all or part of an HSD17B13 protein, wherein the contiguous nucleotides comprise or consists of a segment that is at least about 90%, at least about 95%, at least about 96%, at least about 97%, at least about 98%, at least about 99%, or 100% identical to a corresponding segment present in SEQ ID NO:7, SEQ ID NO:16, SEQ ID NO:25, or SEQ ID NO:34 (Transcript E) that is not present in SEQ ID NO:3, SEQ ID NO:12, SEQ ID NO:21, or SEQ ID NO:30 (Transcript A), optionally wherein the contiguous nucleotides further comprise or consists of a segment that is at least about 90%, at least about 95%, at least about 96%, at least about 97%, at least about 98%, at least about 99%, or 100% identical to a corresponding segment present in SEQ ID NO:7, SEQ ID NO:16, SEQ ID NO:25, or SEQ ID NO:34 (Transcript E) that is not present in SEQ ID NO:11. SEQ ID NO:20, SEQ ID NO:29, or SEQ ID NO:38 (Transcript H).

Embodiment 14

A nucleic acid molecule comprising or consisting of at least 15 contiguous nucleotides encoding all or part of an HSD17B13 protein, wherein the contiguous nucleotides comprise or consist of a segment that is at least about 90%, at least about 95%, at least about 96%, at least about 97%, at least about 98%, at least about 99%, or 100% identical to a corresponding segment present in SEQ ID NO:8, SEQ ID NO:17, SEQ ID NO:26, or SEQ ID NO:35 (Transcript F) that is not present in SEQ ID NO:3, SEQ ID NO: 12, SEQ ID NO:21, or SEQ ID NO:30 (Transcript A).

Embodiment 15

A nucleic acid molecule comprising or consisting of at least 15 contiguous nucleotides encoding all or part of an HSD17B13 protein, wherein the contiguous nucleotides comprise or consist of a segment that is at least about 90%, at least about 95%, at least about 96%, at least about 97%, at least about 98%, at least about 99%, or 100% identical to a corresponding segment present in SEQ ID NO:5, SEQ ID NO: 14. SEQ ID NO:23, or SEQ ID NO:32 (Transcript C) that is not present in SEQ ID NO:3, SEQ ID NO:12, SEQ ID NO:21, or SEQ ID NO:30 (Transcript A).

Embodiment 16

The nucleic acid molecule of any one of embodiments 9 to 15, wherein the HSD17B13 protein is a human HSD17B13 protein.

Embodiment 17

The nucleic acid molecule of any one of embodiments 9 to 16, wherein the isolated nucleic acid molecule comprises or consists of at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, or at least 2000 contiguous nucleotides encoding all or part of an HSD17B13 protein.

Embodiment 18

A nucleic acid molecule comprising or consisting of a sequence at least about 90%, at least about 95%, at least about 96%, at least about 97%, at least about 98%, at least about 99%, or 100% identical to the sequence set forth in: i) SEQ ID NO:5, SEQ ID NO:14, SEQ ID NO:23, or SEQ ID NO:32 (Transcript C), ii) SEQ ID NO:6, SEQ ID NO:15, SEQ ID NO:24, or SEQ ID NO:33 (Transcript D), iii) SEQ ID NO:7, SEQ ID NO:16, SEQ ID NO:25, or SEQ ID NO:34 (Transcript E), iv) SEQ ID NO:8, SEQ ID NO:17, SEQ ID NO:26, or SEQ ID NO:35 (Transcript F), v) SEQ ID NO:10, SEQ ID NO:19, SEQ ID NO:28, or SEQ ID NO:37 (Transcript G), or vi) SEQ ID NO:11, SEQ ID NO:20, SEQ ID NO:29, or SEQ ID NO:38 (Transcript H) and encoding an HSD17B13 protein comprising or consisting of the sequence set forth in SEQ ID NO:41 (Isoform C), SEQ ID NO:42 (Isoform D), SEQ ID NO:43 (Isoform E), SEQ ID NO:44 (Isoform F), SEQ ID NO:46 (Isoform G), or SEQ ID NO:47 (Isoform H).

Embodiment 19

The nucleic acid molecule of any one of embodiments 9 to 18, wherein the contiguous nucleotides comprise or consist of sequences from at least two different exons of an HSD17B13 gene without an intervening intron.

Embodiment 20

A polypeptide encoded by the nucleic acid molecule of any one of embodiments 1 to 19.

Embodiment 21

A nucleic acid molecule comprising or consisting of at least 15 contiguous nucleotides that hybridize to an HSD17B13 gene at a segment that includes or is within 1000, 500, 400, 300, 200, 100, 50, 45, 40, 35, 30, 25, 20, 15, 10, or 5 nucleotides of a position corresponding to position 12666 in SEQ ID NO:2.

Embodiment 22

The nucleic acid molecule of embodiment 21, wherein the segment is at least about 90%, at least about 95%, at least about 96%, at least about 97%, at least about 98%, or at least about 99% identical to a corresponding sequence in SEQ ID NO:2, and having a thymine at a position corresponding to position 12666 of SEQ ID NO:2.

Embodiment 23

The nucleic acid molecule of embodiment 21 or 22, wherein the segment comprises or consists of at least 20, 25, 30, 35, 40, 45, 50, 60, 70, 80, 90, 100, 200, 300, 400, 500, 600, 700, 800, 900, 1000, or 2000 contiguous nucleotides of SEQ ID NO:2.

Embodiment 24

The nucleic acid molecule of any one of embodiments 21 to 23, wherein the segment includes a position corresponding to position 12666 in SEQ ID NO:2.

Embodiment 25

The nucleic acid molecule of any one of embodiments 21 to 24, wherein the HSD17B13 gene is a human HSD17B13 gene.

Embodiment 26

A nucleic acid molecule that hybridizes to at least 15 contiguous nucleotides of a nucleic acid encoding an HSD17B13 protein, wherein the contiguous nucleotides comprise or consist of a segment that is at least about 90%, at least about 95%, at least about 96%, at least about 97%, at least about 98%, at least about 99%, or 100% identical to a corresponding segment present in: i) SEQ ID NO:6, SEQ ID NO:15, SEQ ID NO:24, or SEQ ID NO:33 (Transcript D), ii) SEQ ID NO:10, SEQ ID NO:19, SEQ ID NO:28, or SEQ ID NO:37 (Transcript G), or iii) SEQ ID NO: 11, SEQ ID NO:20, SEQ ID NO:29, or SEQ ID NO:38 (Transcript H), that is not present within SEQ ID NO:3, SEQ ID NO:12, SEQ ID NO:21, or SEQ ID NO:30 (Transcript A).

Embodiment 27

A nucleic acid molecule that hybridizes to at least 15 contiguous nucleotides of a nucleic acid encoding an HSD17B13 protein, wherein the contiguous nucleotides comprise or consist of a segment that is at least about 90%, at least about 95%, at least about 96%, at least about 97%, at least about 98%, or at least about 99% identical to a corresponding segment present in SEQ ID NO:7, SEQ ID NO:16, SEQ ID NO:25, or SEQ ID NO:34 (Transcript E) or SEQ ID NO: 11, SEQ ID NO:20, SEQ ID NO:29, or SEQ ID NO:38 (Transcript H) that is not present in SEQ ID NO:3, SEQ ID NO:12. SEQ ID NO:21, or SEQ ID NO:30 (Transcript A).

Embodiment 28

A nucleic acid molecule that hybridizes to at least 15 contiguous nucleotides of a nucleic acid encoding an HSD17B3 protein, wherein the contiguous nucleotides comprise or consist of a segment that is at least about 90%, at least about 95%, at least about 96%, at least about 97%, at least about 98%, or at least about 99% identical to a corresponding segment in SEQ ID NO:8, SEQ ID NO: 17, SEQ ID NO:26, or SEQ ID NO:35 (Transcript F) that is not present in SEQ ID NO:3, SEQ ID NO: 12. SEQ ID NO:21, or SEQ ID NO:30 (Transcript A).

Embodiment 29

A nucleic acid molecule that hybridizes to at least 15 contiguous nucleotides of a nucleic acid encoding an HSD17B13 protein, wherein the contiguous nucleotides comprise or consist of a segment that is at least about 90%, at least about 95%, at least about 96%, at least about 97%, at least about 98%, or at least about 99% identical to a corresponding segment present in SEQ ID NO:5. SEQ ID NO: 14, SEQ ID NO:23, or SEQ ID NO:32 (Transcript C) that is not present in SEQ ID NO:3, SEQ ID NO:12. SEQ ID NO:21, or SEQ ID NO:30 (Transcript A).

Embodiment 30

The nucleic acid molecule of any one of embodiments 26 to 29, wherein the HSD17B13 protein is a human HSD17B13 protein.

Embodiment 31

The nucleic acid molecule of any one of embodiments 26 to 29, wherein the isolated nucleic acid is an antisense RNA, a short hairpin RNA, or a small-interfering RNA.

Embodiment 32

The nucleic acid molecule of any one of embodiments 21 to 31, wherein the isolated nucleic acid comprises or consists of from 5 up to about 30, 40, 50, 100, 200, 300, 400, 500, 600, 700, 800, 900, or 1000 nucleotides in length.

Embodiment 33

The nucleic acid molecule of any one of embodiments 1 to 19, 21 to 30, and 32, wherein the nucleic acid comprises or consists of DNA.

Embodiment 34

The nucleic acid molecule of any one of embodiments 1 to 19 and 21 to 32, wherein the nucleic acid comprises or consists of RNA.

Embodiment 35

The nucleic acid molecule of any one of embodiments 1 to 19 and 21 to 34, wherein the nucleic acid molecule is linked to a heterologous nucleic acid or comprises a heterologous label.

Embodiment 36

The nucleic acid molecule of embodiment 35, wherein the heterologous label is a fluorescent label.

Embodiment 37

A vector or an exogenous donor sequence comprising the nucleic acid molecule of any one of embodiments 1 to 19 and 21 to 36 and a heterologous nucleic acid molecule.

Embodiment 38

The nucleic acid molecule of any one of embodiments 1 to 19 and 21 to 36, wherein the nucleic acid molecule comprises a non-natural nucleotide.

Embodiment 39

Use of a nucleic acid molecule of any one of embodiments 1 to 19 and 21 to 38 in a method of detecting an HSD17B13 rs72613567 variant in a subject, a method of detecting the presence of an HSD17B13 nucleic acid molecule (Transcript C, D, E, F, G, or H) in a subject, a method of determining a subject's susceptibility to developing a liver disease, or a method of diagnosing a subject with a liver disease or at risk of developing a liver disease.

Embodiment 40

A polypeptide comprising or consisting of at least 8 contiguous amino acids of an HSD17B13 protein, wherein the contiguous amino acids comprise or consist of a segment that is at least about 90%, at least about 95%, at least about 96%, at least about 97%, at least about 98%, at least about 99%, or 100% identical to a corresponding segment present in SEQ ID NO:42 (Isoform D), SEQ ID NO:46 (Isoform G), or SEQ ID NO:47 (Isoform H) that is not present in SEQ ID NO:39 (Isoform A).

Embodiment 41

The polypeptide of embodiment 40, wherein the contiguous amino acids further comprise or consist of a segment that is at least about 90%, at least about 95%, at least about 96%, at least about 97%, at least about 98%, at least about 99%, or 100% identical to a corresponding segment present in SEQ ID NO:42 (Isoform D) that is not present in SEQ ID NO:47 (Isoform H), and wherein the contiguous amino acids further comprise or consist of a segment that is at least about 90%, at least about 95%, at least about 96%, at least about 97%, at least about 98%, at least about 99%, or 100% identical to a corresponding segment present in SEQ ID NO:42 (Isoform D) that is not present in SEQ ID NO:46 (Isoform G).

Embodiment 42

The polypeptide of embodiment 40, wherein the contiguous amino acids further comprise or consist of a segment that is at least about 90%, at least about 95%, at least about 96%, at least about 97%, at least about 98%, at least about 99%, or 100% identical to a corresponding segment present in SEQ ID NO:47 (Isoform H) that is not present in SEQ ID NO:42 (Isoform D).

Embodiment 43

The polypeptide of embodiment 40, wherein the contiguous amino acids further comprise or consist of a segment that is at least about 90%, at least about 95%, at least about 96%, at least about 97%, at least about 98%, at least about 99%, or 100% identical to a corresponding segment present in SEQ ID NO:46 (Isoform G) that is not present in SEQ ID NO:42 (Isoform D).

Embodiment 44

A polypeptide comprising or consisting of at least 8 contiguous amino acids of an HSD17B13 protein, wherein the contiguous amino acids comprise or consist of a segment that is at least about 90%, at least about 95%, at least about 96%, at least about 97%, at least about 98%, at least about 99%, or 100% identical to a corresponding segment present in SEQ ID NO:43 (Isoform E) that is not present in SEQ ID NO:39 (Isoform A), optionally wherein the contiguous amino acids further comprise or consist of a segment that is at least about 90%, at least about 95%, at least about 96%, at least about 97%, at least about 98%, at least about 99%, or 100% identical to a corresponding segment present in SEQ ID NO:43 (Isoform E) that is not present in SEQ ID NO:47 (Isoform H).

Embodiment 45

A polypeptide comprising or consisting of at least 8 contiguous amino acids of an HSD17B13 protein, wherein the contiguous amino acids comprise or consist of a segment that is at least about 90%, at least about 95%, at least about 96%, at least about 97%, at least about 98%, at least about 99%, or 100% identical to a corresponding segment present in SEQ ID NO:44 (HSD17B13) that is not present in SEQ ID NO:39 (Isoform A).

Embodiment 46

A polypeptide comprising or consisting of at least 8 contiguous amino acids of an HSD17B13 protein, wherein the contiguous amino acids comprise or consist of a segment that is at least about 90%, at least about 95%, at least about 96%, at least about 97%, at least about 98%, at least about 99%, or 100% identical to a corresponding segment present in SEQ ID NO:41 (Isoform C) that is not present in SEQ ID NO:39 (Isoform A).

Embodiment 47

A polypeptide comprising or consisting of a sequence at least about 90%, at least about 95%, at least about 96%, at least about 97%, at least about 98%, at least about 99%, or 100% identical to SEQ ID NO:41 (Isoform C), SEQ ID NO:42 (Isoform D), SEQ ID NO:43 (Isoform E), SEQ ID NO:44 (Isoform F), SEQ ID NO:46 (Isoform G), or SEQ ID NO:47 (Isoform H).

Embodiment 48

The polypeptide of any one of embodiments 53 to 60 which is linked to a heterologous molecule.

Embodiment 49

The polypeptide of embodiment 48, wherein the heterologous molecule is an immunoglobulin Fc domain, a peptide tag, a transduction domain, poly(ethylene glycol), polysialic acid, or glycolic acid.

Embodiment 50

A nucleic acid molecule encoding the polypeptide of any one of embodiments 53 to 62.

Embodiment 51

A host cell comprising the nucleic acid molecule of embodiment 50 operably linked to a heterologous promoter active in the host cell.

Embodiment 52

The host cell of embodiment 51, wherein the host cell is a bacterial cell, a yeast cell, an insect cell, or a mammalian cell.

Embodiment 53

A method of producing the isolated polypeptide of any one of embodiments 53 to 62, comprising culturing the host cell of embodiment 51 or 52, whereby the nucleic acid molecule is expressed, and recovering the polypeptide.

Embodiment 54

A composition comprising the polypeptide of any one of embodiments 20 and 40 to 49, or the nucleic acid molecule of any one of embodiments 1 to 19, 21 to 36, 38, and 50, the vector of embodiment 37, or the host cell of embodiment 51 and 52, and a carrier.

Embodiment 55

The composition of embodiment 54, wherein the carrier comprises a poly(lactic acid) (PLA) microsphere, a poly(D, L-lactic-coglycolic-acid) (PLGA) microsphere, a liposome, a micelle, an inverse micelle, a lipid cochleate, or a lipid microtubule.

Embodiment 56

A cell comprising the polypeptide of any one of embodiments 20 and 40 to 49, or the nucleic acid of any one of embodiments 1 to 19, 21 to 36, 38, and 50, or the vector of embodiment 37.

Embodiment 57

The cell of embodiment 56, wherein the cell is a human cell.

Embodiment 58

The cell of embodiment 56 or 57, wherein the cell is a liver cell.

Embodiment 59

The cell of embodiment 56, wherein the cell is a rodent cell, a mouse cell, or a rat cell.

Embodiment 60

The cell of embodiment 59, wherein the cell is a pluripotent cell.

Embodiment 61

A method of detecting an HSD17B13 rs72613567 variant in a human subject, comprising performing an assay on a biological sample comprising an HSD17B13 gene obtained from the human subject, wherein the assay determines whether a thymine is inserted between positions corresponding to positions 12665 and 12666 of SEQ ID NO:1 of the wild type HSD17B13 gene.

Embodiment 62

The method of embodiment 61, wherein the assay comprises or consists of sequencing a portion of the HSD17B13 gene including positions corresponding to positions 12665 and 12666 of SEQ ID NO:1.

Embodiment 63

The method of embodiment 62, wherein the assay comprises or consists of: i) contacting the biological sample with a primer hybridizing to a segment of the HSD17B13 gene that is within about 50 nucleotides of a position of the HSD17B13 gene corresponding to positions 12665 and 12666 of SEQ ID NO:1; ii) extending the primer at least through the position of the HSD17B13 gene corresponding to positions 12665 and 12666 of SEQ ID NO:1: and iii) determining whether a thymine is inserted between the positions corresponding to positions 12665 and 12666 of SEQ ID NO:1 of the wild type HSD17B13 gene in an extension product of the primer.

Embodiment 64

The method of embodiment 61, wherein the assay comprises or consists of contacting the biological sample with a primer or probe that specifically hybridizes to the HSD17B13 rs72613567 variant and not the corresponding wild type HSD17B13 sequence under stringent conditions, and determining whether hybridization has occurred.

Embodiment 65

A method of detecting the presence of one or more of HSD17B13 Transcripts C, D, E, F, G, and H in a human subject, comprising or consisting of performing an assay on a biological sample comprising mRNA or cDNA obtained from the subject, wherein the assay determines the presence of one or more of HSD17B13 Transcripts C, D, E, F, G, and H in the biological sample.

Embodiment 66

The method of embodiment 65, wherein the assay comprises or consists of contacting the biological sample with one or more primers or probes that specifically hybridize to one or more sequences, the combination of which is unique to one or more of: i) SEQ ID NO:5, SEQ ID NO:14, SEQ ID NO:23, or SEQ ID NO:32 (Transcript C), ii) SEQ ID NO:6, SEQ ID NO:15, SEQ ID NO:24, or SEQ ID NO:33 (Transcript D), iii) SEQ ID NO:7, SEQ ID NO:16. SEQ ID NO:25, or SEQ ID NO:34 (Transcript E), iv) SEQ ID NO:8, SEQ ID NO:17, SEQ ID NO:26, or SEQ ID NO:35 (Transcript F), v) SEQ ID NO:10, SEQ ID NO:19, SEQ ID NO:28, or SEQ ID NO:37 (Transcript G), and vi) SEQ ID NO: 11, SEQ ID NO:20, SEQ ID NO:29, or SEQ ID NO:38 (Transcript H), and determining whether hybridization has occurred.

Embodiment 67

The method of embodiment 66, wherein the assay comprises reverse transcription polymerase chain reaction (RT-PCR).

Embodiment 68

The method of embodiment 65 or 66, wherein the one or more primers or probes specifically hybridize to a region corresponding to a region present in: i) SEQ ID NO:6, SEQ ID NO:15, SEQ ID NO:24, or SEQ ID NO:33 (Transcript D), ii) SEQ ID NO:10, SEQ ID NO:19, SEQ ID NO:28, or SEQ ID NO:37 (Transcript G), or iii) SEQ ID NO:11, SEQ ID NO:20, SEQ ID NO:29, or SEQ ID NO:38 (Transcript H) that is not present in SEQ ID NO:3, SEQ ID NO:12. SEQ ID NO:21, or SEQ ID NO:30 (Transcript A).

Embodiment 69

The method of embodiment 68, wherein the one or more primers or probes further specifically hybridize to a region corresponding to a region present in SEQ ID NO:6. SEQ ID NO:15, SEQ ID NO:24, or SEQ ID NO:33 (Transcript D) that is not present in SEQ ID NO: 11, SEQ ID NO:20, SEQ ID NO:29, or SEQ ID NO:38 (Transcript H), and a region present in SEQ ID NO:6, SEQ ID NO:15. SEQ ID NO:24, or SEQ ID NO:33 (Transcript D) that is not present in SEQ ID NO:10, SEQ ID NO:19, SEQ ID NO:28, or SEQ ID NO:37 (Transcript G).

Embodiment 70

The method of embodiment 68, wherein the one or more primers or probes further specifically hybridize to a region corresponding to a region present in SEQ ID NO:11, SEQ ID NO:20, SEQ ID NO:29, or SEQ ID NO:38 (Transcript H) that is not present in SEQ ID NO:6, SEQ ID NO:15, SEQ ID NO:24, or SEQ ID NO:33 (Transcript D).

Embodiment 71

The method of embodiment 68, wherein the one or more primers or probes further specifically hybridize to a region corresponding to a region present in SEQ ID NO:10, SEQ ID NO:19, SEQ ID NO:28, or SEQ ID NO:37 (Transcript G) that is not present in SEQ ID NO:6, SEQ ID NO:15, SEQ ID NO:24, or SEQ ID NO:33 (Transcript D).

Embodiment 72

The method of embodiment 65 or 66, wherein the one or more primers or probes specifically hybridize to a region corresponding to a region present in SEQ ID NO:7, SEQ ID NO:16, SEQ ID NO:25, or SEQ ID NO:34 (Transcript E) that is not present in SEQ ID NO:3, SEQ ID NO:12, SEQ ID NO:21, or SEQ ID NO:30 (Transcript A), optionally wherein the one or more primers or probes further specifically hybridize a region corresponding to a region present in SEQ ID NO:7, SEQ ID NO:16, SEQ ID NO:25, or SEQ ID NO:34 (Transcript E) that is not present in SEQ ID NO:11, SEQ ID NO:20, SEQ ID NO:29, or SEQ ID NO:38 (Transcript H).

Embodiment 73

The method of embodiment 65 or 66, wherein the one or more primers or probes specifically hybridize to a region corresponding to a region present in SEQ ID NO:8, SEQ ID NO:17, SEQ ID NO:26, or SEQ ID NO:35 (Transcript F) that is not present in SEQ ID NO:3, SEQ ID NO: 12, SEQ ID NO:21, or SEQ ID NO:30 (Transcript A).

Embodiment 74

The method of embodiment 65 or 66, wherein the one or more primers or probes specifically hybridize to a region corresponding to a region present in SEQ ID NO:5, SEQ ID NO:14, SEQ ID NO:23, or SEQ ID NO:32 (Transcript C) that is not present in SEQ ID NO:3, SEQ ID NO:12, SEQ ID NO:21, or SEQ ID NO:30 (Transcript A).

Embodiment 75

The method of embodiment 65, wherein the assay comprises RNA sequencing (RNA-Seq).

Embodiment 76

A method of detecting the presence of one or more of HSD17B13 Isoforms C, D, E, F, G, or H in a human subject, comprising or consisting of performing an assay on a biological sample comprising mRNA or cDNA obtained from the human subject, wherein the assay determines the presence of one or more of HSD17B13 Isoforms C, D, E, F, G, or H in the biological sample.

Embodiment 77

A method of determining a human subject's susceptibility to developing a liver disease, comprising or consisting of: a) performing an assay on a biological sample comprising an HSD17B13 gene obtained from the human subject, wherein the assay determines whether a thymine is inserted between positions corresponding to positions 12665 and 12666 of SEQ ID NO:1 of the wild type HSD17B13 gene; and b) classifying the human subject as being at decreased risk for developing the liver disease if a thymine is inserted between the positions corresponding to positions 12665 and 12666 of SEQ ID NO:1 of the wild type HSD17B13 gene, or classifying the human subject as being at increased risk for developing the liver disease if a thymine is not inserted between the positions corresponding to positions 12665 and 12666 of SEQ ID NO:1 of the wild type HSD17B3 gene.

Embodiment 78

The method of embodiment 77, wherein the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH).

Embodiment 79

A method of diagnosing a human subject with fatty liver disease, comprising or consisting of: a) performing an assay on a biological sample comprising an HSD17B13 gene obtained from the human subject, wherein the assay determines whether a thymine is inserted between positions corresponding to positions 12665 and 12666 of SEQ ID NO:1 of the wild type HSD17B13 gene; and b) classifying the human subject as being at decreased risk for progression to more clinically advanced stages of fatty liver disease if a thymine is inserted between the positions corresponding to positions 12665 and 12666 of SEQ ID NO:1 of the wild type HSD17B13 gene, or classifying the human subject as being at increased risk for progression to more clinically advanced stages of fatty liver disease if a thymine is not inserted between the positions corresponding to positions 12665 and 12666 of SEQ ID NO:1 of the wild type HSD17B13 gene.

Embodiment 80

The method of embodiment 79, wherein the assay comprises sequencing a portion of the HSD17B13 gene including positions corresponding to positions 12665 and 12666 of SEQ ID NO:1.

Embodiment 81

The method of any one of embodiments 77 to 80, wherein the assay comprises or consists of: i) contacting the biological sample with a primer hybridizing to a segment of the HSD17B13 gene that is within about 50 nucleotides of positions of the HSD17B13 gene corresponding to positions 12665 and 12666 of SEQ ID NO:1; ii) extending the primer at least through the positions of the HSD17B13 gene corresponding to positions 12665 and 12666 of SEQ ID NO:1; and iii) determining whether a thymine is inserted between the positions corresponding to positions 12665 and 12666 of SEQ ID NO:1 of the wild type HSD17B13 gene in an extension product of the primer.

Embodiment 82

The method of any one of embodiments 77 to 80, wherein the assay comprises or consists of contacting the biological sample with a primer or probe that specifically hybridizes to the HSD17B13 rs72613567 variant and not the corresponding wild type HSD17B13 sequence under stringent conditions, and determining whether hybridization has occurred.

Embodiment 83

A method of determining a human subject's susceptibility to developing a liver disease, comprising or consisting of: a) performing an assay on a biological sample comprising an HSD17B13 mRNA or cDNA obtained from the human subject, wherein the assay determines the presence of one or more of HSD17B13 Transcripts C, D, F, G, and H in the biological sample; and b) classifying the human subject as being at decreased risk for developing the liver disease if HSD17B13 Transcript C, D, F, G, or H is present in the biological sample, or classifying the human subject as being at increased risk for developing the liver disease if HSD17B13 Transcript C, D, F, G, or H is not present in the biological sample.

Embodiment 84

The method of embodiment 83, wherein the assay in step a) determines the presence of HSD17B13 Transcript D.

Embodiment 85

The method of embodiment 83, wherein the assay in step a) determines the expression level of one or more of HSD17B13 Transcripts C, D, F, G, and H in the biological sample, wherein an increased expression level of HSD17B13 Transcript C, D, F, G, or H compared to a control sample from a control human subject homozygous for a wild type HSD17B13 allele indicates a decreased risk for developing the liver disease, and wherein the same or a decreased expression level of HSD17B13 Transcript C, D, F, G, or H compared to the control sample indicates an increased risk for developing the liver disease.

Embodiment 86

The method of embodiment 83, wherein the assay in step a) determines the expression level of one or more of HSD17B13 Transcripts C, D, F, G, and H relative to HSD17B13 Transcript A, B, or E in the biological sample, wherein an increased ratio of HSD17B13 Transcript C, D, F, G, or H expression relative to HSD17B13 Transcript A, B, or E expression compared to the ratio in a control sample from a control human subject homozygous for a wild type HSD17B13 allele indicates a decreased risk for developing the liver disease, or wherein the same or a decreased ratio of HSD17B13 Transcript C, D, F, G. or H expression relative to HSD17B13 Transcript A, B, or E expression compared to the ratio in the control sample indicates an increased risk for developing the liver disease.

Embodiment 87

The method of embodiment 86, wherein the assay in step a) determines the expression level of HSD17B13 Transcript D relative to the expression level of HSD17B13 Transcript A in the biological sample.

Embodiment 88

The method of any one of embodiments 82 to 87, wherein the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH).

Embodiment 89

A method of diagnosing a human subject with fatty liver disease, comprising or consisting of: a) performing an assay on a biological sample comprising an HSD17B13 mRNA or cDNA obtained from the human subject, wherein the assay determines the presence of one or more of HSD17B13 Transcripts C, D, F, G, and H in the biological sample; and b) classifying the human subject as being at decreased risk for progression to more clinically advanced stages of fatty liver disease if HSD17B13 Transcript C, D, F, G, or H is present in the biological sample, or classifying the human subject as being at increased risk for progression to more clinically advanced stages of fatty liver disease if HSD17B13 Transcript C, D, F, G, or H is not present in the biological sample.

Embodiment 90

The method of embodiment 89, wherein the assay in step a) determines the presence of HSD17B13 Transcript D.

Embodiment 91

The method of embodiment 89, wherein the assay in step a) determines the expression level of one or more of HSD17B13 Transcripts C, D, F, G, and H in the biological sample, wherein an increased expression level of HSD17B13 Transcript C, D, F, G, or H compared to a control sample from a control human subject homozygous for a wild type HSD17B13 allele indicates a decreased risk for progression to more clinically advanced stages of liver disease, or wherein the same or a decreased expression level of HSD17B13 Transcript C, D, F, G, or H compared to the control sample indicates an increased risk for progression to more clinically advanced stages of liver disease.

Embodiment 92

The method of embodiment 89, wherein the assay in step a) determines the expression level of one or more of HSD17B13 Transcripts C, D, F, G, and H relative to HSD17B13 Transcript A, B, or E in the biological sample, wherein an increased ratio of HSD17B13 Transcript C, D, F, G, or H expression relative to HSD17B13 Transcript A, B, or E expression compared to the ratio in a control sample from a control human subject homozygous for a wild type HSD17B13 allele indicates a decreased risk for progression to more clinically advanced stages of liver disease, or wherein the same or a decreased ratio of HSD17B13 Transcript C, D, F, G, or H expression relative to HSD17B13 Transcript A, B, or E expression compared to the ratio in the control sample indicates an increased risk for progression to more clinically advanced stages of liver disease.

Embodiment 93

The method of embodiment 92, wherein the assay in step a) determines the expression level of HSD17B13 Transcript D relative to the expression level of HSD17B13 Transcript A in the biological sample.

Embodiment 94

The method of any one of embodiments 83 to 93, wherein the assay in step a) comprises or consists of contacting the biological sample with one or more primers or probes that specifically hybridize to a segment corresponding to a segment present in: i) SEQ ID NO:6, SEQ ID NO:15, SEQ ID NO:24, or SEQ ID NO:33 (Transcript D); ii) SEQ ID NO:10, SEQ ID NO:19, SEQ ID NO:28, or SEQ ID NO:37 (Transcript G); or SEQ ID NO:11, SEQ ID NO:20, SEQ ID NO:29, or SEQ ID NO:38 (Transcript H) that is not present in SEQ ID NO:3, SEQ ID NO: 12, SEQ ID NO:21, or SEQ ID NO:30 (Transcript A), and determining whether hybridization has occurred.

Embodiment 95

The method of any one of embodiments 82 to 93, wherein the assay in step a) comprises or consists of contacting the biological sample with one or more primers or probes that specifically hybridize to a segment corresponding to a segment present within SEQ ID NO:8, SEQ ID NO: 17, SEQ ID NO:26, or SEQ ID NO:35 (Transcript F) that is not present in SEQ ID NO:3, SEQ ID NO:12, SEQ ID NO:21, or SEQ ID NO:30 (Transcript A), and determining whether hybridization has occurred.

Embodiment 96

The method of any one of embodiments 82 to 93, wherein the assay in step a) comprises or consists of contacting the biological sample with one or more primers or probes that specifically hybridize to a segment corresponding to a segment present within SEQ ID NO:5, SEQ ID NO: 14, SEQ ID NO:23, or SEQ ID NO:32 (Transcript C) that is not present in SEQ ID NO:3, SEQ ID NO:12, SEQ ID NO:21, or SEQ ID NO:30 (Transcript A), and determining whether hybridization has occurred.

Embodiment 97

The method of any one of embodiments 82 to 96, wherein the assay in step a) comprises reverse transcription polymerase chain reaction (RT-PCR) or quantitative RT-PCR (qRT-PCR).

Embodiment 98

The method of any one of embodiments 85 to 96, wherein the assay in step a) comprises RNA sequencing (RNA-Seq) followed by determination of the presence and quantity of one or more of HSD17B13 Transcripts C, D, F, G, and H in the biological sample.

Embodiment 99

A method of determining a human subject's susceptibility to developing a liver disease, comprising or consisting of: a) detecting whether one or more of HSD17B13 Isoforms C, D, F, G, and H is present in a biological sample comprising proteins obtained from the human subject; and b) classifying the human subject as being at decreased risk for developing the liver disease if HSD17B13 Isoform C, D, F, G, or H is detected in the biological sample.

Embodiment 100

The method of embodiment 99, wherein the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH).

Embodiment 101

The method of embodiments 99 or 100, wherein the detecting in step a) determines the expression level of one or more of HSD17B13 Isoforms C, D, F, G, and H in the biological sample, wherein an increased expression level of HSD17B13 Isoform C, D, F, G, or H compared to a control sample from a control human subject homozygous for a wild type HSD17B13 allele indicates a decreased risk for developing the liver disease.

Embodiment 102

A method of diagnosing a human subject with fatty liver disease, comprising or consisting of: a) detecting whether one or more of HSD17B13 Isoforms C, D, F, G, or H is present in a biological sample comprising proteins obtained from the human subject; and b) classifying the human subject as being at decreased risk for progression to more clinically advanced stages of liver disease if HSD17B13 Isoform C, D, F, G, or H is detected in the biological sample.

Embodiment 103

The method of embodiment 102, wherein the detecting in step a) determines the expression level of one or more of HSD17B13 Isoforms C, D, F, G, and H in the biological sample, wherein an increased expression level of HSD17B13 Isoform C, D, F, G, or H compared to a control sample from a control human subject homozygous for a wild type HSD17B13 allele indicates a decreased risk for progression to more clinically advanced stages of liver disease.

Embodiment 104

The method of any one of embodiments 77 to 103, further comprising or consisting of administering a therapeutic that prevents or alleviates symptoms associated with progression from simple steatosis to one or more of steatohepatitis, fibrosis, cirrhosis, and hepatocellular carcinoma.

Embodiment 105

An isolated nucleic acid comprising at least 15 contiguous nucleotides of an HSD17B13 gene and having a thymine inserted between nucleotides corresponding to positions 12665 and 12666 of SEQ ID NO:1 when optimally aligned with SEQ ID NO:1.

Embodiment 106

The isolated nucleic acid of embodiment 105, wherein the contiguous nucleotides are at least 90%, at least 95%, at least 96%, at least 97%, at least 98%, or at least 99% identical to a corresponding sequence in SEQ ID NO:2 including position 12666 of SEQ ID NO: 2 when optimally aligned with SEQ ID NO:2.

Embodiment 107

The isolated nucleic acid of embodiment 105 or 106, wherein the HSD17B13 gene is a human HSD17B13 gene.

Embodiment 108

The isolated nucleic acid of any preceding embodiment, wherein the isolated nucleic acid comprises at least 15, at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 11000, at least 12000, at least 13000, at least 14000, at least 15000, at least 16000, at least 17000, at least 18000, or at least 19000 contiguous nucleotides of SEQ ID NO:2.

Embodiment 109

The isolated nucleic acid of any preceding embodiment, wherein the isolated nucleic acid comprises an HSD17B13 minigene in which one or more nonessential segments of the gene have been deleted with respect to a corresponding wild type HSD17B13 gene.

Embodiment 110

The isolated nucleic acid of embodiment 109, wherein the deleted segments comprise one or more intronic sequences.

Embodiment 111

The isolated nucleic acid of embodiment 109 or 110, wherein the isolated nucleic acid further comprises an intron corresponding to intron 6 of SEQ ID NO:2 when optimally aligned with SEQ ID NO:2.

Embodiment 112

The isolated nucleic acid of embodiment 111, wherein the intron is intron 6 of SEQ ID NO:2.

Embodiment 113

An isolated nucleic acid comprising at least 15 contiguous nucleotides encoding all or part of an HSD17B13 protein, wherein the contiguous nucleic acids comprise a segment that is at least 90%, at least 95%, at least 96%, at least 97%, at least 98%, at least 99%, or 100% identical to a segment present in SEQ ID NO:24 (HSD17B13 Transcript D), SEQ ID NO:28 (HSD17B13 Transcript G), and SEQ ID NO:29 (HSD17B13 Transcript H) that is not present in SEQ ID NO:21 (HSD17B13 Transcript A).

Embodiment 114

The isolated nucleic acid of embodiment 113, wherein the contiguous nucleotides further comprise a segment that is at least 90%, at least 95%, at least 96%, at least 97%, at least 98%, at least 99%, or 100% identical to a segment present in SEQ ID NO:24 (HSD17B13 Transcript D) that is not present SEQ ID NO:29 (HSD17B13 Transcript H), and wherein the contiguous nucleotides further comprise a segment that is at least 90%, at least 95%, at least 96%, at least 97%, at least 98%, at least 99%, or 100% identical to a segment present in SEQ ID NO:24 (HSD17B13 Transcript D) that is not present in SEQ ID NO:28 (HSD17B13 Transcript G).

Embodiment 115

The isolated nucleic acid of embodiment 113, wherein the contiguous nucleotides further comprise a segment that is at least 90%, at least 95%, at least 96%, at least 97%, at least 98%, at least 99%, or 100% identical to a segment present in SEQ ID NO:29 (HSD17B13 Transcript H) that is not present in SEQ ID NO:24 (HSD17B13 Transcript D).

Embodiment 116

The isolated nucleic acid of embodiment 113, wherein the contiguous nucleotides further comprise a segment that is at least 90%, at least 95%, at least 96%, at least 97%, at least 98%, at least 99%, or 100% identical to a segment present in SEQ ID NO:28 (HSD17B13 Transcript G) that is not present in SEQ ID NO:24 (HSD17B13 Transcript D).

Embodiment 117

An isolated nucleic acid comprising at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO:25 (HSD17B13 Transcript E) that is not present in SEQ ID NO:21 (HSD17B13 Transcript A), optionally wherein the contiguous nucleotides further comprise a segment that is at least 90%, at least 95%, at least 96%, at least 97%, at least 98%, at least 99%, or 100% identical to a segment present in SEQ ID NO:25 (HSD17B13 Transcript E) that is not present in SEQ ID NO:29 (HSD17B13 Transcript H).

Embodiment 118

An isolated nucleic acid comprising at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO:26 (HSD17B13 Transcript F) that is not present in SEQ ID NO:21 (HSD17B13 Transcript A).

Embodiment 119

An isolated nucleic acid comprising at least 15 contiguous nucleotides encoding all or part of an HSD17B13 protein, wherein the contiguous nucleotides comprise a segment that is at least 90%, at least 95%, at least 96%, at least 97%, at least 98%, at least 99%, or 100% identical to a segment present in SEQ ID NO:23 (HSD17B13 Transcript C) that is not present in SEQ ID NO:21 (HSD17B13 Transcript A).

Embodiment 120

The isolated nucleic acid of any one of embodiments 113-119, wherein the HSD17B13 protein is a human HSD17B13 protein.

Embodiment 121

The isolated nucleic acid of any one of embodiments 13-120, wherein the isolated nucleic acid comprises at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, or at least 2000 contiguous nucleotides encoding all or part of an HSD17B13 protein.

Embodiment 122

An isolated nucleic acid comprising a sequence at least 90%, at least 95%, at least 96%, at least 97%, at least 98%, at least 99%, or 100% identical to the sequence set forth in SEQ ID NO:23, 24, 25, 26, 28, or 29 (HSD17B13 Transcript C, D, E, F, G, or H) and encoding an HSD17B13 protein comprising the sequence set forth in SEQ ID NO:41, 42, 43, 44, 46, or 47 (HSD17B13 Isoform C, D, E, F, G, or H), respectively.

Embodiment 123

The isolated nucleic acid of any one of embodiments 113-122, wherein the contiguous nucleotides comprise sequence from at least two different exons of an HSD17B13 gene without an intervening intron.

Embodiment 124

A protein encoded by the isolated nucleic acid of any preceding embodiment.

Embodiment 125

An isolated nucleic acid comprising at least 15 contiguous nucleotides that hybridize to an HSD17B13 gene at a segment that includes or is within 1000, 500, 400, 300, 200, 100, 50, 45, 40, 35, 30, 25, 20, 15, 10, or 5 nucleotides of a position corresponding to position 12666 in SEQ ID NO:2 when optimally aligned with SEQ ID NO:2.

Embodiment 126

The isolated nucleic acid of embodiment 125, wherein the segment is at least 90%, at least 95%, at least 96%, at least 97%, at least 98%, or at least 99% identical to a corresponding sequence in SEQ ID NO:2 when optimally aligned with SEQ ID NO:2.

Embodiment 127

The isolated nucleic acid of embodiment 125 or 126, wherein the segment comprises at least 20, 25, 30, 35, 40, 45, 50, 60, 70, 80, 90, 100, 200, 300, 400, 500, 600, 700, 800, 900, 1000, or 2000 contiguous nucleotides of SEQ ID NO:2.

Embodiment 128

The isolated nucleic acid of any one of embodiments 125-127, wherein the segment includes position 12666 in SEQ ID NO:2 or a position corresponding to position 12666 in SEQ ID NO:2 when optimally aligned with SEQ ID NO:2.

Embodiment 129

The isolated nucleic acid of any one of embodiments 125-128, wherein the HSD17B13 gene is a human HSD17B13 gene.

Embodiment 130

An isolated nucleic acid that hybridizes to at least 15 contiguous nucleotides of a nucleic acid encoding an HSD17B13 protein, wherein the contiguous nucleotides comprise a segment that is at least 90%, at least 95%, at least 96%, at least 97%, at least 98%, at least 99%, or 100% identical to a segment present in SEQ ID NO:24 (HSD17B13 Transcript D), SEQ ID NO:28 (HSD17B13 Transcript G), and SEQ ID NO:29 (HSD17B13 Transcript H) that is not present within SEQ ID NO:21 (HSD17B13 Transcript A).

Embodiment 131

An isolated nucleic acid that hybridizes to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment present in SEQ ID NO:25 (HSD17B13 Transcript E) and SEQ ID NO:29 (HSD17B13 Transcript H) that is not present in SEQ ID NO:21 (HSD17B13 Transcript A).

Embodiment 132

An isolated nucleic acid that hybridizes to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment in SEQ ID NO:26 (HSD17B13 Transcript F) that is not present in SEQ ID NO:21 (HSD17B13 Transcript A).

Embodiment 133

An isolated nucleic acid that hybridizes to at least 15 contiguous nucleotides of a nucleic acid encoding an HSD17B13 protein, wherein the contiguous nucleotides comprise a segment that is at least 90%, at least 95%, at least 96%, at least 97%, at least 98%, or at least 99% identical to a segment present in SEQ ID NO:23 (HSD17B13 Transcript C) that is not present in SEQ ID NO:21 (HSD17B13 Transcript A).

Embodiment 134

The isolated nucleic acid of any one of embodiments 130-133, wherein the HSD17B13 protein is a human HSD17B13 protein.

Embodiment 135

The isolated nucleic acid of any one of embodiments 130-133, wherein the isolated nucleic acid is an antisense RNA, a short hairpin RNA, or a small-interfering RNA.

Embodiment 136

The isolated nucleic acid of any one of embodiments 125-135, wherein the isolated nucleic acid is up to about 30, 40, 50, 100, 200, 300, 400, 500, 600, 700, 800, 900, or 1000 nucleotides in length.

Embodiment 137

The isolated nucleic acid of any one of embodiments 105-123, 125-134, and 136, wherein the isolated nucleic acid comprises DNA.

Embodiment 138

The isolated nucleic acid of any one of embodiments 105-123 and 125-136, wherein the isolated nucleic acid comprises RNA.

Embodiment 139

The isolated nucleic acid of any one of embodiments 105-123 and 125-138, wherein the isolated nucleic acid is linked to a heterologous nucleic acid or comprises a heterologous label.

Embodiment 140

The isolated nucleic acid of embodiment 139, wherein the heterologous label is a fluorescent label.

Embodiment 141

A vector comprising the isolated nucleic acid of any one of embodiments 105-123 and 125-140 and a heterologous nucleic acid sequence.

Embodiment 142

The isolated nucleic acid of any one of embodiments 105-123 and 125-140, wherein the isolated nucleic acid includes a non-natural nucleotide.

Embodiment 143

Use of the isolated nucleic acid of any one of embodiments 105-123 and 125-142 in a method of detecting an HSD17B13 rs72613567 variant in a subject, a method of detecting the presence of HSD17B13 Transcript C, D, E, F, G, or H in a subject, a method of determining a subject's susceptibility to developing a chronic liver disease, method of diagnosing a subject with fatty liver disease, or a method of modifying an HSD17B13 gene in a cell, a method for altering expression of an HSD17B13 gene in a cell.

Embodiment 144

An isolated polypeptide comprising at least 8 contiguous amino acids of an HSD17B13 protein, wherein the contiguous amino acids comprise a segment that is at least 90%, at least 95%, at least 96%, at least 97%, at least 98%, at least 99%, or 100% identical to a segment present in SEQ ID NO:42 (HSD17B13 Isoform D), SEQ ID NO:46 (HSD17B13 Isoform G), and SEQ ID NO:47 (HSD17B13 Isoform H) that is not present in SEQ ID NO:39 (HSD17B13 Isoform A).

Embodiment 145

The isolated polypeptide of embodiment 144, wherein the contiguous amino acids further comprise a segment that is at least 90%, at least 95%, at least 96%, at least 97%, at least 98%, at least 99%, or 100% identical to a segment present in SEQ ID NO:42 (HSD17B13 Isoform D) that is not present in SEQ ID NO:47 (HSD17B13 Isoform H), and wherein the contiguous amino acids further comprise a segment that is at least 90%, at least 95%, at least 96%, at least 97%, at least 98%, at least 99%, or 100% identical to a segment present in SEQ ID NO:42 (HSD17B13 Isoform D) that is not present in SEQ ID NO:46 (HSD17B13 Isoform G).

Embodiment 146

The isolated polypeptide of embodiment 144, wherein the contiguous amino acids further comprise a segment that is at least 90%, at least 95%, at least 96%, at least 97%, at least 98%, at least 99%, or 100% identical to a segment present in SEQ ID NO:47 (HSD17B13 Isoform H) that is not present in SEQ ID NO:42 (HSD17B13 Isoform D).

Embodiment 147

The isolated polypeptide of embodiment 144, wherein the contiguous amino acids further comprise a segment that is at least 90%, at least 95%, at least 96%, at least 97%, at least 98%, at least 99%, or 100% identical to a segment present in SEQ ID NO:46 (HSD17B13 Isoform G) that is not present in SEQ ID NO:42 (HSD17B13 Isoform D).

Embodiment 148

An isolated polypeptide comprising at least 8 contiguous amino acids of an HSD17B13 protein, wherein the contiguous amino acids comprise a segment that is least 90%, at least 95%, at least 96%, at least 97%, at least 98%, at least 99%, or 100% identical to a segment present in SEQ ID NO:43 (HSD17B13 Isoform E) that is not present in SEQ ID NO:39 (HSD17B13 Isoform A), optionally wherein the contiguous amino acids further comprise a segment that is at least 90%, at least 95%, at least 96%, at least 97%, at least 98%, at least 99%, or 100% identical to a segment present in SEQ ID NO:43 (HSD17B13 Isoform E) that is not present in SEQ ID NO:47 (HSD17B13 Isoform H).

Embodiment 149

An isolated polypeptide comprising at least 8 contiguous amino acids of an HSD17B13 protein, wherein the contiguous amino acids comprise a segment that is least 90%, at least 95%, at least 96%, at least 97%, at least 98%, at least 99%, or 100% identical to a segment present in SEQ ID NO:44 (HSD17B13 Isoform F) that is not present in SEQ ID NO:39 (HSD17B13 Isoform A).

Embodiment 150

An isolated polypeptide comprising at least 8 contiguous amino acids of an HSD17B13 protein, wherein the contiguous amino acids comprise a segment that is at least 90%, at least 95%, at least 96%, at least 97%, at least 98%, at least 99%, or 100% identical to a segment present in SEQ ID NO:41 (HSD17B13 Isoform C) that is not present in SEQ ID NO:39 (HSD17B13 Isoform A).

Embodiment 151

An isolated polypeptide comprising a sequence at least 90%, at least 95%, at least 96%, at least 97%, at least 98%, at least 99%, or 100% identical to SEQ ID NO:41, 42, 43, 44, 46, or 47 (HSD17B13 Isoform C, D, E, F, G, or H) when optimally aligned with SEQ ID NO:41, 42, 43, 44, 46, or 47 (HSD17B13 Isoform C, D, E, F, G, or H), respectively.

Embodiment 152

The isolated polypeptide of any one of embodiments 144-151 which is linked to a heterologous molecule.

Embodiment 153

The isolated polypeptide of embodiment 152, wherein the heterologous molecule is an immunoglobulin Fc domain, a peptide tag, a transduction domain, poly(ethylene glycol), polysialic acid, or glycolic acid.

Embodiment 154

An isolated nucleic acid encoding the isolated polypeptide of any one of embodiments 144-153.

Embodiment 155

A host cell comprising the isolated nucleic acid of embodiment 154 operably linked to a heterologous promoter active in the host cell.

Embodiment 156

The host cell of embodiment 155, wherein the host cell is a bacterial cell, a yeast cell, an insect cell, or a mammalian cell.

Embodiment 157

A method of producing the isolated polypeptide of any one of embodiments 144-153, comprising culturing the host cell of embodiment 155 or 156, whereby the nucleic acid is expressed, and recovering the isolated polypeptide.

Embodiment 158

A composition comprising the isolated polypeptide of any one of embodiments 124 and 144-153, or the isolated nucleic acid of any one of embodiments 105-123, 125-140, 142, and 154, the vector of embodiment 141, and a carrier increasing the stability of the isolated polypeptide, the isolated nucleic acid, or the vector.

Embodiment 159

The composition of embodiment 158, wherein the carrier comprises a poly(lactic acid) (PLA) microsphere, a poly(D, L-lactic-coglycolic-acid) (PLGA) microsphere, a liposome, a micelle, an inverse micelle, a lipid cochleate, or a lipid microtubule.

Embodiment 160

A cell comprising the isolated polypeptide of any one of embodiments 124 and 144-153, or the isolated nucleic acid of any one of embodiments 105-123, 125-140, 142, and 154, or the vector of embodiment 141.

Embodiment 161

The cell of embodiment 160, wherein the cell is a human cell.

Embodiment 162

The cell of embodiment 160 or 161, wherein the cell is a liver cell.

Embodiment 163

The cell of embodiment 160, wherein the cell is a rodent cell, a mouse cell, or a rat cell.

Embodiment 164

The cell of embodiment 163, wherein the cell is a pluripotent cell.

Embodiment 165

A method of detecting an HSD17B13 rs72613567 variant in a human subject, comprising: (a) obtaining a biological sample from the human subject comprising an HSD17B13 gene; and (b) performing an assay on the biological sample that determines that a thymine is inserted between positions of the HSD17B13 gene corresponding to positions 12665 and 12666 of SEQ ID NO:1 when the HSD17B13 gene and SEQ ID NO:1 are optimally aligned.

Embodiment 166

The method of embodiment 165, wherein the assay comprises sequencing a portion of the HSD17B13 gene including positions corresponding to positions 12665 and 12666 of SEQ ID NO:1 when the HSD17B13 gene and SEQ ID NO:1 are optimally aligned.

Embodiment 167

The method of embodiment 166, wherein the assay comprises: (i) contacting the biological sample with a primer hybridizing to a segment of the HSD17B13 gene that is proximate to a position of the HSD17B13 gene corresponding to positions 12665 and 12666 of SEQ ID NO:1 when the HSD17B13 gene and SEQ ID NO:1 are optimally aligned; (ii) extending the primer at least through the position of the HSD17B13 gene corresponding to positions 12665 and 12666 of SEQ ID NO:1; and (iii) determining the whether a thymine is inserted between the positions of the HSD17B13 gene corresponding to positions 12665 and 12666 of SEQ ID NO:1 in an extension product of the primer.

Embodiment 168

The method of embodiment 165, wherein the assay comprises contacting the biological sample with a primer or probe that specifically hybridizes to the HSD17B13 rs72613567 variant and not the corresponding wild type HSD17B13 sequence under stringent conditions, and determining whether hybridization has occurred.

Embodiment 169

A method of detecting the presence of one or more of HSD17B13 Transcripts C, D, E, F, G, and H in a human subject, comprising: (a) obtaining a biological sample from the human subject comprising mRNA or cDNA; and (b) performing an assay on the biological sample that determines the presence of one or more of HSD17B13 Transcripts C, D, E, F, G, and H in the biological sample.

Embodiment 170

The method of embodiment 169, wherein the assay comprises contacting the biological sample with one or more primers or probes that specifically hybridize to one or more sequences, the combination of which is unique to one or more of SEQ ID NOS:23, 24, 25, 26, 28, and 29 (HSD17B13 Transcripts C-H) among SEQ ID NOS:21, 22, 23, 24, 25, 26, 28, and 29 (HSD17B13 Transcripts A-H), and determining whether hybridization has occurred.

Embodiment 171

The method of embodiment 170, wherein the assay comprises reverse transcription polymerase chain reaction (RT-PCR).

Embodiment 172

The method of embodiment 169 or 170, wherein the one or more primers or probes specifically hybridize to a region present in SEQ ID NO:24 (HSD17B13 Transcript D), SEQ ID NO:28 (HSD17B13 Transcript G), and SEQ ID NO:29 (HSD17B13 Transcript H) that is not present in SEQ ID NO:21 (HSD17B13 Transcript A).

Embodiment 173

The method of embodiment 172, wherein the one or more primers or probes further specifically hybridize to a region present in SEQ ID NO:24 (HSD17B13 Transcript D) that is not present in SEQ ID NO:29 (HSD17B13 Transcript H) and a region present in SEQ ID NO:24 (HSD17B13 Transcript D) that is not present in SEQ ID NO:28 (HSD17B13 Transcript G).

Embodiment 174

The method of embodiment 172, wherein the one or more primers or probes further specifically hybridize to a region present in SEQ ID NO:29 (HSD17B13 Transcript H) that is not present in SEQ ID NO:24 (HSD17B13 Transcript D).

Embodiment 175

The method of embodiment 172, wherein the one or more primers or probes further specifically hybridize to a region present in SEQ ID NO:28 (HSD17B13 Transcript G) that is not present in SEQ ID NO:24 (HSD17B13 Transcript D).

Embodiment 176

The method of embodiment 169 or 170, wherein the one or more primers or probes specifically hybridize to a region present in SEQ ID NO:25 (HSD17B13 Transcript E) that is not present in SEQ ID NO:21 (HSD17B13 Transcript A), optionally wherein the one or more primers or probes further specifically hybridize a region present in SEQ ID NO:25 (HSD17B13 Transcript E) that is not present in SEQ ID NO:29 (HSD17B13 Transcript H).

Embodiment 177

The method of embodiment 169 or 170, wherein the one or more primers or probes specifically hybridize to a region present in SEQ ID NO:26 (HSD17B13 Transcript F) that is not present in SEQ ID NO:21 (HSD17B13 Transcript A).

Embodiment 178

The method of embodiment 169 or 170, wherein the one or more primers or probes specifically hybridize to a region present in SEQ ID NO:23 (HSD17B13 Transcript C) that is not present in SEQ ID NO:21 (HSD17B13 Transcript A).

Embodiment 179

The method of embodiment 169, wherein the assay comprises RNA sequencing (RNA-Seq).

Embodiment 180

A method of detecting the presence of one or more of HSD17B13 Isoforms C, D, E, F, G, or H in a human subject, comprising: (a) obtaining a biological sample from the human subject comprising mRNA or cDNA; and (b) performing an assay on the biological sample that determines the presence of one or more of HSD17B13 Isoforms C, D, E, F, G, or H in the biological sample.

Embodiment 181

A method of determining a human subject's susceptibility to developing a chronic liver disease, comprising: (a) obtaining a biological sample from the human subject comprising an HSD17B13 gene; (b) performing an assay on the biological sample that determines whether a thymine is inserted between positions of the HSD17B13 gene corresponding to positions 12665 and 12666 of SEQ ID NO:1 when the HSD17B13 gene and SEQ ID NO:1 are optimally aligned; and (c) classifying the human subject as being at decreased risk for developing the chronic liver disease if a thymine is inserted between the positions of the HSD17B13 gene corresponding to positions 12665 and 12666 of SEQ ID NO:1, or classifying the human subject as being at increased risk for developing the chronic liver disease if a thymine is not inserted between the positions of the HSD17B13 gene corresponding to positions 12665 and 12666 of SEQ ID NO:1.

Embodiment 182

The method of embodiment 181, wherein the chronic liver disease is selected from the group consisting of non-alcoholic fatty liver disease (NAFLD), alcoholic liver fatty liver disease, cirrhosis, and hepatocellular carcinoma.

Embodiment 183

A method of diagnosing a human subject with fatty liver disease, comprising: (a) obtaining a biological sample from the human subject comprising an HSD17B13 gene; (b) performing an assay on the biological sample that determines whether a thymine is inserted between positions of the HSD17B13 gene corresponding to positions 12665 and 12666 of SEQ ID NO:1 when the HSD17B13 gene and SEQ ID NO:1 are optimally aligned; and (c) classifying the human subject as being at decreased risk for progression to more clinically advanced stages of chronic liver disease if a thymine is inserted between the positions of the HSD17B13 gene corresponding to positions 12665 and 12666 of SEQ ID NO:1, or classifying the human subject as being at increased risk for progression to more clinically advanced stages of chronic liver disease if a thymine is not inserted between the positions of the HSD17B13 gene corresponding to positions 12665 and 12666 of SEQ ID NO: 1.

Embodiment 184

The method of embodiment 183, wherein the assay comprises sequencing a portion of the HSD17B13 gene including positions corresponding to positions 12665 and 12666 of SEQ ID NO:1 when the HSD17B13 gene and SEQ ID NO:1 are optimally aligned.

Embodiment 185

The method of any one of embodiments 181-184, wherein the assay comprises: (i) contacting the biological sample with a primer hybridizing to a segment of the HSD17B13 gene that is proximate to positions of the HSD17B13 gene corresponding to positions 12665 and 12666 of SEQ ID NO:1 when the HSD17B13 gene and SEQ ID NO:1 are optimally aligned; (ii) extending the primer at least through the positions of the HSD17B13 gene corresponding to positions 12665 and 12666 of SEQ ID NO: 1; and (iii) determining whether a thymine is inserted between the positions of the HSD17B13 gene corresponding to positions 12665 and 12666 of SEQ ID NO:1 in an extension product of the primer.

Embodiment 186

The method of any one of embodiments 181-184, wherein the assay comprises contacting the biological sample with a primer or probe that specifically hybridizes to the HSD17B13 rs72613567 variant and not the corresponding wild type HSD17B13 sequence under stringent conditions, and determining whether hybridization has occurred.

Embodiment 187

A method of determining a human subject's susceptibility to developing a chronic liver disease, comprising: (a) obtaining a biological sample from the human subject comprising mRNA or cDNA; (b) performing an assay on the biological sample that determines the presence of one or more of HSD17B13 Transcripts C, D, F, G, and H in the biological sample; and (c) classifying the human subject as being at decreased risk for developing the chronic liver disease if HSD17B13 Transcript C, D, F, G, or H is present in the biological sample, or classifying the human subject as being at increased risk for developing the chronic liver disease if HSD17B13 Transcript C, D, F, G, or H is not present in the biological sample.

Embodiment 188

The method of embodiment 187, wherein the assay in step (b) determines the presence of HSD17B13 Transcript D.

Embodiment 189

The method of embodiment 187, wherein the assay in step (b) determines the expression level of one or more of HSD17B13 Transcripts C, D, F, G, and H in the biological sample, wherein an increased expression level of HSD17B13 Transcript C, D, F, G, or H compared to a control sample from a control human subject homozygous for a wild type HSD17B13 allele indicates a decreased risk for developing the chronic liver disease, and wherein the same or a decreased expression level of HSD17B13 Transcript C, D, F, G, or H compared to the control sample indicates an increased risk for developing the chronic liver disease.

Embodiment 190

The method of embodiment 187, wherein the assay in step (b) determines the expression level of one or more of HSD17B13 Transcripts C, D, F, G, and H relative to HSD17B13 Transcript A, B, or E in the biological sample, wherein an increased ratio of HSD17B13 Transcript C, D, F, G, or H expression relative to HSD17B13 Transcript A, B, or E expression compared to the ratio in a control sample from a control human subject homozygous for a wild type HSD17B13 allele indicates a decreased risk for developing the chronic liver disease, or wherein the same or a decreased ratio of HSD17B13 Transcript C, D, F, G, or H expression relative to HSD17B13 Transcript A, B, or E expression compared to the ratio in the control sample indicates an increased risk for developing the chronic liver disease.

Embodiment 191

The method of embodiment 190, wherein the assay in step (b) determines the expression level of HSD17B13 Transcript D relative to the expression level of HSD17B13 Transcript A in the biological sample.

Embodiment 192

The method of any one of embodiments 187-191, wherein the chronic liver disease is selected from the group consisting of nonalcoholic fatty liver disease (NAFLD), alcoholic liver fatty liver disease, cirrhosis, and hepatocellular carcinoma.

Embodiment 193

A method of diagnosing a human subject with fatty liver disease, comprising: (a) obtaining a biological sample from the human subject comprising mRNA or cDNA; (b) performing an assay on the biological sample that determines the presence of one or more of HSD17B13 Transcripts C, D, F, G, and H in the biological sample; and (c) classifying the human subject as being at decreased risk for progression to more clinically advanced stages of chronic liver disease if HSD17B13 Transcript C, D, F, G, or H is present in the biological sample, or classifying the human subject as being at increased risk for progression to more clinically advanced stages of chronic liver disease if HSD17B13 Transcript C, D, F, G, or H is not present in the biological sample.

Embodiment 194

The method of embodiment 193, wherein the assay in step (b) determines the presence of HSD17B13 Transcript D.

Embodiment 195

The method of embodiment 193, wherein the assay in step (b) determines the expression level of one or more of HSD17B13 Transcripts C, D, F, G, and H in the biological sample, wherein an increased expression level of HSD17B13 Transcript C, D, F, G, or H compared to a control sample from a control human subject homozygous for a wild type HSD17B13 allele indicates a decreased risk for progression to more clinically advanced stages of chronic liver disease, or wherein the same or a decreased expression level of HSD17B13 Transcript C, D, F, G, or H compared to the control sample indicates an increased risk for progression to more clinically advanced stages of chronic liver disease.

Embodiment 196

The method of embodiment 193, wherein the assay in step (b) determines the expression level of one or more of HSD17B13 Transcripts C, D, F, G, and H relative to HSD17B13 Transcript A, B, or E in the biological sample, wherein an increased ratio of HSD17B13 Transcript C, D, F, G, or H expression relative to HSD17B13 Transcript A, B, or E expression compared to the ratio in a control sample from a control human subject homozygous for a wild type HSD17B13 allele indicates a decreased risk for progression to more clinically advanced stages of chronic liver disease, or wherein the same or a decreased ratio of HSD17B13 Transcript C, D, F, G, or H expression relative to HSD17B13 Transcript A, B, or E expression compared to the ratio in the control sample indicates an increased risk for progression to more clinically advanced stages of chronic liver disease.

Embodiment 197

The method of embodiment 196, wherein the assay in step (b) determines the expression level of HSD17B13 Transcript D relative to the expression level of HSD17B13 Transcript A in the biological sample.

Embodiment 198

The method of any one of embodiments 187-197, wherein the assay in step (b) comprises contacting the biological sample with one or more primers or probes that specifically hybridize to a segment present in SEQ ID NO:24 (HSD17B13 Transcript D), SEQ ID NO:28 (HSD17B13 Transcript G), and SEQ ID NO:29 (HSD17B13 Transcript H) that is not present in SEQ ID NO:21 (HSD17B13 Transcript A), and determining whether hybridization has occurred.

Embodiment 199

The method of any one of embodiments 187-197, wherein the assay in step (b) comprises contacting the biological sample with one or more primers or probes that specifically hybridize to a segment present within SEQ ID NO:26 (HSD17B13 Transcript F) that is not present in SEQ ID NO:21 (HSD17B13 Transcript A), and determining whether hybridization has occurred.

Embodiment 200

The method of any one of embodiments 187-197, wherein the assay in step (b) comprises contacting the biological sample with one or more primers or probes that specifically hybridize to a segment present within SEQ ID NO:23 (HSD17B13 Transcript C) that is not present in SEQ ID NO:21 (HSD17B13 Transcript A), and determining whether hybridization has occurred.

Embodiment 201

The method of any one of embodiments 187-200, wherein the assay in step (b) comprises reverse transcription polymerase chain reaction (RT-PCR) or quantitative RT-PCR (qRT-PCR).

Embodiment 202

The method of any one of embodiments 187-200, wherein the assay in step (b) comprises RNA sequencing (RNA-Seq) followed by determination of the presence and quantity of one or more of HSD17B13 Transcripts C, D, F, G, and H in the biological sample.

Embodiment 203

A method of determining a human subject's susceptibility to developing a chronic liver disease, comprising: (a) obtaining a biological sample from the human subject comprising proteins; (b) detecting whether one or more of HSD17B13 Isoforms C, D, F, G, and H is present in the biological sample; and (c) classifying the human subject as being at decreased risk for developing the chronic liver disease if HSD17B13 Isoform C, D, F, G, or H is detected in the biological sample.

Embodiment 204

The method of embodiment 203, wherein the chronic liver disease is selected from the group consisting of non-alcoholic fatty liver disease (NAFLD), alcoholic liver fatty liver disease, cirrhosis, and hepatocellular carcinoma.

Embodiment 205

The method of any one of embodiments 203 or 204, wherein the detecting in step (b) determines the expression level of one or more of HSD17B13 Isoforms C, D, F, G, and H in the biological sample, wherein an increased expression level of HSD17B13 Isoform C, D, F, G, or H compared to a control sample from a control human subject homozygous for a wild type HSD17B13 allele indicates a decreased risk for developing the chronic liver disease.

Embodiment 206

A method of diagnosing a human subject with fatty liver disease, comprising: (a) obtaining a biological sample from the human subject comprising proteins; (b) detecting whether one or more of HSD17B13 Isoforms C, D, F, G, or H is present in the biological sample; and (c) classifying the human subject as being at decreased risk for progression to more clinically advanced stages of chronic liver disease if HSD17B13 Isoform C, D, F, G, or H is detected in the biological sample.

Embodiment 207

The method of embodiment 206, wherein the detecting in step (b) determines the expression level of one or more of HSD17B13 Isoforms C, D, F, G, and H in the biological sample, wherein an increased expression level of HSD17B13 Isoform C, D, F, G, or H compared to a control sample from a control human subject homozygous for a wild type HSD17B13 allele indicates a decreased risk for progression to more clinically advanced stages of chronic liver disease.

Embodiment 208

The method of any one of embodiments 181-207, further comprising: (d) administering a therapeutic that prevents or alleviates symptoms associated with progression from simple steatosis to one or more of steatohepatitis, fibrosis, cirrhosis, and hepatocellular carcinoma, or performing the method of any one of embodiments 233-237.

Embodiment 209

A method for decreasing expression of an HSD17B13 gene in a cell, comprising: contacting the genome of the cell with an antisense RNA, an siRNA, or an shRNA that hybridizes to a sequence within exon 7 of SEQ ID NO:21 (HSD17B13 Transcript A) and decreases expression of HSD17B13 Transcript A.

Embodiment 210

The method of embodiment 209, further comprising introducing an expression vector into the cell, wherein the expression vector comprises a recombinant HSD17B13 gene comprising a thymine inserted between nucleotides corresponding to positions 12665 and 12666 of SEQ ID NO:1 when the recombinant HSD17B13 gene is optimally aligned with SEQ ID NO: 1.

Embodiment 211

The method of embodiment 210, wherein the recombinant HSD17B13 gene is a human gene.

Embodiment 212

The method of embodiment 210 or 211, wherein the recombinant HSD17B13 gene is an HSD17B13 minigene in which one or more nonessential segments of the gene have been deleted with respect to a corresponding wild type HSD17B13 gene.

Embodiment 213

The method of embodiment 212, wherein the deleted segments comprise one or more intronic sequences.

Embodiment 214

The method of embodiment 212 or 213, wherein the HSD17B13 minigene comprises an intron corresponding to intron 6 of SEQ ID NO:2 when optimally aligned with SEQ ID NO:2.

Embodiment 215

The method of embodiment 209, further comprising introducing an expression vector into the cell, wherein the expression vector comprises a nucleic acid encoding an HSD17B13 protein that is at least 90%, at least 95%, at least 96%, at least 97%, at least 98%, at least 99%, or 100% identical to SEQ ID NO:42 (HSD17B13 Isoform D).

Embodiment 216

The method of embodiment 215, wherein the nucleic acid encoding the HSD17B13 protein is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 217

The method of embodiment 209, further comprising introducing an HSD17B13 protein or fragment thereof into the cell.

Embodiment 218

The method of embodiment 217, wherein the HSD17B13 protein or fragment thereof is at least 90%, at least 95%, at least 96%, at least 97%, at least 98%, at least 99%, or 100% identical to SEQ ID NO:42 (HSD17B13 Isoform D).

Embodiment 219

A method for modifying a cell, comprising introducing an expression vector into the cell, wherein the expression vector comprises a recombinant HSD17B13 gene comprising a thymine inserted between nucleotides corresponding to positions 12665 and 12666 of SEQ ID NO:1 when the recombinant HSD17B13 gene is optimally aligned with SEQ ID NO:1.

Embodiment 220

The method of embodiment 219, wherein the recombinant HSD17B13 gene is a human gene.

Embodiment 221

The method of embodiment 219 or 220, wherein the recombinant HSD17B13 gene is an HSD17B13 minigene in which one or more nonessential segments of the gene have been deleted with respect to a corresponding wild type HSD17B13 gene.

Embodiment 222

The method of embodiment 221, wherein the deleted segments comprise one or more intronic sequences.

Embodiment 223

The method of embodiment 221 or 222, wherein the HSD17B13 minigene comprises an intron corresponding to intron 6 of SEQ ID NO:2 when optimally aligned with SEQ ID NO:2.

Embodiment 224

A method for modifying a cell, comprising introducing an expression vector into the cell, wherein the expression vector comprises a nucleic acid encoding an HSD17B13 protein that is at least 90%, at least 95%, at least 96%, at least 97%, at least 98%, at least 99%, or 100% identical to SEQ ID NO:42 (HSD17B13 Isoform D).

Embodiment 225

The method of embodiment 224, wherein the nucleic acid encoding the HSD17B13 protein is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 226

A method for modifying a cell, comprising introducing an HSD17B13 protein or fragment thereof into the cell.

Embodiment 227

The method of embodiment 226, wherein the HSD17B13 protein or fragment thereof is at least 90%, at least 95%, at least 96%, at least 97%, at least 98%, at least 99%, or 100% identical to SEQ ID NO:42 (HSD17B13 Isoform D).

Embodiment 228

The method of any one of embodiments 209-227, wherein the cell is a rodent cell, a mouse cell, or a rat cell.

Embodiment 229

The method of any one of embodiments 209-227, wherein the cell is a human cell.

Embodiment 230

The method of any one of embodiments 209-228, wherein the cell is a pluripotent cell.

Embodiment 231

The method of any one of embodiments 209-229, wherein the cell is a differentiated cell.

Embodiment 232

The method of embodiment 231, wherein the cell is a liver cell.

Embodiment 233

A method of treating a subject who is not a carrier of the HSD17B13 rs72613567 variant and has or is susceptible to developing a chronic liver disease comprising introducing into the subject: an antisense RNA, an siRNA, or an shRNA that hybridizes to a sequence within exon 7 or a sequence spanning the exon 6-exon 7 boundary of SEQ ID NO:21 (HSD17B13 Transcript A) and decreases expression of HSD17B13 Transcript A in a liver cell in the subject.

Embodiment 234

The method of embodiment 233, further comprising introducing an expression vector into the subject, wherein the expression vector comprises a recombinant HSD17B13 gene comprising a thymine inserted between nucleotides corresponding to positions 12665 and 12666 of SEQ ID NO:1 when the recombinant HSD17B13 gene is optimally aligned with SEQ ID NO:1, wherein the expression vector expresses the recombinant HSD17B13 gene in the liver cell in the subject.

Embodiment 235

The method of embodiment 233, further comprising introducing an expression vector into the subject, wherein the expression vector comprises a nucleic acid encoding an HSD17B13 protein that is at least 90%, at least 95%, at least 96%, at least 97%, at least 98%, at least 99%, or 100% identical to SEQ ID NO:42 (HSD17B13 Isoform D), wherein the expression vector expresses the nucleic acid encoding the HSD17B13 protein in the liver cell in the subject.

Embodiment 236

The method of embodiment 235, wherein the nucleic acid encoding the HSD17B13 protein is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 237

The method of embodiment 233, further comprising introducing a messenger RNA into the subject, wherein the messenger RNA encodes an HSD17B13 protein that is at least 90%, at least 95%, at least 96%, at least 97%, at least 98%, at least 99%, or 100% identical to SEQ ID NO:42 (HSD17B13 Isoform D), wherein the mRNA expresses the HSD17B13 protein in the liver cell in the subject.

Embodiment 238

The method of embodiment 237, wherein a complementary DNA reverse transcribed from the messenger RNA is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 239

The method of embodiment 233, further comprising introducing an HSD17B13 protein or fragment thereof into the subject.

Embodiment 240

The method of embodiment 239, wherein the HSD17B13 protein or fragment thereof is at least 90%, at least 95%, at least 96%, at least 97%, at least 98%, at least 99%, or 100% identical to SEQ ID NO:42 (HSD17B13 Isoform D).

Embodiment 241

A method of treating a subject who is not a carrier of the HSD17B13 rs72613567 variant and has or is susceptible to developing a chronic liver disease comprising introducing an expression vector into the subject, wherein the expression vector comprises a recombinant HSD17B13 gene comprising a thymine inserted between nucleotides corresponding to positions 12665 and 12666 of SEQ ID NO:1 when the recombinant HSD17B13 gene is optimally aligned with SEQ ID NO:1, wherein the expression vector expresses the recombinant HSD17B13 gene in a liver cell in the subject.

Embodiment 242

The method of any one of embodiments 234 and 241, wherein the recombinant HSD17B13 gene is a human gene.

Embodiment 243

The method of any one of embodiments 234, 241, and 242, wherein recombinant HSD17B13 gene is at least 90%, at least 95%, at least 96%, at least 97%, at least 98%, or at least 99% identical to SEQ ID NO:2 when optimally aligned with SEQ ID NO:2.

Embodiment 244

The method of any one of embodiments 234, 241, and 242, wherein the recombinant HSD17B13 gene is an HSD17B13 minigene in which one or more nonessential segments of the gene have been deleted with respect to a corresponding wild type HSD17B13 gene.

Embodiment 245

The method of embodiment 244, wherein the deleted segments comprise one or more intronic sequences.

Embodiment 246

The method of embodiment 244 or 245, wherein the HSD17B13 minigene comprises an intron corresponding to intron 6 of SEQ ID NO:2 when optimally aligned with SEQ ID NO:2.

Embodiment 247

A method of treating a subject who is not a carrier of the HSD17B13 rs72613567 variant and has or is susceptible to developing a chronic liver disease comprising introducing an expression vector into the subject, wherein the expression vector comprises a nucleic acid encoding an HSD17B13 protein that is at least 90%, at least 95%, at least 96%, at least 97%, at least 98%, at least 99%, or 100% identical to SEQ ID NO:42 (HSD17B13 Isoform D), wherein the expression vector expresses the nucleic acid encoding the HSD17B13 protein in a liver cell in the subject.

Embodiment 248

The method of embodiment 247, wherein the nucleic acid encoding the HSD17B13 protein is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 249

A method of treating a subject who is not a carrier of the HSD17B13 rs72613567 variant and has or is susceptible to developing a chronic liver disease comprising introducing a messenger RNA into the subject, wherein the messenger RNA encodes an HSD17B13 protein that is at least 90%, at least 95%, at least 96%, at least 97%, at least 98%, at least 99%, or 100% identical to SEQ ID NO:42 (HSD17B13 Isoform D), wherein the mRNA expresses the HSD17B13 protein in the liver cell in the subject.

Embodiment 250

The method of embodiment 249, wherein a complementary DNA reverse transcribed from the messenger RNA is at least 90%, at least 95%, at least 96%, at least 97%, at least 98%, at least 99%, or 100% identical to SEQ ID NO:24 (HSD17B13 Transcript D) when optimally aligned with SEQ ID NO:24.

Embodiment 251

A method of treating a subject who is not a carrier of the HSD17B13 rs72613567 variant and has or is susceptible to developing a chronic liver disease comprising introducing an HSD17B13 protein or fragment thereof into the liver of the subject.

Embodiment 252

The method of embodiment 251, wherein the HSD17B13 protein or fragment thereof is at least 90%, at least 95%, at least 96%, at least 97%, at least 98%, at least 99%, or 100% identical to SEQ ID NO:42 (HSD17B13 Isoform D).

Embodiment 253

The method of any one of embodiments 233-252, wherein the subject is a human.

Embodiment 254

The method of any one of embodiments 233-253, wherein the chronic liver disease is nonalcoholic fatty liver disease (NAFLD), alcoholic liver fatty liver disease, cirrhosis, or hepatocellular carcinoma.

Embodiment 255

The method of any one of embodiments 233-254, wherein the introducing into the subject comprises hydrodynamic delivery, virus-mediated delivery, lipid-nanoparticle-mediated delivery, or intravenous infusion.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present embodiments have been described in some detail by way of illustration and example for purposes of clarity and understanding, it will be apparent that certain changes and modifications may be practiced within the scope of the appended claims.

The nucleotide and amino acid sequences recited herein are shown using standard letter abbreviations for nucleotide bases, and one-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

The following examples are provided to describe the embodiments in greater detail. They are intended to illustrate, not to limit, the claimed embodiments.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The diseases identified in the Examples are preferred.

Example 1: Variant 17Beta-Hydroxysteroid Dehydrogenase 13 Protects Against Chronic Liver Disease To identify genetic factors contributing to chronic liver disease, we utilized exome sequence data and electronic health records from 46,544 participants in the DiscovEHR human genetics study. We identified genetic variants associated with established biomarkers of hepatic injury (serum alanine aminotransferase (ALT) and aspartate aminotransferase (AST)) to nominate candidates that might be associated with chronic liver disease. Candidate variants replicating in three additional cohorts (12.527 individuals) were subsequently evaluated for association with clinical diagnoses of chronic liver disease in DiscovEHR and two independent cohorts (total of 37,892 individuals). We also examined the association with histopathological severity of liver disease in an independent bariatric surgery cohort (n=2,391 human liver samples).

A splice variant (rs72613567:TA) in HSD17B13, encoding the hepatic lipid droplet protein 17-beta hydroxysteroid dehydrogenase 13, was reproducibly associated with reduced ALT ($P=4.2\times10^{-12}$) and AST ($P=6.2\times10^{-10}$) levels. In DiscovEHR, this variant was associated with reduced risk of alcoholic and nonalcoholic liver disease (by 38%, 95% confidence interval (CI) 19%-52%; and by 16%, 95% CI 9%-22%, respectively, for each rs72613567:TA allele) and cirrhosis (by 44%, 95% CI 22-59%; and by 26%, 95% CI 12%-38% for alcoholic and nonalcoholic cirrhosis, respectively, for each rs72613567:TA allele) in an allele dosage-dependent manner; associations were confirmed in two independent cohorts. rs72613567:TA was associated with decreased severity of histological features of nonalcoholic steatohepatitis (NASH) (23% reduction, 95% CI 10%-34% for each rs72613567:TA allele among individuals with fatty liver disease). rs72613567:TA results in an unstable and truncated protein with reduced enzymatic activity against steroid substrates.

A loss-of-function variant in HSD17B13 was associated with reduced risk of alcoholic and nonalcoholic liver disease, and progression from steatosis to NASH.

Study Design and Participants

Human genetics studies were conducted as part of the DiscovEHR collaboration of the Regeneron Genetics Center and Geisinger Health System (GHS). The two DiscovEHR study populations (discovery cohort and bariatric surgery cohort) originated from the first 50,726 consented participants ≥18 years of age from the MyCode® Community Health Initiative of GHS. The GHS discovery cohort consisted of 46,544 European individuals recruited from outpatient primary care and specialty clinics between 2007 and 2016, excluding all those recruited to the bariatric surgery cohort. The GHS bariatric surgery cohort consisted of 2,644 European individuals who had been referred for bariatric surgery.

Replication studies of associations with liver transaminases included 1,357 European individuals from the Dallas Heart Study and 8,527 European individuals from the Penn Medicine Biobank. The Dallas Heart Study is a probability-based population cohort study of Dallas County residents aged 30 to 65 years (Victor et al., Am. J. Cardiol., 2004; 93, 1473-80). The Penn Medicine Biobank includes participants recruited from the University of Pennsylvania Health System and consented for biospecimen storage, access to EHR data, and permission to recontact.

Replication studies of the associations with chronic liver disease included 517 individuals from the Dallas Liver Study (DLS) and 447 individuals from the Dallas Pediatric Liver Study (DPLS). The DLS is a biobank of patients with liver disease of non-viral etiology. Recruitment began in January 2015 and is ongoing. Participants were recruited from liver clinics at UT Southwestern and Parkland Health and Hospital System. Dallas. Participants completed a questionnaire on ethnic/racial background, medical history, lifestyle factors, and family history of liver disease and other diseases. Additional clinical information was extracted from medical records by a trained technician. We included all African American. European American, and Hispanic American patients with DNA available at the time of the present study (n=517) with controls from the Dallas Heart Study. The DPLS is a biobank of Hispanic children recruited from pediatric liver clinics at UT Southwestern and Parkland Health and Hospital System, Dallas, and from an obesity clinic at Children's Medical Center, Dallas. Clinical information was extracted from medical records by a trained technician. As more than 95% of the patients were Hispanic Americans, we only included Hispanic American patients and controls in the present study (n=205 patients and 234 controls).

Clinical Measurements and Chronic Liver Disease Definitions in the Discovery Cohort Clinical laboratory measurements for ALT and AST were extracted from EHRs of participants from the GHS discovery cohort and bariatric surgery cohort. Median ALT and AST values were calculated for all participants with two or more measurements, and were $\log_{10}$-transformed to normalize the distribution prior to association analyses.

International Classification of Diseases, Ninth Revision (ICD-9) disease diagnosis codes were extracted from EHRs and collapsed into clinical disease categories for non-viral, nonalcoholic (ICD-9 571.40, 571.41, 571.49, 571.5, 571.8, 571.9) or alcoholic (ICD-9 571.0, 571.1, 571.2, 571.3) liver disease case definitions. Additional case definitions based on single diagnosis codes included: alcoholic cirrhosis (ICD-9 571.2), nonalcoholic cirrhosis (ICD-9 571.5), and HCC (ICD-9 155.0). For these case definitions, a common control group without liver disease ("no liver disease") was defined as participants with no case criteria or single-encounter or problem-list diagnosis code indicating any type of liver disease.

Liver Histopathologic Phenotype Definitions in the Bariatric Surgery Cohort

The GHS bariatric surgery cohort consisted of 2,644 individuals of European descent. Wedge biopsies of the liver were obtained intraoperatively during bariatric surgery from 2,391 of these individuals. The biopsies were consistently obtained 10 cm to the left of falciform ligament prior to any liver retraction or surgery on the stomach. The biopsy was divided into sections, with the primary section delivered to the clinical pathologists for liver histology (fixed in 10% neutral buffered formalin and stained with hematoxylin and eosin for routine histology and Masson's trichrome for assessment of fibrosis) and remaining sections stored within a research biobank (frozen in RNAlater and/or liquid nitrogen). Liver histology was conducted by an experienced pathologist and subsequently re-reviewed by a second experienced pathologist using the NASH Clinical Research Network scoring system (Kleiner et al., Hepatology, 2005, 41, 1313-21) as follows: steatosis grade 0 (<5% parenchymal involvement), 1 (5 to <33%), 2 (34 to <66%), and 3 (>67%); lobular inflammation grade 0 (no foci), grade 1 (mild, <2 foci per 200× field), grade 2 (moderate, 2-4 foci per 200× field), grade 3 (severe, >4 foci per 200× field); fibrosis Stage 0 (none), Stage 1 (perisinusoidal or periportal fibrosis), Stage 2 (perisinusoidal and periportal fibrosis), Stage 3 (bridging fibrosis), and Stage 4 (cirrhosis). These histologic diagnoses were used to defined the following phenotypes: 1) Normal: no evidence of steatosis, NASH, or fibrosis; 2) Simple steatosis: Steatosis (regardless of grade) with no evidence of NASH or fibrosis; 3) NASH: Any presence of lobular inflammation or hepatocyte ballooning (regardless of grade), or any presence of fibrosis (regardless of stage); 4) Fibrosis: Any presence of fibrosis (regardless of stage).

Sample Preparation, Sequencing, and Genotyping

DNA sample preparation and whole exome sequencing for the participants in the DiscovEHR study, the Dallas Heart Study, and the Penn Medicine Biobank were performed at the Regeneron Genetics (Dewey et al., Science In Press, 2016). HSD17B13 rs72613567 was genotyped by Taqman assay (and verified by Sanger sequencing in 5 individuals of each genotype) in the Dallas Liver Study and Dallas Pediatric Liver Study.

In particular, exome capture was performed using NimbleGen probes according to the manufacturer's recommended protocol (Roche NimbleGen). The captured DNA was PCR amplified and quantified by qRT-PCR (Kapa Biosystems). The multiplexed samples were sequenced using 75 bp paired-end sequencing on an Illumina v4 HiSeq 2500 to a coverage depth sufficient to provide greater than 20× haploid read depth of over 85% of targeted bases in 96% of samples (approximately 80× mean haploid read depth of targeted bases). Raw sequence data from each Illumina Hiseq 2500 run were uploaded to the DNAnexus platform (Reid et al., BMC Bioinformatics, 2014, 15, 30) for sequence read alignment and variant identification. In brief, raw sequence data were converted from BCL files to sample-specific FASTQ-files, which were aligned to the human reference build GRCh37.p13 with BWA-mem (Li et al., Bioinformatics, 2009, 25, 1754-60). Single nucleotide variants (SNV) and insertion/deletion (indel) sequence variants were identified using the Genome Analysis Toolkit (McKenna et al., Genome Res., 2010, 20, 1297-303).

Exome-Wide Association Analysis of Liver Enzymes and Chronic Liver Disease Phenotypes We used linear mixed models to test 502,219 biallelic variants that had missing data rate of <1%, Hardy-Weinberg equilibrium P-value >$1.0\times10^{-6}$, and minor allele frequency >0.1% for association with transaminase levels. For variants with exome wide significant associations with transaminases ($p<1\times10^{-7}$) in the GHS discovery cohort, we performed association analyses and meta-analysis, in the European-ancestry replication studies described above. We used a Bonferroni significance threshold determined by the number of variants tested to define replicated associations. Meta-analysis of discovery and replication studies was also performed. All P-values reported in the text correspond to the allelic model.

We subsequently tested transaminase-associated single nucleotide variants for associations with chronic liver disease phenotypes. We used a Bonferroni significance threshold determined by the number of variants and broad chronic liver disease categories tested to determine significance of associations. We further tested replicated novel variants for association with histopathologically defined liver phenotypes from the GHS bariatric surgery cohort. We also performed a phenome-wide study of associations of replicated novel variants with 405 quantitative clinical measurements and 3,168 clinical diagnoses.

In particular, we tested 502,219 biallelic variants with missing data rate <1%, Hardy-Weinberg equilibrium P-value >$1.0\times10^{-6}$, and minor allele frequency >0.1% for association with transaminase levels. $\log_{10}$-transformed median ALT and AST were adjusted for age, age$^2$, sex, BMI, and the first four principal components of ancestry. To account for relatedness among study participants, we also fit a genetic relatedness matrix as a random-effects covariate. Both principal components and the genetic relatedness matrix were constructed from 39,858 non-MHC markers in approximate linkage equilibrium and with minor allele frequency >0.1%. We used linear mixed models as implemented in the GCTA package (Yang et al., Am. J. Hum. Genet., 2011, 88, 76-82) to test for association between trait residuals and single nucleotide variants. All P-values reported in the text correspond to the allelic model.

We attempted to replicate associations in the GHS discovery cohort in three separate European-ancestry cohorts: the GHS bariatric surgery cohort, the Dallas Heart Study, and the Penn Medicine Biobank (described above). ALT and AST measures from the GHS bariatric surgery cohort and from Penn Medicine Biobank were $log_{10}$-transformed and adjusted for age, $age^2$, sex, BMI, and the first four principal components of ancestry. Genetic relatedness matrices were included as random-effects covariates, and analysis was performed using linear mixed models in GCTA. In the Dallas Heart study, $log_{10}$-transformed ALT and AST measures were adjusted for age, $age^2$, sex, BMI, and the first ten principal components of ancestry, and analysis was performed using linear regression implemented in PLINK. Summary statistics for the three replication cohorts were meta-analyzed using METAL (Willer et al., Bioinformatics, 2010, 26, 2190-1) (replication meta-analysis). Summary statistics for the discovery cohort and the three replication cohorts were meta-analyzed similarly (joint meta-analysis).

Association Analysis with Chronic Liver Disease Phenotypes

We analyzed thirteen significant and replicated single nucleotide variants from the liver enzyme ExWAS for associations with chronic liver disease phenotypes defined from the GHS discovery cohort, as described above. We used a Bonferroni significance threshold of $P<0.05/26$ ($P<1.92 \times 10^{-3}$) to account for the thirteen variants and two broad chronic liver disease categories (alcoholic and non-alcoholic) tested. The HSD17B13 rs72613567 variant was further tested for association with histopathologically defined liver phenotypes from the GHS bariatric surgery cohort, as described above. Odds ratios were estimated with the use of Firth's penalized likelihood method of logistic regression after adjustment for age, $age^2$, sex, BMI, and the first four principal components of ancestry. Genotypic odds ratios were estimated for HSD17B13 rs72613567 using the same covariates.

Odds ratios for liver disease in the DLS were estimated by logistic regression, adjusted for age, $age^2$, sex, body mass index, and self-reported ethnicity. Participants from the Dallas Heart Study with available rs72613567 genotypes were used as normal controls (n=4,279). Odds ratios in the DPLS were estimated by logistic regression.

Phenome-Wide Association Study of HSD17B13 rs72613567

We performed a phenome-wide study of associations of HSD17B13 rs72613567 with 405 quantitative EHR-derived anthropometric, vital sign, laboratory, electrocardiographic, echocardiographic, and bone densitometry measurements, and also with 3,168 EHR-derived clinical diagnoses. Median laboratory values for individuals with serial outpatient measures were calculated following removal of likely spurious values that were >3 standard deviations from the intra-individual median value; maximum and minimum values were also calculated. We then calculated trait residuals for all laboratory traits after adjustment for age, $age^2$, sex, and the first ten principal components of ancestry, and applied appropriate transformations prior to association analysis. ICD-9 based diagnosis codes were collapsed to hierarchical clinical disease groups and corresponding controls using a modified version of the groupings proposed by Denny et al (Denny et al., Nature Biotechnology, 2013, 31, 1102-10; and Denny et al., Bioinformatics, 2010, 26, 1205-10). ICD-9 based diagnoses required one or more of the following: a problem list entry of the diagnosis code or an encounter diagnosis code entered for two separate clinical encounters on separate calendar days.

Analyses of association with transformed quantitative clinical measurement residuals were performed using linear regression, and analyses of association with clinical diagnoses were performed using logistic regression adjusted for age, $age^2$, sex, and the first four principal components. Alleles were coded using both additive (0 for reference allele homozygotes, 1 for heterozygotes, and 2 for alternative allele homozygotes) and recessive (0 for reference allele homozygotes and heterozygotes, 1 for alternative allele homozygotes) models.

Software

Genetic association analyses were performed using GCTA software, version 1.25.07 and PLINK, version 1.9.0. Quantile-quantile and Manhattan plots were generated using R software, version 3.2.1 (R Project for Statistical Computing). Regional association plots were generated using LocusZoom (Pruim et al., Bioinformatics, 2010, 26, 2336-7).

RNA Sequencing Studies

RNA quality and concentration was evaluated by running total RNA on an Agilent RNA Nano Bioanalyzer chip; all samples had an RNA integrity number (RIN) greater than 8. Polyadenlylated RNA transcripts were isolated using two rounds of enrichment with oligo(dT)25 beads (Thermo Fisher Scientific). Samples were purified and concentrated with RNAclean XP beads (Beckman Coulter) and heat-fragmented to approximately 140 base pairs. First-strand synthesis was completed with SuperScript III reverse transcriptase (Thermo Fisher Scientific) using random hexamers; dTTP was replaced with dUTP during second-strand synthesis. Samples were processed according to our standard DNA library preparation method referenced above for exomes with the addition of a uracil DNA-glycosylase step to generate strand-specific sequencing libraries.

Identification and Validation of Novel HSD17B13 Transcripts

Figure 7A:
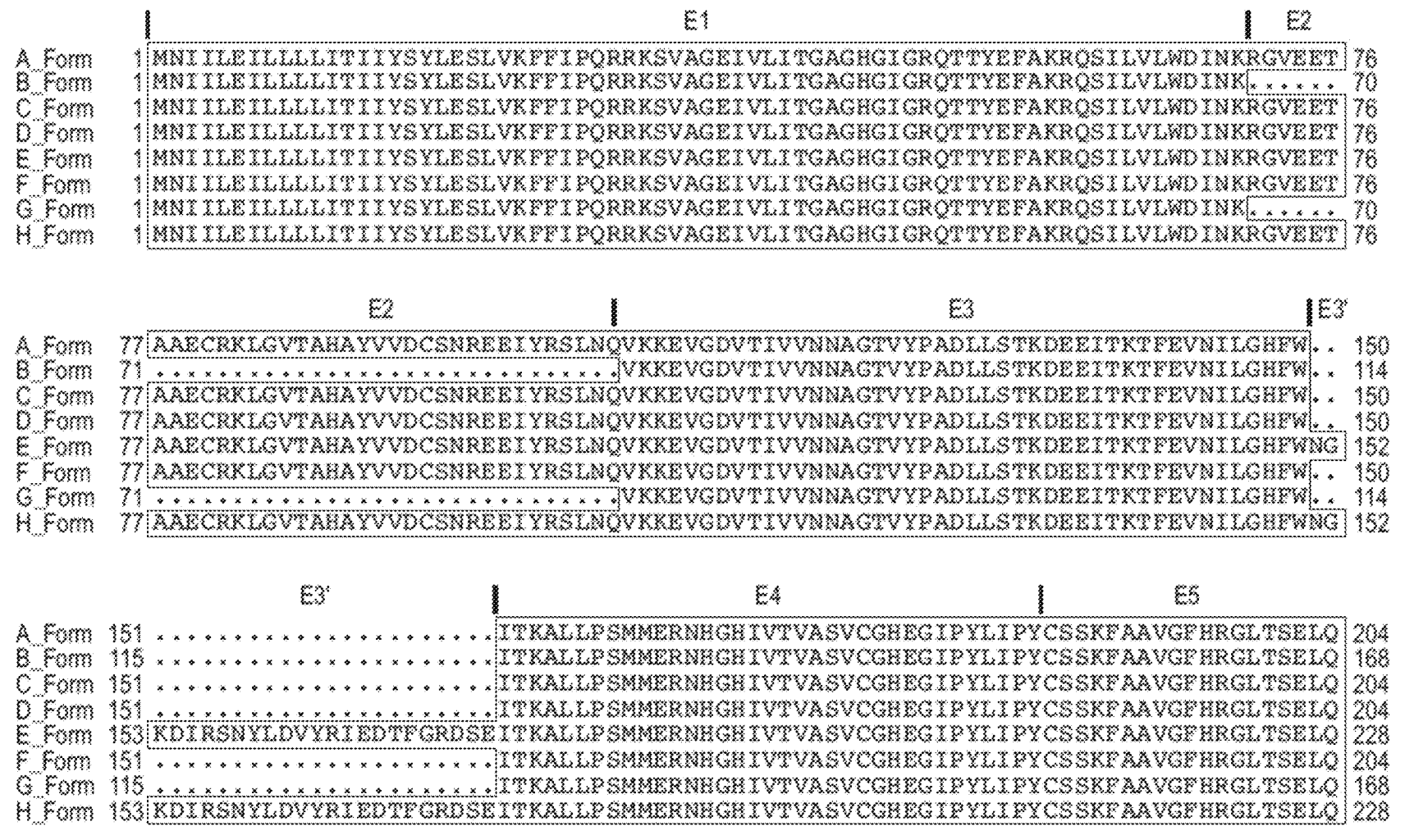
Figure 7B:
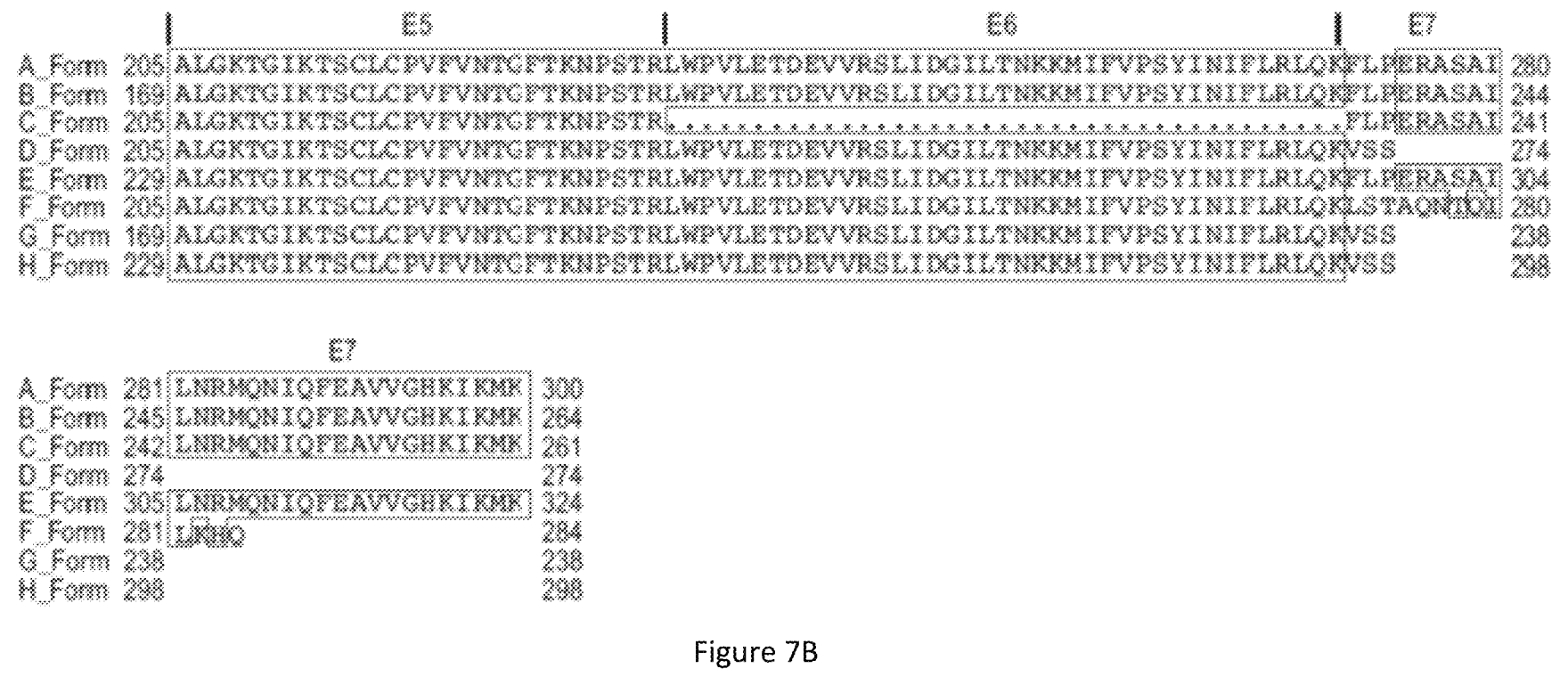

Reads were mapped to the Human.B38 using ArrayStudio® software (OmicSoft®, Cary, N.C.) allowing two mismatches. Two approaches were employed to identify novel HSD17B13 transcripts. Novel exon junctions were discovered based on Gencode v24 using ArrayStudio. De novo transcript assembly was carried out using Trinity (v2.2.0) in default setting. Custom gene models were built to incorporate novel transcripts of HSD17B13, and transcript quantification was estimated by read alignment to the custom gene model. Protein sequence alignment of all identified HSD17B13 isoforms is shown in FIGS. 7A and 7B. RT-PCR was performed on total RNA from human liver samples was performed using the SuperScript™ One-Step RT-PCR System with Platinum™ Taq DNA Polymerase (Thermo Fisher). Each 50 µL RT-PCR reaction contained IX Reaction Mix, 500 nM each forward and reverse primers (PST516: ATGAACATCATCCTAGAAATCCTTC (SEQ ID NO:48) and PST517: ATCATGCATACATCTCTGGCTGGAG (SEQ ID NO:49)), 1 µL of RT/Platinum Taq, and 75 ng RNA. Cycling conditions were: one cycle of 45° C. for 30 minutes; one cycle of 94° C. for 2 minutes; 40 cycles of 94° C. for 20 seconds, 53° C. for 30 seconds, and 72° C. for 90 seconds; one cycle of 72° C. for 5 minutes; then a 10° C. hold. Products were purified using the QIAquick PCR Purification Kit (Qiagen) and submitted for direct Sanger sequencing using the primer DE002 (ATCAGAACTTIC AGGCCTTGG (SEQ ID NO:50)). To identify the B and C transcripts, the RT-PCR products were run out on a 2% agarose gel stained with SYBR GoldSYBR® Gold Nucleic Acid Gel Stain (ThermoFisher), and bands of the expected molecular weight were excised and purified using the QIAquick Gel Extraction Kit (Qiagen), then subjected to cloning with the TOPO® TA Cloning Kit (ThermoFisher). Sequencing of the TOPO clones was performed using M13F and M13R sequencing primers. Sequence analysis was performed using the Sequencher DNA analysis software (Gene Codes Corporation).

Full-length HSD17B13 transcripts were amplified directly from 50 ng of total RNA with the SuperScript III One-step RT-PCR System with Platinum Taq High Fidelity (ThermoFisher Scientific) using gene-specific primers in the first (GCAAAGCCATGAACATCATCC (SEQ ID NO:51)) and last exons (TCTTGATGTA GTGGGAGTCGGATT (SEQ ID NO:52)) to generate an amplicon of about 2.2 kb (maximum predicted size transcript). Amplicons were verified on an Agilent Bioanalyzer. PacBio-compatible barcoded adapters were ligated to the amplicons and cleaned with PacBio PB beads (Pacific Biosciences). Libraries were pooled in equal amounts and sequenced on one SMRT cell for 180 minutes on the PacBio RSII platform. The data was demultiplexed using PacBio software smrtanalysis v2.3 tool labelzmw and then analyzed with ConsensusTools AmpliconAnalysis. Resulting amplicons were compared to HSD17B13 RefSeq genes to determine isoform and genotype status.

Subcellular Localization of HSD17B13 Isoforms

HepG2 cells were cultured in Eagle's Minimum Essential Medium supplemented with 10% fetal bovine serum. HSD17B13 transcripts A and D were sub-cloned into Myc-DDK backbone lentivirus constructs, and lentivirus were generated. HepG2 cells were infected with lentivirus carrying the HSD17B13 transcripts. Stable cell lines expressing each HSD17B13 transcript were selected with 1-3 mg/ml Geneticin G-418 sulfate in complete culture medium for two weeks. Following fixation, HSD17B13 isoforms were detected with mouse anti-Myc antibody. Lipid droplets were labeled with BODIPY FL dye (Sigma). Secondary antibodies for immunofluorescence were Alexa Fluor 488 donkey anti-rabbit IgG and Alexa Fluor 594 donkey anti-mouse IgG (Jackson ImmunoResearch).

Quantification of HSD171B3 Protein Expression in Human Liver Biopsy Tissue and Stable Cell Lines Human liver and cell pellet samples were homogenized in ice-cold 1×RIPA lysis buffer (EMD Millipore) in the presence of protease and phosphatase inhibitor mixtures (ThermoFisher). Supernatant was collected and used for protein concentration using BCA protein assay (ThermoFisher). Human tissue and cell lysates were loaded and separated on SDS/PAGE gels (Bio-Rad) and transferred to PVDF membranes (Bio-Rad). The membranes were blocked for 1 hour with 5% (wt/vol) milk in 1×TBS supplemented with 0.1% Tween20 (Bio-Rad). Membranes were incubated with antibody at 4° C. overnight against HSD17B13 (1:200, ThermoFisher) and B-Actin (1:500, Cell Signaling Technology). Bound antibody was detected using HRP-conjugated anti-rabbit antibody (1:10,000, Jackson ImmunoResearch) and enhanced using chemi-luminescence reagent (ThermoFisher). Band intensities were quantified using Image J software.

Real-Time Semi-Quantitative PCR

RNA was extracted from cell using TRIzol® (Invitrogen, Carlsbad, CA). First-strand cDNA was synthesized using Superscript III RT (Invitrogen) and utilized for Semi-Quantitative PCR based on intron-spanning primers. A QuantStudio 6 Flex Real-Time PCR System was used to measure the expression level of transcripts. Primers of HSD17B13 and TBP were ordered from IDT (Integrated DNA Technologies). Relative gene expression was analyzed with the ΔΔCt method, providing a fold-change of expression normalized to the house-keeping gene TBP (ΔCt).

Lipid Droplet Isolation and Characterization by Western Blotting

Lipid droplets were prepared from HepG2 cells stably expressing HSD17B13 transcript A (IsoA) or transcript D (IsoD) as previously reported (Brasaemle D L, Wolins N E. Isolation of lipid droplets from cells by density gradient centrifugation. Current protocols in cell biology 2006; Chapter 3:Unit 3 15; and Ding et al., Nature Protocols, 2013, 8, 43-51). In brief, HepG2 cells stably expressing HSD17B13 IsoA, IsoD, or the parental line were incubated overnight with 1 mM oleic acid. The following lipid loading, cells were scraped and resuspended in hypotonic lysis buffer (20 mM Tris, pH 7.5, 1 mM EDTA) supplemented with IX Halt™ protease/phosphatase inhibitors (Thermo) and lysed by cavitation at 50 bar for 8 minutes. Lysates were centrifuged at 1000 g/4° C. for 10 minutes, and the post-nuclear supernatant (PNS) was mixed with sucrose to a final volume of 2 mL and concentration of 20% in ultracentrifuge tubes. Then 1.5 mL of 5% sucrose and another 1.5 mL of hypotonic lysis buffer was layered on top of the lysate. Tubes were centrifuged at 182,000 g/4° C. for 40 minutes, and the lipid droplet (LD) layers were transferred to new tubes. The remaining volume in the tube was aspirated, and the pelleted (total membrane, TM) was resuspended in 0.5 mL hypotonic lysis buffer. The PNS, LD, and TM fractions were mixed with 1× radioimmunoprecipitation (RIPA) buffer (EMD)+ NuPAGE™ LDS Sample Buffer (Thermo) and β-mercaptoethanol and sonicated for 3 hours at 37° C. The TM lysate was diluted 2.5-fold to normalize to the PNS. Lysates were run on 4-20% SDS-PAGE gels (Biorad), transferred using the Trans-Blot (Biorad) onto low fluorescence PVDF membranes, and blocked for 1 hour in Odyssey TBS Blocking Buffer. Membranes were incubated overnight with the following antibodies: α-HSD17B13 (Abgent, cat #AP5729a 1:500); LD marker: α-ADRP (Proteintech, 152-94-1-AP, 1:2500); LD marker: α-TIP47 (Proteintech, 10694 1:2000); lysosome marker: α-LAMP1 (Novus, NBP2-25183, 1:1000); cytosolic marker: α-GAPDH (Proteintech, 60004-1-Ig, 1:2000); endoplasmic reticulum marker: α-calreticulin (Abcam, ab92516, 1:1000); mitochondrial marker: α-COX IV (Abcam, ab33985, 1:500); cytoskeleton marker: α-actin (Sigma, A5441, 1:4000). The next day membranes were washed 4 times with Tris-buffered saline+0.1% Tween, then incubated for 1 hour at room temperature with blocking buffer containing IRDye® α-rabbit (800CW) and α-mouse (680RD) secondary antibodies (Li-Cor) at 1:5,000 and 1:10,000 dilutions, respectively. Gels were washed again with TBST and imaged using the Odyssey.

Quantification of Intracellular Triglyceride Content

The triglyceride (TG) content from the stable cells was determined using a TG quantification kit (Abcam). In the assay, TG are converted to free fatty acids and glycerol. The glycerol is then oxidized to generate a product which is quantified (spectrophotometry at $\lambda$=570 nm).

Substrate Screening of Steroid and Bioactive Lipid Libraries Against Purified Recombinant HSD17B13

Reactions were performed in a final volume of 40 μl of assay buffer (0.2 M Tris-HCl, pH 7.5) which contained 500 μM NAD$^+$, 5 μM bioactive lipid or 50 μM steroid (all in a final concentration of 5% DMSO), and 100 ng recombinant human HSD17B13. Reactions were incubated for 3 hours, at 23° C. after which an equal volume NADH-Glo Detection Reagent (Promega) was added. Following a 1 hour incubation at 23° C., the relative light units (RLUs) were measured on an Envision Plate Reader (Perkin Elmer). Raw RLU values were normalized as percent of control (50 µM estradiol) following subtraction of negative control (5% DMSO) using the following formula: Percent of control (POC)=100×(Sample (RLU)−Negative CTRLaverage)/(Positive CTRLaverage−Negative CTRLaverage).

In Vitro and Cellular Characterization of HSD17B13 Enzymatic Activity

Recombinant human HSD17B13 protein was purified from *E. coli* (Genscript) transformed with plasmid DNA harboring HSD17B13 transcript A or transcript D. The HSD17B13 variants contained a 10×His tag at the C terminus and were purified from soluble fraction using a Ni2+ affinity purification. Enzymatic activity was determined through measurement of NADH production using the NAD(P)H-Glo Detection System (Promega). Reactions were performed for 3 hours at 25° C. in 0.2 M Tris-HCl, pH 7.5, 0.5 mM NAD+, 75 µM of substrate (Sigma) and 500 ng purified enzyme in a final volume of 100 µL. After incubation, 20 µL of the reaction was combined with 20 µL luciferase reagent (Promega), incubated at room temperature for 1 hour and read on an Envision Plate Reader (Perkin Elmer).

HEK293 cells overexpressing HSD17B13 transcript A, transcript D or green fluorescent protein (GFP, control) were used to investigate the activity of HSD17B13 against estradiol in a cell-based assay. Estradiol (1 µM) was fed to each cell type. After 48 hours, the media was collected and the concentration of estradiol and its converted product estrone were identified and quantified by LC-MS.

Association of Exonic Variants with Asparatate and Alanine Aminotransferases

Figure 1B:
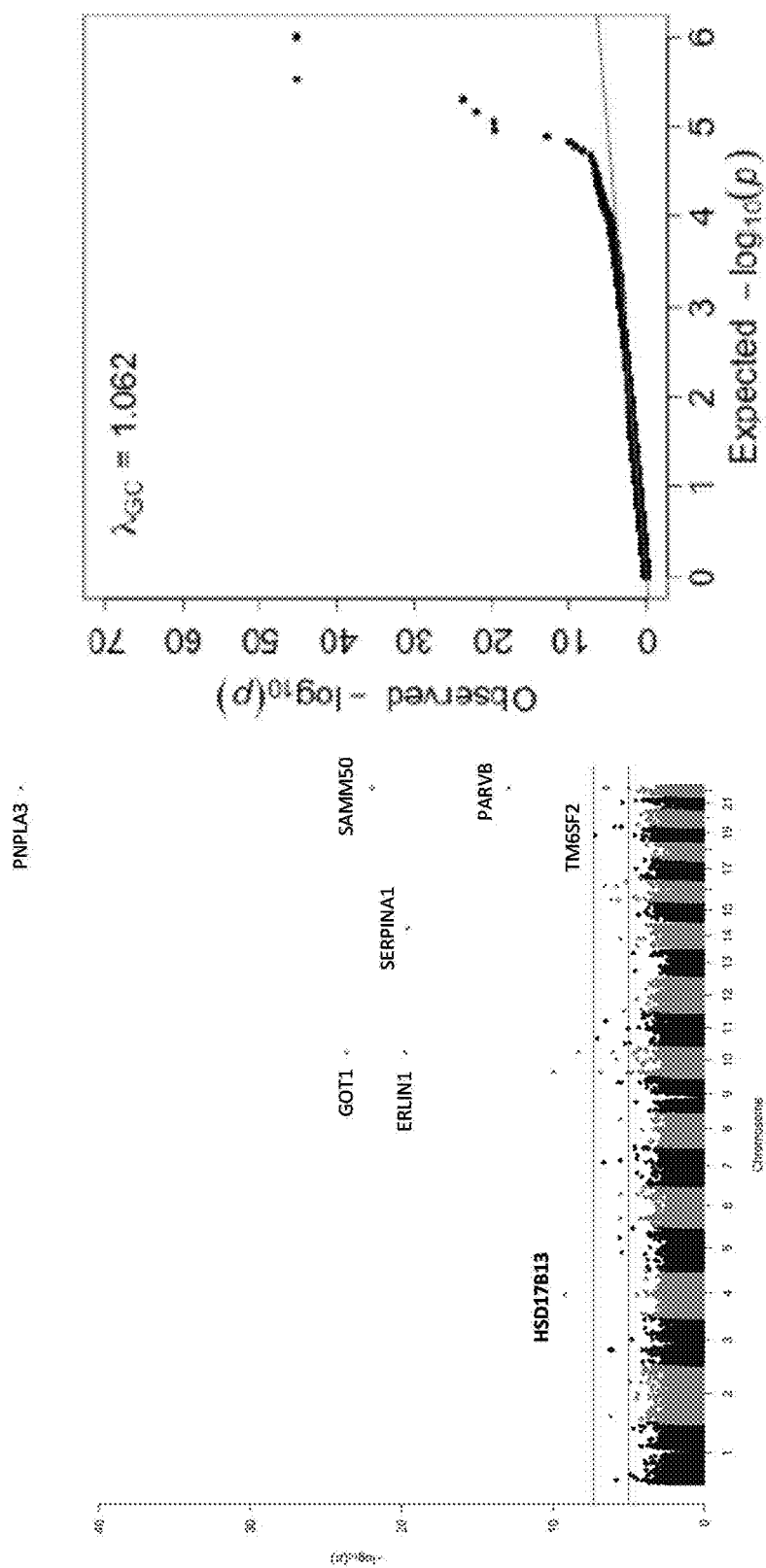

We tested 502,219 biallelic single genetic variants for association with serum ALT or AST levels in 46,544 individuals of European descent from the DiscovEHR study ("GHS discovery cohort"; basic demographics in Table 1). A total of 35 variants in 19 genes were found to be associated with ALT or AST at $P<1.0\times10^{-7}$ (FIGS. 1A and 1B, and Table 2). We performed replication studies in three cohorts of European-ancestry individuals: 1) bariatric surgery patients (n=2,644) from DiscovEHR ("GHS bariatric surgery cohort"); 2) 1,357 individuals from the Dallas Heart Study; and 3) 8,526 individuals from the Penn Medicine Biobank. In meta-analysis of the replication cohorts, thirteen variants in nine genes were significantly associated with serum levels of ALT or AST (Bonferroni significance threshold of $P<1.43\times10^{-3}$ for 35 variants tested, Table 3). These included variants that were previously reported to be associated with elevated transaminase levels, such as PNPLA3[7], TM6SF2[11], SERPINA1[22], SAMM50[23], and ERLIN1[24]. SERPINA1 encodes alpha-1-antitrypsin, whose functional deficiency causes liver disease; the association with SAMM50 is mediated via linkage disequilibrium with variation in PNPLA3, and ERLIN1 has been implicated in liver fat deposition. We also identified variants that were not previously reported to be associated with liver disease. These included several variants in GPT and GOT1, the genes encoding ALT and AST, respectively, and SLC39A12, which encodes solute carrier family 39 member 12.

Figure 5A:
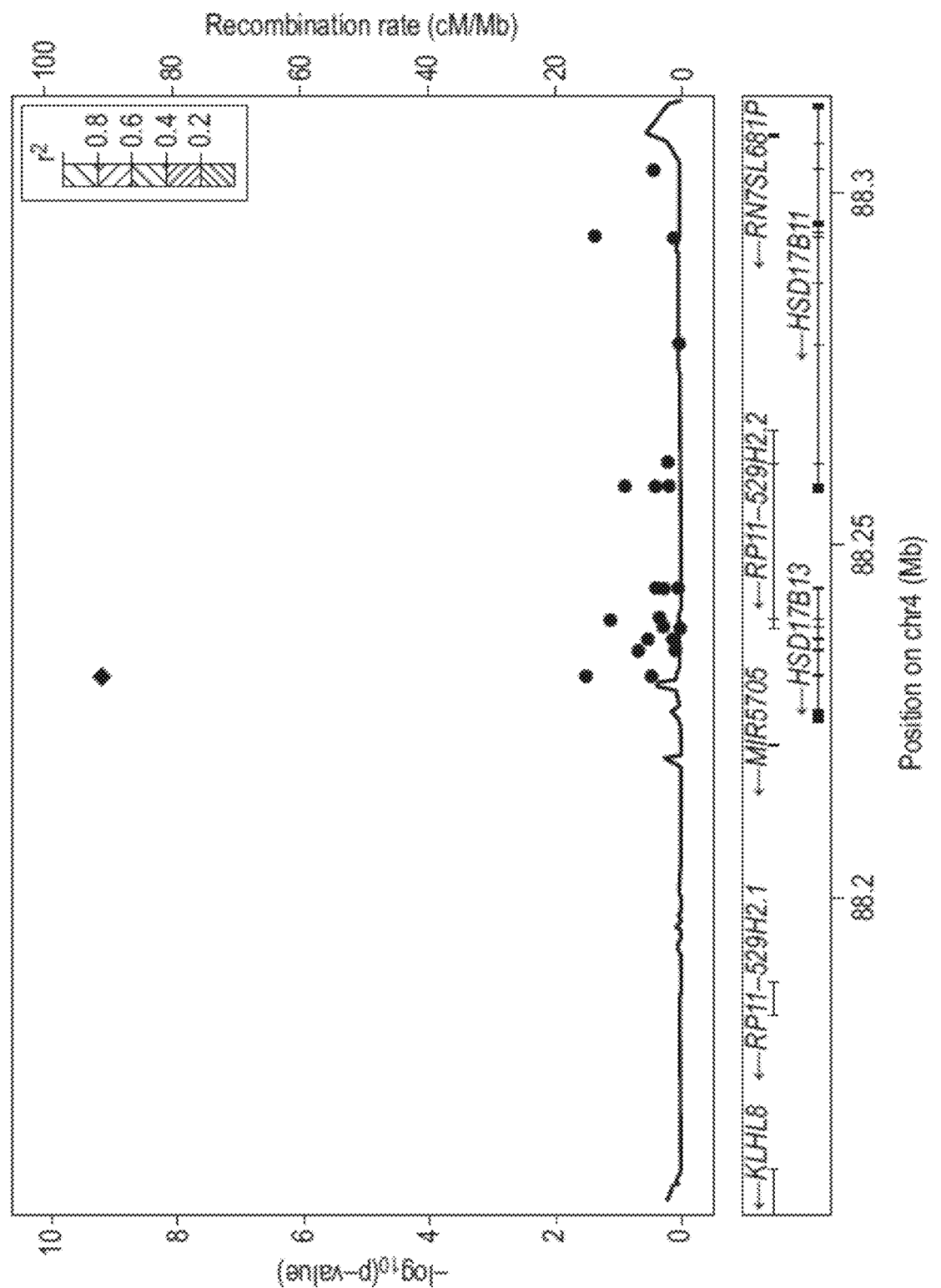
FIGS. 5A and 5B show regional association plots for alanine aminotransferase (ALT; 5A) and aspartate aminotransferase (AST; 5B) levels in the GHS Discovery Cohort in the region around HSD17B13; diamonds indicate the splice variant rs72613567; each circle indicates a single nucleotide variant with the color of the circle indicating the linkage disequilibrium ($r^2$ calculated in the DiscovEHR cohort) between that variant and rs72613567; lines indicate estimated recombination rates in HapMap; the bottom panels show the relative position and the transcribed strand of each gene in the locus; there were no significant associations between ALT or AST and coding or splice region variants in the neighboring gene HSD17B11 (most significant P-values $1.4 \times 10^{-1}$ and $4.3 \times 10^{-2}$ for ALT and AST, respectively).
Figure 5B:
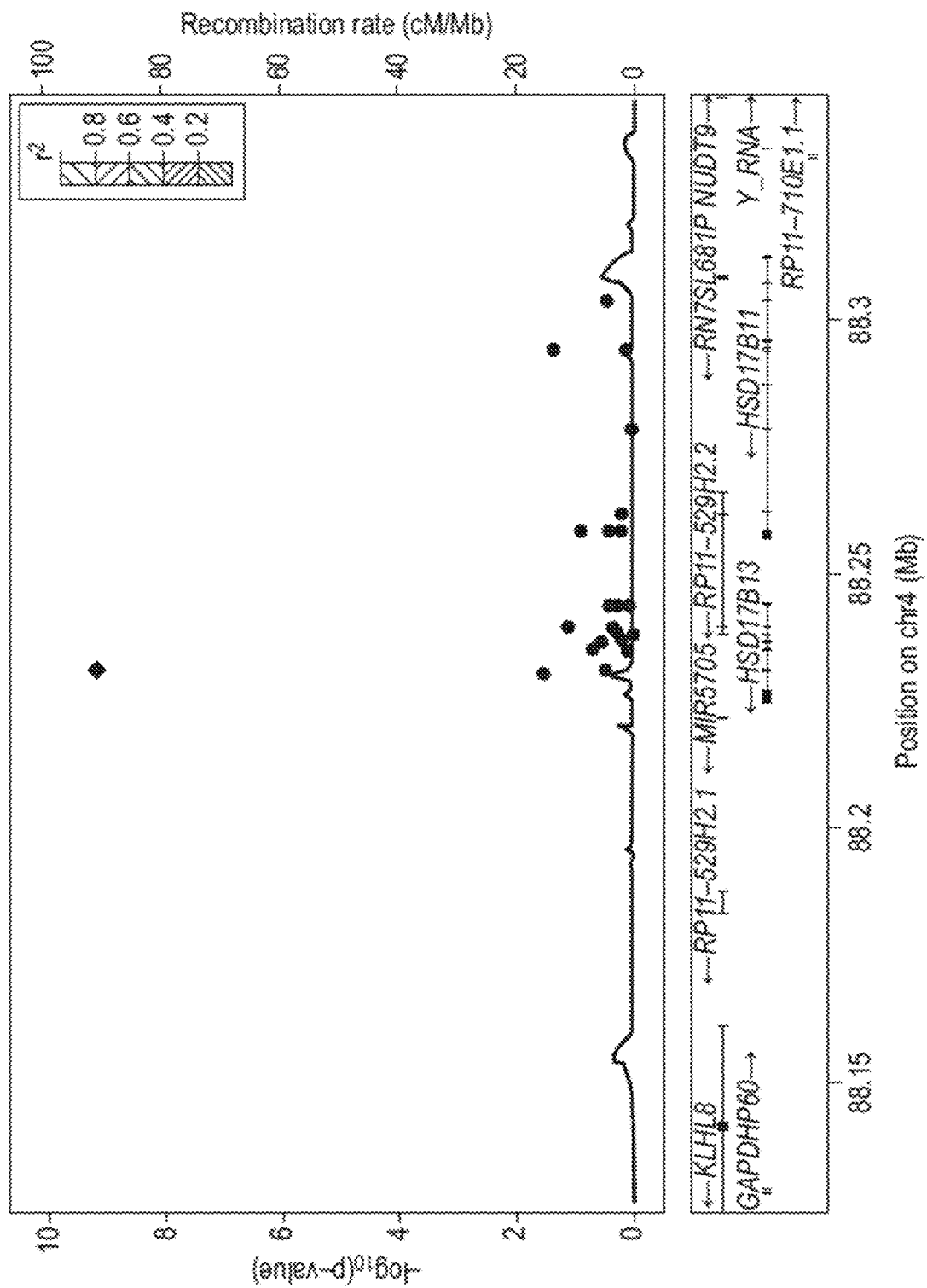
Figure 6A:
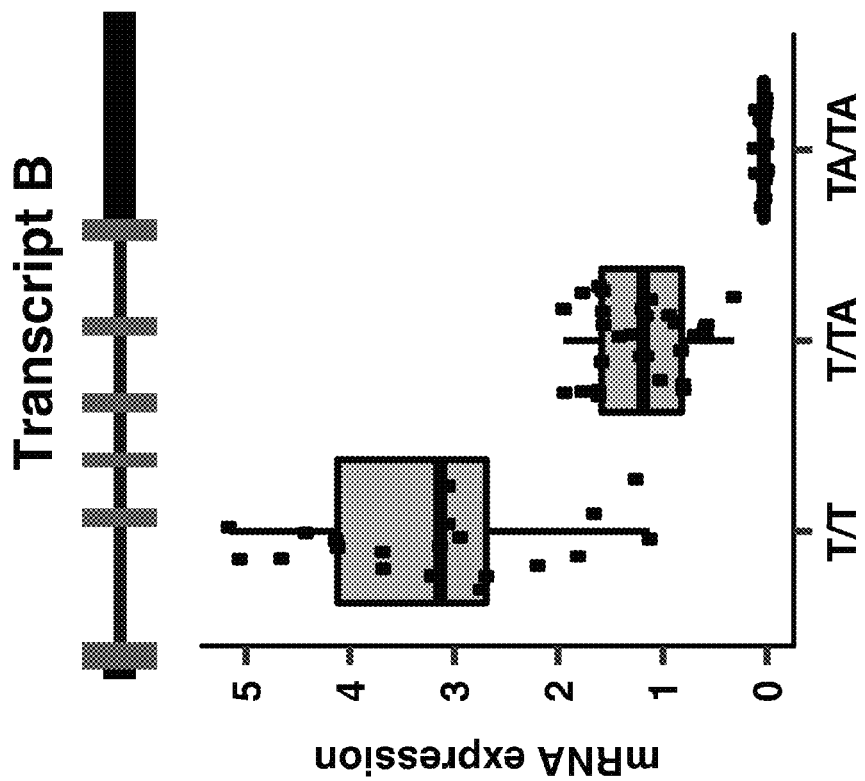
FIGS. 6A, 6B, 6C, 6D, 6E, 6F, 6G, and 6H show mRNA expression of eight HSD17B13 Transcripts (A-H) in homozygous reference (T/T), heterozygous (T/TA), and homozygous alternate (TA/TA) allele carriers of the HSD17B13 splice variant; each transcript is illustrated with a corresponding gene model; coding regions in gene models are indicated in vertical rectangles, untranslated regions as thick lines, and introns as thin lines; the asterisks indicate the A insertion from rs72613567; transcripts are differentially expressed according to HSD17B13 genotype, as shown in the box plots; mRNA expression is displayed in FPKM units (Fragments Per Kilobase of transcript per Million mapped reads).
Figure 6B:
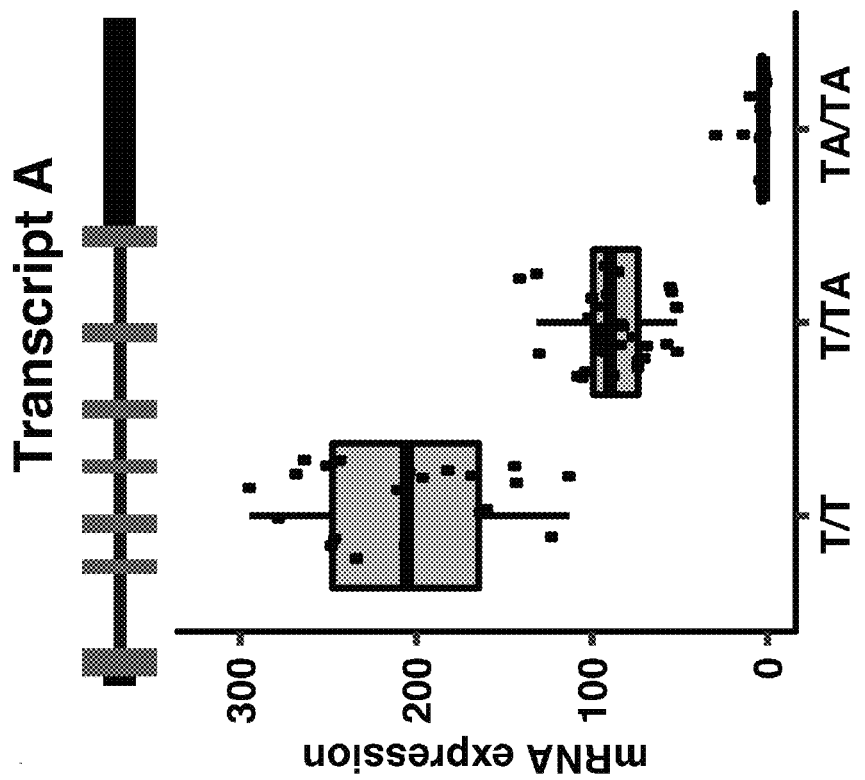
Figures 6C, 6D:
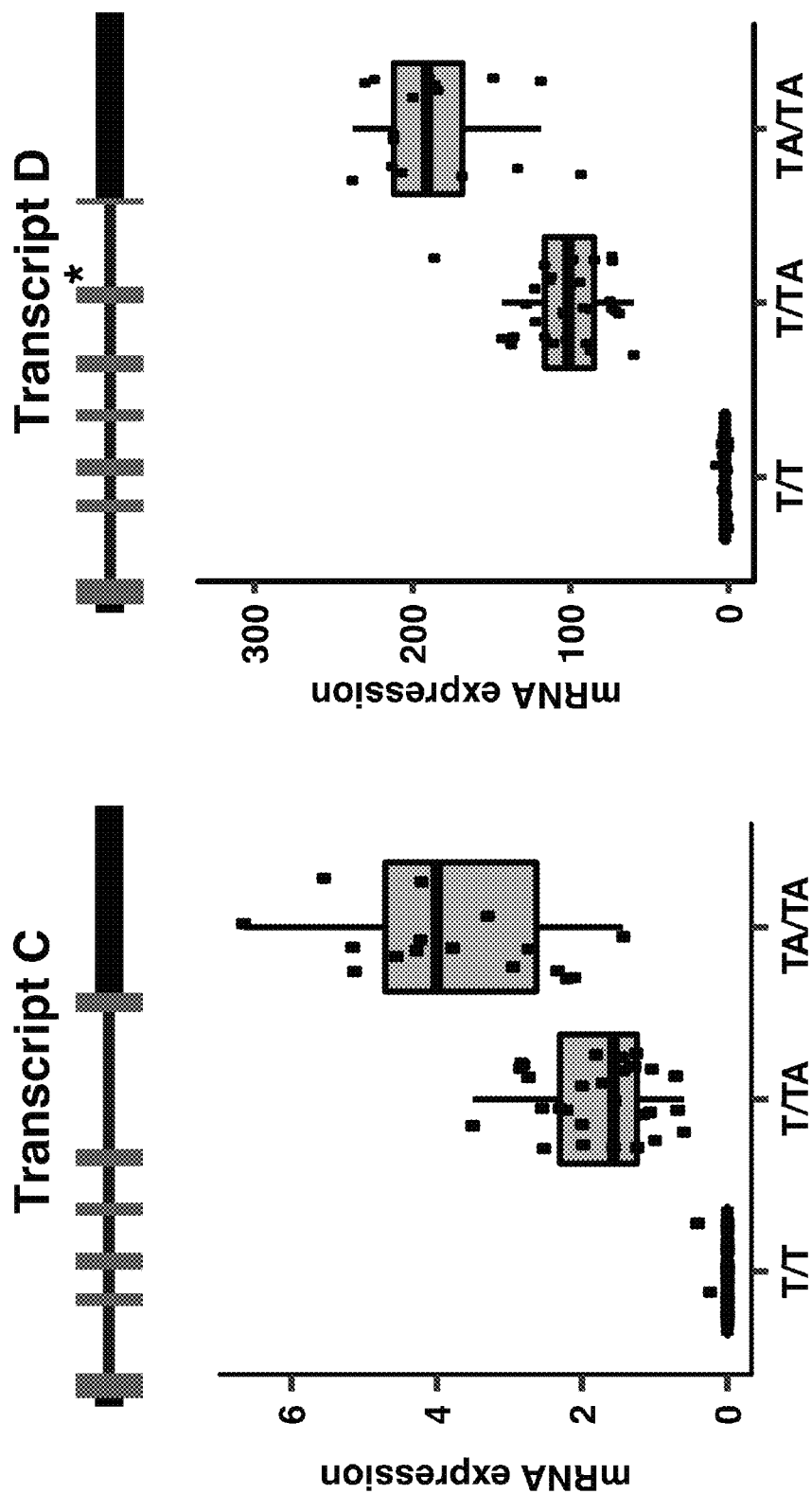
Figure 6E:
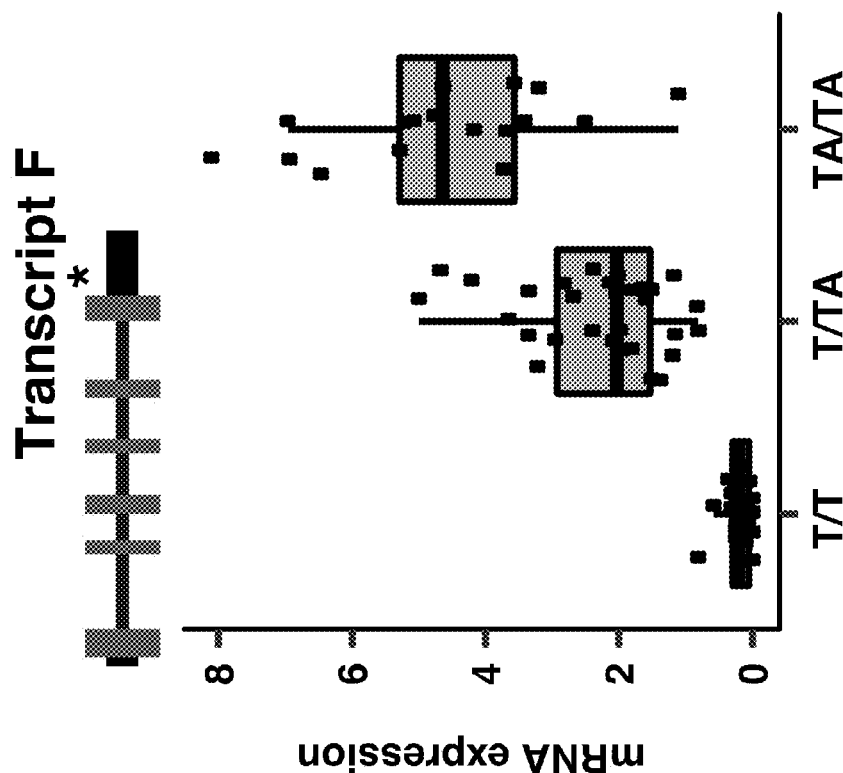
Figure 6F:
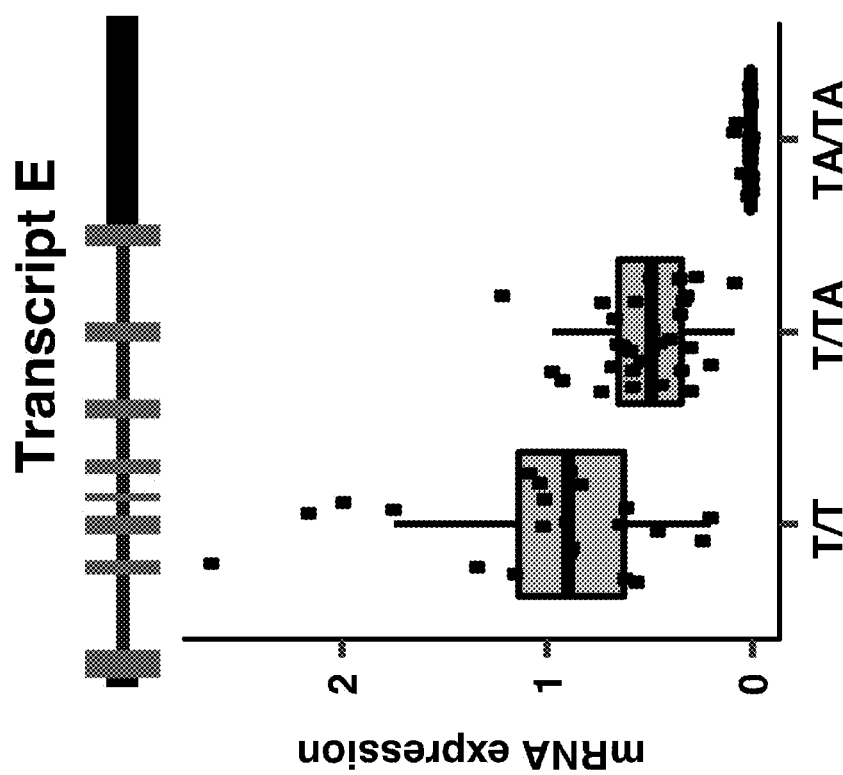
Figures 6G, 6H:
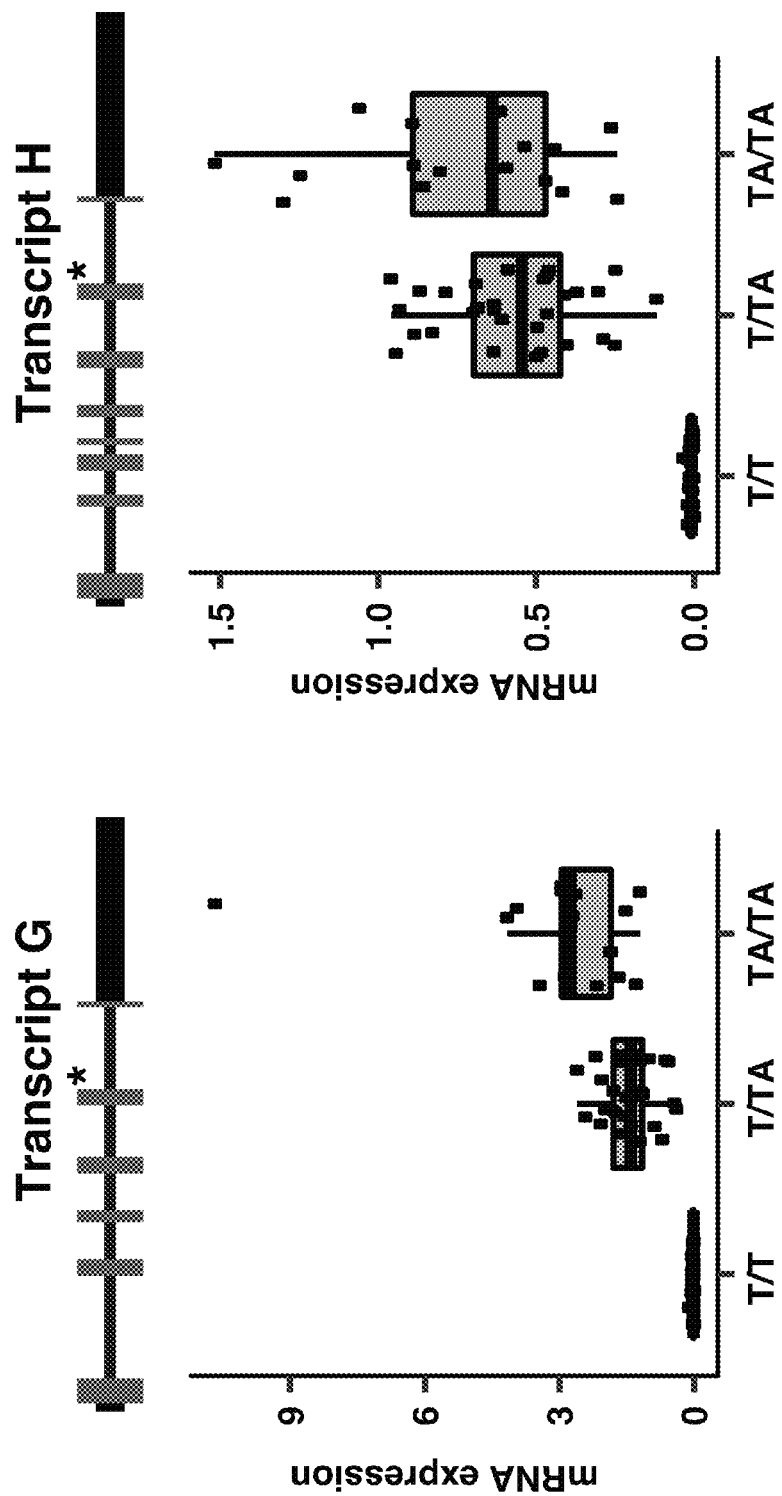

We also identified a reproducible association between a variant in HSD17B13, the gene encoding hydroxysteroid 17-beta dehydrogenase 13, an uncharacterized member of the 17-beta hydroxysteroid dehydrogenase family, and decreased levels of ALT (discovery $P=4.2\times10^{-12}$, replication $P=1.7\times10^{-4}$) and AST (discovery $P=-6.2\times10^{-10}$, replication $P=1.7\times10^{-4}$, Table 3). The associated variant, rs72613567, is an insertion of an adenine adjacent to the donor splice site of exon six (TA allele), and had an allele frequency of 26.0% in the GHS discovery cohort. Previously, Chambers et al. identified a nearby locus at 4q22 (rs6834314) associated with ALT levels (Chambers et al., Nat. Genet., 2011, 43, 1131-1138. doi: 10, 1038/ng.970); rs72613567 has not heretofore been reported to be associated with transaminase levels. HSD17B13 is 30 kb upstream of HSD17B11, another member of the same gene family. We did not observe exome-wide significant associations between coding or splice variants in HSD17B11 and transaminase levels in the discovery cohort (FIGS. 5A and 5B) or in the joint meta-analysis of the discovery cohort and three replication cohorts. Furthermore, linkage disequilibrium of rs72613567 with variants in HSD17B11 was modest across all ancestry groups (r<0.4 with all ascertained variants in HSD17B11 all ancestry groups). Collectively, these findings suggest HSD17B13 as the gene in the genomic region that is most likely to be functionally related to transaminase levels.

TABLE 1

Demographics and clinical characteristics of sequenced European-ancestry individuals from the discovery and replication cohorts.

| Characteristic | Discovery Cohort (N = 46,544) | Bariatric Surgery Cohort (N = 2,644) | Dallas Heart Study (N = 1,357) | Penn Medicine Biobank (N = 8,526) |
|---|---|---|---|---|
| Age (years) - median (IQR) | 62.9 (49.6-73.8) | 52.9 (44.1-61.2) | 46.0 (38.0-54.0) | 68.0 (60.0-76.0) |
| Female sex - number (%) | 26,875 (57.7) | 2,119 (80.1) | 724 (53.4) | 3,242 (38.0) |
| Body mass index - median (IQR) | 29.9 (35.4-44.8) | 47.4 (42.0-53.7) | 28 (25-32) | 30 (25-32) |
| Transaminase level (U/L) - median (IQR) | | | | |
| Alanine aminotransferase (ALT) | 22.0 (17.0-29.0) | 23.0 (17.5-29.5) | 20.0 (15.0-27.0) | 22.0 (17.0-30.0) |
| Aspartate aminotransferase (AST) | 23.0 (20.0-27.5) | 23.0 (20.0-27.0) | 21.0 (18.0-25.0) | 24.0 (20.0-30.5) |
| Presence of liver disease (by ICD-9 code) - N (%) | | | | |
| Alcoholic liver disease | 197 (0.4) | 7 (0.3) | — | — |
| Alcoholic cirrhosis | 130 (0.3) | 3 (0.1) | — | — |
| Nonalcoholic, non-viral liver disease | 1,938 (4.2) | 1,543 (58.4) | — | — |

TABLE 1-continued

Demographics and clinical characteristics of sequenced European-ancestry individuals from the discovery and replication cohorts.

| Characteristic | Discovery Cohort (N = 46,544) | Bariatric Surgery Cohort (N = 2,644) | Dallas Heart Study (N = 1,357) | Penn Medicine Biobank (N = 8,526) |
|---|---|---|---|---|
| Nonalcoholic cirrhosis | 382 (0.8) | 24 (0.9) | — | — |
| Hepatocellular carcinoma | 76 (0.2) | 1 (0.04) | — | — |
| No liver disease | 30,628 (65.8) | 1 (0.04) | — | — |

TABLE 2

Single nucleotide variants associated with serum transaminase levels at $P < 1.0 \times 10^{-7}$ in the discovery cohort.

| Trait | CHR | BP | REF | ALT | rsID | Gene | Annotation | AA Substitution | Beta (SE) |
|---|---|---|---|---|---|---|---|---|---|
| ALT | 1 | 220970028 | A | G | rs2642438 | MARC1 | missense | p.Thr165Ala | 0.008 (0.001) |
| | 4 | 88231392 | T | TA | *rs72613567 | HSD17B13 | splice donor | | -0.009 (0.001) |
| | 8 | 144997604 | C | T | rs371119003 | PLEC | missense | p.Ala2302Thr | -0.160 (0.026) |
| | 8 | 145008502 | G | A | | PLEC | missense | p.Arg522Cys | -0.268 (0.032) |
| | 8 | 145602018 | G | A | rs35968570 | KIFC2 | missense | p.Glu174Lys | -0.033 (0.005) |
| | 8 | 145730072 | G | A | rs143408057 | GPT | missense | p.Arg83His | -0.314 (0.036) |
| | 8 | 145730161 | C | T | rs201815297 | GPT | missense | p.Ala87Val | -0.224 (0.014) |
| | 8 | 145730221 | G | A | rs112574791 | GPT | missense | p.Arg107Lys | -0.033 (0.005) |
| | 8 | 145731636 | T | G | rs145155876 | GPT | stop gained | p.Tyr326* | -0.235 (0.031) |
| | 8 | 145732114 | G | C | rs141505249 | GPT | missense | p.Glu430Gln | -0.224 (0.013) |
| | 8 | 145732151 | G | A | rs143462595 | GPT | missense | p.Arg442His | -0.077 (0.013) |
| | 8 | 145732180 | G | C | rs147998249 | GPT | missense | p.Val452Leu | -0.225 (0.013) |
| | 8 | 145732305 | G | GC | | GPT | frameshift | p.Glu475fs | -0.271 (0.031) |
| | 8 | 145748532 | A | G | rs567402720 | LRRC24 | missense | p.Leu290Ser | -0.185 (0.028) |
| | 9 | 117122202 | C | T | rs3748177 | AKNA | synonymous | p.Glu755Glu | -0.007 (0.001) |
| | 9 | 117124731 | G | A | rs3748176 | AKNA | missense | p.Pro624Leu | -0.007 (0.001) |
| | 10 | 101595996 | T | A | rs17222723 | ABCC2 | missense | p.Val1188Glu | -0.015 (0.003) |
| | 10 | 101606861 | G | T | rs1137968 | ABCC2 | synonymous | p.Val1430Val | -0.015 (0.003) |
| | 10 | 101610533 | C | T | rs8187707 | ABCC2 | synonymous | p.His1496His | -0.015 (0.003) |

TABLE 2-continued

Single nucleotide variants associated with serum transaminase levels at
$P < 1.0 \times 10^{-7}$ in the discovery cohort.

| | | | | | | | | | |
|---|---|---|---|---|---|---|---|---|---|
| | 10 | 101611294 | G | A | rs8187710 | ABCC2 | missense | p.Cys1515Tyr | -0.015 (0.003) |
| | 10 | 101912064 | T | C | *rs2862954 | ERLIN1 | missense | p.Ile291Val | -0.012 (0.001) |
| | 10 | 101977883 | C | T | rs2230804 | CHUK | missense | p.Val268Ile | -0.009 (0.001) |
| | 10 | 113917085 | T | A | rs2254537 | GPAM | synonymous | p.Pro681Pro | -0.008 (0.001) |
| | 10 | 113940329 | T | C | rs2792751 | GPAM | missense | p.Ile43Val | -0.008 (0.001) |
| | 14 | 94844947 | C | T | *rs28929474 | SERPINA1 | missense | p.Glu366Lys | 0.042 (0.005) |
| | 19 | 19379549 | C | T | *rs58542926 | TM6SF2 | missense | p.Glu167Lys | 0.014 (0.002) |
| | 22 | 44324727 | C | G | *rs738409 | PNPLA3 | missense | p.Ile148Met | 0.023 (0.002) |
| | 22 | 44324730 | C | T | *rs738408 | PNPLA3 | synonymous | p.Pro149Pro | 0.023 (0.002) |
| | 22 | 44342116 | A | G | rs2294918 | PNPLA3 | missense | p.Lys434Glu | 0.007 (0.001) |
| | 22 | 44368122 | A | G | *rs3761472 | SAMM50 | missense | p.Asp110Gly | 0.019 (0.002) |
| | 22 | 44395451 | T | C | *rs1007863 | PARVB | missense | p.Trp37Arg | 0.011 (0.001) |
| AST | 4 | 88231392 | T | TA | *rs72613567 | HSD17B13 | splice donor | | -0.005 (0.001) |
| | 10 | 18242311 | A | G | rs10764176 | SLC39A12 | missense | p.Ser36Gly | -0.006 (0.001) |
| | | 101157378 | CGTT | C | | GOT1 | inframe indel | p.Asn389del | -0.221 (0.024) |
| | 10 | 101165533 | G | C | rs374966349 | GOT1 | missense | p.Gln208Glu | 0.271 (0.027) |
| | 10 | 101912064 | T | C | *r52862954 | ERLIN1 | missense | p.Ile291Val | -0.005 (0.001) |
| | 11 | 22271870 | A | T | rs7481951 | ANO5 | missense | p.Leu322Phe | 0.004 (0.001) |
| | 14 | 94844947 | C | T | *rs28929474 | SERPINA1 | missense | p.Glu366Lys | 0.027 (0.003) |
| | 19 | 19379549 | C | T | *rs58542926 | TM6SF2 | missense | p.Glu167Lys | 0.008 (0.002) |
| | 22 | 44324727 | C | G | *rs738409 | PNPLA3 | missense | pIle148Met | 0.014 (0.001) |
| | 22 | 44324730 | C | T | *rs738408 | PNPLA3 | synonymous | p.Pro149Pro | 0.014 (0.001) |

TABLE 2-continued

Single nucleotide variants associated with serum transaminase levels at $P < 1.0 \times 10^{-7}$ in the discovery cohort.

| | | | | | | | | |
|---|---|---|---|---|---|---|---|---|
| 22 | 44368122 | A | G | *rs3761472 | SAMM50 | missense | p.Asp110Gly | 0.011 (0.001) |
| 22 | 44395451 | T | C | *rs1007863 | PARVB | missense | p.Trp37Arg | 0.006 (0.001) |

| | | | | | | | | N | | | Mean AST or ALT level (U/L) | | |
|---|---|---|---|---|---|---|---|---|---|---|---|---|---|
| Trait | CHR | BP | REF | ALT | P | AAF | N | REF/REF | REF/ALT | ALT/ALT | REF/REF | REF/ALT | ALT/ALT |
| ALT | 1 | 220970028 | A | G | 4.67E-08 | 0.7067 | 41,414 | 3,515 | 17,262 | 20,637 | 23.88 | 24.52 | 24.92 |
| | 4 | 88231392 | T | TA | 4.16E-12 | 0.2634 | 41,414 | 22,441 | 16,130 | 2,843 | 25.02 | 24.26 | 24.1 |
| | 8 | 144997604 | C | T | 1.30E-09 | 0.0005 | 41,413 | 41,373 | 40 | 0 | 24.67 | 18.1 | NA |
| | 8 | 145008502 | G | A | 3.26E-17 | 0.0003 | 41,414 | 41,387 | 27 | 0 | 24.67 | 13.8 | NA |
| | 8 | 145692918 | G | A | 1.40E-11 | 0.0139 | 41,414 | 40,271 | 1,133 | 10 | 24.67 | 12.07 | NA |
| | 8 | 145730072 | G | A | 3.28E-18 | 0.0003 | 41,414 | 41,393 | 21 | 0 | 24.67 | 12.07 | NA |
| | 8 | 145730161 | C | T | 6.28E-59 | 0.0018 | 41,414 | 41,270 | 144 | 0 | 24.7 | 14.68 | NA |
| | 8 | 145730221 | G | A | 4.25E-11 | 0.0136 | 41,414 | 40,293 | 1,111 | 10 | 24.71 | 23.09 | 18.35 |
| | 8 | 145731636 | T | G | 1.76E-14 | 0.0004 | 41,394 | 41,364 | 30 | 0 | 24.67 | 14.07 | NA |
| | 8 | 145732114 | G | C | 8.84E-64 | 0.0019 | 41,375 | 41,223 | 150 | 2 | 24.7 | 14.48 | 13.75 |
| | 8 | 145732151 | G | A | 1.18E-09 | 0.0021 | 41,406 | 41,232 | 174 | 0 | 24.68 | 20.87 | NA |
| | 8 | 145732180 | G | C | 8.19E-65 | 0.0019 | 41,413 | 41,254 | 159 | 0 | 24.7 | 14.74 | NA |
| | 8 | 145732305 | G | GC | 1.00E-18 | 0.0004 | 41,414 | 41,385 | 29 | 0 | 24.67 | 14.24 | NA |
| | 8 | 145748532 | A | G | 3.42E-11 | 0.0004 | 41,393 | 41,358 | 35 | 0 | 24.67 | 17.71 | NA |
| | 9 | 117122202 | C | T | 9.51E-09 | 0.5232 | 41,414 | 9,414 | 20,645 | 11,355 | 25.12 | 24.72 | 24.18 |
| | 9 | 117124731 | G | A | 4.31E-09 | 0.5230 | 41,412 | 9,427 | 20,634 | 11,351 | 25.12 | 24.73 | 24.17 |
| | 10 | 101595996 | T | A | 2.97E-08 | 0.0608 | 41,414 | 36,543 | 4,704 | 167 | 24.77 | 23.97 | 22.12 |
| | 10 | 101606861 | G | T | 2.71E-08 | 0.0608 | 41,414 | 36,543 | 4,704 | 167 | 24.77 | 23.97 | 22.04 |
| | 10 | 101610533 | C | T | 2.77E-08 | 0.0608 | 41,414 | 36,542 | 4,706 | 166 | 24.77 | 23.97 | 22.03 |
| | 10 | 101611294 | G | A | 2.15E-08 | 0.0611 | 41,414 | 36,519 | 4,726 | 169 | 24.77 | 23.97 | 21.99 |
| | 10 | 101912064 | T | C | 2.43E-21 | 0.4755 | 41,414 | 11,318 | 20,819 | 9,277 | 25.32 | 24.71 | 23.77 |
| | 10 | 101977883 | C | T | 1.93E-13 | 0.5072 | 41,414 | 10,048 | 20,733 | 10,633 | 25.18 | 24.75 | 24.01 |

TABLE 2-continued

Single nucleotide variants associated with serum transaminase levels at $P < 1.0 \times 10^{-7}$ in the discovery cohort.

| Trait | Chr | Position | Ref | Alt | P | AAF | N | RR | RA | AA | v1 | v2 | v3 |
|---|---|---|---|---|---|---|---|---|---|---|---|---|---|
|  | 10 | 113917085 | T | A | 4.61E-10 | 0.7073 | 41,414 | 3,627 | 16,984 | 20,803 | 25 | 24.97 | 24.36 |
|  | 10 | 113940329 | T | C | 2.54E-10 | 0.7097 | 41,412 | 3,567 | 16,910 | 20,935 | 25 | 24.98 | 24.35 |
|  | 14 | 94844947 | C | T | 9.28E-21 | 0.0171 | 41,414 | 40,006 | 1,399 | 9 | 24.58 | 26.91 | 43.89 |
|  | 19 | 19379549 | C | T | 4.76E-09 | 0.0759 | 41,413 | 35,388 | 5,780 | 245 | 24.52 | 25.46 | 26.84 |
|  | 22 | 44324727 | C | G | 1.34E-50 | 0.2351 | 41,414 | 24,257 | 14,837 | 2,320 | 24.06 | 24.99 | 28.91 |
|  | 22 | 44324730 | C | T | 1.11E-50 | 0.2349 | 41,414 | 24,273 | 14,824 | 2,317 | 24.06 | 24.98 | 28.92 |
|  | 22 | 44342116 | A | G | 8.26E-08 | 0.5986 | 41,412 | 6,691 | 19,833 | 14,888 | 24.15 | 24.47 | 25.15 |
|  | 22 | 44368122 | A | G | 8.85E-30 | 0.1682 | 41,413 | 28,626 | 11,618 | 1,169 | 24.23 | 25.36 | 28.45 |
|  | 22 | 44395451 | T | C | 7.98E-16 | 0.3963 | 41,414 | 15,036 | 19,920 | 6,458 | 24.15 | 24.6 | 26.09 |
| AST | 4 | 88231392 | T | TA | 6.24E-10 | 0.2638 | 40,753 | 22,068 | 15,870 | 2,815 | 24.47 | 24.1 | 23.96 |
|  | 10 | 18242311 | A | G | 1.09E-10 | 0.2881 | 40,753 | 20,645 | 16,738 | 3,370 | 24.47 | 24.15 | 23.85 |
|  | 10 | 101157378 | CGTT | C | 1.96E-20 | 0.0002 | 40,753 | 40,733 | 20 | 0 | 24.29 | 14.7 | NA |
|  | 10 | 101165533 | G | C | 2.43E-24 | 0.0002 | 40,753 | 40,736 | 17 | 0 | 24.28 | 44.5 | NA |
|  | 10 | 101912064 | T | C | 4.82E-09 | 0.4754 | 40,753 | 11,138 | 20,486 | 9,129 | 24.59 | 24.26 | 23.99 |
|  | 11 | 22271870 | A | T | 9.61E-08 | 0.5833 | 40,722 | 7,123 | 19,686 | 13,913 | 24.03 | 24.22 | 24.53 |
|  | 14 | 94844947 | C | T | 2.44E-20 | 0.0172 | 40,753 | 39,361 | 1,384 | 8 | 24.24 | 25.76 | 34.5 |
|  | 19 | 19379549 | C | T | 6.54E-08 | 0.0760 | 40,752 | 34,811 | 5,698 | 243 | 24.21 | 24.74 | 25.43 |
|  | 22 | 44324727 | C | G | 8.31E-46 | 0.2343 | 40,753 | 23,889 | 14,622 | 2,242 | 23.96 | 24.48 | 26.62 |
|  | 22 | 44324730 | C | T | 8.93E-46 | 0.2341 | 40,753 | 23,905 | 14,609 | 2,239 | 23.96 | 24.47 | 26.63 |
|  | 22 | 44368122 | A | G | 1.22E-22 | 0.1680 | 40,752 | 28,170 | 11,450 | 1,132 | 24.07 | 24.64 | 26.24 |
|  | 22 | 44395451 | T | C | 1.31E-13 | 0.3961 | 40,753 | 14,761 | 19,678 | 6,314 | 24.02 | 24.23 | 25.1 |

*Indicates variants having exome-wide significant associations with both ALT and AST.
Abbreviations: AAF, alternate allele frequency; Alt, alternate allele; ALT, alanine aminotransferase; AST, aspartate aminotransferase; Ref, reference allele; SE, standard error.

TABLE 3

Replication and joint meta-analysis of 35 exome-wide significant single nucleotide variants from the discovery cohort in three separate European-ancestry cohorts.

| Trait | Chr | BP | Ref | Alt | RSID | Gene | Ann | AA Substitution | GHS Discovery Cohort Beta (SE) | P | N |
|---|---|---|---|---|---|---|---|---|---|---|---|
| ALT | 1 | 220970028 | A | G | rs2642438 | MARC1 | mis | p.Thr165Ala | 0.008 (0.001) | 4.67E-08 | 41,414 |
|  | 4 | 88231392 | T | TA | rs72613567 | HSD17B13 | spl |  | -0.009 (0.001) | 4.16E-12 | 41,414 |
|  | 8 | 144997604 | C | T | rs371119003 | PLEC | mis | p.Ala2302Thr | -0.160 (0.026) | 1.30E-09 | 41,413 |
|  | 8 | 145008502 | G | A |  | PLEC | mis | p.Arg522Cys | -0.268 (0.032) | 3.26E-17 | 41,414 |
|  | 8 | 145692918 | G | A | rs35968570 | KIFC2 | mis | p.Glu174Lys | -0.033 (0.005) | 1.40E-11 | 41,414 |
|  | 8 | 145730072 | G | A | rs143408057 | GPT | mis | p.Arg83His | -0.314 (0.036) | 3.28E-18 | 41,414 |
|  | 8 | 145730161 | C | T | rs201815297 | GPT | mis | p.Ala87Val | -0.224 (0.014) | 6.28E-59 | 41,414 |
|  | 8 | 145730221 | G | A | rs112574791 | GPT | mis | p.Arg107Lys | -0.033 (0.005) | 4.25E-11 | 41,414 |
|  | 8 | 145731636 | T | G | rs145155876 | GPT | stop | p.Tyr326* | -0.235 (0.031) | 1.76E-14 | 41,394 |
|  | 8 | 145732114 | G | C | rs141505249 | GPT | mis | p.Glu430Gln | -0.224 (0.013) | 8.84E-64 | 41,375 |
|  | 8 | 145732151 | G | A | rs143462595 | GPT | mis | p.Arg442His | -0.077 (0.013) | 1.18E-09 | 41,406 |
|  | 8 | 145732180 | G | C | rs147998249 | GPT | mis | p.Val452Leu | -0.225 (0.013) | 8.19E-65 | 41,413 |
|  | 8 | 145732305 | G | GC |  | GPT | fs | p.Glu475fs | -0.271 (0.031) | 1.00E-18 | 41,414 |
|  | 8 | 145748532 | A | G | rs567402720 | LRRC24 | mis | p.Leu290Ser | -0.185 (0.028) | 3.42E-11 | 41,393 |
|  | 9 | 117122202 | C | T | rs3748177 | AKNA | syn | p.Glu755Gln | -0.007 (0.001) | 9.51E-09 | 41,414 |
|  | 9 | 117124731 | G | A | rs3748176 | AKNA | mis | p.Pro624Leu | -0.007 (0.001) | 4.31E-09 | 41,412 |
|  | 10 | 101595996 | T | A | rs17222723 | ABCC2 | mis | p.Val1188Glu | -0.015 (0.003) | 2.97E-08 | 41,414 |
|  | 10 | 101606861 | G | T | rs1137968 | ABCC2 | syn | p.Val1430Val | -0.015 (0.003) | 2.71E-08 | 41,414 |
|  | 10 | 101610533 | C | T | rs8187707 | ABCC2 | syn | p.His1496His | -0.015 (0.003) | 2.77E-08 | 41,414 |
|  | 10 | 101611294 | G | A | rs8187710 | ABCC2 | mis | p.Cys1515Tyr | -0.015 (0.003) | 2.15E-08 | 41,414 |
|  | 10 | 101912064 | T | C | rs2862954 | ERLIN1 | mis | p.Ile291Val | -0.012 (0.001) | 2.43E-21 | 40,834 |
|  | 10 | 101977883 | C | T | rs2230804 | CHUK | mis | p.Val268Ile | -0.009 (0.001) | 1.93E-13 | 41,414 |
|  | 10 | 113917085 | T | A | rs2254537 | GPAM | syn | p.Pro681Pro | -0.008 (0.001) | 4.61E-10 | 41,414 |
|  | 10 | 113940329 | T | C | rs2792751 | GPAM | mis | p.Ile43Val | -0.008 (0.001) | 2.54E-10 | 41,412 |

TABLE 3-continued

Replication and joint meta-analysis of 35 exome-wide significant single nucleotide variants from the discovery cohort in three separate European-ancestry cohorts.

| Trait | Chr | BP | Ref | Alt | rsID | Gene | Type | Protein | Beta (SE) | P | N |
|---|---|---|---|---|---|---|---|---|---|---|---|
| | 14 | 94844947 | C | T | rs28929474 | SERPINA1 | mis | p.Glu366Lys | 0.042 (0.005) | 9.28E-21 | 41,414 |
| | 19 | 19379549 | C | T | rs58542926 | TM6SF2 | mis | p.Glu167Lys | 0.014 (0.002) | 4.76E-09 | 41,413 |
| | 22 | 44324727 | C | G | rs738409 | PNPLA3 | mis | p.Ile148Met | 0.023 (0.002) | 1.34E-50 | 41,414 |
| | 22 | 44324730 | C | T | rs738408 | PNPLA3 | syn | p.Pro149Pro | 0.023 (0.002) | 1.11E-50 | 41,414 |
| | 22 | 44342116 | A | G | rs2294918 | PNPL43 | mis | p.Lys434Glu | 0.007 (0.001) | 8.26E-08 | 41,412 |
| | 22 | 44368122 | A | G | rs3761472 | SAMM50 | mis | p.Asp110Gly | 0.019 (0.002) | 8.85E-30 | 41,413 |
| | 22 | 44395451 | T | C | rs1007863 | PARVB | mis | p.Trp37Arg | 0.011 (0.001) | 7.98E-16 | 41,414 |
| AST | 4 | 88231392 | T | TA | rs72613567 | HSD17B13 | spl | | -0.005 (0.001) | 6.24E-10 | 40,753 |
| | 10 | 18242311 | A | G | rs10764176 | SLC39A12 | mis | p.Ser36Gly | -0.006 (0.001) | 1.09E-10 | 40,753 |
| | 10 | 101157378 | CGTT | C | | GOT1 | inf | p.Asn389del | -0.221 (0.024) | 1.96E-20 | 40,753 |
| | 10 | 101165533 | G | C | rs374966349 | GOT1 | mis | p.Gln208Glu | 0.271 (0.027) | 2.43E-24 | 40,753 |
| | 10 | 101912064 | T | C | rs2862954 | ERLIN1 | mis | p.Ile291Val | -0.005 (0.001) | 4.82E-09 | 40,753 |
| | 11 | 22271870 | A | T | rs7481951 | ANO5 | mis | p.Leu322Phe | 0.004 (0.001) | 9.61E-08 | 40,722 |
| | 14 | 94844947 | C | T | rs28929474 | SERPINA1 | mis | p.Glu366Lys | 0.027 (0.003) | 2.44E-20 | 40,753 |
| | 19 | 19379549 | C | T | rs58542926 | TM6SF2 | mis | p.Glu167Lys | 0.008 (0.002) | 6.54E-08 | 40,192 |
| | 22 | 44324727 | C | G | rs738409 | PNPLA3 | mis | p.Ile148Met | 0.014 (0.001) | 8.31E-46 | 40,753 |
| | 22 | 44324730 | C | T | rs738408 | PNPLA3 | syn | p.Pro149Pro | 0.014 (0.001) | 8.93E-46 | 40,753 |
| | 22 | 44368122 | A | G | rs3761472 | SAMM50 | mis | p.Asp110Gly | 0.011 (0.001) | 1.22E-22 | 40,752 |
| | 22 | 44395451 | T | C | rs1007863 | PARVB | Mis | p.Trp37Arg | 0.006 (0.001) | 1.31E-13 | 40,753 |

| | | | GHS Bariatric Surgery Cohort | | | Dallas Heart Study | | | U. Penn | | |
|---|---|---|---|---|---|---|---|---|---|---|---|
| Trait | Chr | BP | Beta (SE) | P | N | Beta (SE) | P | N | Beta (SE) | P | N |
| ALT | 1 | 220970028 | 0.005 (0.005) | 3.10E-01 | 2475 | 0.011 (0.008) | 1.76E-01 | 1357 | 0.007 (0.004) | 1.02E-01 | 6158 |
| | 4 | 88231392 | -0.010 (0.005) | 5.57E-02 | 2475 | -0.016 (0.008) | 6.60E-02 | 1357 | -0.013 (0.004) | 1.33E-03 | 6158 |
| | 8 | 144997604 | -0.492 (0.165) | 2.84E-03 | 2475 | NA (NA) | NA | NA | -0.051 (0.072) | 4.79E-01 | 6158 |
| | 8 | 145008502 | -0.161 (0.165) | 3.29E-01 | 2475 | NA (NA) | NA | NA | -0.247 (0.143) | 8.48E-02 | 6158 |
| | 8 | 145692918 | -0.009 (0.020) | 6.48E-01 | 2475 | 0.032 (0.036) | 3.76E-01 | 1356 | -0.053 (0.018) | 3.72E-03 | 6158 |

TABLE 3-continued

Replication and joint meta-analysis of 35 exome-wide significant single nucleotide variants from the discovery cohort in three separate European-ancestry cohorts.

| Chr | Position | Beta (SE) | P | N | Beta (SE) | P | N | Beta (SE) | P | N |
|---|---|---|---|---|---|---|---|---|---|---|
| 8 | 145730072 | −0.189 (0.165) | 2.50E−01 | 2475 | NA (NA) | NA | NA | −0.298 (0.101) | 3.26E−03 | 6158 |
| 8 | 145730161 | −0.341 (0.074) | 3.64E−06 | 2475 | NA (NA) | NA | NA | −0.143 (0.054) | 8.50E−03 | 6158 |
| 8 | 145730221 | −0.009 (0.020) | 6.45E−01 | 2475 | 0.028 (0.036) | 4.37E−01 | 1357 | −0.060 (0.018) | 5.60E−04 | 6158 |
| 8 | 145731636 | −0.314 (0.165) | 5.71E−02 | 2475 | −0.317 (0.140) | 2.35E−02 | 1356 | −0.148 (0.143) | 3.04E−01 | 6157 |
| 8 | 145732114 | −0.273 (0.048) | 9.83E−09 | 2474 | −0.240 (0.075) | 1.36E−03 | 1357 | −0.197 (0.041) | 1.31E−06 | 6157 |
| 8 | 145732151 | −0.115 (0.058) | 4.82E−02 | 2475 | −0.106 (0.099) | 2.86E−01 | 1356 | −0.049 (0.041) | 2.27E−01 | 6157 |
| 8 | 145732180 | −0.273 (0.050) | 4.26E−08 | 2475 | −0.191 (0.070) | 6.58E−03 | 1357 | −0.197 (0.041) | 1.31E−06 | 6158 |
| 8 | 145732305 | −0.161 (0.165) | 3.29E−01 | 2475 | NA (NA) | NA | NA | −0.509 (0.203) | 1.21E−02 | 6158 |
| 8 | 145748532 | −0.161 (0.165) | 3.29E−01 | 2475 | NA (NA) | NA | NA | −0.307 (0.143) | 3.21E−02 | 6158 |
| 9 | 117122202 | −0.004 (0.005) | 4.09E−01 | 2475 | 0.004 (0.008) | 6.18E−01 | 1357 | −0.007 (0.004) | 5.29E−02 | 6158 |
| 9 | 117124731 | −0.004 (0.005) | 3.90E−01 | 2475 | 0.003 (0.008) | 7.33E−01 | 1356 | −0.007 (0.004) | 4.24E−02 | 6158 |
| 10 | 101595996 | −0.002 (0.010) | 8.01E−01 | 2475 | −0.007 (0.017) | 6.88E−01 | 1357 | −0.017 (0.007) | 1.55E−02 | 6158 |
| 10 | 101606861 | −0.003 (0.010) | 7.74E−01 | 2475 | −0.008 (0.017) | 6.28E−01 | 1357 | −0.017 (0.007) | 1.70E−02 | 6158 |
| 10 | 101610533 | −0.003 (0.010) | 7.93E−01 | 2475 | −0.008 (0.017) | 6.28E−01 | 1357 | −0.017 (0.007) | 1.76E−02 | 6158 |
| 10 | 101611294 | −0.001 (0.010) | 9.11E−01 | 2475 | −0.010 (0.017) | 5.40E−01 | 1357 | −0.016 (0.007) | 2.77E−02 | 6158 |
| 10 | 101912064 | −0.010 (0.005) | 2.91E−02 | 2475 | −0.006 (0.007) | 4.02E−01 | 1356 | −0.009 (0.004) | 2.06E−02 | 6158 |
| 10 | 101977883 | −0.006 (0.005) | 2.05E−01 | 2475 | 0.0001 (0.008) | 9.94E−01 | 1357 | −0.011 (0.004) | 3.91E−03 | 6158 |
| 10 | 113917085 | −0.003 (0.005) | 5.80E−01 | 2475 | −0.013 (0.008) | 1.15E−01 | 1357 | −0.008 (0.004) | 5.12E−02 | 6158 |
| 10 | 113940329 | −0.003 (0.005) | 5.61E−01 | 2475 | −0.013 (0.008) | 1.33E−01 | 1357 | −0.008 (0.004) | 4.77E−02 | 6158 |
| 14 | 94844947 | 0.035 (0.020) | 7.97E−02 | 2475 | 0.034 (0.032) | 2.92E−01 | 1357 | 0.054 (0.013) | 1.63E−05 | 6158 |
| 19 | 19379549 | 0.040 (0.010) | 2.40E−05 | 2475 | 0.024 (0.014) | 9.50E−02 | 1357 | 0.013 (0.008) | 7.51E−02 | 6158 |
| 22 | 44324727 | 0.019 (0.006) | 5.54E−04 | 2475 | 0.006 (0.009) | 5.43E−01 | 1357 | 0.016 (0.004) | 2.05E−04 | 6158 |
| 22 | 44324730 | 0.019 (0.006) | 5.51E−04 | 2475 | 0.006 (0.009) | 5.43E−01 | 1357 | 0.016 (0.004) | 2.14E−04 | 6158 |
| 22 | 44342116 | 0.001 (0.005) | 7.77E−01 | 2475 | 0.005 (0.008) | 5.18E−01 | 1357 | 0.005 (0.004) | 2.16E−01 | 6158 |
| 22 | 44368122 | 0.009 (0.006) | 1.66E−01 | 2475 | −0.001 (0.01) | 9.37E−01 | 1357 | 0.018 (0.005) | 4.02E−04 | 6158 |

TABLE 3-continued

Replication and joint meta-analysis of 35 exome-wide significant single nucleotide variants from the discovery cohort in three separate European-ancestry cohorts.

| Trait | Chr | BP | Beta (SE) | P | | Beta (SE) | P | | Beta (SE) | P | |
|---|---|---|---|---|---|---|---|---|---|---|---|
| | 22 | 44395451 | 0.003 (0.005) | 5.22E-01 | 2475 | 0.008 (0.008) | 3.13E-01 | 1357 | 0.009 (0.004) | 2.50E-02 | 6158 |
| AST | 4 | 88231392 | -0.010 (0.003) | 3.12E-03 | 2469 | -0.012 (0.006) | 5.32E-02 | 1357 | -0.007 (0.004) | 5.56E-02 | 6166 |
| | 10 | 18242311 | -0.010 (0.003) | 2.91E-03 | 2469 | -0.003 (0.006) | 5.80E-01 | 1357 | -0.009 (0.004) | 1.03E-02 | 6166 |
| | 10 | 101157378 | -0.205 (0.062) | 8.57E-04 | 2469 | NA (NA) | NA | NA | -0.243 (0.088) | 5.97E-03 | 6165 |
| | 10 | 101165533 | NA (NA) | NA | NA | NA (NA) | NA | NA | 0.339 (0.079) | 1.85E-05 | 6166 |
| | 10 | 101912064 | -0.004 (0.003) | 1.54E-01 | 2469 | -0.007 (0.006) | 2.21E-01 | 1357 | -0.004 (0.003) | 1.94E-01 | 6166 |
| | 11 | 22271870 | -0.001 (0.003) | 7.85E-01 | 2466 | 0.006 (0.006) | 2.85E-01 | 1357 | -0.002 (0.003) | 5.46E-01 | 6165 |
| | 14 | 94844947 | 0.023 (0.013) | 7.79E-02 | 2469 | 0.044 (0.024) | 6.98E-02 | 1357 | 0.055 (0.011) | 4.01E-07 | 6166 |
| | 19 | 19379549 | 0.023 (0.006) | 1.99E-04 | 2469 | 0.010 (0.011) | 3.42E-01 | 1356 | 0.004 (0.007) | 5.94E-01 | 6166 |
| | 22 | 44324727 | 0.014 (0.004) | 1.27E-04 | 2469 | 0.004 (0.007) | 5.44E-01 | 1357 | 0.015 (0.004) | 4.87E-05 | 6166 |
| | 22 | 44324730 | 0.014 (0.004) | 1.32E-04 | 2469 | 0.004 (0.007) | 5.44E-01 | 1357 | 0.015 (0.004) | 4.96E-05 | 6166 |
| | 22 | 44368122 | 0.008 (0.004) | 6.03E-02 | 2469 | -0.001 (0.008) | 9.45E-01 | 1357 | 0.016 (0.004) | 2.64E-04 | 6166 |
| | 22 | 44395451 | 0.003 (0.003) | 4.12E-01 | 2469 | 0.006 (0.006) | 2.95E-01 | 1357 | 0.009 (0.003) | 6.17E-03 | 6166 |

| | | | **Replication Meta-Analysis (N = 3) | | ***Joint Meta-Analysis (N = 4) | |
|---|---|---|---|---|---|---|
| Trait | Chr | BP | Beta (SE) | P | Beta (SE) | P |
| ALT | 1 | 220970028 | 0.007 (0.003) | 2.31E-02 | 0.008 (0.001) | 3.38E-09 |
| | 4 | 88231392 | -0.013 (0.003) | *3.85E-05 | -0.010 (0.001) | 1.17E-15 |
| | 8 | 144997604 | -0.121 (0.066) | 6.56E-02 | -0.155 (0.025) | 2.68E-10 |
| | 8 | 145008502 | -0.210 (0.108) | 5.23E-02 | -0.264 (0.031) | 5.54E-18 |
| | 8 | 145692918 | -0.025 (0.013) | 4.69E-02 | -0.032 (0.005) | 2.25E-12 |
| | 8 | 145730072 | -0.268 (0.086) | 1.88E-03 | -0.308 (0.033) | 2.79E-20 |
| | 8 | 145730161 | -0.213 (0.044) | *1.14E-06 | -0.223 (0.013) | 4.49E-64 |
| | 8 | 145730221 | -0.031 (0.013) | 1.36E-02 | -0.033 (0.005) | 1.92E-12 |
| | 8 | 145731636 | -0.256 (0.086) | 2.79E-03 | -0.237 (0.029) | 1.94E-16 |
| | 8 | 145732114 | -0.231 (0.029) | *7.24E-16 | -0.225 (0.012) | 6.06E-78 |
| | 8 | 145732151 | -0.074 (0.032) | 1.88E-02 | -0.076 (0.012) | 7.03E-11 |

TABLE 3-continued

Replication and joint meta-analysis of 35 exome-wide significant single nucleotide variants from the discovery cohort in three separate European-ancestry cohorts.

|     |    |           |                    |           |                    |          |
|-----|----|-----------|--------------------|-----------|--------------------|----------|
|     | 8  | 145732180 | −0.221 (0.029)     | *1.41E−14 | −0.224 (0.012)     | 1.04E−77 |
|     | 8  | 145732305 | −0.299 (0.128)     | 1.93E−02  | −0.273 (0.030)     | 6.44E−20 |
|     | 8  | 145748532 | −0.244 (0.108)     | 2.40E−02  | −0.189 (0.027)     | 2.93E−12 |
|     | 9  | 117122202 | −0.005 (0.003)     | 8.42E−02  | −0.007 (0.001)     | 3.08E−09 |
|     | 9  | 117124731 | −0.005 (0.003)     | 6.15E−02  | −0.007 (0.001)     | 1.00E−09 |
|     | 10 | 101595996 | −0.012 (0.005)     | 3.43E−02  | −0.014 (0.002)     | 3.44E−09 |
|     | 10 | 101606861 | −0.012 (0.005)     | 3.25E−02  | −0.014 (0.002)     | 2.99E−09 |
|     | 10 | 101610533 | −0.012 (0.005)     | 3.43E−02  | −0.014 (0.002)     | 3.23E−09 |
|     | 10 | 101611294 | −0.011 (0.005)     | 5.21E−02  | −0.014 (0.002)     | 4.09E−09 |
|     | 10 | 101912064 | −0.009 (0.003)     | *1.14E−03 | −0.011 (0.001)     | 1.76E−23 |
|     | 10 | 101977883 | −0.008 (0.003)     | 4.33E−03  | −0.009 (0.001)     | 3.59E−15 |
|     | 10 | 113917085 | −0.007 (0.003)     | 2.07E−02  | −0.008 (0.001)     | 3.28E−11 |
|     | 10 | 113940329 | −0.007 (0.003)     | 2.00E−02  | −0.008 (0.001)     | 1.77E−11 |
|     | 14 | 94844947  | 0.047 (0.010)      | *2.82E−06 | 0.043 (0.004)      | 1.59E−25 |
|     | 19 | 19379549  | 0.024 (0.006)      | *1.37E−05 | 0.016 (0.002)      | 1.15E−12 |
|     | 22 | 44324727  | 0.016 (0.003)      | *7.45E−07 | 0.021 (0.001)      | 3.55E−55 |
|     | 22 | 44324730  | 0.016 (0.003)      | *7.73E−07 | 0.021 (0.001)      | 3.10E−55 |
|     | 22 | 44342116  | 0.004 (0.003)      | 1.91E−01  | 0.006 (0.001)      | 6.24E−08 |
|     | 22 | 44368122  | 0.012 (0.004)      | *7.69E−04 | 0.018 (0.002)      | 1.08E−31 |
|     | 22 | 44395451  | 0.007 (0.003)      | 1.78E−02  | 0.010 (0.001)      | 1.16E−16 |
| AST | 4  | 88231392  | −0.009 (0.002)     | *8.38E−05 | −0.006 (0.001)     | 6.82E−13 |
|     | 10 | 18242311  | −0.009 (0.002)     | *1.16E−04 | −0.006 (0.001)     | 1.10E−13 |
|     | 10 | 101157378 | −0.218 (0.051)     | *1.66E−05 | −0.220 (0.022)     | 1.68E−24 |
|     | 10 | 101165533 | 0.339 (0.079)      | *1.85E−05 | 0.278 (0.025)      | 3.25E−28 |
|     | 10 | 101912064 | −0.005 (0.002)     | 2.51E−02  | −0.005 (0.001)     | 3.68E−10 |
|     | 11 | 22271870  | 0.000 (0.002)      | 8.43E−01  | 0.004 (0.001)      | 1.13E−06 |

TABLE 3-continued

Replication and joint meta-analysis of 35 exome-wide significant single nucleotide variants from the discovery cohort in three separate European-ancestry cohorts.

| | | | | | |
|---|---|---|---|---|---|
| 14 | 94844947 | 0.042 (0.008) | *9.54E-08 | 0.029 (0.003) | 6.71E-26 |
| 19 | 19379549 | 0.014 (0.004) | *1.20E-03 | 0.009 (0.002) | 5.92E-10 |
| 22 | 44324727 | 0.013 (0.002) | *5.51E-08 | 0.014 (0.001) | 3.14E-52 |
| 22 | 44324730 | 0.013 (0.002) | *5.81E-08 | 0.014 (0.001) | 3.55E-52 |
| 22 | 44368122 | 0.010 (0.003) | *3.40E-04 | 0.011 (0.001) | 1.91E-25 |
| 22 | 44395451 | 0.006 (0.002) | 7.34E-03 | 0.006 (0.001) | 3.62E-15 |

*Indicates P-values meeting the Bonferroni significance threshold of $P < 1.43 \times 10^{-3}$.
**Replication meta-analysis includes the three replication cohorts: GHS Bariatric Surgery Cohort, Dallas Heart Study, and Penn Medicine Biobank.
***Joint meta-analysis includes the discovery cohort and the three replication cohorts: GHS Discovery Cohort, GHS Bariatric Surgery Cohort, Dallas Heart Study, and Penn Medicine Biobank.

Abbreviations

AAF, alternate allele frequency; Alt, alternate allele; ALT, alanine aminotransferase; AST, aspartate aminotransferase; Ref, reference allele; SE, standard error; ann, annotation; mis, missense; syn, synonymous; spl, splice donor; stop, stop gained; fs, frameshift; inf, inframe indel.

Association of Exonic Variants with Clinical Diagnoses of Chronic Liver Disease

Figure 2A:
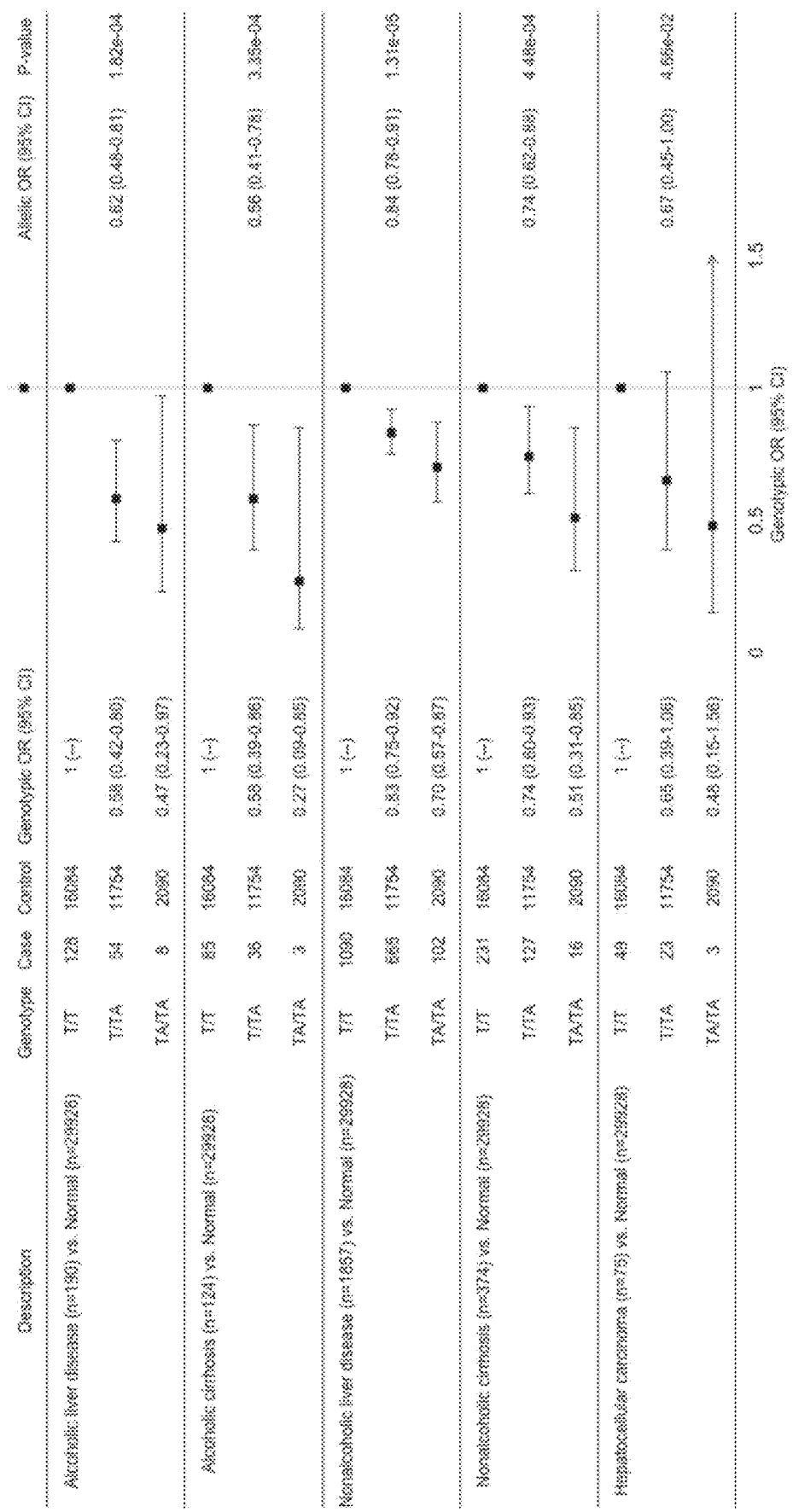
FIGS. 2A and 2B show that HSD17B13 rs72613567:TA is associated with reduced risk of alcoholic and nonalcoholic liver disease phenotypes; 2A: HSD17B13 rs72613567 was associated with lower odds of nonalcoholic and alcoholic liver disease, cirrhosis, and hepatocellular carcinoma in an allele dosage-dependent manner; odds ratios were calculated using logistic regression, with adjustment for age, age$^2$, sex, BMI, and principal components of ancestry; genotypic odds ratios for heterozygous (Het OR) and homozygous (Hom OR) carriers are also shown; 2B: in the Dallas Liver Study, HSD17B13 rs72613567 was associated with lower odds of any liver disease in an allele dosage-dependent manner; similar allele dosage-dependent effects were observed across liver disease subtypes; odds ratios were calculated using logistic regression, with adjustment for age, age$^2$, sex, BMI, and self-reported ethnicity.

Next, we analyzed the relationship between the thirteen transaminase-associated variants in the nine genes found in the discovery and replication cohorts and chronic liver disease, including alcoholic and nonalcoholic (non-viral) liver disease, as well as the most advanced forms of chronic liver disease: alcoholic cirrhosis, nonalcoholic cirrhosis, and hepatocellular carcinoma (HCC). Using a Bonferroni significance threshold of $P<1.92\times10^3$ for the thirteen variants tested, we found significant associations between six variants in five genes (HSD17B13, SERPINA1, TM6SF2, PNPLA3, and SAMM50) and chronic liver disease phenotypes (Table 4). The SERPINA1, TM6SF2, PNPLA3, and SAMM50 associations confirm previously reported associations. In the discovery cohort, HSD17B13 rs72613567:TA was associated with lower odds of all EHR-derived categories of both alcoholic and nonalcoholic liver disease in an allele dosage-dependent manner (FIG. 2A): all categories of alcoholic liver disease, heterozygous odds ratio ($OR_{het}$) (95% confidence interval) 0.58 (0.42-0.80), homozygous OR ($OR_{hom}$) 0.47 (0.23-0.97), allelic OR ($OR_{allelic}$) 0.62 (0.48-0.81), $P=0.8\times10^{-4}$; all categories of nonalcoholic liver disease, $OR_{het}$ 0.83 (0.75-0.92), $OR_{hom}$ 0.70 (0.57-0.87), $OR_{allelic}$ 0.84 (0.78-0.91), $P=1.3\times10^{-5}$. HSD17B13 rs72613567:TA was also associated with lower odds of alcoholic and nonalcoholic cirrhosis, with 42% and 73% lower odds of alcoholic cirrhosis for heterozygotes and homozygotes, respectively, ($OR_{het}$ 0.58 (0.39-0.86), $OR_{hom}$ 0.27 (0.09-0.85), $OR_{allelic}$ 0.56 (0.41-0.78), $P=3.4\times10^{-4}$) and 26% and 49% lower odds of nonalcoholic cirrhosis for heterozygotes and homozygotes, respectively ($OR_{het}$ 0.74 (0.60-0.93), $OR_{hom}$ 0.51 (0.31-0.85), $OR_{allelic}$ 0.74 (0.62-0.88), $P=4.5\times10^{-4}$). HSD17B13 rs72613567:TA was also nominally associated with lower odds of HCC.

Figure 2B:
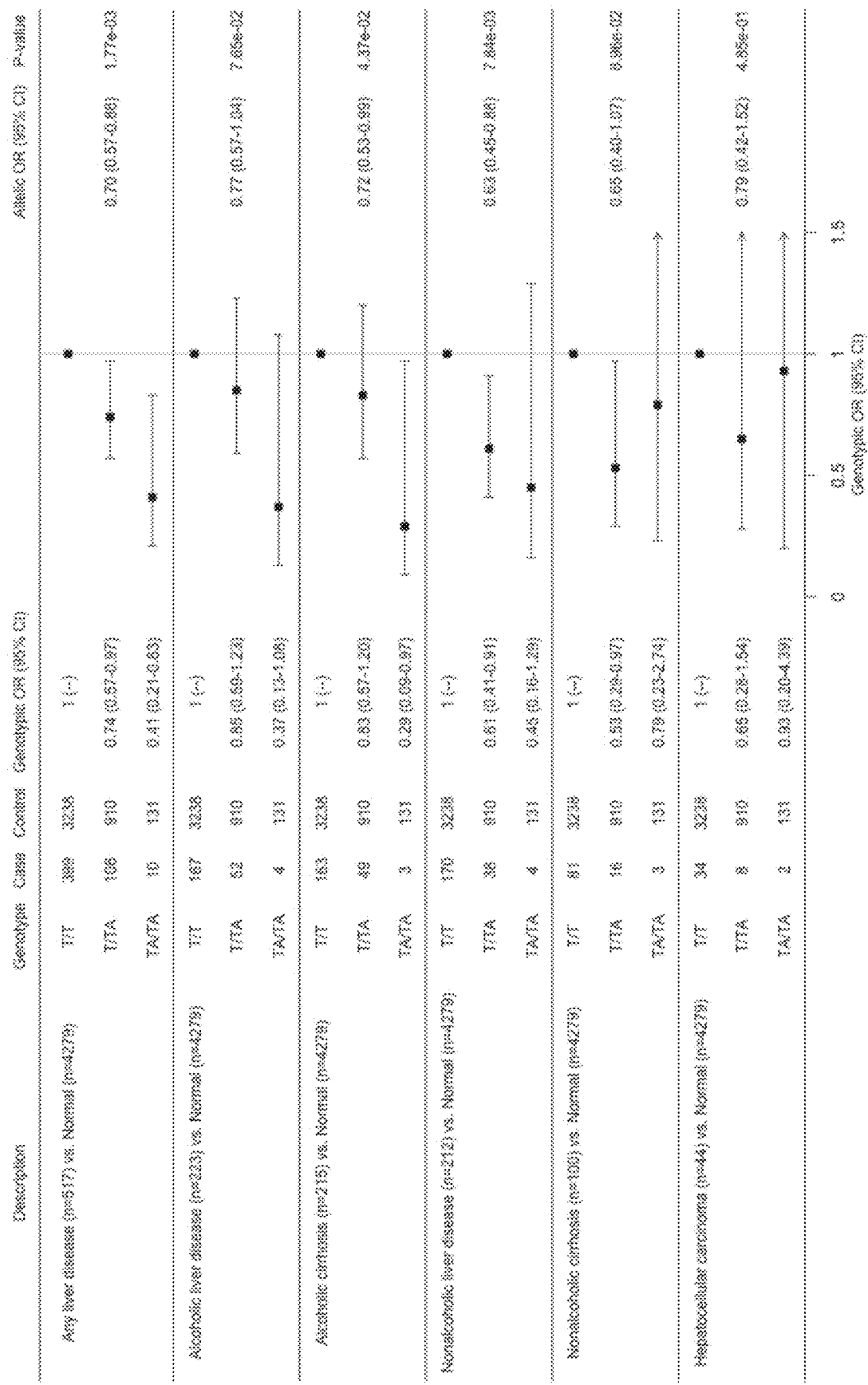

We sought to confirm and extend these findings in the multi-ethnic Dallas Liver Study (DLS) and the Dallas Pediatric Liver Study (DPLS, Table 5). In the DLS, the TA allele was associated with lower odds of any liver disease in an allele-dosage dependent manner ($OR_{het}$ 0.74 (0.57-0.97), $OR_{hom}$ 0.41 (0.21-0.83), $OR_{allelic}$ 0.70 (0.5-0.88), $P=1.8\times10^{-3}$, FIG. 2B). Similar effects were observed across EHR-derived liver disease subtypes, including protective associations with advanced, cirrhotic forms of alcoholic ($OR_{allelic}$ 0.72 (0.53-0.99), $P=4.4\times10^{-2}$) and nonalcoholic ($OR_{allelic}$ 0.65 (0.40-1.07), $P=9.0\times10^{-2}$) liver disease. In subset analyses of individuals grouped by self-reported ethnicity, the association with liver disease was significant in Hispanic Americans (n=326 cases and 722 controls, $OR_{allelic}$ 0.51 (0.35-0.74), $P=4.0\times10^{-4}$); similar numerical trends, which did not achieve statistical significance, were also noted in the African American (n=33 cases and 2,291 controls, $OR_{allelic}$ 0.74 (0.25-2.47), $P=0.67$) and European American (n=158 cases and 1,266 controls, $OR_{allelic}$ 0.87 (0.65-1.15), $P=0.32$) subsets of the DLS. In the DPLS, a separate study of Hispanic American pediatric liver disease patients and obese controls, the TA allele was also associated with lower odds of liver disease ($OR_{allelic}$ 0.61 (0.37-0.99), $P=4.6\times10^{-2}$). Thus, HSD17B13 rs72613567:TA was associated with reduced odds of multiple forms of chronic liver disease, including cirrhosis, in adults and children in three independent populations.

TABLE 4

Association of twelve exome-wide significant and replicating single nucleotide variants with liver disease phenotypes in the discovery cohort.

| CHR:BP:Ref:Alt | Gene | rsID | Alcoholic liver disease OR (95% CI) | P-value | Alcoholic cirrhosis OR (95% CI) | P-value |
|---|---|---|---|---|---|---|
| 4:88231392:T:TA | HSD17B13 | rs72613567 | 0.62 (0.48-0.81) | *1.82E−04 | 0.56 (0.41-0.78) | *3.35E−04 |
| 8:145730161:C:T | GPT | rs201815297 | 3.83 (1.05-13.94) | 8.88E−02 | 6.33 (1.71-23.43) | 2.88E−02 |
| 8:145732114:G:C | GPT | rs141505249 | 0.77 (0.06-10.73) | 8.43E−01 | 1.13 (0.08-15.39) | 9.30E−01 |
| 8:145732180:G:C | GPT | rs147998249 | 0.73 (0.05-11.76) | 8.17E−01 | 1.07 (0.07-17.16) | 9.60E−01 |
| 10:18242311:A:G | SLC39A12 | rs10764176 | 0.85 (0.68-1.07) | 1.64E−01 | 0.92 (0.70-1.22) | 5.80E−01 |
| 10:101157378:CGTT:C | GOT1 |  | 4.60 (0.25-86.41) | 3.93E−01 | 7.11 (0.38-133.19) | 3.00E−01 |
| 10:101165533:G:C | GOT1 | rs374966349 | 2.20 (0.13-37.68) | 6.24E−01 | 3.47 (0.20-59.04) | 4.70E−01 |
| 14:94844947:C:T | SERPINA1 | rs28929474 | 2.49 (1.49-4.17) | 2.30E−03 | 3.35 (1.93-5.83) | *3.01E−04 |
| 19:19379549:C:T | TM6SF2 | rs58542926 | 1.47 (1.06-2.04) | 2.76E−02 | 1.35 (0.89-2.04) | 1.80E−01 |
| 22:44324727:C:G | PNPLA3 | rs738409 | 1.76 (1.43-2.18) | *4.98E−07 | 2.07 (1.60-2.67) | *1.08E−07 |
| 22:44324730:C:T | PNPLA3 | rs738408 | 1.77 (1.43-2.18) | *4.70E−07 | 2.07 (1.61-2.67) | *1.03E−07 |
| 22:44368122:A:G | SAMM50 | rs3761472 | 1.90 (1.52-2.38) | *1.36E−07 | 2.28 (1.75-2.98) | *1.83E−08 |

| CHR:BP:Ref:Alt | Gene | rsID | Nonalcoholic liver disease OR (95% CI) | P-value | Nonalcoholic cirrhosis OR (95% CI) | P-value | Hepatocellular carcinoma OR (95% CI) | P-value |
|---|---|---|---|---|---|---|---|---|
| 4:88231392:T:TA | HSD17B13 | rs72613567 | 0.84 (0.78-0.91) | *1.31E−05 | 0.74 (0.62-0.88) | *4.48E−04 | 0.67 (0.45-1.00) | 4.66E−02 |
| 8:145730161:C:T | GPT | rs201815297 | 0.23 (0.04-1.14) | 1.86E−02 | 1.25 (0.24-6.38) | 7.98E−01 | 3.66 (0.70-19.01) | 2.01E−01 |
| 8:145732114:G:C | GPT | rs141505249 | 1.02 (0.49-2.11) | 9.70E−01 | 0.36 (0.02-5.37) | 3.82E−01 | 1.84 (0.15-23.25) | 6.88E−01 |
| 8:145732180:G:C | GPT | rs147998249 | 1.03 (0.49-2.17) | 9.30E−01 | 0.34 (0.02-5.59) | 3.67E−01 | 1.74 (0.11-27.05) | 7.21E−01 |
| 10:18242311:A:G | SLC9A12 | rs10764176 | 0.92 (0.86 0.99) | 3.43E−02 | 1.03 (0.88-1.21) | 7.15E−01 | 1.29 (0.93-1.79) | 1.37E−01 |
| 10:101157378:CGTT:C | GOT1 |  | 2.37 (0.61-9.27) | 2.50E−01 | 8.27 (1.44-47.49) | 5.92E−02 | 9.81 (0.52-183.54) | 2.43E−01 |
| 10:101165533:G:C | GOT1 | rs374966349 | 1.63 (0.53-4.96) | 4.20E−01 | 1.17 (0.07-20.09) | 9.13E−01 | 5.37 (0.32-91.12) | 3.55E−01 |
| 14:94844947:C:T | SERPINA1 | rs28929474 | 1.50 (1.21-1.87) | *5.29E−04 | 2.99 (2.11-4.24) | *9.08E−08 | 1.86 (0.74-4.67) | 2.40E−01 |
| 19:19379549:C:T | TM6SF2 | rs58542926 | 1.36 (1.21-1.52) | *2.42E−07 | 1.64 (1.31-2.05) | *6.04E−05 | 1.93 (1.22-3.04) | 1.08E−02 |
| 22:44324727:C:G | PNPLA3 | rs738409 | 1.65 (1.54-1.78) | *1.31E−41 | 2.05 (1.76-2.38) | *1.70E−19 | 2.20 (1.60-3.02) | *5.59E−06 |
| 22:44324730:C:T | PNPLA3 | rs738408 | 1.65 (1.54-1.78) | *1.42E−41 | 2.05 (1.77-2.38) | *1.45E−19 | 2.20 (1.60-3.03) | *5.41E−06 |
| 22:44368122:A:G | SAMM50 | rs3761472 | 1.52 (1.41-1.65) | *7.33E−24 | 1.86 (1.58-2.19) | *1.81E−12 | 1.66 (1.16-2.39) | 1.05E−02 |

*Indicates P-values meeting the Bonferroni significance threshold of $P < 2.08 \times 10^{-3}$.

TABLE 5

Demographics and clinical characteristics of genotyped multi-ethnic cases and controls from the Dallas Liver and Pediatric Liver Studies.

| Characteristic | Dallas Liver Study Cases (N = 517) | Dallas Liver Study Controls (N = 4,279) | Dallas Pediatric Liver Study Cases (N = 203) | Dallas Pediatric Liver Study Controls (N = 244) |
|---|---|---|---|---|
| Age (years) -median (IQR) | 55 (48-60) | 44 (36-53) | 12 (10-15) | 12 (11-14) |
| Female sex - number (%) | 277 (54) | 2,494 (58) | 65 (32) | 126 (52) |
| Body mass index - median (IQR) | 30 (27-35) | 30 (26-35) | 30 (27-34) | 31 (28-35) |
| Self-reported ethnicity | | | | |
| African American | 33 (6) | 2,291 (54) | — | — |
| European American | 158 (31) | 1,266 (30) | — | — |
| Hispanic American | 326 (63) | 722 (17) | 203 (100) | 244 (100) |
| Presence of liver disease (by ICD-9 code) - N (%) | | | | |
| Alcoholic liver disease | 223 (43) | — | — | — |
| Alcoholic cirrhosis | 215 (42) | — | — | — |
| Nonalcoholic, non-viral liver disease | 212 (20) | — | — | — |
| Nonalcoholic cirrhosis | 100 (19) | — | — | — |
| Hepatocellular carcinoma | 44 (9) | — | — | — |
| No liver disease | — | 4,279 (100) | — | -244 (100) |

Association of HSD17B13 rs72613567:TA with Liver Pathology

Figure 3A:
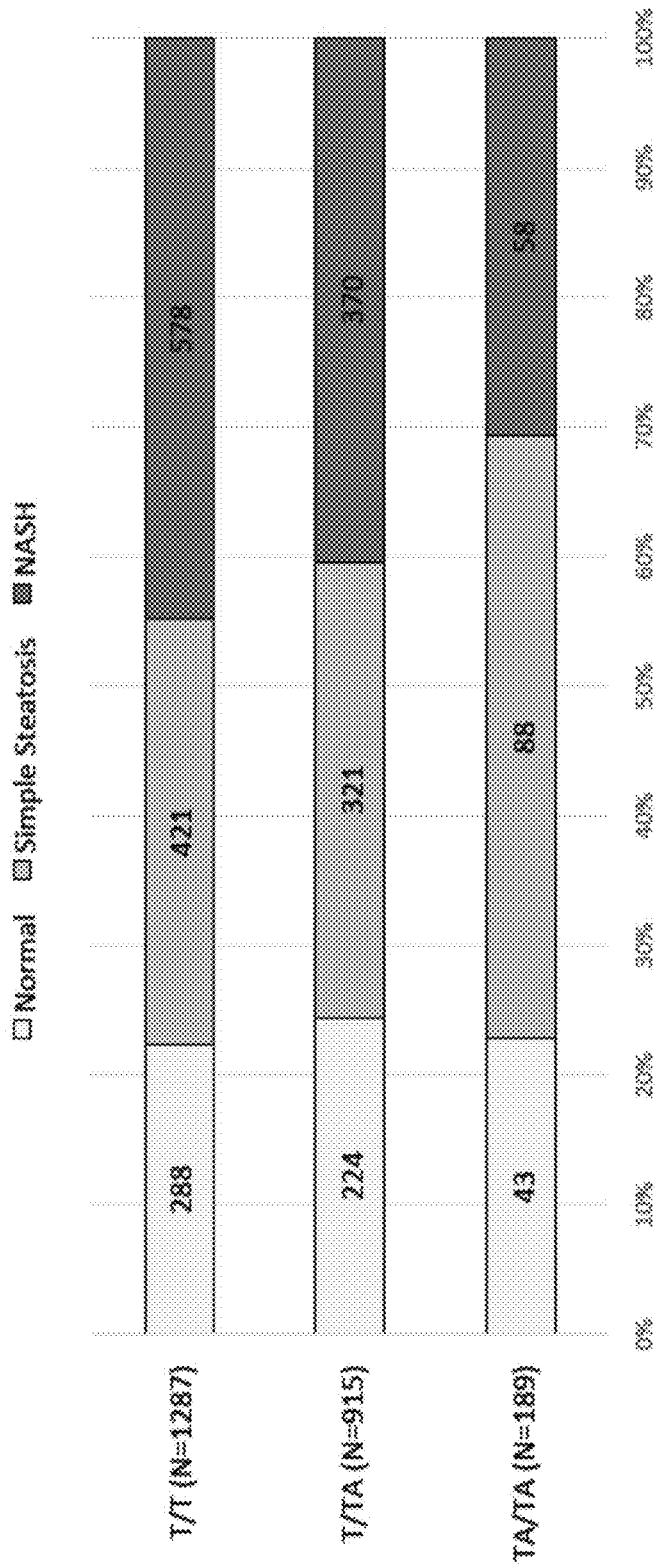
FIGS. 3A and 3B show that HSD17B13 rs72613567:TA is associated with reduced risk of progression from simple steatosis to steatohepatitis and fibrosis; 3A: prevalence of histopathologically-characterized liver disease according to HSD17B13 rs72613567 genotype in 2,391 individuals with liver biopsies from the GHS bariatric surgery cohort; the prevalence of normal liver did not appear to differ by genotype (P=0.5 by Chi-squared test for trend in proportions), but the prevalence of NASH decreased (P=1.6×10) and that of simple steatosis increased ($P=1.1\times10^{-3}$) with each TA allele; 3B: in the GHS bariatric surgery cohort, HSD17B13 rs72613567 was associated with 13% and 52% lower odds of NASH, and 13% and 61% lower odds of fibrosis, in heterozygous and homozygous TA carriers, respectively; odds ratios were calculated using logistic regression, with adjustment for age, age$^2$, sex, BMI, and principal components of ancestry; genotypic odds ratios for heterozygous (Het OR) and homozygous (Hom OR) carriers are also shown.
Figure 3B:
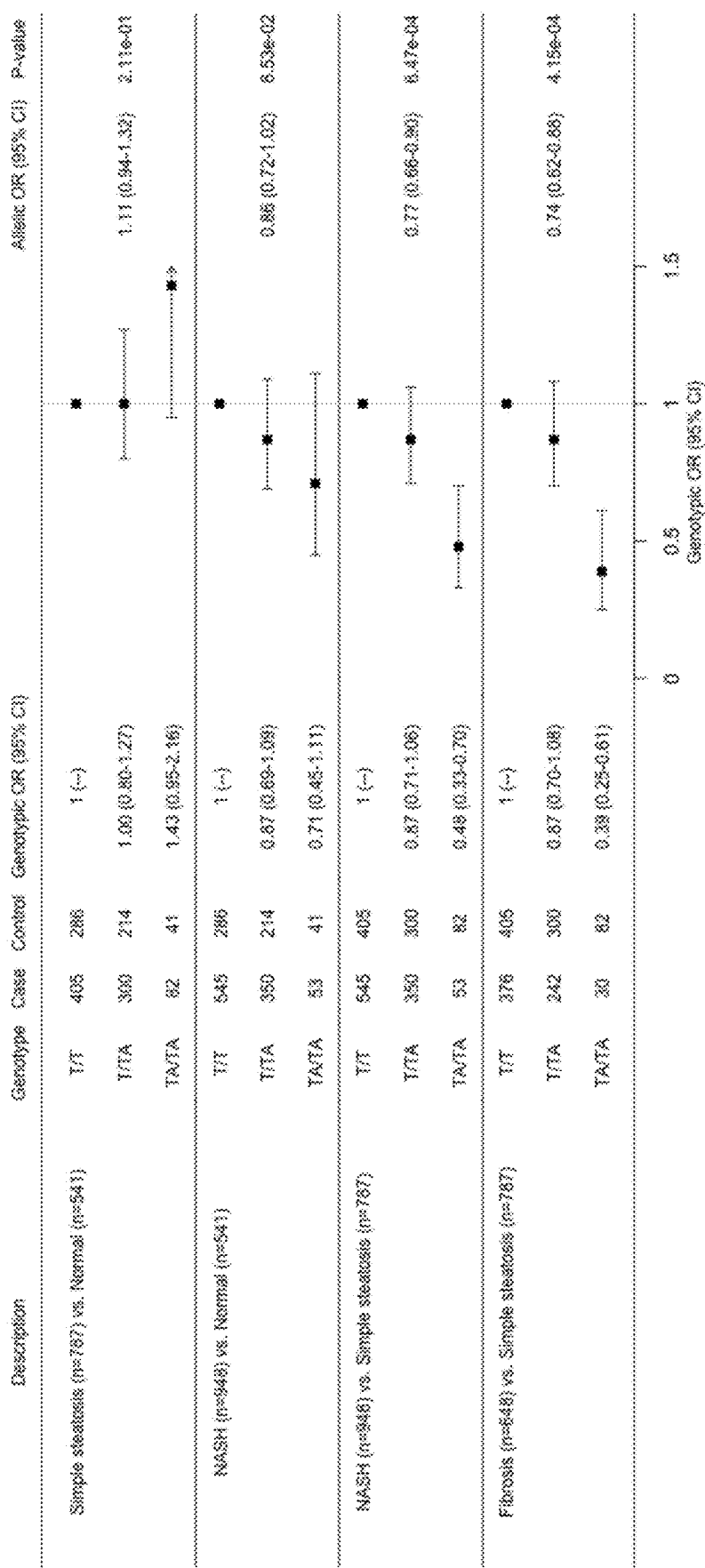

NAFLD describes a disease spectrum ranging from liver fat accumulation without evidence of significant inflammation (simple steatosis), to more clinically impactful NASH. To confirm the association between the HSD17B13 rs72613567:TA and EHR-derived liver disease diagnoses codes, and to further understand its association with histopathological progression of steatosis to NASH, we performed tests of association in the GHS bariatric surgery cohort. In this cohort of 2.391 of the whole exome sequenced individuals assessed by liver biopsy at the time of bariatric surgery, a total of 555 (23%) individuals had no evidence of steatosis, steatohepatitis, or fibrosis ("normal"), 830 (35%) had simple steatosis, and 1006 (42%) had NASH. When comparing prevalence of normal liver, simple steatosis, and NASH by genotype, it was observed that the prevalence of normal liver did not appear to differ by genotype (23%, 24%, and 23% for T/T, T/TA, and TA/TA carriers, respectively, P=0.5 by Chi-squared test for trend in proportions), but that the prevalence of NASH decreased (45%, 40%, and 31% for T/T. T/TA, and TA/TA carriers, respectively, $P=1.6\times10^{-4}$) and that of simple steatosis increased (33%, 35%, and 47% for T/T. T/TA, and TA/TA carriers, respectively, $P=1.1\times10^{-3}$) with each TA allele (FIG. 3A). Among individuals with steatosis, the TA allele was associated with statistically significantly lower odds of both NASH and fibrosis, as compared to simple steatosis ($OR_{allelic}$ 0.77 (0.66-0.90), $P=6.5\times10^{-4}$ for NASH; $OR_{allelic}$ 0.74 (0.62-0.88). $P=4.15\times10^{-4}$ for fibrosis; FIG. 3B), in an allele dosage-dependent manner. Altogether, these data suggest a role for HSD17B13 in mediating NAFLD progression from simple steatosis to more advanced stages of NASH and fibrosis.

Association of HSD17B13 rs72613567: TA with Clinical Quantitative Traits and Diagnoses To more comprehensively examine the clinical consequences of the HSD17B13 splice variant, we performed a phenome-wide study of associations of HSD17B13 rs72613567:TA with 405 quantitative EHR-derived anthropometric, vital sign, laboratory, electrocardiographic, echocardiographic, and bone densitometry measurements, and also with 3,168 EHR-derived clinical diagnoses. Using Bonferroni significance thresholds of $1.23\times10^{-4}$ and $1.58\times10^{-5}$ for associations with quantitative clinical measurements and clinical diagnoses, respectively, we identified statistically significant associations of the HSD17B13 rs72613567:TA allele with higher platelet counts, in addition to the associations with hepatic transaminases (Table 6). There were no statistically significant associations with clinical diagnoses other than chronic liver disease (OR (95% CI)=0.88 (0.84-0.93); $P=9.14\times10^{-6}$; AAF=0.263; N Cases total=4031, T/T=2331, T/TA=1449, TA/TA=251; N Controls Total=35701, T/T=19238, T/TA=13984, TA/TA=2479).

TABLE 6

Phenome-Wide Study of Associations of HSD17B13 rs72613567:TA with Quantitative Clinical Measurements

| Phenotype | Effect | SE | P* | AAF | N Total | N T/T | N T/TA | N TA/TA |
|---|---|---|---|---|---|---|---|---|
| Alanine Aminotransferase median:Adjusted(Residual Log) | −0.009 | 0.001 | 1.74E−12 | 0.264 | 44038 | 23868 | 17115 | 3055 |
| Aspartate Aminotransferase median:Adjusted(Residual Log) | −0.006 | 0.001 | 2.75E−11 | 0.264 | 43370 | 23493 | 16851 | 3026 |

TABLE 6-continued

Phenome-Wide Study of Associations of HSD17B13 rs72613567:TA
with Quantitative Clinical Measurements

| Phenotype | Effect | SE | P* | AAF | N Total | T/T | T/TA | TA/TA |
|---|---|---|---|---|---|---|---|---|
| Alanine Aminotransferase max:Adjusted(Residual Log) | −0.013 | 0.002 | 1.39E−09 | 0.264 | 43905 | 23797 | 17065 | 3043 |
| Aspartate Aminotransferase max:Adjusted(Residual Log) | −0.010 | 0.002 | 8.73E−09 | 0.264 | 42733 | 23145 | 16609 | 2979 |
| Platelets median:Adjusted(Residual Log) | 0.004 | 0.001 | 1.44E−08 | 0.264 | 46182 | 25020 | 17944 | 3218 |
| Alanine Aminotransferase min:Adjusted(Residual Log) | −0.008 | 0.002 | 2.47E−07 | 0.264 | 44029 | 23864 | 17111 | 3054 |
| Platelets min:Adjusted(Residual) | 1.919 | 0.443 | 1.47E−05 | 0.264 | 46181 | 25020 | 17943 | 3218 |
| Platelets max:Adjusted(Residual Log) | 0.004 | 0.001 | 3.03E−05 | 0.264 | 46165 | 25014 | 17936 | 3215 |
| Aspartate Aminotransferase min:Adjusted(Residual Log) | −0.004 | 0.001 | 5.00E−05 | 0.264 | 43327 | 23471 | 16831 | 3025 |

P*: ALL P-values meet the Bonferroni significance threshold of $P < 1.23 \times 10^{-4}$.
Abbreviations: AAF, alternate allele frequency; SE, standard error.

Figure 8C:
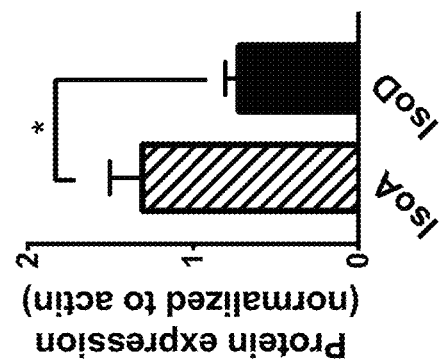
FIGS. 8A, 8B, and 8C show that HSD17B13 isoform D protein has lower molecular weight and is unstable when overexpressed in HEK 293 cells; 8A: RT-PCR of HSD17B13 from HEK 293 cells overexpressing HSD17B13 transcripts A (IsoA) and D (IsoD) indicated that HSD17B13 IsoD RNA level was higher than IsoA RNA level; 8B: Western blot from the same cell lines indicated that HSD17B13 transcript D was translated to a truncated protein with lower molecular weight compared to HSD17B13 transcript A; 8C: HSD17B13 IsoD protein levels were lower than IsoA protein levels although the RNA level was higher; HSD17B13 protein level was normalized to actin; *P<0.05.
Figure 8B:
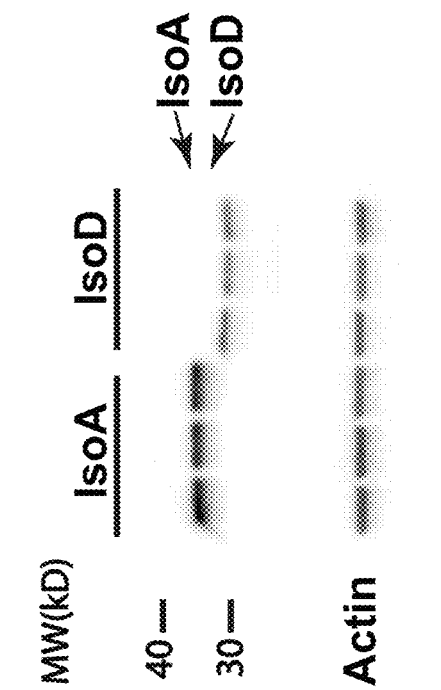
Figure 8A:
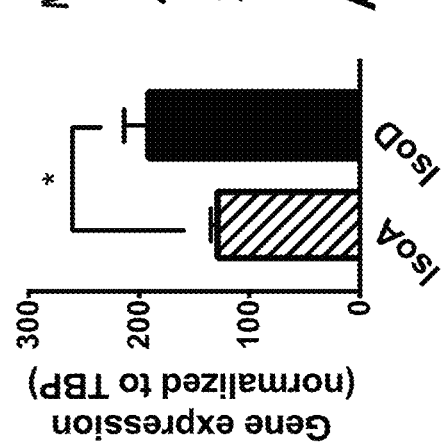

Effect of HSD17B13 rs72613567:TA on HSD17B13 mRNA and HSD17B13 Protein Expression We next examined the effect of the HSD17B13 rs72613567:TA allele on expression of known and novel transcripts of the gene. We used RNA sequencing to assess HSD17B13 mRNA expression in histologically normal liver samples from 22 T/T homozygous, 30 T/TA heterozygous, and 17 TA/TA homozygous carriers of the HSD17B13 rs72613567 splice variant. In addition to the two known HSD17B13 transcripts, A and B, two novel transcripts were identified: transcript C, which lacked exon 6, and transcript D which contained an insertion of a guanine nucleotide at the 3' end of exon 6, which would be predicted to result in premature truncation of the protein. Four additional transcripts (E-H) were expressed at very low levels (FIGS. 6A, 6B, 6C, 6D, 6E, 6F, 6G, and 6H). The transcripts were validated by RT-PCR and Sanger sequencing. The D transcript was also validated using long read cDNA sequencing. Protein sequence alignment of all identified HSD17B13 isoforms (A-H) is shown in FIGS. 7A and 7B. The expression levels of these transcripts varied according to HSD17B13 rs72613567 genotype; levels of transcripts A and B decreased, while those of transcripts C and D increased in an allele dosage-dependent manner with each TA allele (FIG. 4A). Transcript A, which encodes the full-length 300 amino acid protein, was the predominant transcript in T/T homozygotes, while transcript D, which encodes the prematurely truncated protein, was the predominant transcript in TA/TA homozygotes. In human liver biopsy tissue, the truncated isoform D protein was minimally present in heterozygotes and TA/TA homozygotes, and isoform A protein abundance was reduced in an allele dosage-dependent manner (FIG. 4B-4C). Heterologous expression of isoforms A and D in HEK 293 cells indicated reduced abundance of isoform D relative to mRNA expression, suggesting instability of the D isoform when compared to isoform A (FIG. 8). These data are consistent with HSD17B13 rs72613567 altering mRNA splicing, resulting in the synthesis of a truncated form of the protein with substantially reduced expression in human liver.

Expression of HSD17B13 in Human Liver Cells

Figure 4D:
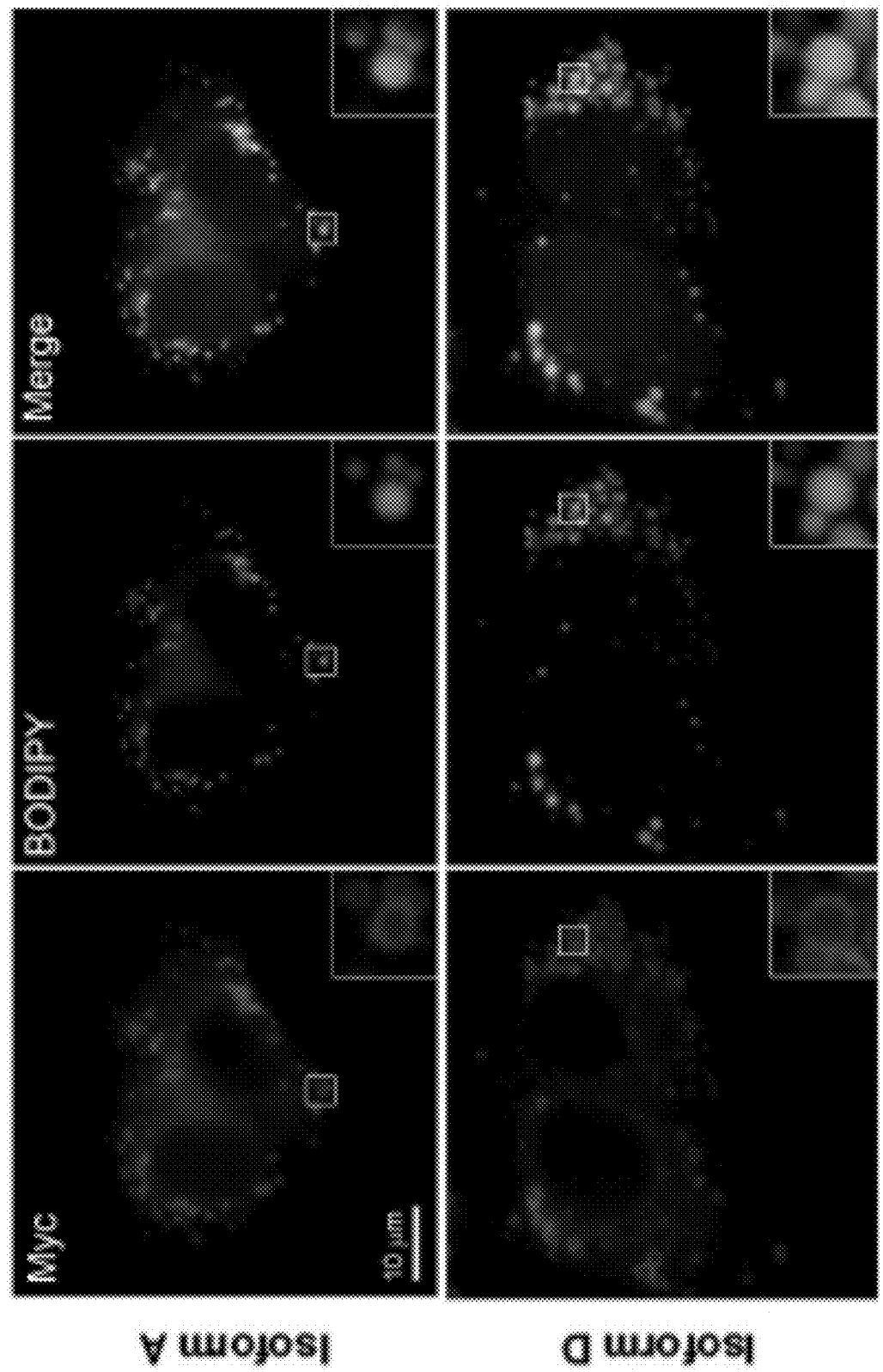
Figure 9:
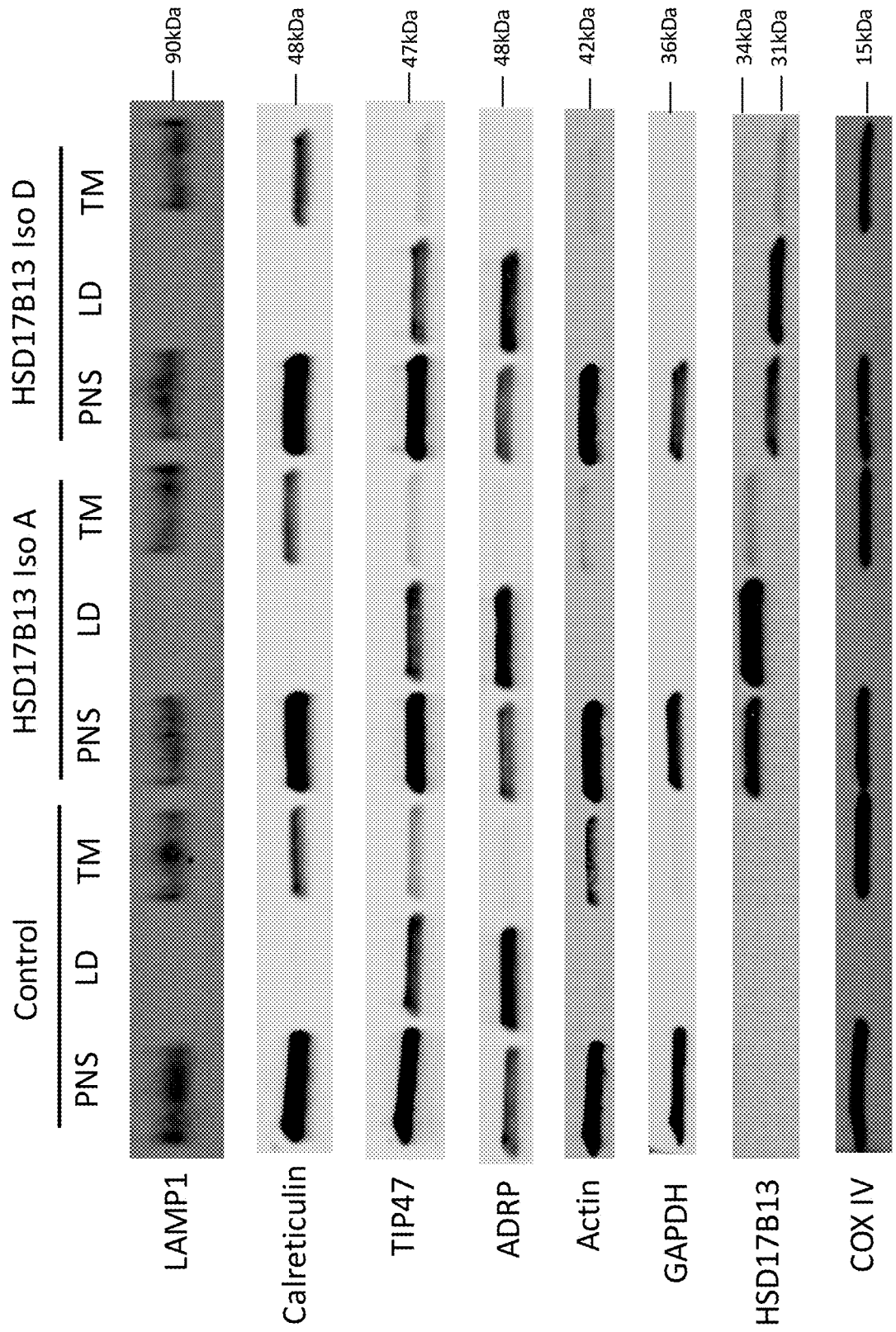
FIG. 9 shows similar localization patterns of HSD17B13 isoform A and isoform D to isolated lipid droplets (LD) derived from HepG2 stable cell lines; ADRP and TIP47 were used as lipid droplet markers; LAMP, calreticulin, and COX IV were used as markers for the lysosomal, endoplasmic reticulum, and mitochondrial compartments, respectively; GAPDH was included as a cytosolic marker; and actin was used as a cytoskeletal marker; this experiment was repeated twice in HepG2 cells, with the above being representative of both runs; PNS=Post-nuclear fraction; TM=total membrane.
Figure 10A:
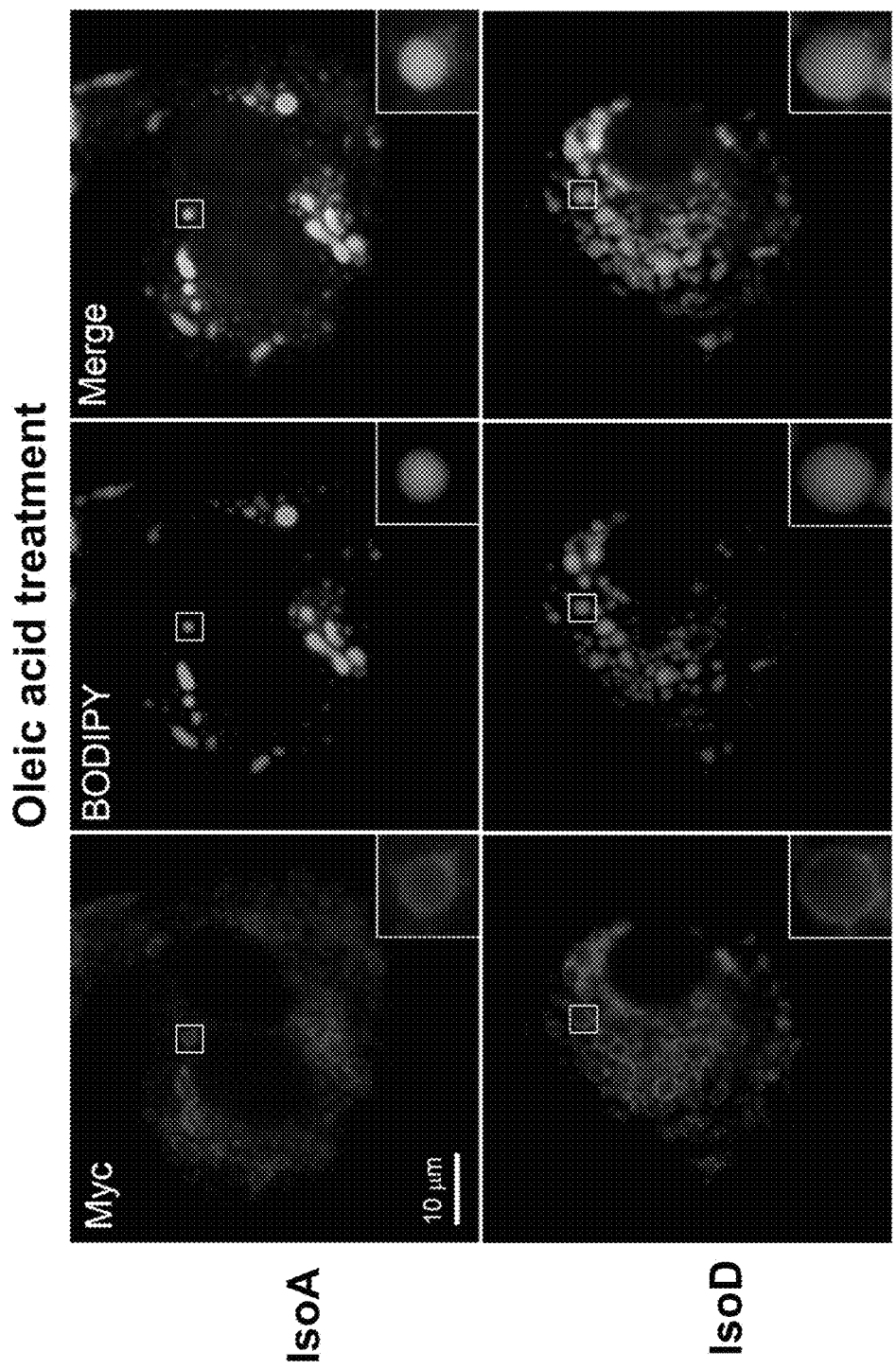
FIGS. 10A, 10B, 10C, 10D, and 10E show oleic acid increased triglyceride content in HepG2 cells overexpressing HSD17B13 Transcript A or D; 10A: oleic acid treatment in lipid droplets in both HSD17B13 transcript A and D expressing HepG2 cell lines to a similar degree; cells were labeled with BODIPY to show lipid droplets and anti-Myc to show HSD17B3 localization; scale bar indicates 10 µm and for all images; insets represent 4× amplification of the original images; 10B: treatment with increasing concentrations of oleic acid increased triglyceride (TG) content to a similar extent in control (GFP overexpressing cells), HSD17B13 transcript A and D cell lines; 10C: HSD17B13 transcripts A and D RNA levels were similar in the cell lines; RNA levels are shown reads per kilobase of transcript per million mapped reads (RPKM); 10D: Western blot from HepG2 cells overexpressing HSD17B13 transcripts A and D; HSD17B13 transcript D was translated to a truncated protein with lower molecular weight compared to HSD17B13 transcript A; 10E: HSD17B13 IsoD protein levels were lower than IsoA protein levels; protein level normalized to actin; **P<0.01.
Figure 10C:
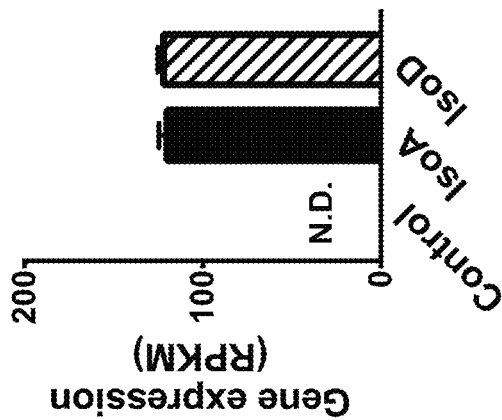
Figure 10B:
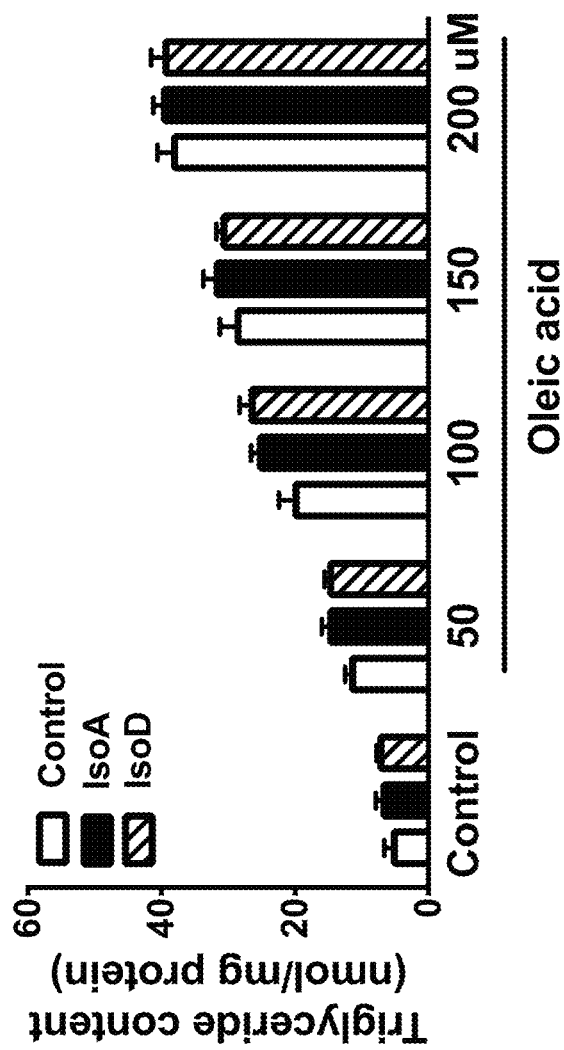
Figure 10E:
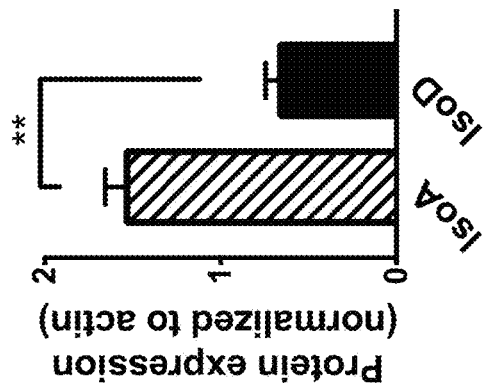
Figure 10D:
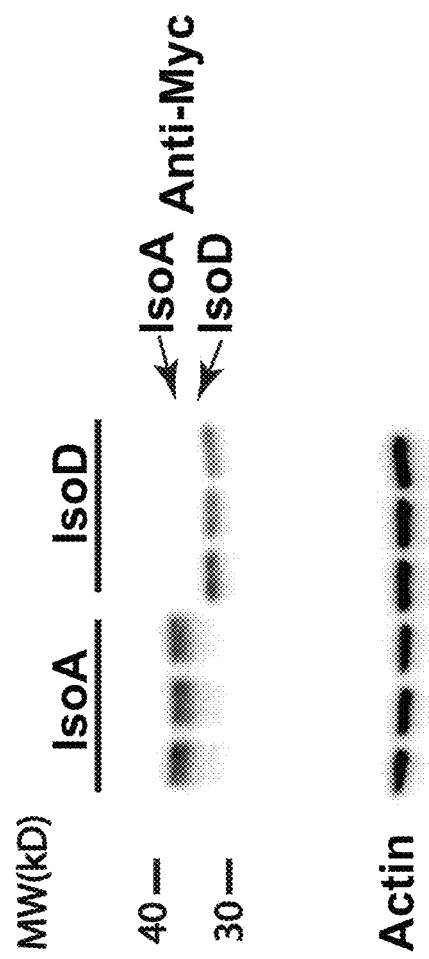

HSD17B13 is expressed primarily in the liver (Liu et al., Acta Biochim. Pol. 2007, 54, 213-218), where it localizes to lipid droplets (Su et al., Proc. Natl. Acad. Sci. USA, 2014, 111, 11437-11442, doi:10.1073/pnas.1410741111), consistent with a role in the pathogenesis of fatty liver disease. We evaluated the expression of HSD17B13 and its localization in an immortalized human liver cell line stably transduced with lentivirus expressing HSD17B13 transcript A or D. HSD17B13 isoform A was mainly detected on membranes surrounding BODIPY-labeled lipid droplets (FIG. 4D). Similar subcellular localization was observed for HSD17B13 isoform D at the lipid droplet surface (FIG. 4D and FIG. 9). No differences in intracellular triglyceride content were observed with oleic acid treatment of cell lines overexpressing GFP control or HSD17B13 isoforms A or D (FIG. 10).

Effect of Rs72613567: TA on HSD17B13 Activity In Vitro and in Cellular Models

Figure 4F:
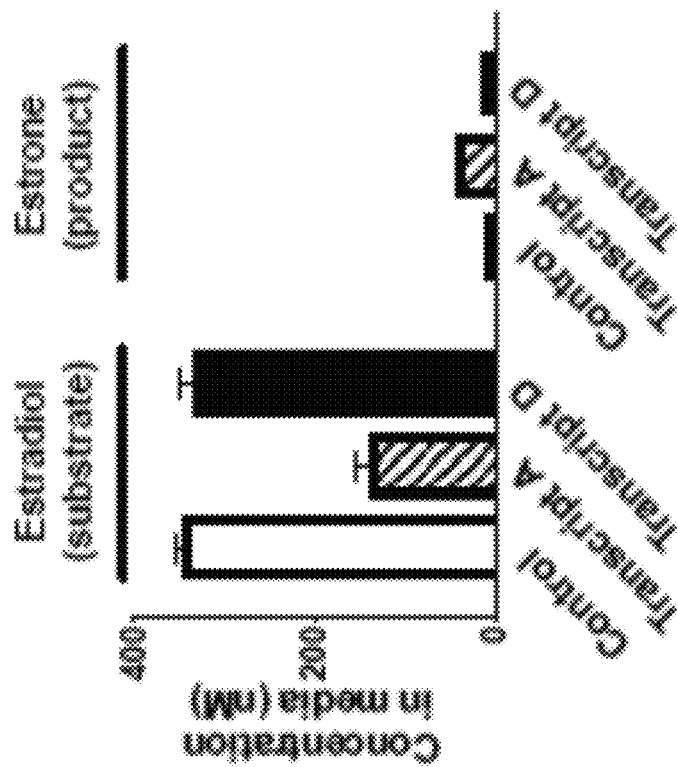
Figure 4E:
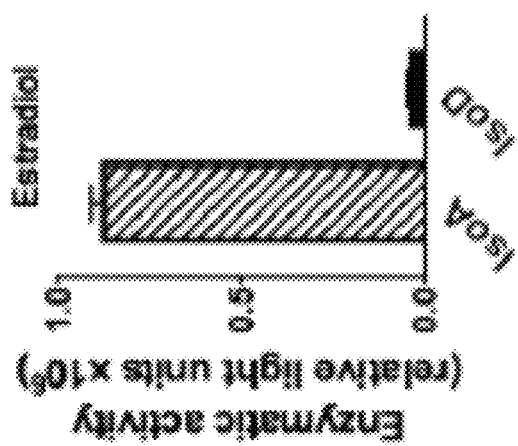
Figure 11:
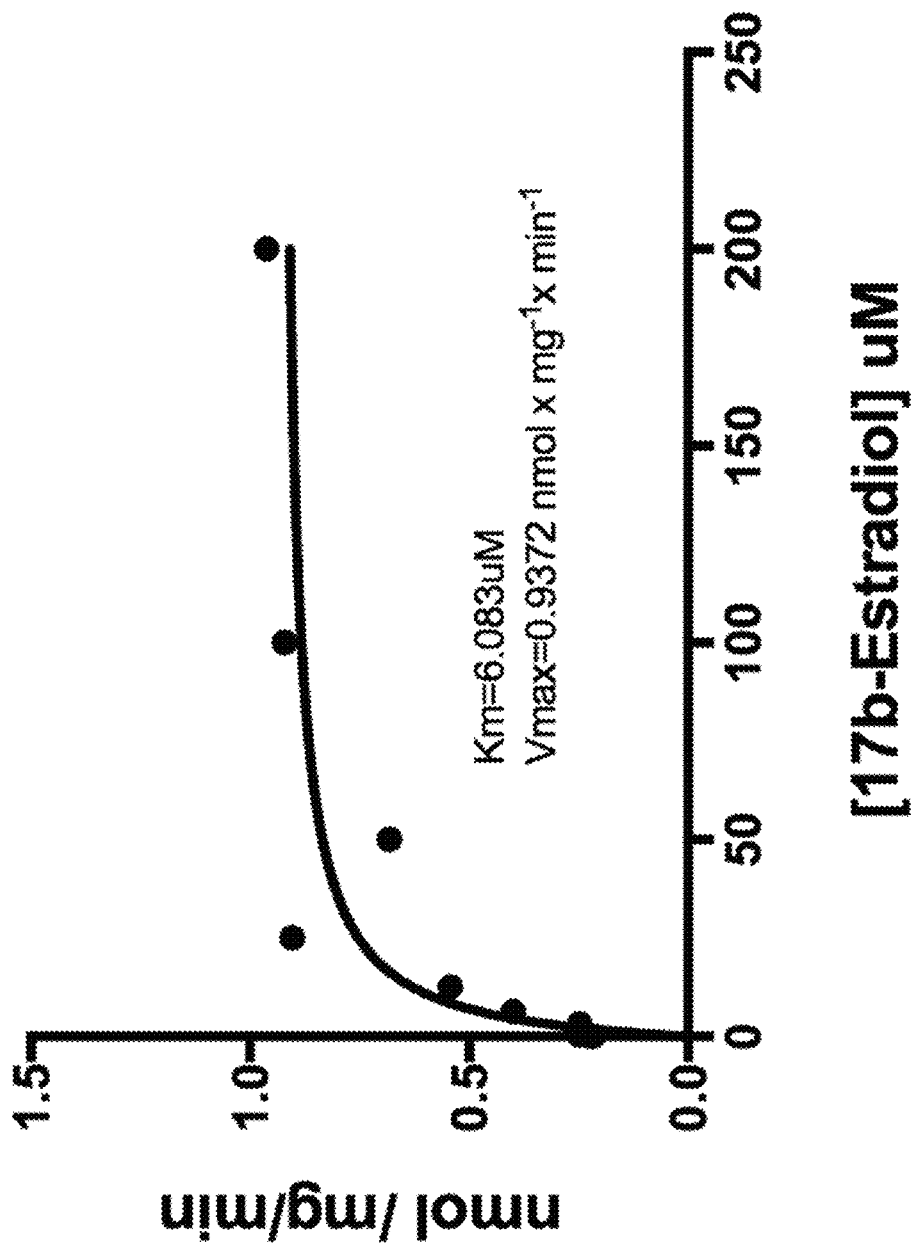
FIG. 11 shows $K_m$ and $V_{max}$ values for estradiol using purified recombinant HSD17B13 protein; for $K_m$ and $V_{max}$ determinations, assays were performed with a dose range of 17β-estradiol between 0.2 µM to 200 µM and time points from 5 minutes to 180 minutes, with 500 µM NAD$^+$ and 228 nM HSD17B13; $V_{max}$ and $K_m$ were then determined using the Michaelis-Menten model and Prism software (GraphPad Software, USA).

To understand the functional consequences of premature truncation of the HSD17B13 protein due to rs72613567:TA, we evaluated the enzymatic activity of isoforms A and D in vitro using recombinant protein and nicotinamide adenosine dinucleotide as cofactor. We tested 265 unique putative substrates, and identified steroid substrates and bioactive lipids (e.g. leukotriene B4) as enzymatic substrates of HS17B13. We focused subsequent characterization of HSD17B13 enzymatic activity on enzymatic conversion of estradiol ($V_{max}$ and $K_m$ values in FIG. 11), which resulted in oxidation of a hydroxyl to a ketone group. HSD17B13 isoform D showed greatly reduced activity towards estradiol in vitro (FIG. 4E) and in cell-based enzymatic conversion assays (FIG. 4F) when compared to HSD17B13 isoform A.

By linking large-scale exome sequencing to EHR-derived clinical phenotypes, we identified a novel association between a splice variant in HSD17B13 and decreased serum transaminase levels, as well as reduced risk of nonalcoholic and alcoholic forms of liver disease. These associations were observed consistently in four independent cohorts, and across several different liver disease categories, including advanced cirrhotic forms of liver disease and HCC. The HSD17B13 rs72613567:TA allele was not associated with simple steatosis, but was associated with reduced risk of NASH and fibrosis, suggesting that this variant allele protects from progression to more clinically advanced stages of chronic liver disease. In a phenome-wide association study, HSD17B13 rs72613567:TA was not significantly associated with clinical diagnoses or measurements other than chronic liver disease and associated clinical measurements (hepatic transaminases and platelet counts), suggesting that the clinical effects of the variant allele may be specific to chronic liver disease.

Other hydroxysteroid 17-beta dehydrogenase family members are involved in sex steroid and fatty acid metabolism (Moeller, Mol. Cell. Endocrinol., 2009, 301, 7-19, doi:10.1016/j.mce.2008.10.040), but little is known about the function of HSD17B13. HSD17B13 overexpression was shown previously to increase lipogenesis in mouse liver, and to increase the number and size of lipid droplets in cultured hepatocytes (Su et al., Proc. Natl. Acad. Sci. USA, 2014, 111, 11437-11442, doi:10.1073/pnas.1410741111). Two previous studies also showed that hepatic expression of HSD17B13 protein is increased in patients with fatty liver (Su et al., Proc. Natl. Acad. Sci. USA, 2014, 111, 11437-11442. doi:10.1073/pnas.1410741111; Kampf et al., FASEB J., 2014, 28, 2901-2914, doi:10.1096/fj.14-250555). Our data suggest that both HSD17B13 isoforms are expressed on the lipid droplet membrane, but do not appear to modulate intracellular neutral fat content, a finding that mirrors the lack of an association between the HSD17B13 rs72613567:TA and simple steatosis in humans. Although the physiological substrates of HSD17B13 are not known, enzymatic studies demonstrate that the HSD17B13 isoform encoded by the HSD17B13 rs72613567:TA allele is catalytically defective against estradiol. While at this time it is not clear if any of the substrates tested are critical for liver disease, it is intriguing that HSD17B13 has enzymatic activity against several bioactive lipid species (e.g. leukotriene B4) that have previously been implicated in lipid-mediated inflammation (Li et al., Nature Medicine, 2015, 21, 239-247, doi:10.1038/nm.3800).

This HSD17B13 variant may provide an avenue to new therapeutic strategies targeting chronic liver disease, similar to genetic variants that have guided the way to new therapeutics in other domains. Our data indicate that HSD17B13 modulates progression of liver disease from steatosis to later stages of NASH, fibrosis, and cirrhosis, which are associated with significant morbidity and mortality, and for which there are currently no effective treatments.

What is claimed is:

1. A cDNA molecule comprising a nucleotide sequence encoding a human Hydroxysteroid 17-Beta Dehydrogenase 13 polypeptide, wherein the nucleotide sequence comprises SEQ ID NO:24 or SEQ ID NO:33.

2. A vector comprising the nucleic acid molecule of claim 1.

3. A cell comprising the nucleic acid molecule of claim 1.

4. A probe molecule comprising a nucleotide sequence and a heterologous label, wherein the nucleotide sequence of the probe consists of 5 to 50 nucleotides, and the probe is hybridized to:
   a) an HSD17B13 Transcript D having at least 95% sequence identity to the nucleotide sequence of SEQ ID NO:6 or 15; or
   b) an HSD17B13 cDNA having at least 95% sequence identity to the nucleotide sequence of SEQ ID NO:24 or 33, or the complement thereof.

5. The probe molecule according to claim 4, where the probe is hybridized to an HSD17B13 Transcript D having at least 95% sequence identity to the nucleotide sequence of SEQ ID NO:6.

6. The probe molecule according to claim 4, where the probe is hybridized to an HSD17B13 Transcript D having at least 95% sequence identity to the nucleotide sequence of SEQ ID NO:15.

7. The probe molecule according to claim 4, where the probe is hybridized to an HSD17B13 cDNA having at least 95% sequence identity to the nucleotide sequence of SEQ ID NO:24 or the complement thereof.

8. The probe molecule according to claim 4, where the probe is hybridized to an HSD17B13 cDNA having at least 95% sequence identity to the nucleotide sequence of SEQ ID NO: 33 or the complement thereof.

9. The probe molecule according to claim 4, wherein the probe is hybridized to an HSD17B13 Transcript D having the nucleotide sequence of SEQ ID NO:6.

10. The probe molecule according to claim 4, wherein the probe is hybridized to an HSD17B13 Transcript D having the nucleotide sequence of SEQ ID NO:15.

11. The probe molecule according to claim 4, wherein the probe is hybridized to an HSD17B13 cDNA having the nucleotide sequence of SEQ ID NO:24 or the complement thereof.

12. The probe molecule according to claim 4, wherein the probe is hybridized to an HSD17B13 cDNA having the nucleotide sequence of SEQ ID NO:33 or the complement thereof.

* * * * *

SEQUENCE LISTING

```
<160> NUMBER OF SEQ ID NOS: 53

<210> SEQ ID NO 1
<211> LENGTH: 19118
<212> TYPE: DNA
<213> ORGANISM: homo sapien

<400> SEQUENCE: 1
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataaggtaat gtatacatct tccaactttt     300
taaagtcaca gagtaagata tgtattttaa gaattatttg acttaccatc tacttatctt     360 tgtattttg tttttcaaag tttgataaat tccctggtcc cttagtctgt atatgtgtca     420
ggttagttag atgaagggaa tgtaattaag aactaagcag cgatttttat gacatggtgt     480
gcaggttgat agaaagactc aggagccagt ctccttccaa gctgctaaat gaggcaagtc     540
acatattatc tctcagcctg ttttcttggc tctgaagtgg ggataataac ttaggggatg     600
ggcaagaacg ggatctgaaa attacagcta caaacaaaag tcaaacgaag aacttgcaac     660
agaaaccttt agtgcctccc ctcatgcaca agcaacacag ttctaaaata tttactgtct     720
gacccTttac agaaaatgtt tgccagtccg tagtcaaaag gattaaataa gtaatatttt     780
cagcacttag catatgataa acgatacgtg gcacatgata aacaataact gtgttaaata     840
aaatatgtgc gcagtgagtc aggcttttcc ttggacatta gtatttttcc tgtgttctta     900
cttgtaaaca ctacattaac aaccccaaat aaaactgaag gaactgaaat cttgtatcat     960
tttctctaaa cttgtaaatt ctggtaaggc catgaaaata tatgcagaga agtgtttaca    1020 ggatttagg attggaaaaa ttgtgaagta ctccttgaga atcacatttt ctgcaaatta    1080
cagtggtttt aattaccatt atattattac tttctcatgt tctttgctgt catgtttagt    1140
tgaaacctaa aatgtctctt acacttagag aactaattct tttctgtttt ttttctgaat    1200
agtgaagaat actatacaaa aaagctacta cattttatt taacagatat gagcatttat    1260
```

-continued

```
ataatagagg agttgatgta tataaaaatg atttgccatc tttttggtct ttgaagaaat    1320
tcgaatgaac tttctggaag atagcaagaa tttacaaata gagaaaattg ttgcctgctg    1380
ttctcaggca tttgtccaaa aatataaata agtataaatc tatgaaaagg gcttgatgaa    1440
atctaacctt caaatctctt tccagatgtg tattttggg gaaagggcta tatttattaa     1500
gttttttta aattttaaaa tttccagaga caagagaaaa gtaaattaga aggaagtcgt     1560
attaaaaatg acttaagggc gggtgcagtg gctcacacct gtaatcccag cactttggga    1620
gacggaggtg ggcagattgc tggagcccag gagttcaaga ccagcctggg cagcacagca    1680
aaaccccaa ctctacaaaa aatacaaaaa ttagctgggt gcggggtgc acccgtag        1740
tcccagctac tcgggaggct gaggtgggag gatcgtttca gttcaggaag ccaaggctgc    1800
aatgagctat gatggcatca ttgcactcca agctgggcaa tagagccagg ctctgtctca    1860
aaaaaataa aaaagactt aagaaaaata ggtaacccaa cctcaaaaat tctctttgaa      1920
tcattaaatt tcatggttaa acatttaagc tactgaatga ttcactctaa ggctgtaatg    1980
taactcagat ctcctttagg cgaggaagat gctggctgag ttttcatcat aactggctcc    2040
ttttgccctg tgagatgaga gacacagtag cagtttggct cttatgcaat ctaaactgtt    2100
gcgttgggaa tacggttcaa aaaacacatt ggagtttaag ctaaagcaag tgttttgcta    2160
acaaaaagac aaggcatcac attttgcaat tgtctagctc agttataaaa cagaagaata    2220
ggccggacgc ggtggctcac gcctgtaatc ccagcacttt gggaggccga gacgggcgga    2280
tcacgaggtc aggagatcga gaccatcctg gataacacag tgaaaccccg tctctactaa    2340
aaatacaaaa aaattagcca ggcgtagtgg cgggcgcctg tagtcccagc tactcgggag    2400
gctgaggcag gagaatggtg tgaacccggg aggcggagct tgcagtgagc cgagatgacg    2460
ccactgcact ccagcctggg cgacagagcg agactccgtc tcaaaaaaaa aaaaaaaaa    2520
aaaactgaag aataattaat tcttcaatca aacatctga tgaatgctct ggtaacttat     2580
gctctctact gacctagaaa caaatgagag agtatggtgt ggtttgtgca atctggcagt    2640
gagcaagcta ccaactaaat cagtgaaaga ctctcctatt cttttttac tcttctgcaa     2700
tcccacaaaa ggctatttga ggggatactg actttgagac tgggtcctaa catccatgtt    2760
tggggagttc aggctgctgc tccagggttt agcctacagt agcgaaatac aaaggaccca    2820
gagaccactc attcaaggtt tgccctaaat agcagcaaca ccactgtcat ctcaatacac    2880
gaagaatagg gcttttcagg tatccttgcc tctttgtcac agagaagagt ttacagattg    2940
tgagacggaa aagtataatt tttaaaacct tataatattt tctataaaag tcacctgagg    3000
tgaaaacttg aaaagaatta taattttcca gaatgtgagt caagaaacat tagagcaatt    3060
ttatcttagg aaagaggtct ttgaatttag gctgaaagta aattgctctg tctccatgtc    3120
ctatggttat gggcaagttt ggtacataaa tgagaaatcc atccagtggc cttgcccatc    3180
tcactcccaa acacctgaag aatgtaatgt tatatctcct agagtagcag catggtctcc    3240
ctatgaaagt ccttcttctt taaggagact tctttccctt ccctcctagg aggatgagtc    3300
agaatcatca agaaaaatat gatgggcaga ggcatacagt ttaccattac cactagttta    3360
gaattactac ttagcacttt actgcctatt acatagttgg tgctcaacaa atgtatgata    3420
aattaatggt tgagtttttc tttcttctcc atattcatct tccatgacac cacgaagagc    3480
aatgttttc aagaatgttc ttcaaggttt gaaagtagcc tgctttagag aaactgccta    3540
ctgtacagcc tccaaccaag aggaaaagct gaaaaaagca tgaagggatt ttgttttgtt    3600
ttgtttgttt tggttttaat atgagcattc cctggcagaa aagccagggg taatctcatt    3660
```

-continued

```
gcaactaggc aatcactctc aagaaatttt ctaacaaata aggaggccaa ttttattttt    3720
attttgagac gaagtcccac tctgtcaccc aggttggagt gcaatggaat gatttcagct    3780
cactgcaacc tccgcctccc gggttcaagt gattctcctg tctaaacttc ccgagtagct    3840
gggattacag gctcccacca ccacgcccag ctaattttt gtattttag tagagatggg      3900 gtttcaccat tttggccaga ctggtctcaa actcctgacc tcaagtgatc caccctcctc    3960
ggcctcctaa agtgctggga ttacaggcgt gagccaccac acctgaccca ggaggccaat    4020
ttttaaaagg ttaactaatc ttcatgtcca aaatgaatgt taattgttca ttttggacat    4080
gaatgttaat ttttttttt ttttttttg agacagagtc tcactctgtt gcccaggctg      4140
gagtccagtg gcactatctc cactcactgc aacttcctcc tcccaggttc aagcaattat    4200
cctgcctcag cctcccaagt agctgggatt acaggcccac accatcaggc ctggctaatt    4260
tttgtatttt tagtagagac ggggtttcac catgttggcc aggctggtct tgaactcctg    4320
acctcgtgat ccgccctcct cggccaacca aagtgctggg attacaggcg tgagccaccg    4380
cgcctagccg aatgttaatt gtctaaaaat tttcttctc caatgtcttc tcctccactt     4440
ttttcggaat ttgtttcttc ctaattacag cgcggtgtgg aggaaactgc agctgagtgc    4500
cgaaaactag gcgtcactgc gcatgcgtat gtggtagact gcagcaacag agaagagatc    4560
tatcgctctc taaatcaggt gagactgcag gttcacaaat ttcttcagat tattttgttt    4620
cctaggacgc tgacgtggaa aatgagaaag gtctttatga ctgcctgatt taaattggat    4680
tttagctgct aactgaagta gttatgtcac caaggaagga tatatacttt ttttcttgta    4740
tgtaatccac tcagctctgc ccattattat tgttcatatt attaatcaat ttcattctga    4800
tcagaagtgt gagcagtggc acagagtgac tgacaaaaga tttatcatca gggaatatgg    4860
atcacttcct agttttgttt tagtcctatt aactttgcag taattccagc ttctctttaa    4920
ttatttccct tgtgagattt tattttggtg ttaatgtagt cttctgtaga aaatgtaata    4980
ttaataatta ttatcacaat tattttaaaa gagtaaatac caaataatca caatgaacta    5040
agcactctaa caaactttac attttttaat tcaatcccta caataactct gtaaacttca    5100
ttttacagat aagcaaatta tgactcagag aggttaagcc agacccaggt catgtagtta    5160
ttaggttatg aaaccaggat ttctcaacca gcactttaga ccaggtgcgg tggttcacac    5220
atgtaatccc agcactttgt gaggccaagg tggaaggatc acatgagacc aagagttcaa    5280
gaccagccca ggcaacatag tgagacccta tctctaaaaa aaaaaaaaaa aaaaaaaaa     5340 aaagtttaaa gaaaaacaca ttttaaaaa atgaacactt taaaaatatt tggtcagaat     5400
ttatatagga atttatcaac ataaatgtta atttcacttt actgataaac ttgcaaaaca    5460
tgatgtgctg ggtactgaaa tttagatgtt aaaagaacag tttatcccac ctttatgaca    5520
gtgttccctt ggcctccacg atttgagctc aacagtctgt cttgcctgaa ctctgagaga    5580
cctcatacaa tagaagaaag actctcatct ttggattata ttggtcccaa aactttgagt    5640
ttgaataata cacccagtga aagtgttctt tcaatttcaa aaggtgaaga aagaagtggg    5700
tgatgtaaca atcgtggtga ataatgctgg gacagtatat ccagccgatc ttctcagcac    5760
caaggatgaa gagattacca agacatttga ggtcaacatc ctaggacatt ttgggtgag    5820 tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
```

```
acacaacaca ccagaatgta agctacttgg tctgtcttgt ccaccagtat ctgacacaaa      6060
gcttggcatg taccaggagc tcaacaaatg tttgtggagg tttgttaagg gttgtcagtg      6120
tacatctttt caatgctgtc acttgtgact tcattttttt ccctccacac catgattttg      6180
taatgtgtcc tcattttgtg gaattttaga atggaaagga catcagaagt aattacttgg      6240
atgtatatag gatcgaggac acttttggac gagactctga ggcaagtgtt ctagatccat      6300
ggggtgctgg aactgagaaa tgcagctata cagacctcat ataattggtt agttttgtgg      6360
gagatggaaa tatcaacttc aactgccttt gtatagaaat ttttatgatt aatcttccag      6420
tgcctcaata ttagtgtaga atctagggca gatctggatt ctagaagaaa gaagaaaaaa      6480
aagagatgtg tcccccttac ctttaccagc tcttcacata tgtgaattgg ctcccatgcc      6540
caccaaacta cacggagacc tcatacatta gctacctata gctgcataac aaattataca      6600
aaacttagtg gtttaaagca acaatgtatg ttcactatcc tctcacagtt tctatgggtt      6660
gggaatttgg aggtagcttg ggttgggagt tctagttcta tgaatttgca taggatttat      6720
taaattctta taaaatttta ttgatgtttc tcacaaaaga ggttttttgga aaaaaagaaa      6780 gacttgtttt ctgtaacatc aacatataat atacaatatt acaaataggg agatagtgaa      6840
ttcaatcatg attcattagt gtggtgtaga actctcagct tacactactc aactgtctta      6900
atacagttac acaagatttc actcttttaa ttagaatgat aaagccccaa accaaaaaat      6960
tatatgacac caaattatca taaggaataa ttttagttct gaaaactctg aattttttccc      7020 ttaatattgt ttagatgaca tatccaaaaa aggatctatt tgattccttc tgaagggaag      7080
gagggggagt actgagatta gtgttggcat ggggcttacc ataccaataa atttgtatct      7140
ttatttctat catttgtaaa gaattaatca tggaatgctt ggaagtattt tatttcattg      7200
tataagttct ctcaaatgcc tttctgtctt aacaaaaata aaactacctg atttggaaac      7260
ctaacgtcta tgtcattgtc tttcttcttt ctgcaatgat ccttaagatc acaaaagcac      7320
ttcttccatc gatgatggag agaaatcatg gccacatcgt cacagtggct tcagtgtgcg      7380
gccacgaagg gattccttac ctcatcccat attggtaagt atcacatgcc agccatgtta      7440
tatattttta tactttgaag ggagcattac acttcaaatt gttaccactg gagagtcctg      7500
gttcttggca tcttgaacaa agaattggac aaaactcacc aacaaagcca ggaaagaatg      7560
aagcaacaaa agcagagatt tattgaaaat gaaagtacgc tttacagggt gggagtgggc      7620
ccaagcacag gggctcaaga gccaattaca gaattttctg gggtttaaat accccctaga      7680
ggtttccact ggttacttgg tgtacgccct atgtaaatga agaggatgaa ttaaagttac      7740
agagtcgttt actcagtgta caccatatgt aaatggagag gatatttcct gtcatagctg      7800 gagtgttttcc atttgattta gttctaggaa gtcagcatga atcggcctta tgttccctgc      7860
ctccagaccc tgttctcctg cctcaagatt acaatgctga gagcagagtg atttggattt      7920
acagaattta aatttatagt agtttagaat gatttttttaa atgacttttt ctaaaacaat      7980
gaaaccaggt tgtaattata tttaagatat ttttagattt ctgcaaactc ctctgtagaa      8040
caatgagaga aaacagtaat gccaagcatg tttccattgt ttcctggaat aagaaacaga      8100
aaccccacag actgagaagc aaaacctaca gaagctaaaa tgaacacatg tctatgtcat      8160
ggccttggtg cccaagataa gacaatcaga gtggtccctg gatcaaaaca ttttacagtg      8220
tgcttgtgcc atgaaagtgt gtgtgtgtgt gtgtgtgtgt gtgtgagaga gagagagaga      8280
gagaaaacga ctctacctga ctaaaagttg cagataccac actccatgca ccaccaaaga      8340
cataaaggga aggaggtgag aggcgttaag gatgtactgc tgtatttgcc aaatatcctt      8400
```

```
tcctgtaaac tcttctccag atcctcataa taaaattaag aggccaaagt ggcaaccatt    8460
gtcaagagaa aaactatcaa ccattgtcaa gagaataact cagttattga gagagagagg    8520
agaaatgagc agagtcctac agaagtctgt caacacagat accagttttg tagaatttct    8580
aaatgtattt ttcctgattc atattttca aaataaaagc agcaataaaa actgattaga     8640
aaacagtttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaatgaa ttgccattta tactctcaga     8820
aaaatcacaa gtggctgatt tttggcttcc acttgttctt aagccaaatg ataccgcctt    8880
ctcacagaaa gctgaggatt ggtttcactc tcccttagct aacaatgctt aataattctc    8940
ttacagttcc agcaaatttg ccgctgttgg ctttcacaga ggtctgacat cagaacttca    9000
ggccttggga aaaactggta tcaaaacctc atgtctctgc ccagttttg tgaatactgg     9060 gttcaccaaa aatccaagca caaggtaagg tcaaaatcaa gttagaatgg gtatgtggta    9120
tgataaattg atatgaaaac taatgagaaa tgtttaggca ggccaactaa tagaagaaaa    9180
tgaagaagga aaaataattt ttcttattat tattattatc ttgaaattaa aggaataaag    9240
ggggaaaaca cattagggac tagcaggaat gatcagccac cgatgaactg ggatatttat    9300
ttgtgtccgg gagaaagcac atacatttga tcaccgttac caccctgtct ttaaaatgca    9360
aatgttccaa ggaccagcaa ataaattgag tatctagctc cttagtcaag gtgaatttct    9420
gcaagaactc ttgtctctgg tgagacagga tttgagacca caagagaaga aaaattagtc    9480
ctgaaaggag aagaaaaaag caggaaggtg tggataagaa cccgaaaatt aagccatctg    9540
cttaacaaat ttttctaatc ctagtatata ttctgctgca ggttaacaaa atatactaag    9600
cttaatgatt cgaaaccaat tttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttgtttt ttatttttgt    9840
tttttttgag acagagtctc actctgtcac ccaggctgga gtacagtggc gcgatctcag    9900
ctcaccgcaa cctccgcctt tctgggttca gcaattctc cttcctcagc ctcctgagta     9960
tttggattac aggcgcccac caccacgcct ggctaatttt tgtattttta gtagagacgg   10020
ggtttcacca tgttggccag gctggtctca aactcctgac ctcaggtgtc ctacctgcct   10080
tggcctccta aaatgctggg attacaggag tgagccacca tgcccggcca aaaaaataag   10140
tttttaaaga attaaaggtc atcctggcta acacagtgaa accccgtctc tactaaaaaa   10200
cacaaaaaaa ttagccgggc gtggtggcgg gcgcctgtag tcccagctgc gcggaggct    10260 gaggcaggag aatggcgtga acccgggagg cggagcttgc agtgagccga tcgcgcca     10320 ctgcactcca gcctgggcga cagagcgaga ctccgtctca aaaaaaaaa aaaaaaaaa     10380 aaaaaaaga attaaaggtg ttaattttat ttagaagcct tactgaagac tacagtcgga   10440
ggcctatagc ctgagagcag ccctttagag aggttcagtt gaactgttct gatagtgggg   10500
gccatgtgct ctatcctgta ttgtcttcaa agcatctttc cagagagctg cacattgtca   10560
cagagtcagg gactttgtga aattatgctg acaaccagaa gtgagtaaac gtggcttctt   10620
acatttgcta cgttgtctca cagtacttaa taagtatgca atatgtaagt aaatactata   10680
gtactattgc aactcctgat tgttttctta gacaaggaat tgggcccaat aaaaaccctc   10740
```

```
ttggtaggca ttcaggcttc gtgtaccatg agctttccta agggtatcct gccactcttg   10800
gggaaggcat gatagatgag gggagtaagg ataatggaac tctgggtaca gggttcctgg   10860
gggctaactt agaggtagac acaggcaatg ctaaatattt gggattgatt ttatagaggt   10920
tgctagattg tgaatttcct tagtaagggc taaggcattg atatgtaatg tcacacttgg   10980
ctccgaggct gggttgttgg atccatgtag atgaaatcag ggagagaaag ggcagaacgg   11040
agtaatttag aaatgtattg atttgtatta ctctctgttg gcttgctatt caaggcagtg   11100
gagaactcaa tcacataata atctgcagca aaccacagat catcccaggg aatgaagttt   11160
taacattcgc tggctcccta actcctcacc cagcctttac attcactggc tgttcagtcc   11220
atgcctggac atcttaattt gaatacaaca ttttaaatcc attttctgt catcatcttg   11280 cactaacaga caattctaca ctaagcctat gtttatgaat atttctcaag agtacatgta   11340
cacagccttc agtataagga aaactggaag tatgacatac ctccagttgt catactcctt   11400
gggcccctct taaattctca ttaaactgca ggataggcaa gtcagaggtg aatctcaaat   11460
acgaaattct taccggaaag gggttccaat ccagacccca agagagggtt cttagatttc   11520
tcgcaagaaa taattcgggg caaggccaca gtgcaaagca aaagcaagtt tattaggaaa   11580 gtaaggagt agagaacagc tactccatgg agaagaatgg cttgagctgc tccaccaagg   11640
gtatttagag ttacttcttg attatatgct aaacaagggg tggattattc atgagttttc   11700
cgggaaaagg gtgagcaatt cccagaactg agatttcctc ccctttttag gccatatagg   11760
gtaacttcct gccattgcca tggtatttgt aaactgtcat agtgctggtg aagtgtctc   11820 ttagcttgct aatgtattat agttagctta taatgagcag tgaggacaac cagaggtcac   11880
tttcatcacc atcttggttt tggtgggttt tggccggctt ctttactgca ccctatttta   11940
tcaacaaggt ctttatgacc tgaatcttgt gccaacctcc tatctcatcc tgtgacaaag   12000
aatgccttaa cttcctggga atgcagccca gtaggtgtca gccttatttt acccagaccc   12060
tattcaagat ggagttgctc tgatttaaac gcctctgaca aaatgacgac ctcaaaacaa   12120
tccagcttta tggaatacct ccacaagaaa gaaagtatac ttagctatag aattttctcc   12180
ttgcatccaa caggctttga gatgtcagat gtttccttcc tgtcccatga ttaatcctag   12240
ccattcctct ttcttgtctg gctccactac tccttaccat ctaatgcctc gccaccattt   12300
tgatattttg actaagtgag ctatgaaaca cacctactgg atatgaaagt ataagtttct   12360
gataacaaaa catcaacatg ggatgtggag gaagtgggta gggtggcatt aatgcagcaa   12420
atcctggaat atttttaaatc ttcattctaa atttagtaaa aatataggat aattttcctg   12480
ccatcattta cttataaaat taaaatttta gaaaataaaa ataatatttt cctctttta   12540 atcacagatt atggcctgta ttggagacag atgaagtcgt aagaagtctg atagatggaa   12600
tacttaccaa taagaaaatg attttttgttc catcgtatat caatatcttt ctgagactac   12660
agaagtaagt acagcacaga acacccaaat actaaaacac caatagagct ttttttttg   12720 cttttttttt tttagacag agtctcactc tgtcaccctg gctggattgc ggtggttgca   12780
gtggcatgat cttggctcac tgcaacctcc gcctcctggg ttcaagcaat tctcatgcct   12840
cagaccccca agtaactggg attataggtg tgtgctgcca cactacaccc agctaatttt   12900
tgtatttttt gatagagaca ggtttcccca tgttggccag gctggactcg aactcctgac   12960
ctcaagttat cctcctgtct cggcctccca aagtgctggg attacagtca tgagccacca   13020
tgcctggccc aatagagcta ttattatgga gcatctttca gttgtgaaaa ttggcatgga   13080
aactctccat ccctggggag aacagttatt tcctctgtta ttttcctacc cagtctataa   13140
```

```
aaagagagtg attcattttc tctaccaaat ctactgtctc tgcccaaact ttgctgaaga    13200
ctattctaac taaaggaaac acagtttaaa aagaatgcaa tatagtgaag tagttaataa    13260
taaagactcc atttttaaaa gtctgctgga agtttggttg ggattgcact gaatctatag    13320
agcaattggg gagtattgac atatcaacaa tattgagttt tctaatccaa gaacataata    13380 tctatttta aaatcttctt caaaatcttt aaatctttaa attgtatttt gtagttttg     13440 gtgtttaagt cttgcacata ttttgtcaga tttattccaa agtatttcac gggttctttt    13500
tttttttttt tttttttttt ttgagacaga gtttcaccct tgttgcccag gctggagtgc    13560
agtggcgtga tcttggctca ctgcagcttc tgcctcctgg cttcaagtga ttctcctgcc    13620
tcagcctccc aagtagctgg gattacaggc acctgccccc tcgcccaact aacttttgt     13680 gtttgtagta gagacagggt ttcaccatgt tggccaggct ggtctcgaac tcctgacctc    13740
atgtgatcca cctgcctcag cctcccaaag tgctgggatt acaggcatga gccatcatgc    13800
ccagccctat ttgacggttt ttgacgctaa tgcaagtggc atttaaaaa attttatatt     13860 tcccattgtt tgttgtcagt atatattgga ttttgtaat ttgatctcat attttgcagt    13920
cttgctaaat tgctaaacct cttttttgcta aactcgataa gctttttttt ttttggtaga    13980
ttcctgggcc tctaattttc tttatgggaa agtttttaat tacaaattta atttctttaa    14040
tagctacatg gctattcaat ttacttatta attcttggta atgtgtgtct ttcaaggaat    14100
ttgtccattt catctaagtt gtagaatttc tttggcataa atttgtacat aacattccct    14160
tattatcctt ttaatgtctt tagaatgtct tatttattta tttatttatt tttattatat    14220 tttttgaga cagagtctcg ctctgttgcc caggctggag tgcagtggca caatcttggc    14280
tcactgcaag ctccgccttc tgggttcatg ccattctcct gcctcagcct ccctagttgc    14340
tgggactaca ggcgcctgca accatgccca gcttatttt tttttttttt tttttttttt    14400
tttttttttt tttttttttt tagtagagac ggggtttcac cctgttagcc aggatggtct    14460
cgatctcctg acctggtgat ccgcccgcct cagcctccca aagtgctggg attacaggcg    14520
tgagccacca gcccagcct atttatttat ttagtagaga cagtctcact tgctgcccca    14580
ggcaacaaag gttttgaatg cctggcctca agcagtcctc ctgccttggc ctcccaaagt    14640
gctgggatta caggcatgag ccactgcacc tggccaaatg aatatgctga taatatcttc    14700
tttataagga tgcataaga ataaaataat gtaatacaaa caaagcccct gtcactgaaa     14760
atgtatagac ttcaaatgtt aaagtcttag agaacagaat ttatatgaaa tagcaacagc    14820
aacaatttcc cagaggaaat actctctcag ctttcttctg aggagcagtt tctaaattga    14880
aattgtatca gtgagaagat aactatacta acttcataag ccttgggcct ttttgaaaca    14940
aatccatata aactatgaac aaacttgaaa tagaacaatt tgagaacagg gtacaaactg    15000
cattggtgta tcaatttcag tatttggttt tagcttaaat agactgactt gagataacat    15060
aaggagaacc ttgaccccca agcaacatca tctcgcgagt tgactaggcc gggtgtggtg    15120
tctcacgcct gtaattccag cactttggga ggccacagca ggcagatcac ttgaggtcag    15180
gcattcgaga ccagcctggc caacatggtg aaaccctcagc tctactaaag atacgaaaat    15240
tagcaggcat agtggcctgc acctgtaata ccaggcactc gcaggagaat cccttgaacc    15300
cggaaggcgg agattgcagt aaaccatgat tgtgccactg cactccagcc tgggcaacag    15360
gagactctgt ctcggaaaaa taatttttt aaaaaaatga aaaaaataa aagttgacta    15420 aattagtgtc ttggtactaa gcactgtagg aagtgagttt catggaaccc caactctctt    15480
```

-continued

```
ggggcccaaa gcaagtcata ttaatattga aaattacatg catatacatg catatgacca    15540
aggtgataaa aacaattatt ctgcctgagt tggagaatag tatcccagta aaataaacaa    15600
gagtctcaaa gtcttttgta tcctttgaag ctgtcatggt ggtttgtaac taggcaacag    15660
gtatatattg ttaatcttct ttgcatttaa ttccttttat agagagacac aattttacga    15720
gcagatgcaa ttactagcat gaaggtttct ttgtgagggt agttaaaagg cccacatgag    15780
ctctcttctt atccttgtcc ttctttcagc cagatcttcc ctgccccttt gctcattcca    15840
tctttcaccc acctaccccc aaaacaagga agtaaatctt gcattagtca acaataccaa    15900
agtgattttc aatatgactt tctctgcaga atgttattat ttctgcctct ttacattcac    15960
atactgtctt ccttttttt tttttttttt tttttttttt tagattgggt ctcactctgt    16020
tgcccaggct ggagtgcagt ggcttgatct cagctcactg taacctccac ctcctgagtt    16080
caagcaattc tcctgcctca gcctcctgag tagctgggat tacaggcatg tgccaccaca    16140
cctggctagt ttttttgtat ttttagtaga cagggtttt caccatgttg gtcaagctgg    16200
tctcgaactc ctgacctcat gatctgacca cctgtgcctc tcaaagtgct gggattacag    16260
gcgtgagcca ccgggccagc cactctcttc ctttcagttg cctactcatc tcttatgcat    16320
tcctggacat cagttgtcct tttgaagctt tcctccacta tcccagccca tgtgaatcct    16380
ccttccagtt atagcccta attctagatg gctgatattt ttcaataatt gttttaagat    16440
gaccatttta gcctatcagc taaacaatat caaagacaat agctatttt caagtacttt    16500 agtttacctt attatagagt gcataataga tattcagtaa atagtaaagg agaggtgaag    16560
gcttgcatag aatggattct ggtggtgtct cttggtgagc ttttagcatc aagattaatc    16620
agcagtttca gcaatgagct cagaccttca gttttagatc tttactcata tcagataaga    16680
gagtgagaag agtggtatgt atcagtgctt tatttatatt tgcatccaat ttgaactatg    16740
aatattacaa aggtgcacac ataggttcag acagattgat ttaaaatgac caaagatgac    16800
ctgtcgtaag caacctgggt atcttaagat gcactccttg gagagggaat gttcctaaaa    16860
acattttcag agggacgaac tgtatgaaat tcagtaaaac ataaatcatg aggaaaactg    16920
attactctct ttttgacatg aaatgagagt tttaatgcat ggttacgatt attaacgtac    16980
tccgctgcaa gacgttaata aagttactgt tttgcaggct agaatgtctt gatgctgtaa    17040
tcagaacaca ctttttcccc tttcttccag cttcaaatgc agattcataa ttgggctgac    17100
ttctaataac tgcaatgttt tctgccttgg gcttgcagca gaagcctgac aaaatagtgt    17160
ttgtttaggc aataatttat ttatttattt attgagatgg agtttcattc ttgtcgccca    17220
ggctggagtg caatggcgtg atctcggctc actgcaacct ctgtgttcag gcaataattt    17280
agactttacc ttacttgtga ttactatagc aattactata gccacaaggc ataattttac    17340
tgtctcattt caattttatg aatttgaatg ttttacact tttcctaatg aagtccacta    17400
tgaagttatg tcaaaaaaaa aaagaaaaa gaaagatgca cacgtaaaag agaggtggtt    17460
gcaagagaag aaaagaacgg aggaaagtta acgcaaacc agataactct cagcgtattc    17520
taaatgacca aaacagaac tctgttgtca agatttaa atggaaaatt tttcaatttt    17580
tttttctttt ttgtacaggt ttcttcctga acgcgcctca gcgatttaa atcgtatgca    17640 gaatattcaa tttgaagcag tggttggcca caaaatcaaa atgaaatgaa taaataagct    17700
ccagccagag atgtatgcat gataatgata tgaatagttt cgaatcaatg ctgcaaagct    17760
ttatttcaca ttttttcagt cctgataata ttaaaaacat tggtttggca ctagcagcag    17820
tcaaacgaac aagattaatt acctgtcttc ctgtttctca agaatattta cgtagttttt    17880
```

```
cataggtctg ttttccttt catgcctctt aaaaacttct gtgcttacat aaacatactt    17940
aaaaggtttt ctttaagata ttttatttt ccatttaaag gtggacaaaa gctacctccc    18000
taaaagtaaa tacaaagaga acttatttac acagggaagg tttaagactg ttcaagtagc    18060
attccaatct gtagccatgc cacagaatat caacaagaac acagaatgag tgcacagcta    18120
agagatcaag tttcagcagg cagctttatc tcaacctgga catattttaa gattcagcat    18180
ttgaaagatt tccctagcct cttccttttt cattagccca aaacggtgca actctattct    18240
ggactttatt acttgattct gtcttctgta taactctgaa gtccaccaaa agtggaccct    18300
ctatatttcc tcccttttta tagtcttata agatacatta tgaaaggtga ccgactctat    18360
tttaaatctc agaattttaa gttctagccc catgataacc ttttctttg taatttatgc    18420 tttcatatat ccttggtccc agagatgttt agacaatttt aggctcaaaa attaaagcta    18480
acacaggaaa aggaactgta ctggctatta cataagaaac aatggaccca agagaagaaa    18540
aggaagaaag aaaggttttt tggtttttgt tttgttttgt tttgttttt gttttttga     18600 gatggagtct cactctttcg cccaggctgg agtgcagtgg tatgatctca gctcactgca    18660
agctccacct cccgggttca cgccattctc ctgcctcagc ctcctgagta gctgggacta    18720
caggcgcccg ccaccacacc cggctaattt tttgtatttt ttgtagagac ggggtttcac    18780
catgttagcc aagatggtct cgatctcctg acctcgtgat ccacctgcct cggcctccca    18840
aagtgctggg attacgggtg tgagccaccg tgcccagcct tttttttttt aatagaaaaa    18900
ataatccgac tcccactaca tcaagactaa tcttgttttg tgtgttttc acatgtatta    18960 tagaatgctt ttgcatggac tatcctcttg tttttattaa aaacaaatga tttttttaaa    19020
agtcacaaaa acaattcact aaaaataaat atgtcattgt gctttaaaaa aataaccctct   19080 tgtagttata aaataaaacg tttgacttct aaactctg                             19118
```

<210> SEQ ID NO 2
<211> LENGTH: 19119
<212> TYPE: DNA
<213> ORGANISM: homo sapien

<400> SEQUENCE: 2

```
agacagtacc tcctccctag gactacacaa ggactgaacc agaaggaaga ggacagagca      60
aagccatgaa catcatccta gaaatccttc tgcttctgat caccatcatc tactcctact     120
tggagtcgtt ggtgaagttt ttcattcctc agaggagaaa atctgtggct ggggagattg     180
ttctcattac tggagctggg catggaatag gcaggcagac tacttatgaa tttgcaaaac     240
gacagagcat attggttctg tgggatatta ataaggtaat gtatacatct tccaactttt     300
taaagtcaca gagtaagata tgtattttaa gaattatttg acttaccatc tacttatctt     360 tgtattttg ttttcaaag tttgataaat tccctggtcc cttagtctgt atatgtgtca      420
ggttagttag atgaagggaa tgtaattaag aactaagcag cgatttttat gacatggtgt     480
gcaggttgat agaaagactc aggagccagt ctccttccaa gctgctaaat gaggcaagtc     540
acatattatc tctcagcctg ttttcttggc tctgaagtgg ggataataac ttaggggatg     600
ggcaagaacg ggatctgaaa attacagcta caaacaaaag tcaaacgaag aacttgcaac     660
agaaaccttt agtgcctccc ctcatgcaca agcaacacag ttctaaaata tttactgtct     720 gacccttac agaaaatgtt tgccagtccg tagtcaaaag gattaaataa gtaatatttt      780
cagcacttag catatgataa acgatacgtg gcacatgata aacaataact gtgttaaata     840
```

```
aaatatgtgc gcagtgagtc aggcttttcc ttggacatta gtattttttcc tgtgttctta    900 cttgtaaaca ctacattaac aaccccaaat aaaactgaag gaactgaaat cttgtatcat    960
tttctctaaa cttgtaaatt ctggtaaggc catgaaaata tatgcagaga agtgtttaca   1020
ggattttagg attggaaaaa ttgtgaagta ctccttgaga atcacatttt ctgcaaatta   1080
cagtggtttt aattaccatt atattattac tttctcatgt tctttgctgt catgtttagt   1140
tgaaacctaa aatgtctctt acacttagag aactaattct tttctgtttt ttttctgaat   1200
agtgaagaat actatacaaa aaagctacta cattttttatt taacagatat gagcatttat   1260
ataatagagg agttgatgta tataaaaatg atttgccatc tttttggtct ttgaagaaat   1320
tcgaatgaac tttctggaag atagcaagaa tttacaaata gagaaaattg ttgcctgctg   1380
ttctcaggca tttgtccaaa aatataaata agtataaatc tatgaaaagg gcttgatgaa   1440
atctaacctt caaatctctt tccagatgtg tattttttggg gaaagggcta tatttattaa   1500
gtttttttta aattttaaaa tttccagaga caagagaaaa gtaaattaga aggaagtcgt   1560
attaaaaatg acttaagggc gggtgcagtg gctcacacct gtaatcccag cactttggga   1620
gacggaggtg ggcagattgc tggagcccag gagttcaaga ccagcctggg cagcacagca   1680
aaaccccaaa ctctacaaaa aatacaaaaa ttagctgggt gcgggggtgc acccgtag    1740 tcccagctac tcgggaggct gaggtgggag gatcgtttca gttcaggaag ccaaggctgc   1800
aatgagctat gatggcatca ttgcactcca agctgggcaa tagagccagg ctctgtctca   1860
aaaaaaataa aaaagactt aagaaaaata ggtaacccaa cctcaaaaat tctctttgaa    1920
tcattaaatt tcatggttaa acatttaagc tactgaatga ttcactctaa ggctgtaatg   1980
taactcagat ctcctttagg cgaggaagat gctggctgag ttttcatcat aactggctcc   2040
ttttgccctg tgagatgaga gacacagtag cagtttggct cttatgcaat ctaaactgtt   2100
gcgttgggaa tacggttcaa aaaacacatt ggagtttaag ctaaagcaag tgttttgcta   2160
acaaaaagac aaggcatcac attttgcaat tgtctagctc agttataaaa cagaagaata   2220
ggccggacgc ggtggctcac gcctgtaatc ccagcacttt gggaggccga gacgggcgga   2280
tcacgaggtc aggagatcga gaccatcctg gataacacag tgaaacccccg tctctactaa   2340 aaatacaaaa aaattagcca ggcgtagtgg cgggcgcctg tagtcccagc tactcgggag   2400
gctgaggcag gagaatggtg tgaacccggg aggcggagct tgcagtgagc cgagatgacg   2460
ccactgcact ccagcctggg cgacagagcg agactccgtc tcaaaaaaaa aaaaaaaaaa   2520
aaaactgaag aataattaat tcttcaatca aaacatctga tgaatgctct ggtaacttat   2580
gctctctact gacctagaaa caaatgagag agtatggtgt ggtttgtgca atctggcagt   2640
gagcaagcta ccaactaaat cagtgaaaga ctctcctatt ctttttttac tcttctgcaa   2700
tcccacaaaa ggctatttga ggggatactg actttgagac tgggtcctaa catccatgtt   2760
tggggagttc aggctgctgc tccagggttt agcctacagt agcgaaatac aaaggaccca   2820
gagaccactc attcaaggtt tgccctaaat agcagcaaca ccactgtcat ctcaatacac   2880
gaagaatagg gcttttcagg tatccttgcc tctttgtcac agagaagagt ttacagattg   2940
tgagacggaa aagtataatt tttaaaacct tataatatttt tctataaaag tcacctgagg   3000
tgaaaacttg aaaagaatta taattttcca gaatgtgagt caagaaacat tagagcaatt   3060
ttatcttagg aaagaggtct ttgaatttag gctgaaagta aattgctctg tctccatgtc   3120
ctatggttat gggcaagttt ggtacataaa tgagaaatcc atccagtggc cttgcccatc   3180
tcactcccaa acacctgaag aatgtaatgt tatatctcct agagtagcag catggtctcc   3240
```

```
ctatgaaagt ccttcttctt taaggagact tctttccctt ccctcctagg aggatgagtc   3300
agaatcatca agaaaaatat gatgggcaga ggcatacagt ttaccattac cactagttta   3360
gaattactac ttagcacttt actgcctatt acatagttgg tgctcaacaa atgtatgata   3420
aattaatggt tgagtttttc tttcttctcc atattcatct tccatgacac cacgaagagc   3480
aatgtttttc aagaatgttc ttcaaggttt gaaagtagcc tgctttagag aaactgccta   3540
ctgtacagcc tccaaccaag aggaaaagct gaaaaaagca tgaagggatt ttgttttgtt   3600
ttgtttgttt tggttttaat atgagcattc cctggcagaa aagccagggg taatctcatt   3660
gcaactaggc aatcactctc aagaaatttt ctaacaaata aggaggccaa ttttttatttt  3720
attttgagac gaagtcccac tctgtcaccc aggttggagt gcaatggaat gatttcagct   3780
cactgcaacc tccgcctccc gggttcaagt gattctcctg tctaaacttc ccgagtagct   3840
gggattacag gctcccacca ccacgcccag ctaattttt gtattttag tagagatggg      3900
gtttcaccat tttggccaga ctggtctcaa actcctgacc tcaagtgatc caccctcctc   3960
ggcctcctaa agtgctggga ttacaggcgt gagccaccac acctgaccca ggaggccaat   4020
ttttaaaagg ttaactaatc ttcatgtcca aaatgaatgt taattgttca ttttggacat   4080
gaatgttaat tttttttttt ttttttttg agacagagtc tcactctgtt gcccaggctg   4140
gagtccagtg gcactatctc cactcactgc aacttcctcc tcccaggttc aagcaattat   4200
cctgcctcag cctcccaagt agctgggatt acaggcccac accatcaggc ctggctaatt   4260
tttgtatttt tagtagagac ggggtttcac catgttggcc aggctggtct tgaactcctg   4320
acctcgtgat ccgccctcct cggccaacca aagtgctggg attacaggcg tgagccaccg   4380
cgcctagccg aatgttaatt gtctaaaaat ttttcttctc caatgtcttc tcctccactt   4440
ttttcggaat ttgtttcttc ctaattacag cgcggtgtgg aggaaactgc agctgagtgc   4500
cgaaaactag gcgtcactgc gcatgcgtat gtggtagact gcagcaacag agaagagatc   4560
tatcgctctc taaatcaggt gagactgcag gttcacaaat ttcttcagat tattttgttt   4620
cctaggacgc tgacgtggaa aatgagaaag gtctttatga ctgcctgatt taaattggat   4680
tttagctgct aactgaagta gttatgtcac caaggaagga tatatacttt ttttcttgta   4740
tgtaatccac tcagctctgc ccattattat tgttcatatt attaatcaat ttcattctga   4800
tcagaagtgt gagcagtggc acagagtgac tgacaaaaga tttatcatca gggaatatgg   4860
atcacttcct agttttgttt tagtcctatt aactttgcag taattccagc ttctctttaa   4920
ttatttccct tgtgagattt tattttggtg ttaatgtagt cttctgtaga aaatgtaata   4980
ttaataatta ttatcacaat tatttttaaaa gagtaaatac caaataatca caatgaacta   5040
agcactctaa caaactttac attttttaat tcaatcccta caataactct gtaaacttca   5100
ttttacagat aagcaaatta tgactcagag aggttaagcc agacccaggt catgtagtta   5160
ttaggttatg aaaccaggat ttctcaacca gcactttaga ccaggtgcgg tggttcacac   5220
atgtaatccc agcactttgt gaggccaagg tggaaggatc acatgagacc aagagttcaa   5280
gaccagccca gcaacatag tgagacccta tctctaaaaa aaaaaaaaaa aaaaaaaaa    5340
aaagtttaaa gaaaaacaca ttttttaaaaa atgaacactt taaaaatatt tggtcagaat  5400
ttatatagga atttatcaac ataaatgtta atttcacttt actgataaac ttgcaaaaca   5460
tgatgtgctg ggtactgaaa tttagatgtt aaaagaacag tttatcccac ctttatgaca   5520
gtgttccctt ggcctccacg atttgagctc aacagtctgt cttgcctgaa ctctgagaga   5580
```

```
cctcatacaa tagaagaaag actctcatct ttggattata ttggtcccaa aactttgagt    5640
ttgaataata cacccagtga aagtgttctt tcaatttcaa aaggtgaaga aagaagtggg    5700
tgatgtaaca atcgtggtga ataatgctgg gacagtatat ccagccgatc ttctcagcac    5760
caaggatgaa gagattacca agacatttga ggtcaacatc ctaggacatt tttgggtgag    5820
tgtgagtcag aaacatttct gatttgtgca ccttctctta agatacatga aacttataac    5880
ggagttcaca tacttctgga caggaaactg gccagatctt tgccttaatc aagaatcatt    5940
aaatttgttt gagtagaaga gccacagagt ctctgacaca aggacacaga attcaagtgg    6000
acacaacaca ccagaatgta agctacttgg tctgtcttgt ccaccagtat ctgcacaaaa    6060
gcttggcatg taccaggagc tcaacaaatg tttgtggagg tttgttaagg gttgtcagtg    6120
tacatctttt caatgctgtc acttgtgact tcattttttt ccctccacac catgattttg    6180
taatgtgtcc tcattttgtg aattttaga atggaaagga catcagaagt aattacttgg    6240
atgtatatag gatcgaggac acttttggac gagactctga ggcaagtgtt ctagatccat    6300
ggggtgctgg aactgagaaa tgcagctata cagacctcat ataattggtt agttttgtgg    6360
gagatggaaa tatcaacttc aactgccttt gtatagaaat ttttatgatt aatcttccag    6420
tgcctcaata ttagtgtaga atctagggca gatctggatt ctagaagaaa gaagaaaaaa    6480
aagagatgtg tccccttac ctttaccagc tcttcacata tgtgaattgg ctcccatgcc    6540
caccaaacta cacggagacc tcatacatta gctacctata gctgcataac aaattataca    6600
aaacttagtg gtttaaagca acaatgtatg ttcactatcc tctcacagtt tctatgggtt    6660
gggaatttgg aggtagcttg ggtgggagt tctagttcta tgaatttgca taggatttat    6720
taaattctta taaaatttta ttgatgtttc tcacaaaaga gttttttgga aaaaaagaaa    6780
gacttgtttt ctgtaacatc aacatataat atacaatatt acaaataggg agatagtgaa    6840
ttcaatcatg attcattagt gtggtgtaga actctcagct tacactactc aactgtctta    6900
atacagttac acaagatttc actcttttaa ttagaatgat aaagcccaa accaaaaat    6960 tatatgacac caaattatca taaggaataa ttttagttct gaaaactctg aattttccc     7020 ttaatattgt ttagatgaca tatccaaaaa aggatctatt tgattccttc tgaagggaag    7080 gaggggagt actgagatta gtgttggcat ggggcttacc ataccaataa atttgtatct    7140
ttatttctat catttgtaaa gaattaatca tggaatgctt ggaagtattt tatttcattg    7200
tataagttct ctcaaatgcc tttctgtctt aacaaaaata aaactacctg atttggaaac    7260
ctaacgtcta tgtcattgtc tttcttcttt ctgcaatgat ccttaagatc acaaaagcac    7320
ttcttccatc gatgatggag agaaatcatg gccacatcgt cacagtggct tcagtgtgcg    7380
gccacgaagg gattccttac ctcatcccat attggtaagt atcacatgcc agccatgtta    7440 tatatttta tactttgaag ggagcattac acttcaaatt gttaccactg gagagtcctg    7500
gttcttggca tcttgaacaa agaattggac aaaactcacc aacaaagcca ggaaagaatg    7560
aagcaacaaa agcagagatt tattgaaaat gaaagtacgc tttacagggt gggagtgggc    7620
ccaagcacag gggctcaaga gccaattaca gaattttctg gggtttaaat accccctaga    7680
ggtttccact ggttacttgg tgtacgccct atgtaaatga agaggatgaa ttaaagttac    7740
agagtcgttt actcagtgta caccatatgt aaatggagag gatatttcct gtcatagctg    7800 gagtgttttcc atttgattta gttctaggaa gtcagcatga atcggcctta tgttccctgc    7860
ctccagaccc tgttctcctg cctcaagatt acaatgctga gagcagagtg atttggattt    7920
acagaattta aatttatagt agtttagaat gatttttaa atgacttttt ctaaaacaat     7980
```

```
gaaaccaggt tgtaattata tttaagatat ttttagattt ctgcaaactc ctctgtagaa    8040
caatgagaga aaacagtaat gccaagcatg tttccattgt ttcctggaat aagaaacaga    8100
aaccccacag actgagaagc aaaacctaca gaagctaaaa tgaacacatg tctatgtcat    8160
ggccttggtg cccaagataa gacaatcaga gtggtccctg gatcaaaaca ttttacagtg    8220
tgcttgtgcc atgaaagtgt gtgtgtgtgt gtgtgtgtgt gtgtgagaga gagagagaga    8280
gagaaaacga ctctacctga ctaaaagttg cagataccac actccatgca ccaccaaaga    8340
cataaaggga aggaggtgag aggcgttaag gatgtactgc tgtatttgcc aaatatcctt    8400
tcctgtaaac tcttctccag atcctcataa taaaattaag aggccaaagt ggcaaccatt    8460
gtcaagagaa aaactatcaa ccattgtcaa gagaataact cagttattga gagagagagg    8520
agaaatgagc agagtcctac agaagtctgt caacacagat accagttttg tagaatttct    8580
aaatgtattt ttcctgattc atattttca aaataaaagc agcaataaaa actgattaga    8640
aaacagtttg aagattcaat ggaaaaacct tacatgtagg atggaaaact gaacattaag    8700
ccaatcaata gagttatttt tgttcttttg ttatcattgt tgtttaagaa atgagatacg    8760
ttcacaattc tgcttaatca tgtaagaaaa tgaaaatgaa ttgccattta tactctcaga    8820
aaaatcacaa gtggctgatt tttggcttcc acttgttctt aagccaaatg ataccgcctt    8880
ctcacagaaa gctgaggatt ggtttcactc tcccttagct aacaatgctt aataattctc    8940
ttacagttcc agcaaatttg ccgctgttgg cttcacaga ggtctgacat cagaacttca    9000
ggccttggga aaaactggta tcaaaacctc atgtctctgc ccagttttg tgaatactgg    9060 gttcaccaaa atccaagca caaggtaagg tcaaaatcaa gttagaatgg gtatgtggta    9120
tgataaattg atatgaaaac taatgagaaa tgtttaggca ggccaactaa tagaagaaaa    9180
tgaagaagga aaaataattt ttcttattat tattattatc ttgaaattaa aggaataaag    9240
ggggaaaaca cattagggac tagcaggaat gatcagccac cgatgaactg ggatatttat    9300
ttgtgtccgg gagaaagcac atacatttga tcaccgttac caccctgtct ttaaaatgca    9360
aatgttccaa ggaccagcaa ataaattgag tatctagctc cttagtcaag gtgaatttct    9420
gcaagaactc ttgtctctgg tgagacagga tttgagacca caagagaaga aaaattagtc    9480
ctgaaaggag aagaaaaaag caggaaggtg tggataagaa cccgaaaatt aagccatctg    9540
cttaacaaat ttttctaatc ctagtatata ttctgctgca ggttaacaaa atatactaag    9600
cttaatgatt cgaaaccaat ttttactgg aagggaatta atcctaaata tattcattca    9660
aaagaactaa acaattctct gttgagtgcc gcctcatttg aggatactga ctcttacagc    9720
ctgagttagc tatgtggtct ctgcagctgg aatcactccc tgccactgga gtccttcatg    9780
gtgttagacc ataggtactg ttgactaaag aaaaaaaaaa gttttgttt ttattttgt    9840 ttttttgag acagagtctc actctgtcac ccaggctgga gtacagtggc gcgatctcag    9900
ctcaccgcaa cctccgcctt tctgggttca agcaattctc cttcctcagc ctcctgagta    9960
tttggattac aggcgcccac caccacgcct ggctaatttt tgtattttta gtagagacgg   10020
ggtttcacca tgttggccag gctggtctca aactcctgac ctcaggtgtc ctacctgcct   10080
tggcctccta aaatgctggg attacaggag tgagccacca tgcccggcca aaaaaataag   10140 ttttttaaaga attaaaggtc atcctggcta acacagtgaa accccgtctc tactaaaaaa   10200
cacaaaaaaa ttagccgggc gtggtggcgg gcgcctgtag tcccagctgc gcggaggct   10260 gaggcaggag aatggcgtga acccgggagg cggagcttgc agtgagccga gatcgcgcca   10320
```

```
ctgcactcca gcctgggcga cagagcgaga ctccgtctca aaaaaaaaaa aaaaaaaaa    10380 aaaaaaaaga attaaaggtg ttaattttat ttagaagcct tactgaagac tacagtcgga    10440
ggcctatagc ctgagagcag cccttttagag aggttcagtt gaactgttct gatagtgggg   10500
gccatgtgct ctatcctgta ttgtcttcaa agcatctttc cagagagctg cacattgtca    10560
cagagtcagg gactttgtga aattatgctg acaaccagaa gtgagtaaac gtggcttctt    10620
acatttgcta cgttgtctca cagtacttaa taagtatgca atatgtaagt aaatactata    10680
gtactattgc aactcctgat tgttttctta gacaaggaat tgggcccaat aaaaaccctc    10740
ttggtaggca ttcaggcttc gtgtaccatg agctttccta agggtatcct gccactcttg    10800
gggaaggcat gatagatgag gggagtaagg ataatggaac tctgggtaca gggttcctgg    10860
gggctaactt agaggtagac acaggcaatg ctaaatattt gggattgatt ttatagaggt    10920
tgctagattg tgaatttcct tagtaagggc taaggcattg atatgtaatg tcacacttgg    10980
ctccgaggct gggttgttgg atccatgtag atgaaatcag ggagagaaag ggcagaacgg    11040
agtaatttag aaatgtattg atttgtatta ctctctgttg gcttgctatt caaggcagtg    11100
gagaactcaa tcacataata atctgcagca aaccacagat catcccaggg aatgaagttt    11160
taacattcgc tggctcccta actcctcacc cagcctttac attcactggc tgttcagtcc    11220
atgcctggac atcttaattt gaatacaaca ttttaaatcc attttctgt catcatcttg     11280 cactaacaga caattctaca ctaagcctat gtttatgaat atttctcaag agtacatgta    11340
cacagccttc agtataagga aaactggaag tatgacatac ctccagttgt catactcctt    11400
gggcccctct taaattctca ttaaactgca ggataggcaa gtcagaggtg aatctcaaat    11460
acgaaattct taccggaaag gggttccaat ccagacccca agagagggtt cttagatttc    11520
tcgcaagaaa taattcgggg caaggccaca gtgcaaagca aaagcaagtt tattaggaaa    11580
gtaaaggagt agagaacagc tactccatgg agaagaatgg cttgagctgc tccaccaagg    11640
gtatttagag ttacttcttg attatatgct aaacaagggg tggattattc atgagttttc    11700
cgggaaaagg gtgagcaatt cccagaactg agatttcctc ccctttttag gccatatagg    11760
gtaacttcct gccattgcca tggtatttgt aaactgtcat agtgctggtg gaagtgtctc    11820
ttagcttgct aatgtattat agttagctta taatgagcag tgaggacaac cagaggtcac    11880
tttcatcacc atcttggttt tggtgggttt tggccggctt cttttactgca ccctatttta    11940 tcaacaaggt ctttatgacc tgaatcttgt gccaacctcc tatctcatcc tgtgacaaag    12000
aatgccttaa cttcctggga atgcagccca gtaggtgtca gccttatttt acccagaccc    12060
tattcaagat ggagttgctc tgatttaaac gcctctgaca aaatgacgac ctcaaaacaa    12120
tccagcttta tggaatacct ccacaagaaa gaaagtatac ttagctatag aattttctcc    12180
ttgcatccaa caggctttga gatgtcagat gttttccttcc tgtcccatga ttaatcctag   12240
ccattcctct ttcttgtctg gctccactac tccttaccat ctaatgcctc gccaccattt    12300
tgatattttg actaagtgag ctatgaaaca cacctactgg atatgaaagt ataagtttct    12360
gataacaaaa catcaacatg ggatgtggag gaagtgggta gggtggcatt aatgcagcaa    12420
atcctggaat atttttaaatc ttcattctaa attagtaaa aatataggat aattttcctg     12480
ccatcattta cttataaaat taaaattta gaaaataaaa ataatatttt cctctttta       12540 atcacagatt atggcctgta ttggagacag atgaagtcgt aagaagtctg atagatggaa    12600
tacttaccaa taagaaaatg attttgtttc catcgtatat caatatcttt ctgagactac    12660
agaagttaag tacagcacag aacacccaaa tactaaaaca ccaatagagc tttttttttt    12720
```

```
gcttttttt  tttttagaca  gagtctcact  ctgtcaccct  ggctggattg  cggtggttgc   12780
agtggcatga  tcttggctca  ctgcaacctc  cgcctcctgg  gttcaagcaa  ttctcatgcc   12840 tcagacccc   aagtaactgg  gattataggt  gtgtgctgcc  acactacacc  cagctaattt   12900
ttgtattttt  tgatagagac  aggttttccc  atgttggcca  ggctggactc  gaactcctga   12960
cctcaagtta  tcctcctgtc  tcggcctccc  aaagtgctgg  gattacagtc  atgagccacc   13020
atgcctggcc  caatagagct  attattatgg  agcatcttc   agttgtgaaa  attggcatgg   13080
aaactctcca  tccctgggga  gaacagttat  ttcctctgtt  attttcctac  ccagtctata   13140 aaagagagt   gattcatttt  ctctaccaaa  tctactgtct  ctgcccaaac  tttgctgaag   13200
actattctaa  ctaaaggaaa  cacagtttaa  aaagaatgca  atatagtgaa  gtagttaata   13260
ataaagactc  cattttaaa   agtctgctgg  aagtttggtt  gggattgcac  tgaatctata   13320
gagcaattgg  ggagtattga  catatcaaca  atattgagtt  ttctaatcca  agaacataat   13380 atctatttt   aaaatcttct  tcaaaatctt  taaatcttta  aattgtattt  tgtagttttt   13440
ggtgtttaag  tcttgcacat  attttgtcag  atttattcca  aagtatttca  cgggttcttt   13500
tttttttttt  ttttttttt   tttgagacag  agtttcaccc  ttgttgccca  ggctggagtg   13560
cagtggcgtg  atcttggctc  actgcagctt  ctgcctcctg  gcttcaagtg  attctcctgc   13620
ctcagcctcc  caagtagctg  ggattacagg  cacctgcccc  ctcgcccaac  taactttttg   13680
tgtttgtagt  agagacaggg  tttcaccatg  ttggccaggc  tggtctcgaa  ctcctgacct   13740
catgtgatcc  acctgcctca  gcctcccaaa  gtgctgggat  tacaggcatg  agccatcatg   13800
cccagcccta  tttgacggtt  tttgacgcta  atgcaagtgg  catttaaaa   aattttatat   13860 ttcccattgt  ttgttgtcag  tatatattgg  attttgtaa   tttgatctca  tattttgcag   13920
tcttgctaaa  ttgctaaacc  tcttttgct   aaactcgata  agctttttt   ttttggtag    13980 attcctgggc  ctctaatttt  ctttatggga  agttttaa    ttacaatttt  aatttcttta   14040
atagctacat  ggctattcaa  tttacttatt  aattcttggt  aatgtgtgtc  tttcaaggaa   14100
tttgtccatt  tcatctaagt  tgtagaattt  ctttggcata  aatttgtaca  taacattccc   14160
ttattatcct  tttaatgtct  ttagaatgtc  ttatttattt  atttatttat  ttttattata   14220 ttttttgag   acagagtctc  gctctgttgc  ccaggctgga  gtgcagtggc  acaatcttgg   14280
ctcactgcaa  gctccgcctt  ctgggttcat  gccattctcc  tgcctcagcc  tcctagttg    14340 ctgggactac  aggcgcctgc  aaccatgccc  agcttatttt  ttttttttt   tttttttt     14400 tttttttt    ttttttttt   ttagtagaga  cggggtttca  ccctgttagc  caggatggtc    14460
tcgatctcct  gacctggtga  tccgcccgcc  tcagcctccc  aaagtgctgg  gattacaggc    14520
gtgagccacc  aagcccagcc  tatttattta  tttagtagag  acagtctcac  tttgctgccc    14580
aggcaacaaa  ggtttgaat   gcctggcctc  aagcagtcct  cctgccttgg  cctcccaaag    14640
tgctgggatt  acaggcatga  gccactgcac  ctggccaaat  gaatatgctg  ataatatctt    14700
ctttataagg  atgacataag  aataaaataa  tgtaatacaa  acaaagcccc  tgtcactgaa    14760
aatgtataga  cttcaaatgt  taaagtctta  gagaacagaa  tttatatgaa  atagcaacag    14820
caacaatttc  ccagaggaaa  tactctctca  gctttcttct  gaggagcagt  ttctaaattg    14880
aaattgtatc  agtgagaaga  taactatact  aacttcataa  gccttgggcc  ttttttgaaac   14940 aaatccatat  aaactatgaa  caaacttgaa  atagaacaat  ttgagaacag  ggtacaaact    15000
gcattggtgt  atcaatttca  gtatttggtt  ttagcttaaa  tagactgact  tgagataaca   15060
```

```
taaggagaac cttgaccccc aagcaacatc atctcgcgag ttgactaggc cgggtgtggt    15120
gtctcacgcc tgtaattcca gcactttggg aggccacagc aggcagatca cttgaggtca    15180
ggcattcgag accagcctgg ccaacatggt gaaacctcag ctctactaaa gatacgaaaa    15240
ttagcaggca tagtggcctg cacctgtaat accaggcact cgcaggagaa tcccttgaac    15300
ccggaaggcg gagattgcag taaaccatga ttgtgccact gcactccagc ctgggcaaca    15360
ggagactctg tctcggaaaa ataaattttt taaaaaaatg aaaaaaaata aaagttgact    15420
aaattagtgt cttggtacta agcactgtag gaagtgagtt tcatggaacc ccaactctct    15480
tggggcccaa agcaagtcat attaatattg aaaattacat gcatatacat gcatatgacc    15540
aaggtgataa aaacaattat tctgcctgag ttggagaata gtatcccagt aaaataaaca    15600
agagtctcaa agtcttttgt atcctttgaa gctgtcatgg tggtttgtaa ctaggcaaca    15660
ggtatatatt gttaatcttc tttgcattta attccttttta tagagagaca caattttacg    15720
agcagatgca attactagca tgaaggtttc tttgtgaggg tagttaaaag gcccacatga    15780
gctctcttct tatccttgtc cttctttcag ccagatcttc cctgcccctt tgctcattcc    15840
atctttcacc cacctacccc caaaacaagg aagtaaatct tgcattagtc aacaatacca    15900
aagtgatttt caatatgact ttctctgcag aatgttatta tttctgcctc tttacattca    15960
catactgtct tccttttttt tttttttttt tttttttttt ttagattggg tctcactctg    16020
ttgcccaggc tggagtgcag tggcttgatc tcagctcact gtaacctcca cctcctgagt    16080
tcaagcaatt ctcctgcctc agcctcctga gtagctggga ttacaggcat gtgccaccac    16140
acctggctag ttttttttgta tttttagtag agacagggtt tcaccatgtt ggtcaagctg    16200
gtctcgaact cctgacctca tgatctgacc acctgtgcct ctcaaagtgc tgggattaca    16260
ggcgtgagcc accgggccag ccactctctt cctttcagtt gcctactcat ctcttatgca    16320
ttcctggaca tcagttgtcc ttttgaagct ttcctccact atcccagccc atgtgaatcc    16380
tccttccagt tatagccctt aattctagat ggctgatatt tttcaataat tgttttaaga    16440
tgaccatttt agcctatcag ctaaacaata tcaaagacaa tagctatttt tcaagtactt    16500
tagtttacct tattatagag tgcataatag atattcagta aatagtaaag gagaggtgaa    16560
ggcttgcata gaatggattc tggtggtgtc tcttggtgag cttttagcat caagattaat    16620
cagcagtttc agcaatgagc tcagaccttc agttttagat cttttactcat atcagataag    16680 agagtgagaa gagtggtatg tatcagtgct ttatttatat ttgcatccaa tttgaactat    16740
gaatattaca aaggtgcaca cataggttca gacagattga tttaaaatga ccaaagatga    16800
cctgtcgtaa gcaacctggg tatcttaaga tgcactcctt ggagagggaa tgttcctaaa    16860 aacatttttca gagggacgaa ctgtatgaaa ttcagtaaaa cataaatcat gaggaaaact    16920
gattactctc ttttttgacat gaaatgagag ttttaatgca tggttacgat tattaacgta    16980
ctccgctgca agacgttaat aaagttactg ttttgcaggc tagaatgtct tgatgctgta    17040
atcagaacac actttttccc ctttcttcca gcttcaaatg cagattcata attgggctga    17100
cttctaataa ctgcaatgtt ttctgccttg ggcttgcagc agaagcctga caaaatagtg    17160
tttgtttagg caataattta tttatttatt tattgagatg gagtttcatt cttgtcgccc    17220
aggctggagt gcaatggcgt gatctcggct cactgcaacc tctgtgttca ggcaataatt    17280
tagactttac cttacttgtg attactatag caattactat agccacaagg cataatttta    17340
ctgtctcatt tcaattttat gaatttgaat gttttttacac ttttcctaat gaagtccact    17400
atgaagttat gtcaaaaaaa aaaagaaaaa agaaagatgc acacgtaaaa gagaggtggt    17460
```

-continued

```
tgcaagagaa gaaaagaacg gaggaaagtt aaacgcaaac cagataactc tcagcgtatt    17520
ctaaatgacc aaaaacagaa ctctgttgtc aaagatttta aatggaaaat ttttcaattt    17580
ttttttcttt tttgtacagg tttcttcctg aacgcgcctc agcgatttta aatcgtatgc    17640
agaatattca atttgaagca gtggttggcc acaaaatcaa aatgaaatga ataaataagc    17700
tccagccaga gatgtatgca tgataatgat atgaatagtt tcgaatcaat gctgcaaagc    17760
tttatttcac attttttcag tcctgataat attaaaaaca ttggtttggc actagcagca    17820
gtcaaacgaa caagattaat tacctgtctt cctgtttctc aagaatattt acgtagtttt    17880
tcataggtct gttttttcctt tcatgcctct taaaaacttc tgtgcttaca taaacatact    17940
taaaaggttt tctttaagat attttatttt tccatttaaa ggtggacaaa agctacctcc    18000 ctaaagtaa  atacaaagag aacttattta cacagggaag gtttaagact gttcaagtag    18060
cattccaatc tgtagccatg ccacagaata tcaacaagaa cacagaatga gtgcacagct    18120
aagagatcaa gttcagcag  gcagctttat ctcaacctgg acatatttta agattcagca    18180
tttgaaagat ttccctagcc tcttcctttt tcattagccc aaaacggtgc aactctattc    18240
tggactttat tacttgattc tgtcttctgt ataactctga agtccaccaa aagtggaccc    18300
tctatatttc ctccctttt  atagtcttat aagatacatt atgaaaggtg accgactcta    18360
ttttaaatct cagaatttta agttctagcc ccatgataac ctttttcttt gtaatttatg    18420
ctttcatata tccttggtcc cagagatgtt tagacaattt taggctcaaa aattaaagct    18480
aacacaggaa aaggaactgt actggctatt acataagaaa caatggaccc aagagaagaa    18540
aaggaagaaa gaaaggtttt tggttttg  ttttgttttg ttttgttttt tgttttttg     18600 agatggagtc tcactctttc gcccaggctg gagtgcagtg gtatgatctc agctcactgc    18660
aagctccacc tcccgggttc acgccattct cctgcctcag cctcctgagt agctgggact    18720
acaggcgccc gccaccacac ccggctaatt ttttgtattt tttgtagaga cggggtttca    18780
ccatgttagc caagatggtc tcgatctcct gacctcgtga tccacctgcc tcggcctccc    18840
aaagtgctgg gattacgggt gtgagccacc gtgcccagcc ttttttttt  taatagaaaa    18900 aataatccga ctcccactac atcaagacta atcttgtttt gtgtgttttt cacatgtatt    18960
atagaatgct tttgcatgga ctatcctctt gttttttatta aaaacaaatg attttttaa    19020 aagtcacaaa aacaattcac taaaaataaa tatgtcattg tgctttaaaa aaataacctc    19080
ttgtagttat aaaataaaac gtttgacttc taaactctg                          19119
```

<210> SEQ ID NO 3
<211> LENGTH: 2397
<212> TYPE: RNA
<213> ORGANISM: homo sapien

<400> SEQUENCE: 3

```
agacaguacc uccucccuag gacuacacaa ggacugaacc agaaggaaga ggacagagca      60
aagccaugaa caucauccua gaaauccuuc ugcuucugau caccaucauc uacuccuacu     120
uggagucguu ggugaaguuu uucauuccuc agaggagaaa aucgugggcu ggggagauug     180
uucucauuac uggagcuggg cauggaauag gcaggcagac uacuuaugaa uuugcaaaac     240
gacagagcau auugguucug ugggauauua auaagcgcgg uguggaggaa acugcagcug     300
agugccgaaa acuaggcguc acugcgcaug cguauguggu agacugcagc aacagagaag     360
agaucuaucg cucucuaaau caggugaaga agaaguggga ugauguaaca aucgugguga     420
```

| | |
|---|---|
| auaaugcugg gacaguauau ccagccgauc uucucagcac caaggaugaa gagauuacca | 480 |
| agacauuuga ggucaacauc cuaggacauu uuuggaucac aaaagcacuu cuuccaucga | 540 |
| ugauggagag aaaucauggc cacaucguca caguggcuuc agugugcggc cacgaaggga | 600 |
| uuccuuaccu caucccauau uguuccagca aauuugccgc uguuggcuuu cacagagguc | 660 |
| ugacaucaga acuucaggcc uugggaaaaa cugguaucaa aaccucaugu cucugcccag | 720 |
| uuuuugugaa uacuggguuc accaaaaauc aagcacaag auuauggccu guauggaga | 780 |
| cagaugaagu cguaagaagu cugauagaug gaauacuuac caauaagaaa augauuuuug | 840 |
| uuccaucgua uaucaauauc uuucugagac uacagaaguu ucuuccugaa cgcgccucag | 900 |
| cgauuuuaaa ucguaugcag aauauucaau ugaagcagu gguuggccac aaaaucaaaa | 960 |
| ugaaaugaau aaauaagcuc cagccagaga uguaugcaug auaaugauau gaauaguuuc | 1020 |
| gaaucaaugc ugcaaagcuu uauuucacau uuuuucaguc cugauaauau uaaaaacauu | 1080 |
| gguuggcac uagcagcagu caaacgaaca agauuaauua ccugucuccc uguuucucaa | 1140 |
| gaauauuuac guaguuuuuc auaggucugu uuuuccuuuc augccucuua aaaacuucug | 1200 |
| ugcuuacaua aacauacuua aaagguuuuc uuuaagauau uuauuuuuc cauuuaaagg | 1260 |
| uggacaaaag cuaccucccu aaaaguaauu acaaagagaa cuuauuuaca cagggaaggu | 1320 |
| uuaagacugu ucaaguagca uuccaaucug uagccaugcc acagaauauc aacaagaaca | 1380 |
| cagaaugagu gcacagcuaa gagaucaagu ucagcaggc agcuuuaucu caaccuggac | 1440 |
| auauuuaag auucagcauu ugaaagauuu cccuagccuc uuccuuuuc auuagcccaa | 1500 |
| aacgguuugcaa cucuauucug gacuuuauua cuugauucug cuucuguau aacucugaag | 1560 |
| uccaccaaaa guggacccuc uauauuuccu cccuuuuuau agucuuauaa gauacauuau | 1620 |
| gaaaggugac cgacucuauu uuaaaucuca gaauuuuaag uucuagcccc augauaaccu | 1680 |
| uuuucuuugu aauuuaugcu ucauauauc cuuggucca gagauguuua gacaauuuua | 1740 |
| ggcucaaaaa uuaagcuaa cacaggaaaa ggaacuguac uggcuauuac auaagaaaca | 1800 |
| auggacccaa gagaagaaaa ggaagaaaga aagguuuuuu gguuuugu uguuuugu | 1860 |
| uuguuuuug uuuuuugag auggagucuc acucuuucgc ccaggcugga gugcaguggu | 1920 |
| augaucucag cucacugcaa gcuccaccuc ccgggucuac gccauucucc ugccucagcc | 1980 |
| uccugaguag cugggacuac aggcgcccgc caccacccc ggcuaauuuu uguauuuuu | 2040 |
| uguagagacg ggguuucacc auguuagcca agauggcucuc gaucccuga ccucgugauc | 2100 |
| caccugccuc ggccucccaa agugcuggga uuacggguug agccaccgu gcccagccuu | 2160 |
| uuuuuuuua auagaaaaaa uaauccgacu cccacuacau caagacuaau cuuguuugu | 2220 |
| guguuuuuca caguguuauau agaaugcuuu ugcauggacu auccucuguu uuuauuaaa | 2280 |
| aacaaaugau uuuuuaaaa gucacaaaaa caauucacua aaaauaaaua ugucauugug | 2340 |
| cuuuaaaaaa auaaccucuu guaguuauaa aauaaaacgu uugacuucua aacucug | 2397 |

<210> SEQ ID NO 4
<211> LENGTH: 2289
<212> TYPE: RNA
<213> ORGANISM: homo sapien

<400> SEQUENCE: 4

| | |
|---|---|
| agacaguacc uccucccuag gacuacacaa ggacugaacc agaaggaaga ggacagagca | 60 |
| aagccaugaa caucuccua gaaauccuuc ugcuucugau caccaucauc uacuccuacu | 120 |
| uggagucguu ggugaaguuu uucauuccuc agaggagaaa aucugugguc uggggagauug | 180 |

| | |
|---|---|
| uucucauuac uggagcuggg cauggaauag gcaggcagac uacuuaugaa uuugcaaaac | 240 |
| gacagagcau auugguucug ugggauauua auaaggugaa gaaagaagug ggugauguaa | 300 |
| caaucguggu gaauaaugcu gggacaguau auccagccga ucuucucagc accaaggaug | 360 |
| aagagauuac caagacauuu gaggucaaca uccuaggaca uuuuggauc acaaaagcac | 420 |
| uucuuccauc gaugauggag agaaaucaug ccacaucgu cacaguggcu ucagugugcg | 480 |
| gccacgaagg gauuccuuac cucaucccau auuguuccag caaauuugcc gcuguuggcu | 540 |
| uucacagagg ucugacauca gaacuucagg ccuugggaaa aacugguauc aaaaccucau | 600 |
| gucucugccc aguuuugug aauacgggu ucaccaaaaa uccaagcaca agauuauggc | 660 |
| cuguauugga gacagaugaa gucguagaa gucugauaga uggaauacuu accaauaaga | 720 |
| aaaugauuuu uguccaucg uaucaaua ucuuucugag acuacagaag uuucuuccug | 780 |
| aacgcgccuc agcgauuuua aaucguaugc agaauauuca auugaagca gugguuggcc | 840 |
| acaaaaucaa aaugaaauga auaaauaagc uccagccaga gauguaugca ugauaaugau | 900 |
| augaauaguu ucgaaucaau gcugcaaagc uuuauucac auuuucag uccugauaau | 960 |
| auuaaaaaca uugguuugc acuagcagca gucaaacgaa caagauuaau uaccugucuu | 1020 |
| ccuguuucuc aagaauauuu acguaguuuu ucauaggucu guuuuccuu ucaugccucu | 1080 |
| uaaaaacuuc ugugcuuaca uaaacauacu uaaaagguuu ucuuuaagau auuuuauuuu | 1140 |
| uccauuuaaa gguggacaaa agcuaccucc cuaaaaguaa auacaaagag aacuuauuua | 1200 |
| cacagggaag guuuaagacu guucaaguag cauuccaauc uguagccaug ccacagaaua | 1260 |
| ucaacaagaa cacagaauga gugcacagcu aagagaucaa guucagcag gcagcuuuau | 1320 |
| cucaaccugg acauauuuua agauucagca uuugaaagau ucccuagcc ucuuccuuuu | 1380 |
| ucauuagccc aaaacggugc aacucuauuc uggacuuuau uacuugauuc ugucuuccugu | 1440 |
| auaacucuga aguccaccaa aaguggaccc ucuauauuuc cucccuuuuu auagucuuau | 1500 |
| aagauacauu augaaaggug accgacucua uuuuaaaucu cagaauuuua aguucuagcc | 1560 |
| ccaugauaac cuuuuucuuu guaauuuaug cuuucauaua uccuuggucc cagagauguu | 1620 |
| uagacaauuu uaggcucaaa aauuaaagcu aacacaggaa aaggaacugu acuggcuauu | 1680 |
| acauaagaaa caauggaccc aagagaagaa aaggaagaaa gaaagguuuu uugguuuug | 1740 |
| uuuuguuuug uuuuguuuuu uguuuuuug agauggaguc ucacucuuuc gcccaggcug | 1800 |
| gagugcagug guaugaucuc agcucacugc aagcuccacc ucccgggguuc acgccauucu | 1860 |
| ccugccucag ccuccugagu agcugggacu acaggcgccc gccaccacac ccggcuaauu | 1920 |
| uuuuguauuu uuuguagaga cggguuuca ccauguuagc caagaugguc ucgaucccu | 1980 |
| gaccucguga uccaccugcc ucggccuccc aagugcugg gauuacgggu gugagccacc | 2040 |
| gugcccagcc uuuuuuuuu uaauagaaaa aauaauccga cucccacuac aucaagacua | 2100 |
| aucuuguuuu gugguguuuu cacauguauu auagaaugcu uugcaugga cuauccucuu | 2160 |
| guuuuauua aaacaaaug auuuuuuaa aagucacaaa aacaauucac uaaaaauaaa | 2220 |
| uaugucauug ugcuuuaaaa aaauaacccuc uuguaguuau aaaauaaaac guuugacuuc | 2280 |
| uaaacucug | 2289 |

<210> SEQ ID NO 5
<211> LENGTH: 2280
<212> TYPE: RNA
<213> ORGANISM: homo sapien

```
<400> SEQUENCE: 5
agacaguacc uccucccuag gacuacacaa ggacugaacc agaaggaaga ggacagagca      60
aagccaugaa caucauccua gaaauccuuc ugcuucugau caccaucauc uacuccuacu     120
uggagucguu ggugaaguuu ucauuccuc agaggagaaa aucguggcu ggggagauug       180
uucucauuac uggagcuggg cauggaauag gcaggcagac uacuuaugaa uuugcaaaac     240
gacagagcau auugguucug ugggauauua auaagcgcgg uggaggaa acugcagcug       300
agugccgaaa acuaggcguc acugcgcaug cguauguggu agacugcagc aacagagaag     360
agaucuaucg cucucuaaau caggugaaga aagaaguggg ugauguaaca aucgugguga     420
auaaugcugg gacaguauau ccagccgauc uucucagcac caaggaugaa gagauuacca     480
agacauuuga ggucaacauc cuaggacauu uuuggaucac aaaagcacuu cuuccaucga     540
ugauggagag aaaucauggc cacaucguca caguggcuuc agugugcggc cacgaaggga     600
uccuuaccu cauccauau uguuccagca aauugccgc uguuggcuuu cacagaggu        660
ugacaucaga acuucaggcc uugggaaaaa cugguaucaa aaccucaugu cucugcccag     720
uuuuugugaa uacugggguuc accaaaaauc caagcacaag guuucuuccu gaacgcgccu    780
cagcgauuuu aaaucguaug cagaauauuc aauuugaagc aguggguugc cacaaaauca    840
aaaugaaaug aauaaauaag cuccagccag agauguaugc augauaauga uaugaauagu    900
uucgaaucaa ugcugcaaag cuuuauuuca cauuuuuca guccugauaa uauuaaaaac     960
auugguuugg cacuagcagc agucaaacga acaagauuaa uuaccugucu uccuguuucu    1020
caagaauauu uacguaguuu uucauagguc uguuuuccu uucaugccuc uuaaaaacuu     1080
cugugcuuac auaaacauac uuaaaagguu ucuuaaga auuuuauuu uuccauuuaa       1140
aggggacaa aagcuaccuc ccuaaaagua aauacaaaga gaacuauuu acacagggaa      1200
gguuuaagac uguucaagua gcauccaau cuguagccau gccacagaau aucaacaaga    1260
acacagaaug agugcacagc uaagagauca aguucagca ggcagcuuua ucucaaccug     1320
gacauauuuu aagauucagc auuugaaaga uuucccuagc cucuuccuuu uucauuagcc    1380
caaaacggug caacucuauu cuggacuuua uuacuugauu cugucuucug uauaacucug    1440
aaguccacca aagguggacc cucuauauuu ccucccuuuu uauagucuua uaagauacau    1500
uaugaaaggu gaccgacucu auuuuaaauc ucagaauuuu aaguucuagc cccaugauaa    1560
ccuuuuucuu uguaauuuau gcuuucauau auccuugguc ccagagaugu uuagacaauu    1620
uuaggcucaa aaauuaaagc uaacacagga aaggaacug uacuggcuau uacauaagaa     1680
acaauggacc caagagaaga aaaggaagaa agaaagguuu uuggguuuu guuuuguuuu    1740
guuuuguuuu uuguuuuuuu gagauggagu cucacucuuu cgcccaggcu ggagugcagu    1800
gguaugaucu cagcucacug caagcuccac cucccggguu cacgccauuc uccugccuca    1860
gccuccugag uagcugggac uacaggcgcc cgccaccaca cccggcuaau uuuuuguauu    1920
uuuuguagag acgggguuuc accauguuag ccaagauggu cucgaucucc ugaccucgug    1980
auccaccugc cucggccucc caaagugcug ggauuacggg ugugagccac cgugcccagc    2040
cuuuuuuuuu uuaauagaaa aaauaaaaccg acucccacua caucaagacu aaucuuguuu    2100
ugugguuu ucacauguau uauagaaugc uuuugcaugg acuauccucu uguuuuauu       2160
aaaaacaaau gauuuuuuua aaagucacaa aacaauuca cuaaaaauaa auaugucauu    2220
gugcuuuaaa aaaauaaccu cuuguaguua uaaaauaaaa cguuugacuu cuaaacucug    2280
```

<210> SEQ ID NO 6
<211> LENGTH: 2398
<212> TYPE: RNA
<213> ORGANISM: homo sapien

<400> SEQUENCE: 6

| | | | | | |
|---|---|---|---|---|---|
| agacaguacc | uccucccuag | gacuacacaa | ggacugaacc | agaaggaaga | ggacagagca | 60 |
| aagccaugaa | caucauccua | gaaauccuuc | ugcuucugau | caccaucauc | uacuccuacu | 120 |
| uggagucguu | ggugaaguuu | ucauuccuc | agaggagaaa | aucguggcu | ggggagauug | 180 |
| uucucauuac | uggagcuggg | cauggaauag | gcaggcagac | uacuuaugaa | uuugcaaaac | 240 |
| gacagagcau | auugguucug | ugggauauua | auaagcgcgg | uguggaggaa | acugcagcug | 300 |
| agugccgaaa | acuaggcguc | acugcgcaug | cguauggu | agacugcagc | aacagagaag | 360 |
| agaucuaucg | cucucuaaau | caggugaaga | agaaguggg | ugauguaaca | aucgguguga | 420 |
| auaaugcugg | gacaguauau | ccagccgauc | uucucagcac | caaggaugaa | gagauuacca | 480 |
| agacauuuga | ggucaacauc | cuaggacauu | uuuggaucac | aaaagcacuu | cuuccaucga | 540 |
| ugauggagag | aaaucauggc | cacaucguca | caguggcuuc | agugugcggc | cacgaaggga | 600 |
| uuccuuaccu | caucccauau | uguuccagca | aauuugccgc | uguggcuuu | cacagagguc | 660 |
| ugacaucaga | acuucaggcc | uugggaaaaa | cugguaucaa | aaccucaugu | cucugcccag | 720 |
| uuuuugugaa | uacuggguuc | accaaaaaac | caagcacaag | auuauggccu | guauggaga | 780 |
| cagaugaagu | cguagaagu | cugauagaug | gaauacuuac | caauaagaaa | augauuuug | 840 |
| uuccaucgua | uaucaauauc | uuucugagac | uacagaaggu | ucuuccuga | acgcgccuca | 900 |
| gcgauuuuaa | aucguaugca | gaauauucaa | uuugaagcag | ugguuggcca | caaaaucaaa | 960 |
| augaaaugaa | uaaauaagcu | ccagccagag | auguaugcau | gauaaugaua | ugaauaguuu | 1020 |
| cgaaucaaug | cugcaaagcu | uuauucaca | uuuuucagu | ccugauaaua | uuaaaaacau | 1080 |
| ugguuuggca | cuagcagcag | ucaaacgaac | aagauuaauu | accgucuuc | cuguuucuca | 1140 |
| agaauauuua | cguaguuuuu | cauaggucug | uuuuuccuuu | caugccucuu | aaaaacuucu | 1200 |
| gugcuuacau | aaacauacuu | aaaagguuuu | cuuuaagaua | uuuuauuuuu | ccauuuaaag | 1260 |
| guggacaaaa | gcuaccuccc | uaaaaguaaa | uacaaagaga | acuauuuac | acagggaagg | 1320 |
| uuuaagacug | uucaaguagc | auccaaucu | guagccaugc | cacagaauau | caacaagaac | 1380 |
| acagaaugag | ugcacagcua | agagaucaag | uuucagcagg | cagcuuuauc | ucaaccugga | 1440 |
| cauauuuuaa | gauucagcau | uugaaagauu | ucccuagccu | cuuccuuuuu | cauuagccca | 1500 |
| aaacggugca | acucuauucu | ggacuuuauu | acuugauucu | gcuucugua | aacucugaa | 1560 |
| guccaccaaa | aguggacccu | cuauauuucc | uccuuuuua | uagucuuaua | agauacauua | 1620 |
| ugaaggguga | ccgacucuau | uuuaaaucuc | agaauuuuaa | guucuagccc | caugauaacc | 1680 |
| uuuucuuug | uaauuuaugc | uuucauauau | ccuuggaccc | agagauguuu | agacaauuuu | 1740 |
| aggcucaaaa | auuaaagcua | acacaggaaa | aggaacugua | cuggcuauua | cauaagaaac | 1800 |
| aauggaccca | agagaagaaa | aggaagaaag | aaagguuuuu | ugguuuugu | uuguuuugu | 1860 |
| uuuguuuuuu | guuuuuuga | gauggagucu | cacucuuucg | cccaggcugg | agucagugg | 1920 |
| uaugaucuca | gcucacugca | agcuccaccu | cccgggguca | cgccauucuc | cugccucagc | 1980 |
| cuccugagua | gcugggacua | caggcgcccg | ccaccacacc | cggcuaauuu | uuuguauuuu | 2040 |
| uuguagagac | ggggguuucac | caguguuagcc | aagaugguccu | cgaucccug | accucgugau | 2100 |
| ccaccugccu | cggccuccca | aagugcuggg | auuacgggug | ugagccaccg | ugcccagccu | 2160 |

| | |
|---|---|
| uuuuuuuuuu aauagaaaaa auaauccgac ucccacuaca ucaagacuaa ucuuguuuug | 2220 |
| uguguuuuuc acauguauua uagaaugcuu uugcauggac uauccucuug uuuuuauuaa | 2280 |
| aaacaaauga uuuuuuuaaa agucacaaaa acaauucacu aaaaauaaau augucauugu | 2340 |
| gcuuuaaaaa aauaaccucu uguaguuaua aaauaaaacg uuugacuucu aaacucug | 2398 |

<210> SEQ ID NO 7
<211> LENGTH: 2469
<212> TYPE: RNA
<213> ORGANISM: homo sapien

<400> SEQUENCE: 7

| | |
|---|---|
| agacaguacc uccucccuag gacuacacaa ggacugaacc agaaggaaga ggacagagca | 60 |
| aagccaugaa caucauccua gaauccuuuc ugcuucugau caccaucauc uacuccuacu | 120 |
| uggagucguu ggugaaguuu ucauuccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug uggauauua auaagcgcgg uguggaggaa acugcagcug | 300 |
| agugccgaaa acuaggcguc acugcgcaug cguaugggu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuggauugg aaaggacauc agaaguaauu | 540 |
| acuuggaugu auauaggauc gaggacacuu uggacgaga cucugagauc acaaaagcac | 600 |
| uucuuccauc gaugauggag agaaaucaug gccacaucgu cacaguggcu ucagugugcg | 660 |
| gccacgaagg gauuccuuac cucauccccau auuguccag caaauuugcc gcuguuggcu | 720 |
| uucacagagg ucugacauca gaacuucagg ccuugggaaa aacugguauc aaaaccucau | 780 |
| gucucugccc aguuuuugug aauacgggu ucaccaaaaa uccaagcaca agauuauggc | 840 |
| cuguauugga gacagaugaa gucguaagaa gucugauaga uggaauacuu accaauaaga | 900 |
| aaaugauuuu uguccaucg uauaucaaua ucuuucugag acuacagaag uuucuuccug | 960 |
| aacgcgccuc agcgauuuua aaucguaugc agaauauuca auuugaagca gugguuggcc | 1020 |
| acaaaaucaa aaugaaauga auaaauaagc uccagccaga gauguaugca ugauaaugau | 1080 |
| augaauaguu ucgaaucaau gcugcaaagc uuuauuucac auuuuucag uccgauaauu | 1140 |
| auuaaaaaca uugguuuggc acuagcagca gucaaacgaa caagauuaau uaccugucuu | 1200 |
| ccuguuucuc aagaauauuu acguaguuuu cuuagggcu guuuuccuu ucaugccucu | 1260 |
| uaaaaacuuc ugugcuuaca uaaacauacu uaaaggguuu ucuuuaagau auuuuuauuuu | 1320 |
| uccauuuaaa gguggacaaa agcuacccc cuaaaaguaa auacaaagag aacuauuuua | 1380 |
| cacagggaag guuuaagacu guucaaguag cauuccaauc uguagccaug ccacagaaua | 1440 |
| ucaacaagaa cacagaauga gugcacagcu aagagaucaa guuucagcag gcagcuuuau | 1500 |
| cucaaccugg acauauuuua agauucagca uuugaaagau ucccuagcc ucuuccuuuu | 1560 |
| ucauuagccc aaaacggugc aacucuauuc uggacuuuau acuugauuc ugucuucgu | 1620 |
| auaacucuga agccaccaa aagguggaccc ucuauauuuc cucccuuuuu auagucuuau | 1680 |
| aagauacauu augaaaggug accgacucua uuuuaaaucu cagaauuuua aguucuagcc | 1740 |
| ccaugauaac cuuuuucuuu guaauuuaug cuuucauaua uccuuggucc cagagaguguu | 1800 |
| uagcaauuu uaggcucaaa aauuaaagcu aacacaggaa aaggaacugu acuggcuauu | 1860 |
| acauaagaaa caauggaccc aagagaagaa aaggaagaaa gaaaggguuuu uuggguuuug | 1920 |

| | |
|---|---|
| uuuuguuuug uuuuguuuuu uguuuuuuug agauggaguc ucacucuuuc gcccaggcug | 1980 |
| gagugcagug guaugaucuc agcucacugc aagcuccacc ucccgggcuu acgccauucu | 2040 |
| ccugccucag ccuccugagu agcugggacu acaggcgccc gccaccacac ccggcuaauu | 2100 |
| uuuuguauuu uuuguagaga cgggguuuca ccauguuagc caagaugguc ucgaucuccu | 2160 |
| gaccucguga uccaccugcc ucggccuccc aaagugcugg gauuacgggu gugagccacc | 2220 |
| gugcccagcc uuuuuuuuuu aauagaaaa aauaauccga cucccacuac aucaagacua | 2280 |
| aucuguuuu guguguuuuu cacauguauu auagaaugcu uuugcaugga cuauccucuu | 2340 |
| guuuuuauua aaacaaaug auuuuuuuaa aagucacaaa aacaauucac uaaaaauaaa | 2400 |
| uaugucauug ugcuuuaaaa aaauaaccuc uuguaguuau aaaauaaaac guuugacuuc | 2460 |
| uaaacucug | 2469 |

<210> SEQ ID NO 8
<211> LENGTH: 1715
<212> TYPE: RNA
<213> ORGANISM: homo sapien

<400> SEQUENCE: 8

| | |
|---|---|
| agacaguacc uccucccuag dacuacacaa ggacugaacc agaaggaaga ggacagagca | 60 |
| aagccaugaa caucauccua gaaauccuuc ugcuucugau caccaucauc uacuccuacu | 120 |
| uggagucguu ggugaaguuu ucauuccuc agaggagaaa aucuguggcu ggggagauug | 180 |
| uucucauuac uggagcuggg cauggaauag gcaggcagac uacuuaugaa uuugcaaaac | 240 |
| gacagagcau auugguucug uggauauua auaagcgcgg uguggaggaa acugcagcug | 300 |
| agugccgaaa acuaggcguc acugcgcaug cguaugugu agacugcagc aacagagaag | 360 |
| agaucuaucg cucucuaaau caggugaaga agaaguggg ugauguaaca aucgugguga | 420 |
| auaaugcugg gacaguauau ccagccgauc uucucagcac caaggaugaa gagauuacca | 480 |
| agacauuuga ggucaacauc cuaggacauu uuuggaucac aaaagcacuu cuccaucga | 540 |
| ugauggagag aaaucauggc cacaucguca caguggcuuc agugugcggc cacgaaggga | 600 |
| uccuuaccu cauccccauau uguuccagca aauuugccgc uguggcuuu cacagaagguc | 660 |
| ugacaucaga acuucaggcc uugggaaaaa cugguaucaa aaccucaugu cucugcccag | 720 |
| uuuuugaa uacgggguuc accaaaaauc caagcacaag auuauggccu guauggaga | 780 |
| cagaugaagu cguaagaagu cugauagaug gaauacuuac caauaagaaa augauuuuug | 840 |
| uuccaucgua uaucaauauc uuucugagac uacagaaguu aaguacagca cagaacaccc | 900 |
| aaauacuaaa acaccaauag agcuuuuuu uugcuuuuu uuuuuuuag acagagucuc | 960 |
| acucugucac ccuggcugga uugcgguggu ugcaguggca ugaucuuggc ucacugcaac | 1020 |
| cuccgccucc ugggguucaag caauucucau gccucagacc cccaaguaac ugggauuaua | 1080 |
| ggugugugcu gccacacuac acccagcuaa uuuuuguauu uuugauaga cagguuuc | 1140 |
| cccauguugg ccaggcugga cucgaacccc ugaccucaag uuauccuccu gucucggccu | 1200 |
| cccaaagugc ugggauuaca gucaugagcc accaugccug cccaauaga gcauuauua | 1260 |
| uggagcaucu uucaguugug aaaauuggca uggaaacucu ccaucccugg ggagaacagu | 1320 |
| uauuucccucu guuauuuccc uacccagucu auaaaaagag agugauucau uuucucuacc | 1380 |
| aaaucuacug ucucugcccaa aacuuugcug aagacuauuc uaacuaaagg aaacacaguu | 1440 |
| uaaaagaau gcaauauagu gaaguaguua auaauaaga cuccauuuuu aaaagucugc | 1500 |

```
uggaaguuug guugggauug cacugaaucu auagagcaau uggggaguau ugacauauca    1560
acaauauuga guuucuaau ccaagaacau aauaucuauu uuuaaaaucu cuucaaaau     1620 cuuuaaaucu uuaaauugua uuuguaguu uuuguguuu aagucuugca cauauuugu      1680 cagauuuauu ccaaaguauu cacggguuc uuuuu                                1715

<210> SEQ ID NO 9
<211> LENGTH: 1714
<212> TYPE: RNA
<213> ORGANISM: homo sapien

<400> SEQUENCE: 9
agacaguacc uccucccuag gacuacacaa ggacugaacc agaaggaaga ggacagagca     60
aagccaugaa caucauccua gaaauccuuc ugcuucugau caccaucauc uacuccuacu    120
uggagucguu ggugaaguuu ucauuccuc agaggagaaa aucuguggcu ggggagauug     180
uucucauuac uggagcuggg caugaauag gcaggcagac uacuuaugaa uuugcaaaac    240
gacagagcau auugguucug ugggauauua auaagcgcgg uggaggaa acugcagcug      300 agugccgaaa acuaggcguc acugcgcaug cguauguggu agacugcagc aacagagaag    360
agaucuaucg cucucuaaau caggugaaga agaaguggg ugauguaaca aucgugguga    420
auaaugcugg gacaguauau ccagccgauc uucucagcac caaggaugaa gagauuacca    480
agacauuuga ggucaacauc cuaggacauu uuuggaucac aaaagcacuu cuuccaucga    540
ugauggagag aaaucauggc cacaucguca cagugcuuc agugugcggc cacgaaggga    600
uuccuuaccu cauccauau uguuccagca aauugccgc uguuggcuuu cacagagguc     660
ugacaucaga acuucaggcc uugggaaaaa cugguaucaa aaccucaugu cucugcccag    720
uuuuugugaa uacgggguuc accaaaaauc caagcacaag auuaugggccu guaugggaga    780 cagaugaagu cguaagaagu cugauagaug gaauacuuac caauaagaaa augauuuug     840 uuccaucgua uaucaauauc uuucugagac uacagaagua aguacagcac agaacaccca    900
aauacuaaaa caccaauaga gcuuuuuuuu uugcuuuuuu uuuuuuaga cagagucuca    960 cucugucacc cuggcuggau gcggugguu gcaguggcau gaucuuggcu cacugcaacc   1020
uccgccuccu ggguucaagc aauucucaug ccucagaccc ccaaguaacu gggauuauag   1080
gugugugcug ccacacuaca cccagcuaau uuuguauuu uuugauagag acagguuucc   1140
ccauguuggc caggcuggac ucgaacuccu gaccucaagu uauccuccug ucucggccuc   1200
ccaaagugcu gggauuacag ucaugagcca ccaugccugg cccaauagag cuauuauuau   1260
ggagcaucuu ucaguuguga aauuggcau ggaaacucuc caucccuggg gagaacaguu   1320 auuccucug uuauuuuccu acccagucua uaaaaagaga gugauucauu ucucuacca    1380 aaucuacugu cucugcccaa acuuugcuga agacuauucu aacuaaagga aacacaguuu   1440
aaaaagaaug caauauagug aaguaguuaa uaauaaagac uccauuuuua aaagucugcu   1500
ggaaguuugg uugggauugc acugaaucua uagagcaauu gggaguauu gacauaucaa    1560 caauauugag uuucuaaauc caagaacaua auaucuauu uuaaaaucuu cucaaaauc    1620 uuuaaaucuu uaaauuguau uuuguaguuu ugguguuua agucuugcac auauuugc    1680 agauuuauuc caaaguauuu cacggguucu uuuu                                1714

<210> SEQ ID NO 10
<211> LENGTH: 2290
<212> TYPE: RNA
<213> ORGANISM: homo sapien
```

<400> SEQUENCE: 10

```
agacaguacc uccucccuag dacuacacaa ggacugaacc agaaggaaga ggacagagca      60
aagccaugaa caucauccua gaaauccuuc ugcuucugau caccaucauc uacuccuacu     120
uggagucguu ggugaaguuu ucauuccuc agaggagaaa aucguggcu ggggagauug      180
uucucauuac uggagcuggg cauggaauag gcaggcagac uacuuaugaa uuugcaaaac     240
gacagagcau auugguucug ugggauauua auaaggugaa gaaagaagug ggugauguaa     300
caaucguggu gaauaaugcu gggacaguau uccagccga ucuucucagc accaaggaug     360
aagagauuac caagacauuu gaggucaaca uccuaggaca uuuuuggauc acaaaagcac     420
uucuuccauc gaugauggag agaaaucaug gccacaucgu cacagugcgu ucagugugcg     480
gccacgaagg gauuccuuac cucaucccau auuguccag caaauuugcc gcuguuggcu     540
uucacagagg ucugacauca gaacuucagg ccuugggaaa aacugguauc aaaaccucau     600
gucucugccc aguuuugug aauacugggu ucaccaaaaa uccaagcaca agauuauggc     660
cuguauugga gacagaugaa gucguaagaa gucugauaga uggaauacuu accaauaaga     720
aaaugauuuu uguccaucg uauaucaaua ucuuucugag acuacagaag guuucuccu      780
gaacgcgccu cagcgauuuu aaaucguaug cagaauauuc aauugaagc aguggguggc     840
cacaaaauca aaaugaaaug aauaauaaag cccagccag agauguuagc augauaauga     900
uaugaauagu uucgaaucaa ugcugcaaag cuuuauuuca cauuuuuca guccugauaa     960
uauuaaaaac auugguuugg cacuagcagc agucaaacga acaagauuaa uuaccuugcu    1020
uccuguuucu caagaauauu uacguaguuu ucauagguc uguuuuccu uucaugccuc     1080
uuaaaaacuu cugugcuuac auaaacauac uuaaaaggguu ucuuaaga uauuuuauuu     1140
uuccauuuaa agguggacaa agcuaccuc ccuaaaagua aauacaaaga gaacuuauuu     1200
acacaagggaa gguuuaagac uguucaagua gcauuccaau cuguagccau gccacagaau     1260
aucaacaaga acacagaaug agugcacagc uaagagauca aguuucagca ggcagcuuua     1320
ucucaaaccug gacauauuuu aagauucagc auuugaaaga uucccuagc cucuuccuuu    1380
uucauuagcc caaaacggug caacucuauu cuggacuuuu uuacuugauu cugucuucug    1440
uauaacucug aaguccacca aaaguggacc cucuauauuu ccucccuuuu uauagucuua    1500
uaagauacau uaugaaggu gaccgacucu auuuaaauc ucagaauuu aaguucuagc      1560
cccaugauaa ccuuuuucuu uguaauuuau gcuuucauau auccuugguc ccagagaugu     1620
uuagacaauu uuaggcucaa aaauuaaagc uaacacagga aaaggaacug uacuggcuau    1680
uacauaagaa acaauggacc caagagaaga aaaggaagaa agaaagguuu uuugguuuuu     1740
guuuuguuuu guuuuguuuu uuguuuuuu gagauggagu cucacucuuu cgcccaggcu    1800
ggagugcagu gguaugaucu cagcucacug caagcuccac cucccggguu cacgccauuc     1860
uccugccuca gccucugagu agcugggac uacagggcgcc cgccaccaca cccggcuaau    1920
uuuuuguauu uuuuguagag acgggguuuc accauguuag ccaugauggu cucgaucucc    1980
ugaccucgug auccaccgc cucggccucc caaagugcug ggauuacggg ugugagccac    2040
cgugcccagc cuuuuuuuu uuaauagaaa aaauaaccg acuccacua caucaagacu     2100
aaucuuguuu ugugguuuu ucacauguau uauagaaugc uuuugcaugg acuauccucu     2160
uguuuuauu aaaacaaau gauuuuuua aagucacaa aaacaauuca cuaaaaauaa     2220
auaugucauu gugcuuuaaa aaauuaaccu cuuguaguua uaaaauaaaa cguuugacuu     2280
```

| | |
|---|---|
| cuaaacucug | 2290 |

<210> SEQ ID NO 11
<211> LENGTH: 2470
<212> TYPE: RNA
<213> ORGANISM: homo sapien

<400> SEQUENCE: 11

| | | | | | |
|---|---|---|---|---|---|
| agacaguacc | uccucccuag | gacuacacaa | ggacugaacc | agaaggaaga | ggacagagca | 60 |
| aagccaugaa | caucauccua | gaaauccuuc | ugcuucugau | caccaucauc | uacuccuacu | 120 |
| uggagucguu | ggugaaguuu | uucauuccuc | agaggagaaa | aucguggcu | ggggagauug | 180 |
| uucucauuac | uggagcuggg | cauggaauag | gcaggcagac | uacuuaugaa | uuugcaaaac | 240 |
| gacagagcau | auugguucug | ugggauauua | uaagcgcgg | uggaggaa | acugcagcug | 300 |
| agugccgaaa | acuaggcguc | acugcgcaug | cguauguggu | agacugcagc | aacagagaag | 360 |
| agaucuaucg | cucucuaaau | caggugaaga | aagaaguggg | ugauguaaca | aucgugguga | 420 |
| auaaugcugg | gacaguauau | ccagccgauc | uucucagcac | caaggaugaa | gagauuacca | 480 |
| agacauuuga | ggucaacauc | cuaggacauu | uuuggaaugg | aaaggacauc | agaaguaauu | 540 |
| acuuggaugu | auauaggauc | gaggacacuu | uggacgaga | cucugagauc | acaaaagcac | 600 |
| uucuuccauc | gaugauggag | agaaaucaug | gccacaucgu | cacaguggcu | ucagugugcg | 660 |
| gccacgaagg | gauccuuuac | cucaucccau | auugguccag | caaauuugcc | gcuguuggcu | 720 |
| uucacagagg | ucugacauca | gaacuucagg | ccuugggaaa | aacgguauc | aaaaccucau | 780 |
| gucucugccc | aguuuugug | aauacuggu | ucaccaaaaa | uccaagcaca | agauuauggc | 840 |
| cuguauugga | gacagaugaa | gucguaagaa | gucugauaga | uggaauacuu | accaauaaga | 900 |
| aaaugauuuu | uguccaucg | uauaucaaua | ucuuucugag | acuacagaag | guuucuuccu | 960 |
| gaacgcgccu | cagcgauuuu | aaaucguaug | cagaauauuc | aauuugaagc | aguggouggc | 1020 |
| cacaaaauca | aaaugaaaug | aauaaauaag | cuccagccag | agauguaugc | augauaauga | 1080 |
| uaugaauagu | uucgaaucaa | ugcugcaaag | cuuuauuuca | cauuuuca | guccugauaa | 1140 |
| uauuaaaaac | auugguuugg | cacuagcagc | agucaaacga | acaagauuaa | uuaccugucu | 1200 |
| uccuguuucu | caagaauauu | uacguaguu | ucauagguc | uguuuuccu | uucaugccuc | 1260 |
| uuaaaaacuu | cugugcuuac | auaaacauac | uuaaaagguu | ucuuaaga | uauuuauuu | 1320 |
| uuccauuuaa | aggggacaa | aagcuaccuc | ccuaaaagua | aauacaaaga | gaacuuauuu | 1380 |
| acacagggaa | gguuuaagac | uguucaagua | gcauuccaau | cuguagccau | gccacagaau | 1440 |
| aucaacaaga | acacagaaug | agugcacagc | uaagagauca | aguucagca | ggcagcuuua | 1500 |
| ucucaaccug | gacauauuuu | aagauucagc | auuugaaaga | uucccuagc | cucuccuuu | 1560 |
| uucauuagcc | caaaacggug | caacucuauu | cuggacuuua | uuacuugauu | cugucuucug | 1620 |
| uauaacucug | aaguccacca | aaaguggacc | cucuauauuu | ccucccuuuu | uauagcuuua | 1680 |
| uaagauacau | uauugaaaggu | gaccgacucu | auuuuaaauc | ucagaauuuu | aaguucuagc | 1740 |
| cccaugauaa | ccuuuuucuu | uguaauuau | gcuuucauau | auccuugguc | ccagagaugu | 1800 |
| uuagacaauu | uuaggcucaa | aaauuaaagc | uaacacagga | aaaggaacug | uacugguau | 1860 |
| uacauaagaa | acaauggacc | caagagaaga | aaaggaagaa | agaaagguuu | uugguuuuu | 1920 |
| guuuuguuuu | guuuuguuuu | uuguuuuuu | gagauggagu | cucacucuuu | cgcccaggcu | 1980 |
| ggagugcagu | gguaugaucu | cagcucacug | caagcuccac | cucccggguu | cacgccauuc | 2040 |
| uccugccuca | gccuccugag | uagcugggac | uacaggcgcc | cgccaccaca | cccggcuaau | 2100 |

-continued

| | |
|---|---|
| uuuuuguauu uuuugugagag acggggguuuc accauguuag ccaagauggu cucgaucucc | 2160 |
| ugaccucgug auccaccugc cucggccucc caaagugcgg ggauuacggg ugugagccac | 2220 |
| cgugcccagc cuuuuuuuu uuaauagaaa aaauaauccg acucccacua caucaagacu | 2280 |
| aaucuuguuu ugugguuu ucacauguau uauagaaugc uuuugcaugg acuauccucu | 2340 |
| uguuuuuauu aaaacaaau gauuuuuua aaagucacaa aaacaauuca cuaaaauaa | 2400 |
| auaugucauu gugcuuuaaa aaauaaccu cuguaguua uaaauaaaa cguuugacuu | 2460 |
| cuaaacucug | 2470 |

<210> SEQ ID NO 12
<211> LENGTH: 900
<212> TYPE: DNA
<213> ORGANISM: homo sapien

<400> SEQUENCE: 12

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucguggga uauuaauaag cgcggugugg aggaaacugc agcugagugc | 240 |
| cgaaaacuag gcgucacugc gcaugcguau guggagacu gcagcaacag agaagagauc | 300 |
| uaucgcucuc uaaaucaggu gaagaaagaa gugggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aucacaaaag cacuucuucc aucgaugaug | 480 |
| gagagaaauc auggccacau cgucacagug gcuucagugu gcggccacga agggauuccu | 540 |
| uaccucaucc cauauuguuc cagcaaauuu gccgcguuug gcuuuacag aggucugaca | 600 |
| ucagaacuuc aggccuuggg aaaaacuggu aucaaaaccu caugucucug cccaguuuuu | 660 |
| gugaauacug gguucaccaa aaauccaagc acaagauuau ggccuguauu ggagacagau | 720 |
| gaagucguaa aagcucugau agauggaaua cuuaccaaua agaaaugau uuuugucca | 780 |
| ucguauauca auaucuuucu gagacuacag aaguuucuuc cugaacgcgc cucagcgauu | 840 |
| uuaaaucgua ugcagaauau ucaauugaa gcaguggцug ccacaaaaau caaaaugaaa | 900 |

<210> SEQ ID NO 13
<211> LENGTH: 792
<212> TYPE: DNA
<213> ORGANISM: homo sapien

<400> SEQUENCE: 13

| | |
|---|---|
| augaacauca uccuagaaau ccuucugcuu cugaucacca ucaucuacuc cuacuuggag | 60 |
| ucguugguga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucguggga uauuaauaag gugaagaaag aagugggauga guaacaauc | 240 |
| guggugaaua augcugggac aguauaucca gccgaucuuc ucagcaccaa ggaugaagag | 300 |
| auuaccaaga cauuugaggu caacauccua ggacauuuuu ggaucacaaa agcacuucuu | 360 |
| ccaucgauga uggagagaaa ucauggccac aucgucacag uggcuucagu gugcggccac | 420 |
| gaagggauuc cuuaccucau cccauauugu uccagcaaau uugccgcguu uggcuuuac | 480 |
| agaggucuga caucagaacu ucaggccuug ggaaaaacug guaucaaaac cucaugucuc | 540 |

| | |
|---|---|
| ugcccaguuu uugugaauac uggguucacc aaaaauccaa gcacaagauu auggccugua | 600 |
| uuggagacag augaagucgu aagaagucug auagauggaa acuuaccaa uaagaaaaug | 660 |
| auuuuuguuc caucguauau caauaucuuu cugagacuac agaaguuucu uccugaacgc | 720 |
| gcccucagcga uuuuaaaucg uaugcagaau auucaauuug aagcaguggu uggccacaaa | 780 |
| aucaaaauga aa | 792 |

<210> SEQ ID NO 14
<211> LENGTH: 783
<212> TYPE: DNA
<213> ORGANISM: homo sapien

<400> SEQUENCE: 14

| | |
|---|---|
| augaacauca uccuagaaau ccuucugcuu cugaucacca ucaucuacuc cuacuuggag | 60 |
| ucguuggnga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau gugguagacu gcagcaacag agaagagauc | 300 |
| uaucgcucuc uaaaucaggu gaagaaagaa ggggugaug uaacaaucgu ggugaauaau | 360 |
| gcugggacag auauuccagc cgaucuucuc agcaccaagg augaagagau uaccaagaca | 420 |
| uuugagguca cauccuagg acauuuuugg aucacaaaag cacuucuucc aucgaugaug | 480 |
| gagagaaauc auggccacau cgucacagug gcuucagugu gcggccacga agggauuccu | 540 |
| uaccucauc cauauuguuc cagcaaauuu gccgcguuug gcuuucacag aggucugaca | 600 |
| ucagaacuuc aggccuuggg aaaaacuggu aucaaaaccu caugucucug cccaguuuuu | 660 |
| gugaauacg gguucaccaa aaauccaagc acaagguuuc uuccugaacg cgccucagcg | 720 |
| auuuuaaauc guaugcagaa uauucaauuu gaagcagugg uuggccacaa aaucaaaaug | 780 |
| aaa | 783 |

<210> SEQ ID NO 15
<211> LENGTH: 822
<212> TYPE: DNA
<213> ORGANISM: homo sapien

<400> SEQUENCE: 15

| | |
|---|---|
| augaacauca uccuagaaau ccuucugcuu cugaucacca ucaucuacuc cuacuuggag | 60 |
| ucguuggnga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucuguggga uauuaauaag cgcggugugg aggaaacugc agcugagugc | 240 |
| cgaaaacuag gcgucacugc gcaugcguau gugguagacu gcagcaacag agaagagauc | 300 |
| uaucgcucuc uaaaucaggu gaagaaagaa ggggugaug uaacaaucgu ggugaauaau | 360 |
| gcugggacag auauuccagc cgaucuucuc agcaccaagg augaagagau uaccaagaca | 420 |
| uuugagguca cauccuagg acauuuuugg aucacaaaag cacuucuucc aucgaugaug | 480 |
| gagagaaauc auggccacau cgucacagug gcuucagugu gcggccacga agggauuccu | 540 |
| uaccucauc cauauuguuc cagcaaauuu gccgcguuug gcuuucacag aggucugaca | 600 |
| ucagaacuuc aggccuuggg aaaaacuggu aucaaaaccu caugucucug cccaguuuuu | 660 |
| gugaauacg gguucaccaa aaauccaagc acaagauuau ggccuguauu ggagacagau | 720 |
| gaagucguaa gaagucugau agauggaaua cuuaccaaua agaaaaugau uuuuguucca | 780 |

```
ucguauauca auaucuuucu gagacuacag aagguuucuu cc              822
```

<210> SEQ ID NO 16
<211> LENGTH: 972
<212> TYPE: DNA
<213> ORGANISM: homo sapien

<400> SEQUENCE: 16

```
augaacauca uccuagaaau ccuucugcuu cugaucacca ucaucuacuc cuacuuggag    60
ucguuggmuga aguuuucau uccucagagg agaaaaucug uggcugggga gauuguucuc   120
auuacuggag cugggcaugg aauaggcagg cagacuacuu augaauuugc aaaacgacag   180
agcauauugg uucguggga auuaauaag cgcggugugg aggaaacugc agcugagugc    240
cgaaaacuag gcgucacugc gcaugcguau gugguagacu gcagcaacag agaagagauc   300
uaucgcucuc uaaaucaggu gaagaaagaa gugggugaug uaacaaucgu ggugaauaau   360
gcugggacag uauauccagc cgaucuucuc agcaccaagg augaagagau uaccaagaca   420
uuugagguca acauccuagg acauuuuugg aauggaaagg acaucagaag uaauuacuug   480
gauguauaua ggaucgagga cacuuuugga cgagacucug agaucacaaa agcacuucuu   540
ccaucgauga uggagagaaa ucauggccac aucgucacag uggcuucagu gucggccac   600
gaagggauuc cuaccucau cccauauugu ccagcaaauu ugccgcugu ggcuucac     660
agagucuga caucagaacu ucaggccuug ggaaaaacug guaucaaaac cucaugucuc   720
ugcccaguuu uugugaauac ugggnuucacc aaaaauccaa gcacaagauu auggcccugua   780
uuggagacag augaagucgu aagaagucug auagauggaa uacuuaccaa uaagaaaaug   840
auuuuuguuc caucguauau caauaucuuu cugagacuac agaaguuucu uccgaacgc   900
gccucagcga uuuuaaaucg uaugcagaau auucaauuug aagcaguggu uggccacaaa   960
aucaaaauga aa                                                      972
```

<210> SEQ ID NO 17
<211> LENGTH: 852
<212> TYPE: DNA
<213> ORGANISM: homo sapien

<400> SEQUENCE: 17

```
augaacauca uccuagaaau ccuucugcuu cugaucacca ucaucuacuc cuacuuggag    60
ucguuggmuga aguuuucau uccucagagg agaaaaucug uggcugggga gauuguucuc   120
auuacuggag cugggcaugg aauaggcagg cagacuacuu augaauuugc aaaacgacag   180
agcauauugg uucguggga auuaauaag cgcggugugg aggaaacugc agcugagugc    240
cgaaaacuag gcgucacugc gcaugcguau gugguagacu gcagcaacag agaagagauc   300
uaucgcucuc uaaaucaggu gaagaaagaa gugggugaug uaacaaucgu ggugaauaau   360
gcugggacag uauauccagc cgaucuucuc agcaccaagg augaagagau uaccaagaca   420
uuugagguca acauccuagg acauuuuugg aucacaaaag cacuucuucc aucgaugaug   480
gagagaaauc auggccacau cgucacagug gcuucagugu gcggccacga agggauuccu   540
uaccucaucc cauauuguuc agcaaauuu gccgcguuug gcuucacag aggucugaca   600
ucagaacuuc aggccuuggg aaaaacuggu aucaaaaccu caugucucug cccaguuuuu   660
gugaauacug gguucaccaa aaauccaagc acaagauuau ggccuguauu ggagacagau   720
gaagucguaa gaagucugau agauggaaua cuuaccaaua agaaaaugau uuuuguucca   780
```

| | |
|---|---|
| ucguauauca auaucuuucu gagacuacag aaguuaagua cagcacagaa cacccaaaua | 840 |
| cuaaaacacc aa | 852 |

<210> SEQ ID NO 18
<211> LENGTH: 813
<212> TYPE: DNA
<213> ORGANISM: homo sapien

<400> SEQUENCE: 18

| | |
|---|---|
| augaacauca uccuagaaau ccuucugcuu cugaucacca ucaucuacuc cuacuuggag | 60 |
| ucguuggüga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucguggga uauuaauaag cgcggugugg aggaaacugc agcgagugc | 240 |
| cgaaaacuag gcgucacugc gcaugcguau guguagacu gcagcaacag agaagagauc | 300 |
| uaucgcucuc uaaaucaggu gaagaaagaa gugggugaug uaacaaucgu ggugaauaau | 360 |
| gcugggacag uauauccagc cgaucuucuc agcaccaagg augaagagau uaccaagaca | 420 |
| uuugaggüca acauccuagg acauuuuugg aucacaaaag cacuucuccc aucgaugaug | 480 |
| gagagaaauc auggccacau cgucacagüg gcuucagügu gcggcacga agggauuccu | 540 |
| uaccucaucc cauauuguuc cagcaaauuu gccgcuguug gcuuuacag aggucugaca | 600 |
| ucagaacuuc aggccuuggg aaaaacuggu aucaaaaccu caugcucug cccaguuuu | 660 |
| gugaauacug gguucaccaa aaauccaagc acaagauuau ggccuguauu ggagacagau | 720 |
| gaagucguaa gaagcugau agauggaaua cuuaccaaua agaaaaugau uuuguucca | 780 |
| ucguauauca auaucuuucu gagacuacag aag | 813 |

<210> SEQ ID NO 19
<211> LENGTH: 714
<212> TYPE: DNA
<213> ORGANISM: homo sapien

<400> SEQUENCE: 19

| | |
|---|---|
| augaacauca uccuagaaau ccuucugcuu cugaucacca ucaucuacuc cuacuuggag | 60 |
| ucguuggüga aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucguggga uauuaauaag gugaagaaag aagugggüga guaacaauc | 240 |
| guggugaaua augcugggac aguauaucca gccgaucuuc ucagcaccaa ggaugaagag | 300 |
| auuaccaaga cauuugaggu caacauccua ggacauuuuu ggaucacaaa agcacuucuu | 360 |
| ccaucgauga uggagagaaa ucauggccac aucgucacag uggcuucagu gugcggccac | 420 |
| gaagggauuc cuuaccucau cccauauugu ccagcaaau uugccgcugu uggcuuucac | 480 |
| agaggucuga caucagaacu ucaggccuug ggaaaaacug guaucaaaac cucaugcucu | 540 |
| ugcccaguuu uugugaauac uggguucacc aaaaauccaa gcacaagauu auggccugua | 600 |
| uuggagacag augaagucgu aagaagcugu auagauggaa acuuaccaa uaagaaaaug | 660 |
| auuuuuguuc caucguauau caauaucuuu cugagacuac agaagguuuc uucc | 714 |

<210> SEQ ID NO 20
<211> LENGTH: 894
<212> TYPE: DNA
<213> ORGANISM: homo sapien

<400> SEQUENCE: 20

-continued

| | | |
|---|---|---|
| augaacauca uccuagaaau ccuucugcuu cugaucacca ucaucuacuc cuacuuggag | 60 |
| ucguuggugu aguuuuucau uccucagagg agaaaaucug uggcugggga gauuguucuc | 120 |
| auuacuggag cugggcaugg aauaggcagg cagacuacuu augaauuugc aaaacgacag | 180 |
| agcauauugg uucguguggu auuaauaag cgcggugugg aggaaacugc agcugagugc | 240 |
| cgaaaacuag gcgucacugc gcaugcguau ugguagacu gcagcaacag agaagagauc | 300 |
| uaucgcucuc uaaaucaggu gaagaaagaa ggggugaug uaacaaucgu ggugaauaau | 360 |
| gcugggacag uauauccagc cgaucuucuc agcaccaagg augaagagau uaccaagaca | 420 |
| uuugagguca acauccuagg acauuuuugg aauggaaagg acaucagaag uaauuacuug | 480 |
| gauguauaua ggaucgagga cacuuuugga cgagacucug agaucacaaa agcacuucuu | 540 |
| ccaucgauga uggagagaaa ucauggccac aucgucacag uggcuucagu gugcggccac | 600 |
| gaagggauuc cuuaccucau cccauauugu uccagcaaau uugccgcugu uggcuuucac | 660 |
| agaggucuga caucgaacu ucaggccuug ggaaaaacug guaucaaaac cucaugcucu | 720 |
| ugcccaguuu uugugaauac uggguucacc aaaaauccaa gcacaagauu auggccugua | 780 |
| uuggagacag augaagucgu aagaagucug auagauggaa uacuuaccaa uaagaaaaug | 840 |
| auuuuuguuc caucguauau caauaucuuu cugagacuac agaagguuuc uucc | 894 |

<210> SEQ ID NO 21
<211> LENGTH: 2397
<212> TYPE: DNA
<213> ORGANISM: homo sapien

<400> SEQUENCE: 21

| | | |
|---|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta taagcgcgg tgtggaggaa actgcagctg | 300 |
| agtgccgaaa actaggcgtc actgcgcatg cgtatgtggt agactgcagc aacagagaag | 360 |
| agatctatcg ctctctaaat caggtgaaga agaagtggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggatcac aaaagcactt cttccatcga | 540 |
| tgatggagag aaatcatggc cacatcgtca gtggcttca gtgtgcggc cacgaaggga | 600 |
| ttccttacct catcccatat tgttccagca aatttgccgc tgttggcttt cacagaggtc | 660 |
| tgacatcaga acttcaggcc ttgggaaaaa ctggtatcaa acctcatgt ctctgcccag | 720 |
| tttttgtgaa tactgggttc accaaaaatc caagcacaag attatggcct gtattggaga | 780 |
| cagatgaagt cgtaagaagt ctgatagatg aatacttac caataagaaa atgatttttg | 840 |
| ttccatcgta tatcaatatc tttctgagac tacagaagtt tcttcctgaa cgcgcctcag | 900 |
| cgattttaaa tcgtatgcag aatattcaat ttgaagcagt ggttggccac aaaatcaaaa | 960 |
| tgaaatgaat aaataagctc cagccagaga tgtatgcatg ataatgatat gaatagtttc | 1020 |
| gaatcaatgc tgcaaagctt tatttcacat tttttcagtc ctgataatat taaaaacatt | 1080 |
| ggtttggcac tagcagcagt caaacgaaca agattaatta cctgtcttcc tgtttctcaa | 1140 |
| gaatatttac gtagtttttc ataggtctgt ttttcctttc atgcctctta aaaacttctg | 1200 |

-continued

| | |
|---|---|
| tgcttacata aacatactta aaaggttttc tttaagatat tttattttc catttaaagg | 1260 |
| tggacaaaag ctacctccct aaaagtaaat acaaagagaa cttatttaca cagggaaggt | 1320 |
| ttaagactgt tcaagtagca ttccaatctg tagccatgcc acagaatatc aacaagaaca | 1380 |
| cagaatgagt gcacagctaa gagatcaagt ttcagcaggc agctttatct caacctggac | 1440 |
| atattttaag attcagcatt tgaaagattt ccctagcctc ttcctttttc attagcccaa | 1500 |
| aacggtgcaa ctctattctg gactttatta cttgattctg tcttctgtat aactctgaag | 1560 |
| tccaccaaaa gtggaccctc tatatttcct ccctttttat agtcttataa gatacattat | 1620 |
| gaaaggtgac cgactctatt ttaaatctca gaattttaag ttctagcccc atgataacct | 1680 |
| ttttctttgt aatttatgct ttcatatatc cttggtccca gagatgttta gacaatttta | 1740 |
| ggctcaaaaa ttaaagctaa cacaggaaaa ggaactgtac tggctattac ataagaaaca | 1800 |
| atggacccaa gagaagaaaa ggaagaaaga aaggtttttt ggttttgtt ttgttttgtt | 1860 |
| ttgtttttg tttttttgag atggagtctc actctttcgc ccaggctgga gtgcagtggt | 1920 |
| atgatctcag ctcactgcaa gctccactc ccgggttcac gccattctcc tgcctcagcc | 1980 |
| tcctgagtag ctgggactac aggcgcccgc caccacaccc ggctaatttt ttgtattttt | 2040 |
| tgtagagacg gggtttcacc atgttagcca agatggtctc gatctcctga cctcgtgatc | 2100 |
| cacctgcctc ggcctcccaa agtgctggga ttacgggtgt gagccaccgt gcccagcctt | 2160 |
| ttttttttta atagaaaaaa taatccgact cccactacat caagactaat cttgttttgt | 2220 |
| gtgttttca catgtattat agaatgcttt tgcatggact atcctcttgt ttttattaaa | 2280 |
| aacaaatgat tttttaaaa gtcacaaaaa caattcacta aaaataaata tgtcattgtg | 2340 |
| ctttaaaaaa ataacctctt gtagttataa aataaaacgt ttgacttcta aactctg | 2397 |

<210> SEQ ID NO 22
<211> LENGTH: 2289
<212> TYPE: DNA
<213> ORGANISM: homo sapien

<400> SEQUENCE: 22

| | |
|---|---|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catggaatag gcaggcagac tacttatgaa tttgcaaaac | 240 |
| gacagagcat attggttctg tgggatatta ataaggtgaa gaagaagtg ggtgatgtaa | 300 |
| caatcgtggt gaataatgct gggacagtat atccagccga tcttctcagc accaaggatg | 360 |
| aagagattac caagcatttt gaggtcaaca tcctaggaca ttttggatc acaaaagcac | 420 |
| ttcttccatc gatgatggag agaaatcatg gccacatcgt cacagtggct tcagtgtgcg | 480 |
| gccacgaagg gattccttac ctcatcccat attgttccag caaatttgcc gctgttggct | 540 |
| tcacagagg tctgacatca gaacttcagg ccttgggaaa aactggtatc aaaacctcat | 600 |
| gtctctgccc agttttttgtg aatactgggt tcaccaaaaa tccaagcaca agattatggc | 660 |
| ctgtattgga gacagatgaa gtcgtaagaa gtctgataga tggaatactt accaataaga | 720 |
| aaatgatttt tgttccatcg tatatcaata tctttctgag actacagaag tttcttcctg | 780 |
| aacgcgcctc agcgatttta aatcgtatgc agaatattca atttgaagca gtggttggcc | 840 |
| acaaaatcaa aatgaaatga ataaataagc tccagccaga gatgtatgca tgataatgat | 900 |
| atgaatagtt tcgaatcaat gctgcaaagc tttatttcac attttttcag tcctgataat | 960 |

| | |
|---|---:|
| attaaaaaca ttggtttggc actagcagca gtcaaacgaa caagattaat tacctgtctt | 1020 |
| cctgtttctc aagaatattt acgtagtttt tcataggtct gttttccctt tcatgcctct | 1080 |
| taaaaacttc tgtgcttaca taaacatact taaaaggttt tctttaagat atttttatttt | 1140 |
| tccatttaaa ggtggacaaa agctacctcc ctaaaagtaa atacaaagag aacttattta | 1200 |
| cacagggaag gtttaagact gttcaagtag cattccaatc tgtagccatg ccacagaata | 1260 |
| tcaacaagaa cacagaatga gtgcacagct aagagatcaa gtttcagcag gcagctttat | 1320 |
| ctcaacctgg acatatttta agattcagca tttgaaagat ttccctagcc tcttccttttt | 1380 |
| tcattagccc aaaacggtgc aactctattc tggactttat tacttgattc tgtcttctgt | 1440 |
| ataactctga agtccaccaa aagtggaccc tctatatttc ctcccttttt atagtcttat | 1500 |
| aagatacatt atgaaaggtg accgactcta ttttaaatct cagaattttta agttctagcc | 1560 |
| ccatgataac cttttttcttt gtaatttatg ctttcatata tccttggtcc cagagatgtt | 1620 |
| tagacaattt taggctcaaa aattaaagct aacacaggaa aaggaactgt actggctatt | 1680 |
| acataagaaa caatggaccc aagagaagaa aaggaagaaa gaaaggtttt ttggttttttg | 1740 |
| ttttgttttg ttttgttttt tgttttttttg agatggagtc tcactctttc gcccaggctg | 1800 |
| gagtgcagtg gtatgatctc agctcactgc aagctccacc tcccgggttc acgccattct | 1860 |
| cctgcctcag cctcctgagt agctgggact acaggcgccc gccaccacac ccggctaatt | 1920 |
| ttttgtatttt tttgtagaga cggggtttca ccatgttagc caagatggtc tcgatctcct | 1980 |
| gacctcgtga tccacctgcc tcggcctccc aaagtgctgg gattacgggt gtgagccacc | 2040 |
| gtgcccagcc ttttttttttt taatagaaaa aataatccga ctcccactac atcaagacta | 2100 |
| atcttgttttt gtgtgttttt cacatgtatt atagaatgct tttgcatgga ctatcctctt | 2160 |
| gtttttatta aaaacaaatg atttttttaa aagtcacaaa aacaattcac taaaaataaa | 2220 |
| tatgtcattg tgctttaaaa aaataaccctc ttgtagttat aaaataaaac gtttgacttc | 2280 |
| taaactctg | 2289 |

<210> SEQ ID NO 23
<211> LENGTH: 2280
<212> TYPE: DNA
<213> ORGANISM: homo sapien

<400> SEQUENCE: 23

| | |
|---|---:|
| agacagtacc tcctccctag gactacacaa ggactgaacc agaaggaaga ggacagagca | 60 |
| aagccatgaa catcatccta gaaatccttc tgcttctgat caccatcatc tactcctact | 120 |
| tggagtcgtt ggtgaagttt ttcattcctc agaggagaaa atctgtggct ggggagattg | 180 |
| ttctcattac tggagctggg catgaataag gcagcagac tacttatgaa tttgcaaaac | 240 |
| gacagagcat attggttctg tgggatatta ataagcgcgg tgtggaggaa actgcagctg | 300 |
| agtgccgaaa actaggcgtc actgcgcatg cgtatgtggt agactgcagc aacagagaag | 360 |
| agatctatcg ctctctaaat caggtgaaga agaagtgggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggatcac aaaaagcactt cttccatcga | 540 |
| tgatggagag aaatcatggc cacatcgtca cagtggcttc agtgtgcggc cacgaaggga | 600 |
| ttccttacct catcccatat tgttccagca aatttgccgc tgttggcttt cacagaggtc | 660 |
| tgacatcaga acttcaggcc ttgggaaaaa ctggtatcaa aacctcatgt ctctgcccag | 720 |

| | | |
|---|---|---|
| ttttttgtgaa tactgggttc accaaaaatc caagcacaag gtttcttcct gaacgcgcct | 780 | |
| cagcgatttt aaatcgtatg cagaatattc aatttgaagc agtggttggc cacaaaatca | 840 | |
| aaatgaaatg aataaataag ctccagccag agatgtatgc atgataatga tatgaatagt | 900 | |
| ttcgaatcaa tgctgcaaag ctttatttca catttttttca gtcctgataa tattaaaaac | 960 | |
| attggtttgg cactagcagc agtcaaacga acaagattaa ttacctgtct tcctgtttct | 1020 | |
| caagaatatt tacgtagttt ttcataggtc tgttttttcct ttcatgcctc ttaaaaactt | 1080 | |
| ctgtgcttac ataaacatac ttaaaaggtt ttctttaaga tattttatttt ttccatttaa | 1140 | |
| aggtggacaa aagctacctc cctaaaagta aatacaaaga gaacttattt acacagggaa | 1200 | |
| ggtttaagac tgttcaagta gcattccaat ctgtagccat gccacagaat atcaacaaga | 1260 | |
| acacagaatg agtgcacagc taagagatca agtttcagca ggcagcttta tctcaacctg | 1320 | |
| gacatatttt aagattcagc atttgaaaga tttccctagc ctcttccttt ttcattagcc | 1380 | |
| caaaacggtg caactctatt ctggacttta ttacttgatt ctgtcttctg tataactctg | 1440 | |
| aagtccacca aaagtggacc ctctatattt cctcccttttt tatagtctta taagatacat | 1500 | |
| tatgaaaggt gaccgactct attttaaatc tcagaatttt aagttctagc cccatgataa | 1560 | |
| cctttttctt tgtaatttat gctttcatat atccttggtc ccagagatgt ttagacaatt | 1620 | |
| ttaggctcaa aaattaaagc taacacagga aaaggaactg tactggctat acataagaa | 1680 | |
| acaatggacc caagagaaga aaaggaagaa agaaaggttt tttggttttt gttttgtttt | 1740 | |
| gttttgttttt tgtttttttt gagatggagt ctcactcttt cgcccaggct ggagtgcagt | 1800 | |
| ggtatgatct cagctcactg caagctccac ctcccgggtt cacgccattc tcctgcctca | 1860 | |
| gcctcctgag tagctgggac tacaggcgcc cgccaccaca cccggctaat ttttttgtatt | 1920 | |
| ttttgtagag acggggtttc accatgttag ccaagatggt ctcgatctcc tgacctcgtg | 1980 | |
| atccacctgc ctcggcctcc caaagtgctg ggattacggg tgtgagccac cgtgcccagc | 2040 | |
| ctttttttttt ttaatagaaa aaataatccg actcccacta catcaagact aatcttgttt | 2100 | |
| tgtgtgtttt tcacatgtat tatagaatgc ttttgcatgg actatcctct tgttttttatt | 2160 | |
| aaaaacaaat gattttttta aaagtcacaa aaacaattca ctaaaaataa atatgtcatt | 2220 | |
| gtgctttaaa aaaataacct cttgtagtta taaaataaaa cgtttgactt ctaaactctg | 2280 | |

<210> SEQ ID NO 24
<211> LENGTH: 2398
<212> TYPE: DNA
<213> ORGANISM: homo sapien

<400> SEQUENCE: 24

| | | |
|---|---|---|
| agacagtacc tcctccctag gactacacaa ggactgaacc agaaggaaga ggacagagca | 60 | |
| aagccatgaa catcatccta gaaatccttc tgcttctgat caccatcatc tactcctact | 120 | |
| tggagtcgtt ggtgaagttt ttcattcctc agaggagaaa atctgtggct ggggagattg | 180 | |
| ttctcattac tggagctggg catggaatag gcaggcagac tacttatgaa tttgcaaaac | 240 | |
| gacagagcat attggttctg tgggatatta ataagcgcgg tgtggaggaa actgcagctg | 300 | |
| agtgccgaaa actaggcgtc actgcgcatg cgtatgtggt agactgcagc aacagagaag | 360 | |
| agatctatcg ctctctaaat caggtgaaga agaagtgggg tgatgtaaca atcgtggtga | 420 | |
| ataatgctgg gacagtatat ccagccgatc ttctcagcac caaggatgaa gagattacca | 480 | |
| agacatttga ggtcaacatc ctaggacatt tttggatcac aaaaagcactt cttccatcga | 540 | |
| tgatggagag aaatcatggc cacatcgtca cagtggcttc agtgtgcggc cacgaaggga | 600 | |

```
ttccttacct catcccatat tgttccagca aatttgccgc tgttggcttt cacagaggtc    660
tgacatcaga acttcaggcc ttgggaaaaa ctggtatcaa aacctcatgt ctctgcccag    720
tttttgtgaa tactgggttc accaaaaatc caagcacaag attatggcct gtattggaga    780
cagatgaagt cgtaagaagt ctgatagatg aatacttac caataagaaa atgattttg    840 ttccatcgta tatcaatatc tttctgagac tacagaaggt tcttcctga acgcgcctca    900 gcgattttaa atcgtatgca gaatattcaa tttgaagcag tggttggcca caaaatcaaa    960
atgaaatgaa taaataagct ccagccagag atgtatgcat gataatgata tgaatagttt   1020
cgaatcaatg ctgcaaagct ttatttcaca ttttttcagt cctgataata ttaaaaacat   1080
tggtttggca ctagcagcag tcaaacgaac aagattaatt acctgtcttc ctgtttctca   1140
agaatattta cgtagttttt cataggtctg ttttccttt catgcctctt aaaaacttct   1200
gtgcttacat aaacatactt aaaggttttt ctttaagata ttttattttt ccatttaaag   1260
gtggacaaaa gctacctccc taaaagtaaa tacaagagag acttatttac acagggaagg   1320
tttaagactg ttcaagtagc attccaatct gtagccatgc cacagaatat aacaagaac    1380 acagaatgag tgcacagcta agagatcaag tttcagcagg cagctttatc tcaacctgga   1440
catattttaa gattcagcat ttgaaagatt tccctagcct cttccttttt cattagccca   1500
aaacggtgca actctattct ggactttatt acttgattct gtcttctgta taactctgaa   1560
gtccaccaaa agtggaccct ctatatttcc tcccttttta tagtcttata agatacatta   1620
tgaaaggtga ccgactctat tttaaatctc agaattttaa gttctagccc catgataacc   1680
tttttctttg taatttatgc tttcatatat ccttggtccc agagatgttt agacaattt    1740 aggctcaaaa attaaagcta acacaggaaa aggaactgta ctggctatta cataagaaac   1800
aatggaccca agagaagaaa aggaagaaag aaaggtttt tggttttgt tttgttttgt   1860 tttgttttt gttttttga gatggagtct cactctttcg cccaggctgg agtgcagtgg    1920
tatgatctca gctcactgca agctccacct cccgggttca cgccattctc ctgcctcagc   1980
ctcctgagta gctgggacta caggcgcccg ccaccacacc cggctaattt ttgtattt     2040 ttgtagagac ggggttcac catgttagcc aagatggtct cgatctcctg acctcgtgat   2100
ccacctgcct cggcctccca agtgctggg attacgggtg tgagccaccg tgcccagcct   2160 tttttttt aatagaaaaa ataatccgac tcccactaca tcaagactaa tcttgttttg    2220 tgtgttttc acatgtatta tagaatgctt ttgcatggac tatcctcttg ttttattaa    2280 aaacaaatga ttttttaaa agtcacaaaa acaattcact aaaaataaat atgtcattgt    2340
gctttaaaaa aataaccttct tgtagttata aaataaaacg tttgacttct aaactctg    2398
```

<210> SEQ ID NO 25
<211> LENGTH: 2469
<212> TYPE: DNA
<213> ORGANISM: homo sapien

<400> SEQUENCE: 25

```
agacagtacc tcctccctag gactacacaa ggactgaacc agaaggaaga ggacagagca    60
aagccatgaa catcatccta gaaatccttc tgcttctgat caccatcatc tactcctact    120
tggagtcgtt ggtgaagttt ttcattcctc agaggagaaa atctgtggct ggggagattg    180
ttctcattac tggagctggg catggaatag gcaggcagac tacttatgaa tttgcaaaac    240
gacagagcat attggttctg tgggatatta ataagcgcgg tgtggaggaa actgcagctg    300
```

| | |
|---|---|
| agtgccgaaa actaggcgtc actgcgcatg cgtatgtggt agactgcagc aacagagaag | 360 |
| agatctatcg ctctctaaat caggtgaaga aagaagtggg tgatgtaaca atcgtggtga | 420 |
| ataatgctgg gacagtatat ccagccgatc ttctcagcac caaggatgaa gagattacca | 480 |
| agacatttga ggtcaacatc ctaggacatt tttggaatgg aaaggacatc agaagtaatt | 540 |
| acttggatgt ataggatc gaggacactt ttggacgaga ctctgagatc acaaaagcac | 600 |
| ttcttccatc gatgatggag agaaatcatg gccacatcgt cacagtggct tcagtgtgcg | 660 |
| gccacgaagg gattccttac ctcatcccat attgttccag caaatttgcc gctgttggct | 720 |
| ttcacagagg tctgacatca gaacttcagg ccttgggaaa aactggtatc aaaacctcat | 780 |
| gtctctgccc agttttgtg aatactgggt tcaccaaaaa tccaagcaca agattatggc | 840 |
| ctgtattgga gacagatgaa gtcgtaagaa gtctgataga tggaatactt accaataaga | 900 |
| aaatgatttt tgttccatcg tatatcaata tctttctgag actacagaag tttcttcctg | 960 |
| aacgcgcctc agcgatttta aatcgtatgc agaatattca atttgaagca gtggttggcc | 1020 |
| acaaaatcaa aatgaaatga ataaataagc tccagccaga gatgtatgca tgataatgat | 1080 |
| atgaatagtt tcgaatcaat gctgcaaagc tttatttcac atttttttcag tcctgataat | 1140 |
| attaaaaaca ttggtttggc actagcagca gtcaaacgaa caagattaat tacctgtctt | 1200 |
| cctgttctc aagaatattt acgtagtttt tcataggtct gttttcctt tcatgcctct | 1260 |
| taaaaacttc tgtgcttaca taacatact taaaaggttt tctttaagat attttattt | 1320 |
| tccatttaaa ggtggacaaa agctacctcc ctaaaagtaa atacaaagag aacttattta | 1380 |
| cacagggaag gtttaagact gttcaagtag cattccaatc tgtagccatg ccacagaata | 1440 |
| tcaacaagaa cacagaatga gtgcacagct aagagatcaa gtttcagcag gcagctttat | 1500 |
| ctcaacctgg acatatttta agattcagca tttgaaagat ttccctagcc tcttcctttt | 1560 |
| tcattagccc aaaacggtgc aactctattc tggactttat tacttgattc tgtcttctgt | 1620 |
| ataactctga gtccaccaa aagtggaccc tctatatttc ctccctttt atagtcttat | 1680 |
| aagatacatt atgaaaggtg accgactcta ttttaaatct cagaatttta agttctagcc | 1740 |
| ccatgataac cttttctttt gtaatttatg ctttcatata tccttggtcc cagagatgtt | 1800 |
| tagacaattt taggctcaaa aattaaagct aacacaggaa aaggaactgt actggctatt | 1860 |
| acataagaaa caatggaccc aagagaagaa aaggaagaaa gaaaggtttt ttggttttg | 1920 |
| ttttgttttg ttttgttttt tgtttttttg agatggagtc tcactctttc gcccaggctg | 1980 |
| gagtgcagtg gtatgatctc agctcactgc aagctccacc tcccgggttc acgccattct | 2040 |
| cctgcctcag cctcctgagt agctgggact acaggcgccc gccaccacac ccggctaatt | 2100 |
| ttttgtattt tttgtagaga cggggtttca ccatgttagc caagatggtc tcgatctcct | 2160 |
| gacctcgtga tccacctgcc tcggcctccc aaagtgctgg gattacgggt gtgagccacc | 2220 |
| gtgcccagcc ttttttttt taatagaaaa aataatccga ctcccactac atcaagacta | 2280 |
| atcttgtttt gtgtgttttt cacatgtatt atagaatgct tttgcatgga ctatcctctt | 2340 |
| gtttttatta aaacaaatg atttttttaa aagtcacaaa acaattcac taaaaataaa | 2400 |
| tatgtcattg tgctttaaaa aaataaccte ttgtagttat aaaataaaac gtttgacttc | 2460 |
| taaactctg | 2469 |

<210> SEQ ID NO 26
<211> LENGTH: 1715
<212> TYPE: DNA
<213> ORGANISM: homo sapien

<400> SEQUENCE: 26

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta taagcgcgg tgtggaggaa actgcagctg    300
agtgccgaaa actaggcgtc actgcgcatg cgtatgtggt agactgcagc aacagagaag   360
agatctatcg ctctctaaat caggtgaaga agaagtggg tgatgtaaca atcgtggtga    420
ataatgctgg gacagtatat ccagccgatc ttctcagcac caaggatgaa gagattacca   480
agacatttga ggtcaacatc ctaggacatt tttggatcac aaaagcactt cttccatcga   540
tgatggagag aaatcatggc cacatcgtca cagtggcttc agtgtgcggc cacgaaggga   600
ttccttacct catcccatat tgttccagca aatttgccgc tgttggcttt cacagaggtc   660
tgacatcaga acttcaggcc ttgggaaaaa ctggtatcaa aacctcatgt ctctgcccag   720
ttttttgtgaa tactgggttc accaaaaaatc caagcacaag attatggcct gtattggaga  780
cagatgaagt cgtaagaagt ctgatagatg aatacttac caataagaaa atgattttg    840
ttccatcgta tatcaaatatc tttctgagac tacagaagtt aagtacagca cagaacaccc   900
aaatactaaa acaccaatag agcttttttt tttgcttttt tttttttag acagagtctc   960
actctgtcac cctggctgga ttgcggtggt gcagtggca tgatcttggc tcactgcaac   1020
ctccgcctcc tgggttcaag caattctcat gcctcagacc cccaagtaac tgggattata   1080
ggtgtgtgct gccacactac acccagctaa ttttttgtatt ttttgataga acaggtttc   1140
cccatgttgg ccaggctgga ctcgaactcc tgacctcaag ttatcctcct gtctcggcct   1200
cccaaagtgc tgggattaca gtcatgagcc accatgcctg cccaataga gctattatta    1260
tggagcatct ttcagttgtg aaaattggca tggaaactct ccatccctgg ggagaacagt   1320
tatttcctct gttattttcc tacccagtct ataaaaagag agtgattcat tttctctacc   1380
aaatctactg tctctgccca aactttgctg aagactattc taactaaagg aaacacagtt   1440
taaaaagaat gcaatatagt gaagtagtta ataataaaga ctccattttt aaaagtctgc   1500
tggaagtttg gttgggattg cactgaatct atagagcaat gggagtat tgacatatca    1560
acaatattga gttttctaat ccaagaacat aatatctatt tttaaaatct tcttcaaaat   1620
ctttaaatct ttaaattgta ttttgtagtt tttggtgttt aagtcttgca catatttgt    1680
cagatttatt ccaaagtatt tcacgggttc ttttt                              1715
```

<210> SEQ ID NO 27
<211> LENGTH: 1714
<212> TYPE: DNA
<213> ORGANISM: homo sapien

<400> SEQUENCE: 27

```
agacagtacc tcctccctag gactacacaa ggactgaacc agaaggaaga ggacagagca    60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta taagcgcgg tgtggaggaa actgcagctg    300
```

```
agtgccgaaa actaggcgtc actgcgcatg cgtatgtggt agactgcagc aacagagaag        360
agatctatcg ctctctaaat caggtgaaga aagaagtggg tgatgtaaca atcgtggtga        420
ataatgctgg gacagtatat ccagccgatc ttctcagcac caaggatgaa gagattacca        480
agacatttga ggtcaacatc ctaggacatt tttggatcac aaaagcactt cttccatcga        540
tgatggagag aaatcatggc cacatcgtca cagtggcttc agtgtgcggc cacgaaggga        600
ttccttacct catcccatat tgttccagca aatttgccgc tgttggcttt cacagaggtc        660
tgacatcaga acttcaggcc ttgggaaaaa ctggtatcaa aacctcatgt ctctgcccag        720
tttttgtgaa tactgggttc accaaaaatc caagcacaag attatggcct gtattggaga        780
cagatgaagt cgtaagaagt ctgatagatg gaatacttac caataagaaa atgattttg        840 ttccatcgta tatcaatatc tttctgagac tacagaagta agtacagcac agaacaccca        900
aatactaaaa caccaataga gcttttttt ttgcttttt ttttttaga cagagtctca        960 ctctgtcacc ctggctggat tgcggtggt gcagtggcat gatcttggct cactgcaacc       1020
tccgcctcct gggttcaagc aattctcatg cctcagaccc ccagtaact gggattatag       1080 gtgtgtgctg ccacactaca cccagctaat ttttgtattt tttgatagag acaggttcc       1140 ccatgttggc caggctggac tcgaactcct gacctcaagt tatcctcctg tctcggcctc       1200
ccaaagtgct gggattacag tcatgagcca ccatgcctgg cccaatagag ctattattat       1260
ggagcatctt tcagttgtga aaattggcat ggaaactctc catccctggg gagaacagtt       1320
atttcctctg ttattttcct acccagtcta taaaagaga gtgattcatt ttctctacca       1380
aatctactgt ctctgcccaa actttgctga agactattct aactaaagga aacacagttt       1440
aaaaagaatg caatatagtg aagtagttaa taataaagac tccattttta aaagtctgct       1500
ggaagtttgg ttgggattgc actgaatcta tagagcaatt ggggagtatt gacatatcaa       1560
caatattgag ttttctaatc caagaacata atatctattt ttaaaatctt cttcaaaatc       1620
tttaaatctt taaattgtat tttgtagttt tggtgtttta agtcttgcac atattttgtc       1680
agatttattc caaagtattt cacgggttct tttt                                   1714

<210> SEQ ID NO 28
<211> LENGTH: 2290
<212> TYPE: DNA
<213> ORGANISM: homo sapien

<400> SEQUENCE: 28
agacagtacc tcctccctag gactacacaa ggactgaacc agaaggaaga ggacagagca         60
aagccatgaa catcatccta gaaatccttc tgcttctgat caccatcatc tactcctact        120
tggagtcgtt ggtgaagttt ttcattcctc agaggagaaa atctgtggct ggggagattg        180
ttctcattac tggagctggg catggaatag gcaggcagac tacttatgaa tttgcaaaac        240
gacagagcat attggttctg tgggatatta ataaggtgaa gaaagaagtg ggtgatgtaa        300
caatcgtggt gaataatgct gggacagtat atccagccga tcttctcagc accaaggatg        360
aagagattac caagacattt gaggtcaaca tcctaggaca ttttggatc acaaaagcac        420 ttcttccatc gatgatggag agaaatcatg gccacatcgt cacagtggct tcagtgtgcg        480
gccacgaagg gattccttac ctcatcccat attgttccag caaatttgcc gctgttggct        540
ttcacagagg tctgacatca gaacttcagg ccttgggaaa aactggtatc aaaacctcat        600
gtctctgccc agttttgtg aatactgggt tcaccaaaaa tccaagcaca agattatggc        660
ctgtattgga gacagatgaa gtcgtaagaa gtctgataga tggaatactt accaataaga        720
```

```
aaatgatttt tgttccatcg tatatcaata tctttctgag actacagaag gtttcttcct    780
gaacgcgcct cagcgatttt aaatcgtatg cagaatattc aatttgaagc agtggttggc    840
cacaaaatca aaatgaaatg aataaataag ctccagccag agatgtatgc atgataatga    900
tatgaatagt ttcgaatcaa tgctgcaaag ctttatttca catttttca gtcctgataa     960 tattaaaaac attggtttgg cactagcagc agtcaaacga acaagattaa ttacctgtct   1020
tcctgtttct caagaatatt tacgtagttt tcataggtc tgttttcct ttcatgcctc     1080 ttaaaaactt ctgtgcttac ataaacatac ttaaaaggtt ttctttaaga tattttattt   1140
ttccatttaa aggtggacaa aagctacctc cctaaaagta aatacaaaga gaacttattt   1200
acacagggaa ggtttaagac tgttcaagta gcattccaat ctgtagccat gccacagaat   1260
atcaacaaga acacagaatg agtgcacagc taagagatca agtttcagca ggcagcttta   1320
tctcaacctg gacatatttt aagattcagc atttgaaaga tttccctagc ctcttccttt   1380
ttcattagcc caaaacggtg caactctatt ctggacttta ttacttgatt ctgtcttctg   1440
tataactctg aagtccacca aaagtggacc ctctatattt cctcccttt tatagtctta   1500 taagatacat tatgaaaggt gaccgactct atttaaatc tcagaatttt aagttctagc   1560
cccatgataa ccttttttctt tgtaatttat gctttcatat atccttggtc ccagagatgt   1620
ttagacaatt ttaggctcaa aaattaaagc taacacagga aaaggaactg tactggctat   1680
tacataagaa acaatggacc caagagaaga aaaggaagaa agaaaggttt tttggttttt   1740
gttttgtttt gttttgtttt ttgtttttt gagatggagt ctcactcttt cgcccaggct   1800
ggagtgcagt ggtatgatct cagctcactg caagctccac ctcccgggtt cacgccattc   1860
tcctgcctca gcctcctgag tagctgggac tacaggcgcc cgccaccaca cccggctaat   1920 ttttttgtatt ttttgtagag acggggtttc accatgttag ccaagatggt ctcgatctcc   1980
tgacctcgtg atccacctgc ctcggcctcc caaagtgctg ggattacggg tgtgagccac   2040
cgtgcccagc cttttttttt taatagaaa aaataatccg actcccacta catcaagact   2100
aatcttgttt tgtgtgtttt tcacatgtat tatagaatgc ttttgcatgg actatcctct   2160 tgttttatt aaaacaaat gattttttta aaagtcacaa aaacaattca ctaaaaataa   2220
atatgtcatt gtgctttaaa aaaataaccct cttgtagtta taaaataaaa cgtttgactt   2280
ctaaactctg                                                          2290

<210> SEQ ID NO 29
<211> LENGTH: 2470
<212> TYPE: DNA
<213> ORGANISM: homo sapien

<400> SEQUENCE: 29
agacagtacc tcctccctag gactacacaa ggactgaacc agaaggaaga ggacagagca     60
aagccatgaa catcatccta gaaatccttc tgcttctgat caccatcatc tactcctact   120
tggagtcgtt ggtgaagttt ttcattcctc agaggagaaa atctgtggct ggggagattg   180
ttctcattac tggagctggg catggaatag gcaggcagac tacttatgaa tttgcaaaac   240
gacagagcat attggttctg tgggatatta ataagcgcgg tgtggaggaa actgcagctg   300
agtgccgaaa actaggcgtc actgcgcatg cgtatgtggt agactgcagc aacagagaag   360
agatctatcg ctctctaaat caggtgaaga agaagtggg tgatgtaaca atcgtggtga   420
ataatgctgg gacagtatat ccagccgatc ttctcagcac caaggatgaa gagattacca   480
```

| | |
|---|---|
| agacatttga ggtcaacatc ctaggacatt tttggaatgg aaaggacatc agaagtaatt | 540 |
| acttggatgt ataggatc gaggacactt ttggacgaga ctctgagatc acaaaagcac | 600 |
| ttcttccatc gatgatggag agaaatcatg ccacatcgt cacagtggct tcagtgtgcg | 660 |
| gccacgaagg gattccttac ctcatcccat attgttccag caaatttgcc gctgttggct | 720 |
| ttcacagagg tctgacatca gaacttcagg ccttgggaaa aactggtatc aaaacctcat | 780 |
| gtctctgccc agttttttgtg aatactgggt tcaccaaaaa tccaagcaca agattatggc | 840 |
| ctgtattgga gacagatgaa gtcgtaagaa gtctgataga tggaatactt accaataaga | 900 |
| aaatgatttt tgttccatcg tatatcaata tctttctgag actacagaag gtttcttcct | 960 |
| gaacgcgcct cagcgatttt aaatcgtatg cagaatattc aatttgaagc agtggttggc | 1020 |
| cacaaaatca aaatgaaatg aataaataag ctccagccag agatgtatgc atgataatga | 1080 |
| tatgaatagt ttcgaatcaa tgctgcaaag ctttatttca cattttttca gtcctgataa | 1140 |
| tattaaaaac attggtttgg cactagcagc agtcaaacga acaagattaa ttacctgtct | 1200 |
| tcctgtttct caagaatatt tacgtagttt ttcataggtc tgttttttcct ttcatgcctc | 1260 |
| ttaaaaactt ctgtgcttac ataaacatac ttaaaaggtt ttctttaaga tattttatt | 1320 |
| ttccatttaa aggtggacaa aagctacctc cctaaaagta aatacaaaga gaacttattt | 1380 |
| acacagggaa ggtttaagac tgttcaagta gcattccaat ctgtagccat gccacagaat | 1440 |
| atcaacaaga acacagaatg agtgcacagc taagagatca agtttcagca ggcagcttta | 1500 |
| tctcaacctg gacatatttt aagattcagc atttgaaaga tttccctagc ctcttccttt | 1560 |
| ttcattagcc caaacggtg caactctatt ctggactta ttacttgatt ctgtcttctg | 1620 |
| tataactctg aagtccacca aaagtggacc ctctatattt cctccctttt tatagtctta | 1680 |
| taagatacat tatgaaaggt gaccgactct atttttaaatc tcagaatttt aagttctagc | 1740 |
| cccatgataa ccttttttctt tgtaatttat gctttcatat atccttggtc ccagagatgt | 1800 |
| ttagacaatt ttaggctcaa aaattaaagc taacacagga aaaggaactg tactggctat | 1860 |
| tacataagaa acaatggacc caagagaaga aaaggaagaa agaaaggttt tttggttttt | 1920 |
| gttttgttttt gttttgtttt ttgttttttt gagatggagt ctcactcttt cgcccaggct | 1980 |
| ggagtgcagt ggtatgatct cagctcactg caagctccac ctcccgggtt cacgccattc | 2040 |
| tcctgcctca gcctcctgag tagctgggac tacaggcgcc cgccaccaca cccggctaat | 2100 |
| ttttttgtatt ttttgtagag acggggtttc accatgttag ccaagatggt ctcgatctcc | 2160 |
| tgacctcgtg atcccacctgc ctcggcctcc caaagtgctg ggattacggg tgtgagccac | 2220 |
| cgtgcccagc ctttttttttt ttaatagaaa aaataatccg actcccacta catcaagact | 2280 |
| aatcttgttt tgtgtgtttt tcacatgtat tatagaatgc ttttgcatgg actatcctct | 2340 |
| tgttttatt aaaacaaat gattttttta aaagtcacaa aaacaattca ctaaaaataa | 2400 |
| atatgtcatt gtgctttaaa aaataaccct cttgtagtta taaaataaaa cgtttgactt | 2460 |
| ctaaactctg | 2470 |

<210> SEQ ID NO 30
<211> LENGTH: 900
<212> TYPE: DNA
<213> ORGANISM: homo sapien

<400> SEQUENCE: 30

| | |
|---|---|
| atgaacatca tcctagaaat ccttctgctt ctgatcacca tcatctactc ctacttggag | 60 |
| tcgttggtga agttttcat tcctcagagg agaaaatctg tggctgggga gattgttctc | 120 |

```
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttttgg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg ctttcacag aggtctgaca    600 tcagaacttc aggccttggg aaaaactggt atcaaaacct catgtctctg cccagttttt    660
gtgaatactg ggttcaccaa aaatccaagc acaagattat ggcctgtatt ggagacagat    720
gaagtcgtaa aagtctgat agatggaata cttaccaata gaaaatgat ttttgttcca    780 tcgtatatca atatctttct gagactacag aagtttcttc ctgaacgcgc ctcagcgatt    840
ttaaatcgta tgcagaatat tcaatttgaa gcagtggttg ccacaaaaat caaaatgaaa    900
```

<210> SEQ ID NO 31
<211> LENGTH: 792
<212> TYPE: DNA
<213> ORGANISM: homo sapien

<400> SEQUENCE: 31

```
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag gtgaagaaag aagtgggtga tgtaacaatc    240
gtggtgaata atgctgggac agtatatcca gccgatcttc tcagcaccaa ggatgaagag    300
attaccaaga catttgaggt caacatccta ggacatttttt ggatcacaaa agcacttctt    360
ccatcgatga tggagagaaa tcatggccac atcgtcacag tggcttcagt gtgcggccac    420
gaagggattc cttacctcat cccatattgt tccagcaaat ttgccgctgt tggctttcac    480
agaggtctga catcagaact tcaggccttg ggaaaaactg gtatcaaaac ctcatgtctc    540
tgcccagttt ttgtgaatac tggggttcacc aaaaatccaa gcacaagatt atggcctgta    600
ttggagacag atgaagtcgt aagaagtctg atagatggaa tacttaccaa taagaaaatg    660 attttttgttc catcgtatat caatatcttt ctgagactac agaagtttct tcctgaacgc    720
gcctcagcga ttttaaatcg tatgcagaat attcaatttg aagcagtggt tgccacaaaa    780
atcaaaatga aa                                                        792
```

<210> SEQ ID NO 32
<211> LENGTH: 783
<212> TYPE: DNA
<213> ORGANISM: homo sapien

<400> SEQUENCE: 32

```
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
```

```
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttttgg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg gctttcacag aggtctgaca    600
tcagaacttc aggccttggg aaaaactggt atcaaaacct catgtctctg cccagttttt    660
gtgaatactg ggttcaccaa aaatccaagc acaaggtttc ttcctgaacg cgcctcagcg    720
attttaaatc gtatgcagaa tattcaattt gaagcagtgg ttggccacaa aatcaaaatg    780
aaa                                                                  783

<210> SEQ ID NO 33
<211> LENGTH: 822
<212> TYPE: DNA
<213> ORGANISM: homo sapien

<400> SEQUENCE: 33
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttttgg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg gctttcacag aggtctgaca    600
tcagaacttc aggccttggg aaaaactggt atcaaaacct catgtctctg cccagttttt    660
gtgaatactg ggttcaccaa aaatccaagc acaagattat ggcctgtatt ggagacagat    720
gaagtcgtaa aagtctgat agatggaata cttaccaata agaaaatgat ttttgttcca    780
tcgtatatca atatctttct gagactacag aaggtttctt cc                       822

<210> SEQ ID NO 34
<211> LENGTH: 972
<212> TYPE: DNA
<213> ORGANISM: homo sapien

<400> SEQUENCE: 34
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttttgg aatggaaagg acatcagaag taattacttg    480
```

```
gatgtatata ggatcgagga cacttttgga cgagactctg agatcacaaa agcacttctt    540
ccatcgatga tggagagaaa tcatggccac atcgtcacag tggcttcagt gtgcggccac    600
gaagggattc cttacctcat cccatattgt tccagcaaat ttgccgctgt tggctttcac    660
agaggtctga catcagaact tcaggccttg ggaaaaactg gtatcaaaac ctcatgtctc    720
tgcccagttt ttgtgaatac tgggttcacc aaaaatccaa gcacaagatt atggcctgta    780
ttggagacag atgaagtcgt aagaagtctg atagatggaa tacttaccaa taagaaaatg    840
atttttgttc catcgtatat caatatcttt ctgagactac agaagtttct tcctgaacgc    900
gcctcagcga ttttaaatcg tatgcagaat attcaatttg aagcagtggt tggccacaaa    960
atcaaaatga aa                                                        972

<210> SEQ ID NO 35
<211> LENGTH: 852
<212> TYPE: DNA
<213> ORGANISM: homo sapien

<400> SEQUENCE: 35
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
tttgaggtca acatcctagg acattttgg atcacaaaag cacttcttcc atcgatgatg    480
gagagaaatc atggccacat cgtcacagtg gcttcagtgt gcggccacga agggattcct    540
tacctcatcc catattgttc cagcaaattt gccgctgttg gctttcacag aggtctgaca    600
tcagaacttc aggccttggg aaaaactggt atcaaaacct catgtctctg cccagttttt    660
gtgaatactg ggttcaccaa aaatccaagc acaagattat ggcctgtatt ggagacagat    720
gaagtcgtaa gaagtctgat agatggaata cttaccaata agaaaatgat ttttgttcca    780
tcgtatatca atatctttct gagactacag aagttaagta cagcacagaa cacccaaata    840
ctaaaacacc aa                                                        852

<210> SEQ ID NO 36
<211> LENGTH: 813
<212> TYPE: DNA
<213> ORGANISM: homo sapien

<400> SEQUENCE: 36
atgaacatca tcctagaaat ccttctgctt ctgatcacca tcatctactc ctacttggag     60
tcgttggtga agttttttcat tcctcagagg agaaaatctg tggctgggga gattgttctc    120
attactggag ctgggcatgg aataggcagg cagactactt atgaatttgc aaaacgacag    180
agcatattgg ttctgtggga tattaataag cgcggtgtgg aggaaactgc agctgagtgc    240
cgaaaactag gcgtcactgc gcatgcgtat gtggtagact gcagcaacag agaagagatc    300
tatcgctctc taaatcaggt gaagaaagaa gtgggtgatg taacaatcgt ggtgaataat    360
gctgggacag tatatccagc cgatcttctc agcaccaagg atgaagagat taccaagaca    420
```

| | |
|---|---|
| tttgaggtca acatcctagg acattttttgg atcacaaaag cacttcttcc atcgatgatg | 480 |
| gagagaaatc atggccacat cgtcacagtg gcttcagtgt gcggccacga agggattcct | 540 |
| tacctcatcc catattgttc cagcaaattt gccgctgttg gctttcacag aggtctgaca | 600 |
| tcagaacttc aggccttggg aaaaactggt atcaaaacct catgtctctg cccagttttt | 660 |
| gtgaatactg ggttcaccaa aaatccaagc acaagattat ggcctgtatt ggagacagat | 720 |
| gaagtcgtaa aagtctgat agatggaata cttaccaata agaaaatgat ttttgttcca | 780 |
| tcgtatatca atatctttct gagactacag aag | 813 |

<210> SEQ ID NO 37
<211> LENGTH: 714
<212> TYPE: DNA
<213> ORGANISM: homo sapien

<400> SEQUENCE: 37

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag gtgaagaaag aagtgggtga tgtaacaatc | 240 |
| gtggtgaata tgctgggac agtatatcca gccgatcttc tcagcaccaa ggatgaagag | 300 |
| attaccaaga catttgaggt caacatccta ggacattttt ggatcacaaa agcacttctt | 360 |
| ccatcgatga tggagagaaa tcatggccac atcgtcacag tggcttcagt gtgcggccac | 420 |
| gaagggattc cttacctcat cccatattgt tccagcaaat ttgccgctgt tggctttcac | 480 |
| agaggtctga catcagaact tcaggccttg ggaaaaactg gtatcaaaac ctcatgtctc | 540 |
| tgcccagttt ttgtgaatac tgggttcacc aaaaatccaa gcacaagatt atggcctgta | 600 |
| ttggagacag atgaagtcgt aagaagtctg atagatggaa tacttaccaa taagaaaatg | 660 |
| attttttgttc catcgtatat caatatcttt ctgagactac agaaggtttc ttcc | 714 |

<210> SEQ ID NO 38
<211> LENGTH: 894
<212> TYPE: DNA
<213> ORGANISM: homo sapien

<400> SEQUENCE: 38

| | |
|---|---|
| atgaacatca tcctagaaat ccttctgctt ctgatcacca tcatctactc ctacttggag | 60 |
| tcgttggtga agttttttcat tcctcagagg agaaaatctg tggctgggga gattgttctc | 120 |
| attactggag ctgggcatgg aataggcagg cagactactt atgaatttgc aaaacgacag | 180 |
| agcatattgg ttctgtggga tattaataag cgcggtgtgg aggaaactgc agctgagtgc | 240 |
| cgaaaactag gcgtcactgc gcatgcgtat gtggtagact gcagcaacag agaagagatc | 300 |
| tatcgctctc taaatcaggt gaagaaagaa gtgggtgatg taacaatcgt ggtgaataat | 360 |
| gctgggacag tatatccagc cgatcttctc agcaccaagg atgaagagat accaagaca | 420 |
| tttgaggtca acatcctagg acattttttgg aatggaaagg acatcagaag taattacttg | 480 |
| gatgtatata ggatcgagga cacttttgga cgagactctg atcacaaa agcacttctt | 540 |
| ccatcgatga tggagagaaa tcatggccac atcgtcacag tggcttcagt gtgcggccac | 600 |
| gaagggattc cttacctcat cccatattgt tccagcaaat ttgccgctgt tggctttcac | 660 |
| agaggtctga catcagaact tcaggccttg ggaaaaactg gtatcaaaac ctcatgtctc | 720 |
| tgcccagttt ttgtgaatac tgggttcacc aaaaatccaa gcacaagatt atggcctgta | 780 |

```
ttggagacag atgaagtcgt aagaagtctg atagatggaa tacttaccaa taagaaaatg    840 attttttgttc catcgtatat caatatcttt ctgagactac agaaggtttc ttcc          894
```

<210> SEQ ID NO 39
<211> LENGTH: 300
<212> TYPE: PRT
<213> ORGANISM: homo sapien

<400> SEQUENCE: 39

```
Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285

Phe Glu Ala Val Val Gly His Lys Ile Lys Met Lys
    290                 295                 300
```

<210> SEQ ID NO 40
<211> LENGTH: 264
<212> TYPE: PRT
<213> ORGANISM: homo sapien

<400> SEQUENCE: 40

```
Met Asn Ile Ile Leu Glu Ile Leu Leu Leu Leu Ile Thr Ile Ile Tyr
```

```
            1               5                  10                 15
        Ser Tyr Leu Glu Ser Leu Val Lys Phe Phe Ile Pro Gln Arg Arg Lys
                        20                 25                 30

Ser Val Ala Gly Glu Ile Val Leu Ile Thr Gly Ala Gly His Gly Ile
                        35                 40                 45

Gly Arg Gln Thr Thr Tyr Glu Phe Ala Lys Arg Gln Ser Ile Leu Val
                    50                 55                 60

Leu Trp Asp Ile Asn Lys Val Lys Glu Val Gly Asp Val Thr Ile
         65                 70                 75                 80

Val Val Asn Asn Ala Gly Thr Val Tyr Pro Ala Asp Leu Leu Ser Thr
                        85                 90                 95

Lys Asp Glu Glu Ile Thr Lys Thr Phe Glu Val Asn Ile Leu Gly His
                       100                105                110

Phe Trp Ile Thr Lys Ala Leu Leu Pro Ser Met Met Glu Arg Asn His
                       115                120                125

Gly His Ile Val Thr Val Ala Ser Val Cys Gly His Glu Gly Ile Pro
                       130                135                140

Tyr Leu Ile Pro Tyr Cys Ser Ser Lys Phe Ala Ala Val Gly Phe His
        145                150                155                160

Arg Gly Leu Thr Ser Glu Leu Gln Ala Leu Gly Lys Thr Gly Ile Lys
                       165                170                175

Thr Ser Cys Leu Cys Pro Val Phe Val Asn Thr Gly Phe Thr Lys Asn
                       180                185                190

Pro Ser Thr Arg Leu Trp Pro Val Leu Glu Thr Asp Glu Val Val Arg
                       195                200                205

Ser Leu Ile Asp Gly Ile Leu Thr Asn Lys Lys Met Ile Phe Val Pro
                       210                215                220

Ser Tyr Ile Asn Ile Phe Leu Arg Leu Gln Lys Phe Leu Pro Glu Arg
        225                230                235                240

Ala Ser Ala Ile Leu Asn Arg Met Gln Asn Ile Gln Phe Glu Ala Val
                       245                250                255

Val Gly His Lys Ile Lys Met Lys
                       260

<210> SEQ ID NO 41
<211> LENGTH: 261
<212> TYPE: PRT
<213> ORGANISM: homo sapien

<400> SEQUENCE: 41

Met Asn Ile Ile Leu Glu Ile Leu Leu Leu Ile Thr Ile Tyr
         1               5                  10                 15

Ser Tyr Leu Glu Ser Leu Val Lys Phe Phe Ile Pro Gln Arg Arg Lys
                        20                 25                 30

Ser Val Ala Gly Glu Ile Val Leu Ile Thr Gly Ala Gly His Gly Ile
                        35                 40                 45

Gly Arg Gln Thr Thr Tyr Glu Phe Ala Lys Arg Gln Ser Ile Leu Val
                    50                 55                 60

Leu Trp Asp Ile Asn Lys Arg Gly Val Glu Glu Thr Ala Ala Glu Cys
         65                 70                 75                 80

Arg Lys Leu Gly Val Thr Ala His Ala Tyr Val Val Asp Cys Ser Asn
                        85                 90                 95

Arg Glu Glu Ile Tyr Arg Ser Leu Asn Gln Val Lys Lys Glu Val Gly
                       100                105                110
```

```
Asp Val Thr Ile Val Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Phe Leu Pro Glu Arg Ala Ser Ala
225                 230                 235                 240

Ile Leu Asn Arg Met Gln Asn Ile Gln Phe Glu Ala Val Val Gly His
                245                 250                 255

Lys Ile Lys Met Lys
            260

<210> SEQ ID NO 42
<211> LENGTH: 274
<212> TYPE: PRT
<213> ORGANISM: homo sapien

<400> SEQUENCE: 42

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
            115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220
```

```
Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
            245                 250                 255

Ile Phe Val Pro Ser Tyr Ile Asn Ile Phe Leu Arg Leu Gln Lys Val
            260                 265                 270

Ser Ser

<210> SEQ ID NO 43
<211> LENGTH: 324
<212> TYPE: PRT
<213> ORGANISM: homo sapien

<400> SEQUENCE: 43

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn
        275                 280                 285

Ile Phe Leu Arg Leu Gln Lys Phe Leu Pro Glu Arg Ala Ser Ala Ile
290                 295                 300

Leu Asn Arg Met Gln Asn Ile Gln Phe Glu Ala Val Val Gly His Lys
305                 310                 315                 320
```

Ile Lys Met Lys

<210> SEQ ID NO 44
<211> LENGTH: 284
<212> TYPE: PRT
<213> ORGANISM: homo sapien

<400> SEQUENCE: 44

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Leu
            260                 265                 270

Ser Thr Ala Gln Asn Thr Gln Ile Leu Lys His Gln
        275                 280

<210> SEQ ID NO 45
<211> LENGTH: 271
<212> TYPE: PRT
<213> ORGANISM: homo sapien

<400> SEQUENCE: 45

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
50                      55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
        210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys
            260                 265                 270

<210> SEQ ID NO 46
<211> LENGTH: 238
<212> TYPE: PRT
<213> ORGANISM: homo sapien

<400> SEQUENCE: 46

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
50                      55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
        115                 120                 125

Gly His Ile Val Thr Val Ala Ser Val Cys Gly His Glu Gly Ile Pro
130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
            165                 170                 175

Thr Ser Cys Leu Cys Pro Val Phe Val Asn Thr Gly Phe Thr Lys Asn
        180                 185                 190

Pro Ser Thr Arg Leu Trp Pro Val Leu Glu Thr Asp Glu Val Val Arg
    195                 200                 205

Ser Leu Ile Asp Gly Ile Leu Thr Asn Lys Lys Met Ile Phe Val Pro
210                 215                 220

Ser Tyr Ile Asn Ile Phe Leu Arg Leu Gln Lys Val Ser Ser
225                 230                 235

<210> SEQ ID NO 47
<211> LENGTH: 298
<212> TYPE: PRT
<213> ORGANISM: homo sapien

<400> SEQUENCE: 47

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205

Tyr Cys Ser Ser Lys Phe Ala Ala Val Gly Phe His Arg Gly Leu Thr
210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
            260                 265                 270

Gly Ile Leu Thr Asn Lys Lys Met Ile Phe Val Pro Ser Tyr Ile Asn

-continued

```
            275                 280                 285

Ile Phe Leu Arg Leu Gln Lys Val Ser Ser
        290                 295
```

<210> SEQ ID NO 48
<211> LENGTH: 25
<212> TYPE: DNA
<213> ORGANISM: artificial sequence
<220> FEATURE:
<223> OTHER INFORMATION: Forward Primer for HSD17B13

<400> SEQUENCE: 48
atgaacatca tcctagaaat ccttc                                      25

<210> SEQ ID NO 49
<211> LENGTH: 25
<212> TYPE: DNA
<213> ORGANISM: artificial sequence
<220> FEATURE:
<223> OTHER INFORMATION: Reverse Primer for HSD17B13

<400> SEQUENCE: 49
atcatgcata catctctggc tggag                                      25

<210> SEQ ID NO 50
<211> LENGTH: 20
<212> TYPE: DNA
<213> ORGANISM: artificial sequence
<220> FEATURE:
<223> OTHER INFORMATION: Primer DE002 for HSD17B13

<400> SEQUENCE: 50
atcagaactt caggccttgg                                            20

<210> SEQ ID NO 51
<211> LENGTH: 21
<212> TYPE: DNA
<213> ORGANISM: artificial sequence
<220> FEATURE:
<223> OTHER INFORMATION: Primer for first exon of HSD17B13

<400> SEQUENCE: 51
gcaaagccat gaacatcatc c                                          21

<210> SEQ ID NO 52
<211> LENGTH: 24
<212> TYPE: DNA
<213> ORGANISM: artificial sequence
<220> FEATURE:
<223> OTHER INFORMATION: Primer for last exon of HSD17B13

<400> SEQUENCE: 52
tcttgatgta gtgggagtcg gatt                                       24

<210> SEQ ID NO 53
<211> LENGTH: 600
<212> TYPE: DNA
<213> ORGANISM: artificial sequence
<220> FEATURE:
<223> OTHER INFORMATION: Endogenous HSD17B13 Promoter

<400> SEQUENCE: 53
cactgcacca cgaactcatg gactgaagca atcctcctgc ctcagcctcc tgggtagctg    60
ggactacaga cacatgccac catatccagc taatttttt ctatagtttt ttttttttt   120

```
tttgagacag ggtcttacta tgttgcccag actggtctcg aactcctggg ctcaagcaat    180
cctctgcctc agcctcccaa agtgctggga ttacagatgt gagccactgc acctggcccc    240
tagaattgtt tctagaggtg aaacttcaag gtgaaatata gtacataact gcttttcaga    300
taaacaagtc cagagagcac actctcttgt gctcttggca tcacttggca tcacttcata    360
tttgaggtgt ttcaaaccca ttagaacacg tgaacaaggc ctgcttccaa agctggcttc    420
catctggtag tcccattaac aactgggcac accccttccc tagagctctg tgtagacagt    480
acctcctccc taggactaca caaggactga accagaagga agaggacaga gcaaagccat    540
gaacatcatc ctagaaatcc ttctgcttct gatcaccatc atctactcct acttggagtc    600
```